(12) United States Patent
Land et al.

(10) Patent No.: US 8,613,907 B2
(45) Date of Patent: Dec. 24, 2013

(54) COMPOSITIONS THAT INHIBIT PROLIFERATION OF CANCER CELLS

(75) Inventors: Hartmut Land, Rochester, NY (US); Laurent Deleu, Rochester, NY (US)

(73) Assignee: University of Rochester, Rochester, NY (US)

( * ) Notice: Subject to any disclaimer, the term of this patent is extended or adjusted under 35 U.S.C. 154(b) by 1723 days.

(21) Appl. No.: 10/392,113

(22) Filed: Mar. 17, 2003

(65) Prior Publication Data

US 2003/0224993 A1 Dec. 4, 2003

Related U.S. Application Data

(63) Continuation-in-part of application No. PCT/US01/32127, filed on Oct. 12, 2001.

(60) Provisional application No. 60/365,078, filed on Mar. 15, 2002, provisional application No. 60/242,812, filed on Oct. 24, 2000, provisional application No. 60/239,705, filed on Oct. 12, 2000.

(51) Int. Cl.
*A61K 39/00* (2006.01)
*A61K 39/395* (2006.01)
*A61K 49/00* (2006.01)
*G01N 33/00* (2006.01)
*G01N 33/48* (2006.01)

(52) U.S. Cl.
USPC ....... 424/9.34; 424/9.1; 424/9.35; 424/130.1; 424/134.1; 424/138.1; 424/178.1; 424/179.1; 436/64; 436/86

(58) Field of Classification Search
None
See application file for complete search history.

(56) References Cited

U.S. PATENT DOCUMENTS 6,387,903 B1 * 5/2002 Dinsmore et al. ....... 514/254.05
6,458,026 B1 * 10/2002 Hart ............................. 435/69.1

FOREIGN PATENT DOCUMENTS

WO WO 96 10646 4/1996
WO WO 98 46265 A 10/1998

OTHER PUBLICATIONS

Kumar C.C. Oncogene 17:1365-1373, 1998.*
Bachelder R.E. et al. Journal of Biological Chemistry 274(29): 20733-20737, 1999.*
Hardan I. et al. International Journal of Cancer 55: 1023-1028, 1993.*
Spinardi L. et al. Journal of Cell Biology 129(2): 473-487, 1995.*
Huang F. et al. Oncogene 9(12): 3701-3706, 1994.*
Kauffmann-Zeh A. et al. Nature 385: 544-548, 1997.*
Pomroy N.C. et al. Analytical Biochemistry 275: 224-230, 1999.*
Yamaoka M. et al. Cancer Research 53: 5233-5236, 1993.*
Pyke C. et al. American Journal of Pathology 145(4): 782-791, 1994.*
Gonzales M. et al. Molecular Biology of the Cell 10: 259-270, 1999.*
Abarzua et al. (1995) Microinjection of monoclonal antibody PAb421 into human SW480 colorectal carcinoma cells restores the transcription activation function to mutant p53. *Cancer Res*, 55, 3490-4.
Akiyama et al. (1990) Cell surface receptors for extracellular matrix components. *Biochimica Biophys Acta*, 1031, 91-110.
Braselmann et al. (1993) A selective transcriptional induction system for mammalian cells based on Gal4-estrogen receptor fusion proteins. *Proc Natl Acad Sci U S A*, 90, 1657-61.
Cherif et al. (1988) Chromosomal localization of amplified c-myc in a human colon adenocarcinoma cell line with a biotinylated probe. *Cancer Genet Cytogenet*, 33, 245-9.
Clark and Brugge (1995) Integrins and signal transduction pathways: the road taken. *Science*, 268, 233-9.
D'Abaco et al. Synergy between Apc$^{min}$ and an activated *ras* mutation is sufficient to induce colon carcinomas. *Mol Cell Biol*, 16(3), 884-91 (1996).
Dedhar et al. (1993) Specific alterations in the expression of α3β1 and α6β4 integrins in highly invasive and metastatic variants of human prostate carcinoma cells selected by in vitro invasion through reconstituted basement membrane. *Clin Exp Metastasis*, 11, 391-400.
Efrat et al. (1995) Conditional transformation of a pancreatic βcell line derived from transgenic mice expressing a tetracycline-regulated oncogene. *Proc Natl Acad Sci U S A*, 92, 3576-80.
Freundlieb et al. (1999) A tetracycline controlled activation/repression system with increased potential for gene transfer into mammalian cells. *J Gene Med*, 1, 4-12.
Fujita et al. (1988) Detection of *ras* oncogenes by analysis of p21 proteins in human tumor cell lines. *Urol Res*, 16, 415-8.
Giancotti and Mainiero (1994) Integrin-mediated adhesion and signaling in tumorigenesis. *Biochim Biophys Acta*, 1198, 47-64.
Giancotti and Ruoslahti (1999) Integrin signaling. *Science*, 285, 1028-32.
Gossen, et al. (1995) Transcriptional activation by tetracyclines in mammalian cells. *Science*, 268, 1766-9.
He et al. (1998) Identification of c-MYC as a target of the APC pathway. *Science*, 281, 1509-12.
Hynes, R.O. (1992) Integrins: versatility, modulation, and signaling in cell adhesion. *Cell*, 69, 11-25.
Jat et al. (1991) Direct derivation of conditionally immortal cell lines from an H-2K$^b$-tsA58 transgenic mouse. *Proc Natl Acad Sci U S A*, 88, 5096-100.
Kamijo et al. (1997) Tumor suppression at the mouse INK4a locus mediated by the alternative reading frame product p19$^{ARF}$. *Cell*, 91, 649-59.
Kauffmann-Zeh et al. (1997) Suppression of c-Myc-induced apoptosis by Ras signalling through PI(3)K and PKB. *Nature*, 385, 544-8.
Kennel et al. (1989) Analysis of the tumor-associated antigen TSP-180. Identity with α$^6$-β$_4$ in the integrin superfamily. *J Biol Chem*, 264, 15515-21.
Khwaja et al. . (1997) Matrix adhesion and Ras transformation both activate a phosphoinositide 3-OH kinase and protein kinase B/Akt cellular survival pathway. *Embo J*, 16, 2783-93.

(Continued)

Primary Examiner — Alana Harris Dent
(74) *Attorney, Agent, or Firm* — Ballard Spahr LLP

(57) ABSTRACT

Disclosed are compositions and methods for reducing the proliferation of cancer cells through targeted interactions with integrins.

33 Claims, 10 Drawing Sheets

(56) References Cited

OTHER PUBLICATIONS

Figure 1C:
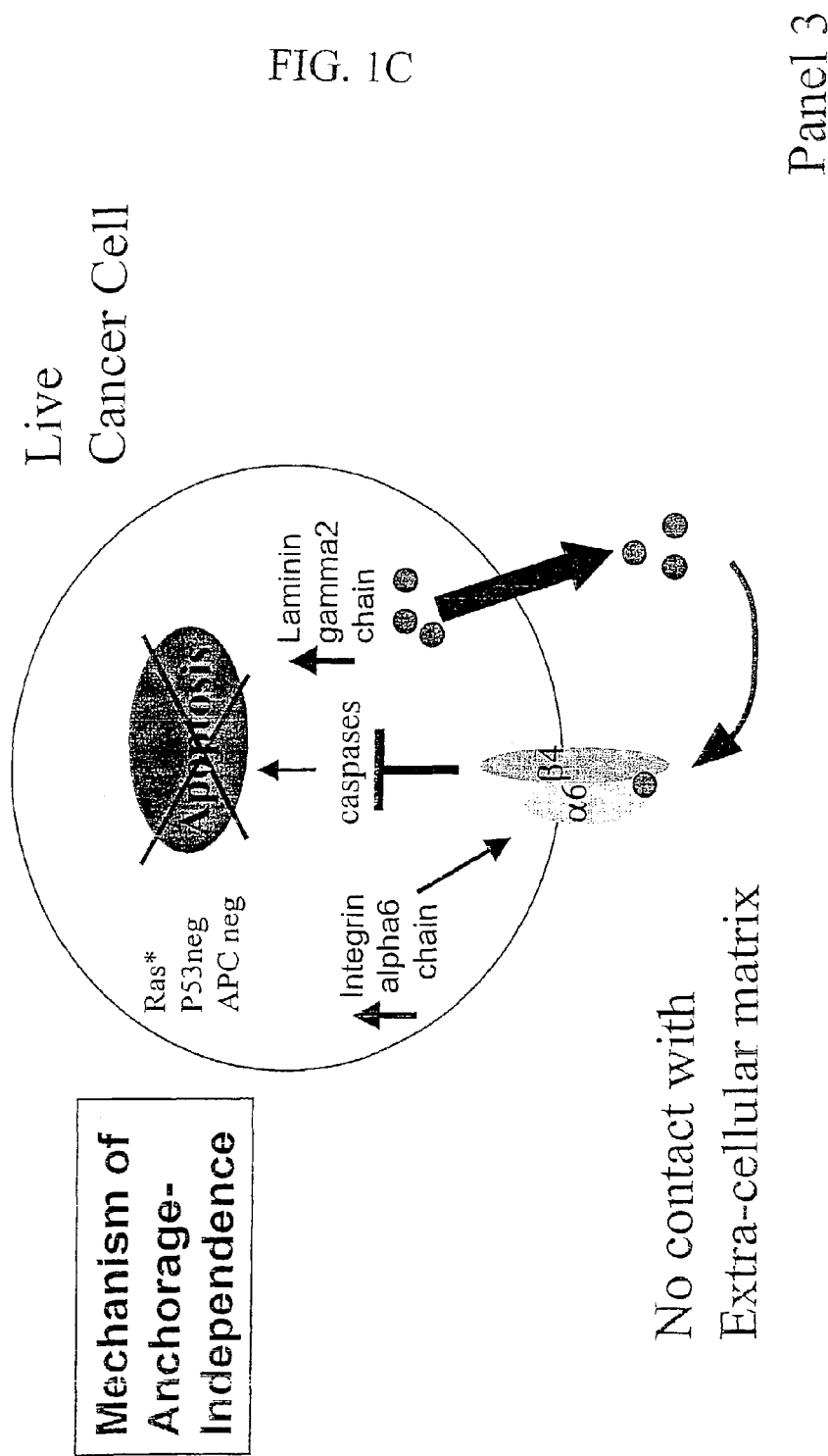

Kikkawa et al. (2000) Integrin binding specificity of laminin-10/11: laminin-10/11 are recognized by α3β1, α6β1 and α6 β 4 integrins. *J Cell Sci*, 113, 869-76.
Koshikawa et al. (1999) Overexpression of laminin gamma2 chain monomer in invading gastric carcinoma cells. *Cancer Res*, 59, 5596-601.
Land et al. (1983) Tumorigenic conversion of primary embryo fibroblasts requires at least two cooperating oncogenes. *Nature*, 304, 596-602.
Lee and Juliano. (2000) α5β1 integrin protects intestinal epithelial cells from apoptosis through a phosphatidylinositol 3-kinase and protein kinase B- dependent pathway. *Mol Biol Cell*, 11, 1973-87.
Lin and Bissell (1993) Multi-faceted regulation of cell differentiation by extracellular matrix. *Faseb J*, 7, 737-43.
Littlewood et al. (1995) A modified oestrogen receptor ligand-binding domain as an improved switch for the regulation of heterologous proteins. *Nucleic Acids Res*, 23, 1686-90.
Lloyd et al. (1997) Cooperating oncogenes converge to regulate cyclin/cdk complexes. *Genes Dev*, 11, 663-77.
Lohi et al. (2000) Basement membrane laminin-5 is deposited in colorectal adenomas and carcinomas and serves as a ligand for alpha3beta1 integrin. *Apmis*, 108, 161-72.
Mainiero et al. (1997) The coupling of $\alpha_6\beta_4$ integrin to Ras-MAP kinase pathways mediated by Shc controls keratinocyte proliferation. *Embo J*, 16, 2365-75.
Mainiero et al. (1995) Signal transduction by the alpha 6 beta 4 integrin: distinct beta 4 subunit sites mediate recruitment of Shc/Grb2 and association with the cytoskeleton of hemidesmosomes. *Embo J*, 14, 4470-81.
Malinda and Kleinman (1996) The laminins. *Int J Biochem Cell Biol*, 28, 957-9.
Marshall, (1995) Ras target proteins in eukaryotic cells. *Faseb J*, 9, 1311-8.
Morgenstern and Land (1990) Advanced mammalian gene transfer: high titre retroviral vectors with multiple drug selection markers and a complementary helper-free packaging cell line. *Nucleic Acids Res*, 18, 3587-96.
Mukhopadhyay et al. (1999) Increased levels of α6 integrins are associated with the metastatic phenotype of human breast cancer cells. *Clin Exp Metastasis*, 17, 325-32.
Munemitsu et al. (1995) Regulation of intracellular β-catenin levels by the adenomatous polyposis coli (APC) tumor-suppressor protein. *Proc Natl Acad Sci U S A*, 92, 3046-50.
Nejjari et al. (1999) α6β1 integrin expression in hepatocarcinoma cells: regulation and role in cell adhesion and migration. *Int J Cancer*, 83, 518-25.
Niessen et al. (1994) The α6β4 integrin is a receptor for both laminin and kalinin. *Exp Cell Res*, 211, 360-7.
Parise, L.V., Lee, J. and Juliano, R.L. (2000) New aspects of integrin signaling in cancer. *Semin Cancer Biol*, 10, 407-14.
Pawson and Scott (1997) Signaling through scaffold, anchoring, and adaptor proteins. *Science*, 278, 2075-80.
Pelengaris et al. (1999) Reversible activation of c-Myc in skin: induction of a complex neoplastic phenotype by a single oncogenic lesion. *Mol Cell*, 3, 565-77.
Perez-Roger et al. (1999) Cyclins D1 and D2 mediate myc-induced proliferation via sequestration of $p27^{Kip1}$ and $p21^{Cip1}$. *Embo J*, 18, 5310-20.
Perez-Roger et al. (1997) Myc activation of cyclin E/Cdk2 kinase involves induction of cyclin E gene transcription and inhibition of $p27^{Kip1}$ binding to newly formed complexes. *Oncogene*, 14, 2373-81.
Ray et al. (1997) Regulated overexpression of interleukin 11 in the lung. Use to dissociate development-dependent and -independent phenotypes. *J Clin Invest*, 100, 2501-11.
Resnicoff et al. (1998) The baculovirus anti-apoptotic p35 protein promotes transformation of mouse embryo fibroblasts. *J Biol Chem*, 273, 10376-80.
Roper et al. (2001) $p19^{ARF}$-independent induction of p53 and cell cycle arrest by Raf in murine keratinocytes. *EMBO Rep*, 2, 145-50.
Ruley, (1983) Adenovirus early region 1A enables viral and cellular transforming genes to transform primary cells in culture. *Nature*, 304, 602-6.
Sewing et al. . (1997) High-intensity Raf signal causes cell cycle arrest mediated by $p21^{Cip1}$. *Mol Cell Biol*, 17, 5588-97.
Shaw et al. (1997) Activation of phosphoinositide 3-OH kinase by the α6β4 integrin promotes carcinoma invasion. *Cell*, 91, 949-60.
Sonnenberg et al. (1990) The α6β1 (VLA-6) and α6β4 protein complexes: tissue distribution and biochemical properties. *J Cell Sci*, 96, 207-17.
Spinardi et al. (1993) The β4 subunit cytoplasmic domain mediates the interaction of α6β4 integrin with the cytoskeleton of hemidesmosomes. *Mol Biol Cell*, 4, 871-84.
Thompson et al. (1989) Multistage carcinogenesis induced by ras and myc oncogenes in a reconstituted organ. *Cell*, 56, 917-30.
Treisman (1996) Regulation of transcription by MAP kinase cascades. *Curr Opin Cell Biol*, 8, 205-15.
Van Waes and Carey (1992) Overexpression of the A9 antigen/α6β4 integrin in head and neck cancer. *Otolaryngol Clin North Am*, 25, 1117-39.
Wary et al. (1996) The adaptor protein Shc couples a class of integrins to the control of cell cycle progression. *Cell*, 87, 733-43.
Zhu et al. (2001) Use of the tetracycline controlled transcriptional silencer (tTS) to eliminate transgene leak in inducible overexpression transgenic mice. *J Biol Chem*, 30, 30.
Tagliabue E. et al., "Prognostic value of alpha 6 beta 4 integrin expression in breast carcinomas is affected by laminin production from tumor cells," pp. 407-410, Feb. 1998, Clinical Cancer Research: An Official Journal of the American Association for Cancer Research, United States.
Fields et al., "Integrins: cell adhesion molecules in cancer," pp. 633-644, Aug. 1998, Expert Opinion on Therapeutic Patents, Ashley Publications, GB.
Nickols A. et al., "Antiangiogenic and Anticancer Activities of Antagonists of Integrinalphavbeta3," p. 206, Proceedings of the 88th Annual Meeting of the American Association for Cancer Research, San Diego, Apr. 12-16, 1997, Proceedings of the Annual Meeting of the American Association for Cancer Research, Philadelphia, AACR, US, vol. 38, Mar. 1, 1997.
Bachelder Robin E. et al., p53 Inhibits alpha6beta4 integrin survival signaling by promoting the caspase 3-dependent cleavage of AKT/PKB, pp. 1063-1072, Journal of Cell Biology, vol. 147, No. 5, Nov. 29, 1999.
Rabinovitz Isaac et al., "The integrin alpha-6-beta-4 and the biology of carcinoma," pp. 811-821, Biochemistry and Cell Biology, vol. 74, No. 6, 1996.
Mercurio Arthur M. et al., "Towards a mechanistic understanding of tumor invasion: Lessons from the alpha6beta4 integrin," pp. 129-141, Seminars in Cancer Biology, vol. 11, No. 2, Apr. 2001.
O'Connor Kathleen L. et al., "Release of cAMP gating by the alpha6beta4 integrin stimulates lamellae formation and the chemotactic migration of invasive carcinoma cells," pp. 1749-1760, Journal of Cell Biology, vol. 143, No. 6, Dec. 14, 1998.
Clarke Astrid S. et al., "Activation of the p21 pathway of growth arrest and apoptosis by the beta-4 integrin cytoplasmic domain," pp. 22673-22676, Journal of Biological Chemistry, vol. 270, No. 39, 1995.
Carico et al. (1993) Integrin β4 Expression in the Neoplastic Progression of Cervical Epithelium. *Gynecologic Oncology* 49: 61-63.
Halatsch et al. (1997) Increased expression of $\alpha_6$-integrin receptors and of mRNA encoding the putative 37 kDa laminin receptor precursor in pancreatic carcinoma. *Cancer Letters* 118: 7-11.
Response to Communication filed Dec. 11, 2012 with the European Patent Office for Application No. 01977754 filed Oct. 12, 2001 (Applicant—University of Rochester//1st Named Inventor—Land) (15 pages).
Response to Communication filed Dec. 19, 2012 with the European Patent Office for Application No. 10012959 filed Oct. 12, 2001 (Applicant—University of Rochester//1st Named Inventor—Land) (19 pages).
Office Action issued Oct. 15, 2012 by the Japanese Patent Office for Application No. 2002-533904 filed Oct. 12, 2001 (Applicant—University of Rochester//1st Named Inventor—Land) (Includes Translation) (4 pages).

(56) References Cited

OTHER PUBLICATIONS

Response to Communication filed Oct. 10, 2010 with the European Patent Office for Application No. 01977754.9 filed Oct. 12, 2001 (Applicant—University of Rochester//1st Named Inventor—Land) (12 pages).
Communication mailed Jun. 1, 2012 by the European Patent Office for Application No. 01977754.9 filed Oct. 12, 2001 (Applicant—University of Rochester//1st Named Inventor—Land) (6 pages).
European Search Report issued Apr. 26, 2011 by the European Patent Office for Application No. 10012959.2 filed Oct. 12, 2001 (Applicant—University of Rochester//1st Named Inventor—Land) (10 pages).
Claims Amendment in Response to European Search Report filed Dec. 22, 2011 with the European Patent Office for Application No. 10012959.2 filed Oct. 12, 2001 (Applicant—University of Rochester//1st Named Inventor—Land) (16 pages).
Communication mailed Jun. 1, 2012 by the European Patent Office for Application No. 10012959.2 filed Oct.12, 2001 (Applicant—University of Rochester//1st Named Inventor—Land) (6 pages).
Official Action mailed Aug. 8, 2011 by the Canadian Intellectual Property Office for Application No. 2,425,779 filed Oct. 12, 2001 (Applicant—University of Rochester//1st Named Inventor—Land) (2 pages).
Response to Official Action filed Feb. 8, 2012 with the Canadian Intellectual Property Office for Application No. 2,425,779 filed Oct. 12, 2001 (Applicant—University of Rochester//1st Named Inventor—Land) (12 pages).
Amended Claims filed with the Japanese Patent Office on Jul. 1, 2011 for Application No. 2002-533904 filed Oct. 12, 2001 (Applicant—University of Rochester//1st Named Inventor—Land) (38 pages).
Official Action mailed Oct. 31, 2011 by the Japanese Patent Office for Application No. 2002-533904 filed Oct. 12, 2001 (Applicant—University of Rochester//1st Named Inventor—Land) (8 pages).
Amended Claims filed with the Japanese Patent Office on Feb. 9, 2012 for Application No. 2002-533904 filed Oct. 12, 2001 (Applicant—University of Rochester//1st Named Inventor—Land) (45 pages).
European Examination Report (Communication under Article 94(3) EPC) mailed on Mar. 31, 2011 for EP 01977754.9.
Japanese Office Action mailed on Mar. 2, 2011 for Japanese Patent Application No. 2002-533904.
International Search Report for PCT Application No. PCT/US01/32127 issued on Nov. 25, 2002.
International Preliminary Examination Report for PCT Application No. PCT/US01/32127 issued on Oct. 27, 2004.
European Examiner's Report mailed on Jun. 9, 2006.
Response to Jun. 9, 2006 European Examiner's Report filed on Dec. 18, 2006.
European Examiner's Report mailed on Apr. 9, 2008.
Response to Apr. 9, 2008 European Examiner's Report filed on Oct. 21, 2008.
European Examiner's Report mailed on Oct. 12, 2009.
Response to Oct. 12, 2009 European Examiner's Report filed on Apr. 22, 2010.
Japanese Office Action mailed on Jun. 3, 2008.
Response to Jun. 3, 2008 Japanese Office Action filed on Dec. 3, 2008.
Japanese Office Action mailed on Feb. 4, 2010.
Response to Feb. 4, 2010 Japanese Office Action filed on Jun. 8, 2010.
Canadian Official Action mailed on Jul. 29, 2008.
Response to Jul. 29, 2008 Canadian Official Action filed on Jan. 29, 2009.
Canadian Official Action mailed on May 28, 2010.
Response to May 28, 2010 Canadian Official Action filed on Nov. 29, 2010.
Australian Examiner's Report filed on Oct. 7, 2005.
Response to Oct. 7, 2005 Australian Examiner's Report filed on Jun. 4, 2007.
Australian Examiner's Report filed on Jun. 7, 2007.
Response to Jun. 7, 2007 Australian Examiner's Report filed on Jun. 21, 2007.
Notice of Acceptance from Australian Patent Office mailed on Jun. 22, 2007.

* cited by examiner

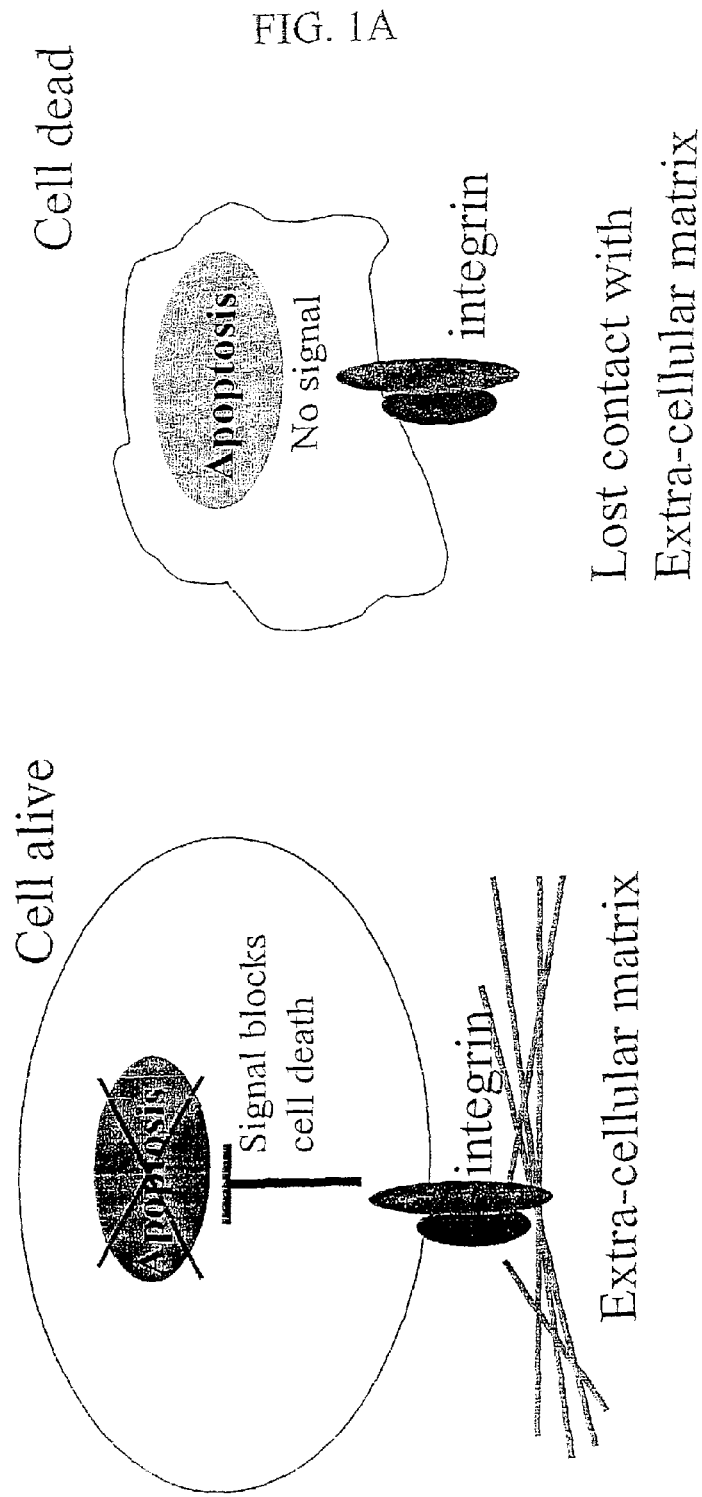

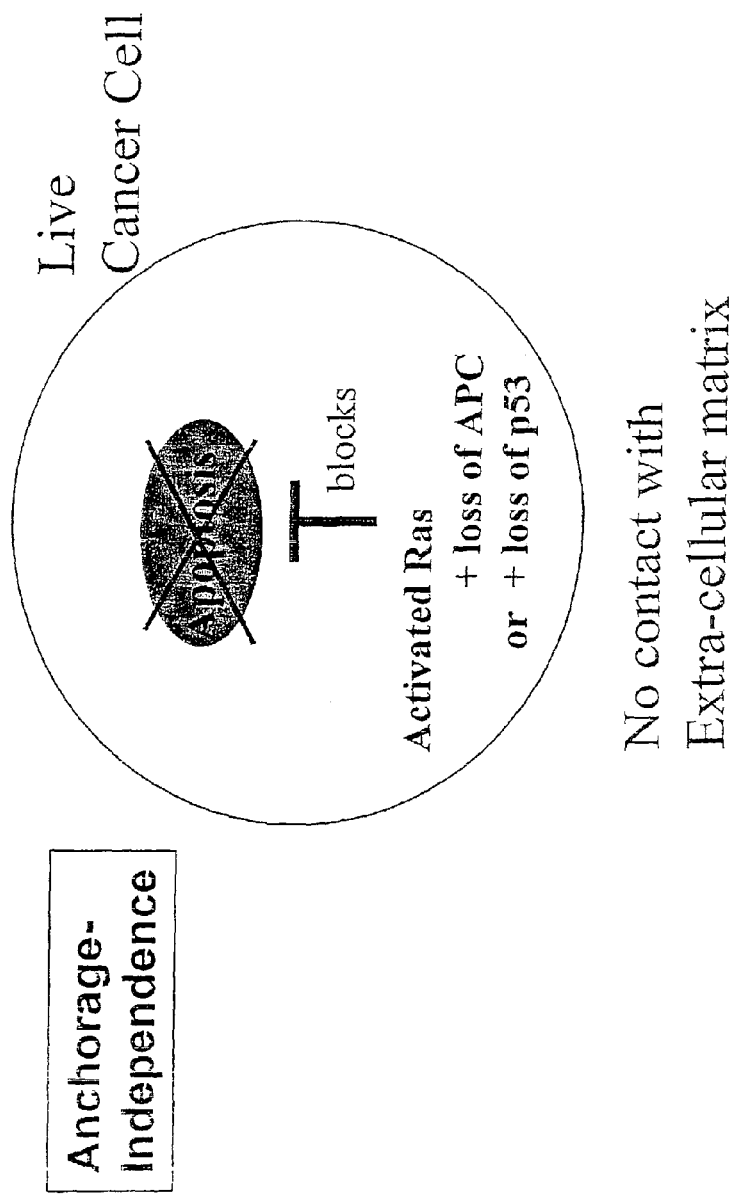

SEQUENCE LISTING

```
<160> NUMBER OF SEQ ID NOS: 45

<210> SEQ ID NO 1
<211> LENGTH: 3222
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 1
atggccgccg ccgggcagct gtgcttgctc tacctgtcgg cggggctcct gtcccggctc        60
ggcgcagcct tcaacttgga cactcgggag gacaacgtga tccggaaata tggagacccc       120
gggagcctct tcggcttctc gctggccatg cactggcaac tgcagcccga ggacaagcgg       180
ctgttgctcg tgggggcccc gcgcggagaa gcgcttccac tgcagagagc caacagaacg       240
ggagggctgt acagctgcga catcaccgcc cgggggccat gcacgcggat cgagtttgat       300
aacgatgctg accccacgtc agaaagcaag gaagatcagt ggatggggggt caccgtccag       360 agccaaggtc caggggggcaa ggtcgtgaca tgtgctcacc gatatgaaaa aaggcagcat       420
gttaatacga agcaggaatc ccgagacatc tttggcggt gttatgtcct gagtcagaat        480
ctcaggattg aagacgatat ggatggggga gattggagct tttgtgatgg gcgattgaga       540
ggccatgaga aatttggctc ttgccagcaa ggtgtagcag ctacttttac taaagacttt       600
cattacattg tatttggagc cccgggtact tataactgga agggattgt tcgtgtagag        660 caaaagaata acactttttt tgacatgaac atctttgaag atgggcctta tgaagttggt       720
ggagagactg agcatgatga agtctcgtt cctgttcctg ctaacagtta cttaggtttt       780
tctttggact cagggaaagg tattgttct aaagatgaga tcacttttgt atctggtgct       840
cccagagcca atcacagtgg agccgtggtt ttgctgaaga gagacatgaa gtctgcacat       900
ctcctccctg agcacatatt cgatggagaa ggtctggcct cttcatttgg ctatgatgtg       960
gcggtggtgg acctcaacaa ggatgggtgg caagatatag ttattggagc cccacagtat      1020
tttgatagag atggagaagt tggaggtgca gtgtatgtct acatgaacca gcaaggcaga      1080
```

```
tggaataatg tgaagccaat tcgtcttaat ggaaccaaag attctatgtt tggcattgca      1140
gtaaaaaata ttggagatat taatcaagat ggctacccag atattgcagt ggagctccg       1200 tatgatgact tgggaaaggt ttttatctat catggatctg caaatggaat aaataccaaa      1260
ccaacacagg ttctcaaggg tatatcacct tattttggat attcaattgc tggaaacatg      1320
gaccttgatc gaaattccta ccctgatgtt gctgttggtt ccctctcaga ttcagtaact      1380
attttcagat cccggcctgt gattaatatt cagaaaacca tcacagtaac tcctaacaga      1440
attgacctcc gccagaaaac agcgtgtggg gcgcctagtg ggatatgcct ccaggttaaa      1500
tcctgttttg aatatactgc taaccccgct ggttataatc cttcaatatc aattgtgggc      1560
acacttgaag ctgaaaaaga aagaagaaaa tctgggctat cctcaagagt tcagtttcga      1620
aaccaaggtt ctgagcccaa atatactcaa gaactaactc tgaagaggca gaaacagaaa      1680
gtgtgcatgg aggaaacccct gtggctacag ataatatca gagataaact gcgtcccatt      1740
cccataactg cctcagtgga gatccaagag ccaagctctc gtaggcgagt gaattcactt      1800
ccagaagttc ttccaattct gaattcagat gaacccaaga cagctcatat tgatgttcac      1860
ttcttaaaag agggatgtgg agacgacaat gtatgtaaca gcaaccttaa actagaaata      1920
aaattttgca cccgagaagg aaatcaagac aaattttctt atttaccaat tcaaaaaggt      1980
gtaccgaaac tagttctaaa agatcagaag gatattgctt tagaaataac agtgacaaac      2040
agcccttcca acccaaggaa tcccacaaaa gatggcgatg acgcccatga ggctaaactg      2100
attgcaacgt ttccagacac tttaacctat tctgcatata gagaactgag ggcttcccct      2160
gagaaacagt tgagttgtgt tgccaaccag aatggctcgc aagctgactg tgagctcgga      2220
aatcctttta aaagaaattc aaatgtcact ttttattgg ttttaagtac aactgaagtc      2280 accttgaca ccccatatct ggatattat ctgaagttag aaacaacaag caatcaagat      2340 aattggctc caattacagc taaagcaaaa gtggttattg aactgctttt atcggtctcg      2400
ggagttgcta aaccttccca ggtgtatttt ggaggtacag ttgttggcga gcaagctatg      2460
aaatctgaag atgaagtggg aagtttaata gagtatgaat tcagggtaat aaacttaggt      2520
aaacctctta caaacctcgg cacagcaacc ttgaacattc agtggccaaa agaaattagc      2580
aatgggaaat ggttgcttta tttggtgaaa gtagaatcca aaggattgga aaaggtaact      2640
tgtgagccac aaaaggagat aaactccctg aacctaacgg agtctcacaa ctcaagaaag      2700
aaacgggaaa ttactgaaaa acagatagat gataacagaa atttttcttt atttgctgaa      2760
agaaaatacc agactcttaa ctgtagcgtg aacgtgaact gtgtgaacat cagatgcccg      2820 ctgcggggc tggacagcaa ggcgtctctt attttgcgct cgaggttatg gaacagcaca      2880
tttctagagg aatattccaa actgaactac ttggacattc tcatgcgagc cttcattgat      2940
gtgactgctg ctgccgaaaa tatcaggctg ccaaatgcag gcactcaggt tcgagtgact      3000
gtgtttccct caaagactgt agctcagtat tcggagtac cttggtggat catcctagtg      3060
gctattctcg ctgggatctt gatgcttgct ttattagtgt ttatactatg gaagtgtggt      3120
ttcttcaaga gaaataagaa agatcattat gatgccacat atcacaaggc tgagatccat      3180
gctcagccat ctgataaaga gaggcttact tctgatgcat ag                        3222
```

<210> SEQ ID NO 2
<211> LENGTH: 1073
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 2

```
Met Ala Ala Ala Gly Gln Leu Cys Leu Leu Tyr Leu Ser Ala Gly Leu
 1               5                  10                  15
Leu Ser Arg Leu Gly Ala Ala Phe Asn Leu Asp Thr Arg Glu Asp Asn
             20                  25                  30
Val Ile Arg Lys Tyr Gly Asp Pro Gly Ser Leu Phe Gly Phe Ser Leu
         35                  40                  45
Ala Met His Trp Gln Leu Gln Pro Glu Asp Lys Arg Leu Leu Leu Val
     50                  55                  60
Gly Ala Pro Arg Gly Glu Ala Leu Pro Leu Gln Arg Ala Asn Arg Thr
 65                  70                  75                  80
Gly Gly Leu Tyr Ser Cys Asp Ile Thr Ala Arg Gly Pro Cys Thr Arg
                 85                  90                  95
Ile Glu Phe Asp Asn Asp Ala Asp Pro Thr Ser Glu Ser Lys Glu Asp
            100                 105                 110
Gln Trp Met Gly Val Thr Val Gln Ser Gln Gly Pro Gly Gly Lys Val
        115                 120                 125
Val Thr Cys Ala His Arg Tyr Glu Lys Arg Gln His Val Asn Thr Lys
    130                 135                 140
Gln Glu Ser Arg Asp Ile Phe Gly Arg Cys Tyr Val Leu Ser Gln Asn
145                 150                 155                 160
Leu Arg Ile Glu Asp Asp Met Asp Gly Gly Asp Trp Ser Phe Cys Asp
                165                 170                 175
Gly Arg Leu Arg Gly His Glu Lys Phe Gly Ser Cys Gln Gln Gly Val
            180                 185                 190
Ala Ala Thr Phe Thr Lys Asp Phe His Tyr Ile Val Phe Gly Ala Pro
        195                 200                 205
Gly Thr Tyr Asn Trp Lys Gly Ile Val Arg Val Glu Gln Lys Asn Asn
    210                 215                 220
Thr Phe Phe Asp Met Asn Ile Phe Glu Asp Gly Pro Tyr Glu Val Gly
225                 230                 235                 240
Gly Glu Thr Glu His Asp Glu Ser Leu Val Pro Val Pro Ala Asn Ser
                245                 250                 255
Tyr Leu Gly Phe Ser Leu Asp Ser Gly Lys Gly Ile Val Ser Lys Asp
            260                 265                 270
Glu Ile Thr Phe Val Ser Gly Ala Pro Arg Ala Asn His Ser Gly Ala
        275                 280                 285
Val Val Leu Leu Lys Arg Asp Met Lys Ser Ala His Leu Leu Pro Glu
    290                 295                 300
His Ile Phe Asp Gly Glu Gly Leu Ala Ser Ser Phe Gly Tyr Asp Val
305                 310                 315                 320
Ala Val Val Asp Leu Asn Lys Asp Gly Trp Gln Asp Ile Val Ile Gly
                325                 330                 335
Ala Pro Gln Tyr Phe Asp Arg Asp Gly Glu Val Gly Gly Ala Val Tyr
            340                 345                 350
Val Tyr Met Asn Gln Gln Gly Arg Trp Asn Asn Val Lys Pro Ile Arg
        355                 360                 365
Leu Asn Gly Thr Lys Asp Ser Met Phe Gly Ile Ala Val Lys Asn Ile
    370                 375                 380
Gly Asp Ile Asn Gln Asp Gly Tyr Pro Asp Ile Ala Val Gly Ala Pro
385                 390                 395                 400
Tyr Asp Asp Leu Gly Lys Val Phe Ile Tyr His Gly Ser Ala Asn Gly
                405                 410                 415
```

-continued

```
Ile Asn Thr Lys Pro Thr Gln Val Leu Lys Gly Ile Ser Pro Tyr Phe
            420                 425                 430
Gly Tyr Ser Ile Ala Gly Asn Met Asp Leu Asp Arg Asn Ser Tyr Pro
            435                 440                 445
Asp Val Ala Val Gly Ser Leu Ser Asp Ser Val Thr Ile Phe Arg Ser
450                 455                 460
Arg Pro Val Ile Asn Ile Gln Lys Thr Ile Thr Val Thr Pro Asn Arg
465                 470                 475                 480
Ile Asp Leu Arg Gln Lys Thr Ala Cys Gly Ala Pro Ser Gly Ile Cys
            485                 490                 495
Leu Gln Val Lys Ser Cys Phe Glu Tyr Thr Ala Asn Pro Ala Gly Tyr
            500                 505                 510
Asn Pro Ser Ile Ser Ile Val Gly Thr Leu Glu Ala Glu Lys Glu Arg
            515                 520                 525
Arg Lys Ser Gly Leu Ser Ser Arg Val Gln Phe Arg Asn Gln Gly Ser
530                 535                 540
Glu Pro Lys Tyr Thr Gln Glu Leu Thr Leu Lys Arg Gln Lys Gln Lys
545                 550                 555                 560
Val Cys Met Glu Glu Thr Leu Trp Leu Gln Asp Asn Ile Arg Asp Lys
            565                 570                 575
Leu Arg Pro Ile Pro Ile Thr Ala Ser Val Glu Ile Gln Glu Pro Ser
            580                 585                 590
Ser Arg Arg Arg Val Asn Ser Leu Pro Glu Val Leu Pro Ile Leu Asn
            595                 600                 605
Ser Asp Glu Pro Lys Thr Ala His Ile Asp Val His Phe Leu Lys Glu
610                 615                 620
Gly Cys Gly Asp Asp Asn Val Cys Asn Ser Asn Leu Lys Leu Glu Tyr
625                 630                 635                 640
Lys Phe Cys Thr Arg Glu Gly Asn Gln Asp Lys Phe Ser Tyr Leu Pro
            645                 650                 655
Ile Gln Lys Gly Val Pro Glu Leu Val Leu Lys Asp Gln Lys Asp Ile
            660                 665                 670
Ala Leu Glu Ile Thr Val Thr Asn Ser Pro Ser Asn Pro Arg Asn Pro
            675                 680                 685
Thr Lys Asp Gly Asp Asp Ala His Glu Ala Lys Leu Ile Ala Thr Phe
690                 695                 700
Pro Asp Thr Leu Thr Tyr Ser Ala Tyr Arg Glu Leu Arg Ala Phe Pro
705                 710                 715                 720
Glu Lys Gln Leu Ser Cys Val Ala Asn Gln Asn Gly Ser Gln Ala Asp
            725                 730                 735
Cys Glu Leu Gly Asn Pro Phe Lys Arg Asn Ser Asn Val Thr Phe Tyr
            740                 745                 750
Leu Val Leu Ser Thr Thr Glu Val Thr Phe Asp Thr Pro Tyr Leu Asp
            755                 760                 765
Ile Asn Leu Lys Leu Glu Thr Thr Ser Asn Gln Asp Asn Leu Ala Pro
            770                 775                 780
Ile Thr Ala Lys Ala Lys Val Val Ile Glu Leu Leu Leu Ser Val Ser
785                 790                 795                 800
Gly Val Ala Lys Pro Ser Gln Val Tyr Phe Gly Gly Thr Val Val Gly
            805                 810                 815
Glu Gln Ala Met Lys Ser Glu Asp Val Gly Ser Leu Ile Glu Tyr
            820                 825                 830
Glu Phe Arg Val Ile Asn Leu Gly Lys Pro Leu Thr Asn Leu Gly Thr
```

```
                    835                 840                 845
Ala Thr Leu Asn Ile Gln Trp Pro Lys Glu Ile Ser Asn Gly Lys Trp
850                 855                 860
Leu Leu Tyr Leu Val Lys Val Glu Ser Lys Gly Leu Glu Lys Val Thr
865                 870                 875                 880
Cys Glu Pro Gln Lys Glu Ile Asn Ser Leu Asn Leu Thr Glu Ser His
                    885                 890                 895
Asn Ser Arg Lys Lys Arg Glu Ile Thr Glu Lys Gln Ile Asp Asp Asn
                900                 905                 910
Arg Lys Phe Ser Leu Phe Ala Glu Arg Lys Tyr Gln Thr Leu Asn Cys
            915                 920                 925
Ser Val Asn Val Asn Cys Val Asn Ile Arg Cys Pro Leu Arg Gly Leu
        930                 935                 940
Asp Ser Lys Ala Ser Leu Ile Leu Arg Ser Arg Leu Trp Asn Ser Thr
945                 950                 955                 960
Phe Leu Glu Glu Tyr Ser Lys Leu Asn Tyr Leu Asp Ile Leu Met Arg
                    965                 970                 975
Ala Phe Ile Asp Val Thr Ala Ala Glu Asn Ile Arg Leu Pro Asn
                980                 985                 990
Ala Gly Thr Gln Val Arg Val Thr Val Phe Pro Ser Lys Thr Val Ala
            995                 1000                1005
Gln Tyr Ser Gly Val Pro Trp Trp Ile Ile Leu Val Ala Ile Leu Ala
        1010                1015                1020
Gly Ile Leu Met Leu Ala Leu Leu Val Phe Ile Leu Trp Lys Cys Gly
1025                1030                1035                1040
Phe Phe Lys Arg Asn Lys Lys Asp His Tyr Asp Ala Thr Tyr His Lys
                    1045                1050                1055
Ala Glu Ile His Ala Gln Pro Ser Asp Lys Glu Arg Leu Thr Ser Asp
                1060                1065                1070
Ala

<210> SEQ ID NO 3
<211> LENGTH: 3222
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 3
atggccgtcg cgggccagtt gtgcctgctc tacctgtccg cggggcttct agcccggctg        60
ggtacagcct tcaacctgga cacccgcgag acaacgtga tccggaaatc gggggatccc       120
gggagcctct tcggcttctc gctcgccatg cactggcagt gcagccgga ggacaagcgg       180 ctgttgcttg tggggcacc tcgggcagaa gcactcccgc tgcagagggc gaacagaaca       240
gggggcctgt acagctgtga catcacctcc cgaggacctt gtacacggat tgaatttgat       300
aatgacgctg atcctatgtc agaaagcaag gaagaccagt ggatgggagt cactgtccag       360
agccaaggtc caggggcaa agtggtgacg tgtgcacatc gatatgagaa acggcagcac       420
gtcaacacga agcaggagtc gcgggatatc tttggaagat gttatgtcct gagtcagaat       480
ctcagaattg aagatgatat ggacggagga gactggagtt tctgcgatgg ccggttgaga       540
ggccatgaaa agtttggctc ctgtcagcaa ggagtagcgg ctactttcac taaggacttt       600
cattacattt ttttggagc cccagggact acaactggaa agggatcgt ccgtgtagaa       660 caaaagaata acactttttt tgacatgaac atctttgaag atgggcccta tgaagttggt       720
```

```
ggagagacag atcatgatga aagtctcgtg cccgttcctg ctaacagtta cctaggcttt      780
tcgctggact cagggaaggg tattgtttct aaagatgaca tcacttttgt gtctggtgct      840
ccaagagcca atcacagtgg ggctgtagtg ttgctaaaaa gagacatgaa gtccgcacat      900
ctgctccctg agtatatatt tgacggagaa ggcctggctt cctcgtttgg ctatgatgtg      960
gcagtggtgg acctcaatgc agatgggtgg caagacatcg ttatcggagc tccacagtat     1020
tttgataggg atggtgaagt cgggggtgca gtttacgtct acattaacca gcaaggcaaa     1080
tggagtaatg tgaagccgat tcgtctaaat gggaccaaag actcgatgtt tggaatctct     1140
gtgaaaaata taggtgatat taaccaagat ggctatccag atattgctgt tggagctccc     1200
tatgatgatc tggggaaggt tttttatctat catggatccc cgactggcat aattaccaag     1260
ccaacacagg ttctcgaggg gacatcgcct tacttcggct attcaatcgc tgggaatatg     1320
gacctggatc ggaattccta ccccgacctt gctgtgggct ccctctcaga ctcggtcact     1380
attttcagat cccggccagt gattaacatt ctaaaaacca tcacagtgac tcctaacaga     1440
attgacctcc gccagaagtc catgtgtggc tcacctagcg ggatatgcct caaggttaaa     1500
gcctgttttg aatatactgc gaaaccttcc ggttataacc ctccaatatc aattttgggt     1560
attcttgaag ctgaaaaga aagaagaaaa tcagggttgt catcgagagt tcagtttcga     1620
aaccaaggtt ccgagccaaa gtatactcag gagctgaccc tgaatcggca gaagcagcgg     1680
gcgtgcatgg aggagaccct ctggctgcag gagaacatca gagacaagct gcgtcccatc     1740
cccatcacgg cttctgtgga gatccaggag cccacgtctc gccggcgggt gaactcactc     1800
cccgaagttc ttcccatcct gaattcaaat gaagccaaaa cggtccagac agatgtccac     1860
ttcttaaagg aaggatgtgg agacgacaat gtctgtaaca gcaaccttaa gctagagtat     1920
aaatttggta cccgagaagg aaatcaagac aaattctctt accttccaat tcaaaaaggc     1980
atcccagaat tagtcctaaa agatcagaaa gatatagctc tggaaataac ggtgaccaac     2040
agcccttcgg atccaaggaa tccccggaaa gatggcgacg atgcccatga agccaaactc     2100
atcgccacgt ttccagacac tctgacatat tccgcttaca gagaactgag ggctttccct     2160
gagaagcagc tgagctgtgt ggccaaccag aatggctccc aagccgactg tgagctcgga     2220 aatccttttca agagaaattc cagtgttact ttctatctga ttttaagtac aaccgaggtc     2280
acctttgaca ccacagatct ggatattaat ctgaagttgg aaacaacaag caatcaggat     2340
aaattggctc caattacagc gaaggcaaaa gtggttattg aattgctttt atccctctcc     2400
ggagtcgcta agccttcgca ggtgtatttt ggaggtacag ttgttggtga gcaagctatg     2460
aaatctgaag atgaagtagg aagtttaata gagtatgaat ttagggtgat taacttaggc     2520
aagcctctta aaaacctcgg cacagcaacc ttgaatatac agtggcccaa ggagattagc     2580
aatggcaaat ggttgcttta tttgatgaaa gttgaatcca aaggtttgga gcagattgtt     2640
tgtgagccac acaatgaaat aaactacctg aagctgaagg agtctcacaa ctcaagaaag     2700
aaacgggaac ttcctgaaaa acagatagat gacagcagga aattttcttt atttcctgaa     2760
agaaaatacc agactctcaa ctgcagcgtc aacgtcaggt gtgtgaacat caggtgccca     2820
ctgcgagggc tggacacgaa ggcctctctc gttctgtgtt ccaggttgtg aacagcaca      2880 tttctagagg aatattccaa actgaactac ttggacattc tcgtgagggc ttccatagat     2940
gtcaccgctg ctgctcagaa tatcaagctc cctcacgcgg gcactcaggt tcgagtgacg     3000
gtgtttccct caaagactgt agctcagtat tcaggagtag cttggtggat catcctcctg     3060
gctgttcttg ccgggattct gatgctggct ctattagtgt ttttactgtg gaagtgtggc     3120
```
ttcttcaaga gaaataagaa agatcattac gatgccacct atcacaaggc tgagatccat    3180
actcagccgt ctgataaaga gaggcttact tccgatgcat ag                       3222

<210> SEQ ID NO 4
<211> LENGTH: 1073
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 4

```
Met Ala Val Ala Gly Gln Leu Cys Leu Leu Tyr Leu Ser Ala Gly Leu
1               5                   10                  15

Leu Ala Arg Leu Gly Thr Ala Phe Asn Leu Asp Thr Arg Glu Asp Asn
                20                  25                  30

Val Ile Arg Lys Ser Gly Asp Pro Gly Ser Leu Phe Gly Phe Ser Leu
            35                  40                  45

Ala Met His Trp Gln Leu Gln Pro Glu Asp Lys Arg Leu Leu Leu Val
        50                  55                  60

Gly Ala Pro Arg Ala Glu Ala Leu Pro Leu Gln Arg Ala Asn Arg Thr
65                  70                  75                  80

Gly Gly Leu Tyr Ser Cys Asp Ile Thr Ser Arg Gly Pro Cys Thr Arg
                85                  90                  95

Ile Glu Phe Asp Asn Asp Ala Asp Pro Met Ser Glu Ser Lys Glu Asp
            100                 105                 110

Gln Trp Met Gly Val Thr Val Gln Ser Gln Gly Pro Gly Gly Lys Val
        115                 120                 125

Val Thr Cys Ala His Arg Tyr Glu Lys Arg Gln His Val Asn Thr Lys
    130                 135                 140

Gln Glu Ser Arg Asp Ile Phe Gly Arg Cys Tyr Val Leu Ser Gln Asn
145                 150                 155                 160

Leu Arg Ile Glu Asp Asp Met Asp Gly Gly Asp Trp Ser Phe Cys Asp
                165                 170                 175

Gly Arg Leu Arg Gly His Glu Lys Phe Gly Ser Cys Gln Gln Gly Val
            180                 185                 190

Ala Ala Thr Phe Thr Lys Asp Phe His Tyr Ile Val Phe Gly Ala Pro
        195                 200                 205

Gly Thr Tyr Asn Trp Lys Gly Ile Val Arg Val Glu Gln Lys Asn Asn
    210                 215                 220

Thr Phe Phe Asp Met Asn Ile Phe Glu Asp Gly Pro Tyr Glu Val Gly
225                 230                 235                 240

Gly Glu Thr Asp His Asp Glu Ser Leu Val Pro Val Pro Ala Asn Ser
                245                 250                 255

Tyr Leu Gly Phe Ser Leu Asp Ser Gly Lys Gly Ile Val Ser Lys Asp
            260                 265                 270

Asp Ile Thr Phe Val Ser Gly Ala Pro Arg Ala Asn His Ser Gly Ala
        275                 280                 285

Val Val Leu Leu Lys Arg Asp Met Lys Ser Ala His Leu Leu Pro Glu
    290                 295                 300

Tyr Ile Phe Asp Gly Glu Gly Leu Ala Ser Ser Phe Gly Tyr Asp Val
305                 310                 315                 320

Ala Val Val Asp Leu Asn Ala Asp Gly Trp Gln Asp Ile Val Ile Gly
                325                 330                 335

Ala Pro Gln Tyr Phe Asp Arg Asp Gly Glu Val Gly Gly Ala Val Tyr
```

```
                    340             345             350
Val Tyr Ile Asn Gln Gln Gly Lys Trp Ser Asn Val Lys Pro Ile Arg
                355                 360                 365

Leu Asn Gly Thr Lys Asp Ser Met Phe Gly Ile Ser Val Lys Asn Ile
        370                 375                 380

Gly Asp Ile Asn Gln Asp Gly Tyr Pro Asp Ile Ala Val Gly Ala Pro
385                 390                 395                 400

Tyr Asp Asp Leu Gly Lys Val Phe Ile Tyr His Gly Ser Pro Thr Gly
                    405                 410                 415

Ile Ile Thr Lys Pro Thr Gln Val Leu Glu Gly Thr Ser Pro Tyr Phe
                420                 425                 430

Gly Tyr Ser Ile Ala Gly Asn Met Asp Leu Asp Arg Asn Ser Tyr Pro
                435                 440                 445

Asp Leu Ala Val Gly Ser Leu Ser Asp Ser Val Thr Ile Phe Arg Ser
        450                 455                 460

Arg Pro Val Ile Asn Ile Leu Lys Thr Ile Thr Val Thr Pro Asn Arg
465                 470                 475                 480

Ile Asp Leu Arg Gln Lys Ser Met Cys Gly Ser Pro Ser Gly Ile Cys
                    485                 490                 495

Leu Lys Val Lys Ala Cys Phe Glu Tyr Thr Ala Lys Pro Ser Gly Tyr
                500                 505                 510

Asn Pro Pro Ile Ser Ile Leu Gly Ile Leu Glu Ala Glu Lys Glu Arg
            515                 520                 525

Arg Lys Ser Gly Leu Ser Ser Arg Val Gln Phe Arg Asn Gln Gly Ser
        530                 535                 540

Glu Pro Lys Tyr Thr Gln Glu Leu Thr Leu Asn Arg Gln Lys Gln Arg
545                 550                 555                 560

Ala Cys Met Glu Glu Thr Leu Trp Leu Gln Glu Asn Ile Arg Asp Lys
                    565                 570                 575

Leu Arg Pro Ile Pro Ile Thr Ala Ser Val Glu Ile Gln Glu Pro Thr
                580                 585                 590

Ser Arg Arg Arg Val Asn Ser Leu Pro Glu Val Leu Pro Ile Leu Asn
            595                 600                 605

Ser Asn Glu Ala Lys Thr Val Gln Thr Asp Val His Phe Leu Lys Glu
        610                 615                 620

Gly Cys Gly Asp Asp Asn Val Cys Asn Ser Asn Leu Lys Leu Glu Tyr
625                 630                 635                 640

Lys Phe Gly Thr Arg Glu Gly Asn Gln Asp Lys Phe Ser Tyr Leu Pro
                    645                 650                 655

Ile Gln Lys Gly Ile Pro Glu Leu Val Leu Lys Asp Gln Lys Asp Ile
                660                 665                 670

Ala Leu Glu Ile Thr Val Thr Asn Ser Pro Ser Asp Pro Arg Asn Pro
        675                 680                 685

Arg Lys Asp Gly Asp Ala His Glu Ala Lys Leu Ile Ala Thr Phe
690                 695                 700

Pro Asp Thr Leu Thr Tyr Ser Ala Tyr Arg Glu Leu Arg Ala Phe Pro
705                 710                 715                 720

Glu Lys Gln Leu Ser Cys Val Ala Asn Gln Asn Gly Ser Gln Ala Asp
                    725                 730                 735

Cys Glu Leu Gly Asn Pro Phe Lys Arg Asn Ser Ser Val Thr Phe Tyr
                740                 745                 750

Leu Ile Leu Ser Thr Thr Glu Val Thr Phe Asp Thr Thr Asp Leu Asp
        755                 760                 765
```

| | | | | | | | | | | | | |
|---|---|---|---|---|---|---|---|---|---|---|---|---|
|Ile|Asn|Leu|Lys|Leu|Glu|Thr|Thr|Ser|Asn|Gln|Asp|Lys|Leu|Ala|Pro|
| |770| | | | |775| | | |780| | | | | |

Ile Thr Ala Lys Ala Lys Val Val Ile Glu Leu Leu Ser Leu Ser
785             790             795             800

Gly Val Ala Lys Pro Ser Gln Val Tyr Phe Gly Gly Thr Val Val Gly
                805             810             815

Glu Gln Ala Met Lys Ser Glu Asp Glu Val Gly Ser Leu Ile Glu Tyr
                820             825             830

Glu Phe Arg Val Ile Asn Leu Gly Lys Pro Leu Lys Asn Leu Gly Thr
            835             840             845

Ala Thr Leu Asn Ile Gln Trp Pro Lys Glu Ile Ser Asn Gly Lys Trp
    850             855             860

Leu Leu Tyr Leu Met Lys Val Glu Ser Lys Gly Leu Glu Gln Ile Val
865             870             875             880

Cys Glu Pro His Asn Glu Ile Asn Tyr Leu Lys Leu Lys Glu Ser His
                885             890             895

Asn Ser Arg Lys Lys Arg Glu Leu Pro Glu Lys Gln Ile Asp Asp Ser
                900             905             910

Arg Lys Phe Ser Leu Phe Pro Glu Arg Lys Tyr Gln Thr Leu Asn Cys
            915             920             925

Ser Val Asn Val Arg Cys Val Asn Ile Arg Cys Pro Leu Arg Gly Leu
    930             935             940

Asp Thr Lys Ala Ser Leu Val Leu Cys Ser Arg Leu Trp Asn Ser Thr
945             950             955             960

Phe Leu Glu Glu Tyr Ser Lys Leu Asn Tyr Leu Asp Ile Leu Val Arg
                965             970             975

Ala Ser Ile Asp Val Thr Ala Ala Gln Asn Ile Lys Leu Pro His
                980             985             990

Ala Gly Thr Gln Val Arg Val Thr Val Phe Pro Ser Lys Thr Val Ala
            995             1000            1005

Gln Tyr Ser Gly Val Ala Trp Trp Ile Ile Leu Leu Ala Val Leu Ala
        1010            1015            1020

Gly Ile Leu Met Leu Ala Leu Leu Val Phe Leu Leu Trp Lys Cys Gly
1025            1030            1035            1040

Phe Phe Lys Arg Asn Lys Lys Asp His Tyr Asp Ala Thr Tyr His Lys
            1045            1050            1055

Ala Glu Ile His Thr Gln Pro Ser Asp Lys Glu Arg Leu Thr Ser Asp
            1060            1065            1070

Ala

<210> SEQ ID NO 5
<211> LENGTH: 5622
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 5
atggcagggc cacgccccag cccatgggcc aggctgctcc tggcagcctt gatcagcgtc    60
agcctctctg ggaccttgaa ccgctgcaag aaggccccag tgaagagctg cacggagtgt    120
gtccgtgtgg ataaggactg cgcctactgc acagacgaga tgttcaggga ccggcgctgc    180
aacacccagg cggagctgct ggccgcgggc tgccagcggg agagcatcgt ggtcatggag    240
agcagcttcc aaatcacaga ggagacccag attgacacca ccctgcggcg cagccagatg    300

```
tccccccaag gcctgcgggt ccgtctgcgg cccggtgagg agcggcattt tgagctggag      360
gtgtttgagc cactggagag ccccgtggac ctgtacatcc tcatggactt ctccaactcc      420
atgtccgatg atctggacaa cctcaagaag atggggcaga acctggctcg ggtcctgagc      480
cagctcacca gcgactacac tattggattt ggcaagtttg tggacaaagt cagcgtcccg      540
cagacggaca tgaggcctga aagctgaag gagccttggc ccaacagtga cccccccttc       600
tccttcaaga acgtcatcag cctgacagaa gatgtggatg agttccggaa taaactgcag      660
ggagagcgga tctcaggcaa cctggatgct cctgagggcg gcttcgatgc catcctgcag      720
acagctgtgt gcacgaggga cattggctgg cgcccggaca gcacccacct gctggtcttc      780
tccaccgagt cagccttcca ctatgaggct gatggcgcca acgtgctggc tggcatcatg      840
agccgcaacg atgaacggtg ccacctggac accacgggca cctacaccca gtacaggaca      900
caggactacc cgtcggtgcc caccctggtg cgcctgctcg ccaagcacaa catcatcccc      960
atctttgctg tcaccaacta ctcctatagc tactacgaga agcttcacac ctatttccct     1020
gtctcctcac tgggggtgct gcaggaggac tcgtccaaca tcgtggagct gctggaggag     1080
gccttcaatc ggatccgctc caacctggac atccgggccc tagacagccc ccgaggcctt     1140
cggacagagg tcacctccaa gatgttccag aagacgagga ctgggtcctt tcacatccgg     1200
cggggggaag tgggtatata ccaggtgcag ctgcgggccc ttgagcacgt ggatgggacg     1260
cacgtgtgcc agctgccgga ggaccagaag ggcaacatcc atctgaaacc ttccttctcc     1320
gacggcctca agatggacgc gggcatcatc tgtgatgtgt gcacctgcga gctgcaaaaa     1380
gaggtgcggt cagctcgctg cagcttcaac ggagacttcg tgtgcggaca gtgtgtgtgc     1440
agcgagggct ggagtggcca gacctgcaac tgctccaccg gctctctgag tgacattcag     1500
ccctgcctgc gggagggcga ggacaagccg tgctccggcc gtggggagtg ccagtgcggg     1560
cactgtgtgt gctacggcga aggccgctac gagggtcagt tctgcgagta tgacaacttc     1620
cagtgtcccc gcacttccgg gttcctctgc aatgaccgag acgctgctc catgggccag     1680 tgtgtgtgtg agcctggttg acaggcccca agctgtgact gtcccctcag caatgccacc     1740
tgcatcgaca gcaatggggg catctgtaat ggacgtggcc actgtgagtg tggccgctgc     1800
cactgccacc agcagtcgct ctacacggac accatctgcg agatcaacta ctcggcgtcc     1860
acccgggcct ctgcgaggac ctacgctcct gcgtgcagtg ccaggcgtgg ggcaccggcg     1920
agaagaaggg gcgcacgtgt gaggaatgca acttcaaggt caagatggtg gacgagctta     1980
agagaggcga ggaggtggtg gtgcgctgct ccttccggga cgaggatgac gactgcacct     2040
acagctacac catggaaggt gacggcgccc ctgggcccaa cagcactgtc ctggtgcaca     2100
agaagaaggg actgccctcc gggctccttc tggtggctca tcccctgct cctcctcctc      2160 ctgccgctcc tggccctgct actgctgcta tgctggaagt actgtgcctg ctgcaaggcc     2220
tgcctggcac ttctcccgtg ctgcaaccga ggtcacatgg tgggctttaa ggaagaccac     2280
tacatgctgc gggagaacct gatggcctct gaccacttgg acacgcccat gctgcgcagc     2340
gggaacctca agggccgtga cgtggtccgc tggaaggtca ccaacaacat gcagcggcct     2400
ggctttgcca ctcatgccgc cagcatcaac cccacagagc tggtgcccta cgggctgtcc     2460
ttgcgcctgg cccgcctttg caccgagaac ctgctgaagc ctgacactcg ggagtgcgcc     2520
cagctgcgcc aggaggtgga ggagaacctg aacgaggtct acaggcagat ctccggtgta     2580
cacaagctcc agcagaccaa gttccggcag cagcccaatg ccgggaaaaa gcaagaccac     2640
accattgtgg acacagtgct gatggcgccc cgctcggcca agccggccct gctgaagctt     2700
```

```
acagagaagc aggtggaaca gagggccttc cacgacctca aggtggcccc cggctactac    2760
accctcactg cagaccagga cgcccggggc atggtggagt tccaggaggg cgtggagctg    2820
gtggacgtac gggtgcccct ctttatccgg cctgaggatg acgacgagaa gcagctgctg    2880
gtggaggcca tcgacgtgcc cgcaggcact gccaccctcg gccgccgcct ggtaaacatc    2940
accatcatca aggagcaagc cagagacgtg gtgtcctttg agcagcctga gttctcggtc    3000
agccgcgggg accaggtggc ccgcatccct gtcatccggc gtgtcctgga cggcgggaag    3060
tcccaggtct cctaccgcac acaggatggc accgcgcagg gcaaccggga ctacatcccc    3120
gtggagggtg agctgctgtt ccagcctggg gaggcctgga agagctgca ggtgaagctc    3180 ctggagctgc aagaagttga ctccctcctg cggggccgcc aggtccgccg tttccacgtc    3240
cagctcagca accctaagtt tggggcccac ctgggccagc ccactccac caccatcatc    3300 atcagggacc cagatgaact ggaccggagc ttcacgagtc agatgttgtc atcacagcca    3360 cccccctcacg cgacctggg cgccccgcag aaccccaatg ctaaggccgc tgggtccagg    3420
aagatccatt tcaactggct gccccttcct ggcaagccaa tggggtacag ggtaaagtac    3480
tggattcagg gtgactccga atccgaagcc cacctgctcg acagcaaggt gccctcagtg    3540
gagctcacca acctgtaccc gtattgcgac tatgagatga aggtgtgcgc ctacggggct    3600
cagggcgagg gaccctacag ctcctggtg tcctgccgca cccaccagga agtgcccagc    3660
gagccagggc gtctggcctt caatgtcgtc tcctccacgg tgacccagct gagctgggct    3720
gagccggctg agaccaacgg tgagatcaca gcctacgagg tctgctatgg cctggtcaac    3780
gatgacaacc gacctattgg gcccatgaag aaagtgctgg ttgacaaccc taagaaccgg    3840
atgctgctta ttgagaacct tcgggagtcc cagccctacc gctacacggt gaaggcgcgc    3900 aacgggggccg gctgggggcc tgagcgggag gccatcatca acctgccac ccagcccaag    3960 aggcccatgt ccatccccat catccctgac atccctatcg tggacgccca gagcggggag    4020
gactacgaca gcttccttat gtacagcgat gacgttctac gctctccatc gggcagccag    4080
aggcccagcg tctccgatga cactggctgc ggctggaagt tcgagcccct gctggggag    4140 gagctggacc tgcggcgcgt cacgtggcgg ctgcccccgg agctcatccc gcgcctgtcg    4200
gccagcagcg ggcgctcctc cgacgccgag gcgccccacg ggccccggga cgacggcggc    4260
gcgggcggga agggcggcag cctgcccgc agtgcgacac ccgggccccc cggagagcac    4320
ctggtgaatg gccggatgga ctttgccttc ccgggcagca ccaactccct gcacaggatg    4380
accacgacca gtgctgctgc ctatggcacc cacctgagcc cacacgtgcc ccaccgcgtg    4440
ctaagcacat cctccaccct cacacgggac tacaactcac tgacccgctc agaacactca    4500
cactcgacca cactgccgag ggactactcc accctcacct ccgtctcctc ccacggcctc    4560
cctcccatct gggaacacgg gaggagcagg cttccgctgt cctgggccct ggggtcccgg    4620
agtcgggctc agatgaaagg gttcccccct tccaggggcc cacgagactc tataatcctg    4680
gctgggaggc cagcagcgcc ctcctggggc ccagactctc gcctgactgc tggtgtgccc    4740
gacacgccca cccgcctggt gttctctgcc ctggggccca tctctcag agtgagctgg    4800 caggagccgc ggtgcgagcg gccgctgcag ggctacagtg tggagtacca gctgctgaac    4860
ggcggtgagc tgcatcggct caacatcccc aaccctgccc agacctcggt ggtggtggaa    4920
gacctcctgc ccaaccactc ctacgtgttc cgcgtgcggg cccagagcca ggaaggctgg    4980
ggccgagagc gtgagggtgt catcaccatt gaatcccagg tgcacccgca gagcccactg    5040 tgtccctgc caggctccgc cttcacttg agcactccca gtgccccagg cccgctggtg    5100
```

-continued

```
ttcactgccc tgagcccaga ctcgctgcag ctgagctggg agcggccacg gaggcccaat    5160
ggggatatcg tcggctacct ggtgacctgt gagatggccc aaggaggagg tccagccacc    5220
gcattccggg tggatggaga cagccccgag agccggctga ccgtgccggg cctcagcgag    5280
aacgtgccct acaagttcaa ggtgcaggcc aggaccactg agggcttcgg gccagagcgc    5340
gagggcatca tcaccataga gtcccaggat ggaggtccct tcccgcagct gggcagccgt    5400
gccgggctct tccagcaccc gctgcaaagc gagtacagca gcatctccac cacccacacc    5460
agcgccaccg agcccttcct agtgggtccg accctggggg cccagcacct ggaggcaggc    5520
ggctccctca cccggcatgt gacccaggag tttgtgagcc ggacactgac caccagcgga    5580
acccttagca cccacatgga ccaacagttc ttccaaactt ga                      5622
```

<210> SEQ ID NO 6
<211> LENGTH: 1873
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 6

```
Met Ala Gly Pro Arg Pro Ser Pro Trp Ala Arg Leu Leu Leu Ala Ala
1               5                   10                  15

Leu Ile Ser Val Ser Leu Ser Gly Thr Leu Asn Arg Cys Lys Lys Ala
            20                  25                  30

Pro Val Lys Ser Cys Thr Glu Cys Val Arg Val Asp Lys Asp Cys Ala
        35                  40                  45

Tyr Cys Thr Asp Glu Met Phe Arg Asp Arg Arg Cys Asn Thr Gln Ala
    50                  55                  60

Glu Leu Leu Ala Ala Gly Cys Gln Arg Glu Ser Ile Val Val Met Glu
65                  70                  75                  80

Ser Ser Phe Gln Ile Thr Glu Glu Thr Gln Ile Asp Thr Thr Leu Arg
                85                  90                  95

Arg Ser Gln Met Ser Pro Gln Gly Leu Arg Val Arg Leu Arg Pro Gly
            100                 105                 110

Glu Glu Arg His Phe Glu Leu Glu Val Phe Glu Pro Leu Glu Ser Pro
        115                 120                 125

Val Asp Leu Tyr Ile Leu Met Asp Phe Ser Asn Ser Met Ser Asp Asp
    130                 135                 140

Leu Asp Asn Leu Lys Lys Met Gly Gln Asn Leu Ala Arg Val Leu Ser
145                 150                 155                 160

Gln Leu Thr Ser Asp Tyr Thr Ile Gly Phe Gly Lys Phe Val Asp Lys
                165                 170                 175

Val Ser Val Pro Gln Thr Asp Met Arg Pro Glu Lys Leu Lys Glu Pro
            180                 185                 190

Trp Pro Asn Ser Asp Pro Pro Phe Ser Phe Lys Asn Val Ile Ser Leu
        195                 200                 205

Thr Glu Asp Val Asp Glu Phe Arg Asn Lys Leu Gln Gly Glu Arg Ile
    210                 215                 220

Ser Gly Asn Leu Asp Ala Pro Glu Gly Gly Phe Asp Ala Ile Leu Gln
225                 230                 235                 240

Thr Ala Val Cys Thr Arg Asp Ile Gly Trp Arg Pro Asp Ser Thr His
                245                 250                 255

Leu Leu Val Phe Ser Thr Glu Ser Ala Phe His Tyr Glu Ala Asp Gly
            260                 265                 270
```

```
Ala Asn Val Leu Ala Gly Ile Met Ser Arg Asn Asp Glu Arg Cys His
        275                 280                 285

Leu Asp Thr Thr Gly Thr Tyr Thr Gln Tyr Arg Thr Gln Asp Tyr Pro
    290                 295                 300

Ser Val Pro Thr Leu Val Arg Leu Leu Ala Lys His Asn Ile Ile Pro
305                 310                 315                 320

Ile Phe Ala Val Thr Asn Tyr Ser Tyr Ser Tyr Tyr Glu Lys Leu His
                325                 330                 335

Thr Tyr Phe Pro Val Ser Ser Leu Gly Val Leu Gln Glu Asp Ser Ser
                340                 345                 350

Asn Ile Val Glu Leu Leu Glu Glu Ala Phe Asn Arg Ile Arg Ser Asn
            355                 360                 365

Leu Asp Ile Arg Ala Leu Asp Ser Pro Arg Gly Leu Arg Thr Glu Val
    370                 375                 380

Thr Ser Lys Met Phe Gln Lys Thr Arg Thr Gly Ser Phe His Ile Arg
385                 390                 395                 400

Arg Gly Glu Val Gly Ile Tyr Gln Val Gln Leu Arg Ala Leu Glu His
                405                 410                 415

Val Asp Gly Thr His Val Cys Gln Leu Pro Glu Asp Gln Lys Gly Asn
            420                 425                 430

Ile His Leu Lys Pro Ser Phe Ser Asp Gly Leu Lys Met Asp Ala Gly
        435                 440                 445

Ile Ile Cys Asp Val Cys Thr Cys Glu Leu Gln Lys Glu Val Arg Ser
450                 455                 460

Ala Arg Cys Ser Phe Asn Gly Asp Phe Val Cys Gly Gln Cys Val Cys
465                 470                 475                 480

Ser Glu Gly Trp Ser Gly Gln Thr Cys Asn Cys Ser Thr Gly Ser Leu
                485                 490                 495

Ser Asp Ile Gln Pro Cys Leu Arg Glu Gly Glu Asp Lys Pro Cys Ser
            500                 505                 510

Gly Arg Gly Glu Cys Gln Cys Gly His Cys Val Cys Tyr Gly Glu Gly
        515                 520                 525

Arg Tyr Glu Gly Gln Phe Cys Glu Tyr Asp Asn Phe Gln Cys Pro Arg
    530                 535                 540

Thr Ser Gly Phe Leu Cys Asn Asp Arg Gly Arg Cys Ser Met Gly Gln
545                 550                 555                 560

Cys Val Cys Glu Pro Gly Trp Thr Gly Pro Ser Cys Asp Cys Pro Leu
                565                 570                 575

Ser Asn Ala Thr Cys Ile Asp Ser Asn Gly Gly Ile Cys Asn Gly Arg
            580                 585                 590

Gly His Cys Glu Cys Gly Arg Cys His Cys His Gln Gln Ser Leu Tyr
        595                 600                 605

Thr Asp Thr Ile Cys Glu Ile Asn Tyr Ser Ala Ser Thr Arg Ala Ser
    610                 615                 620

Ala Arg Thr Tyr Ala Pro Ala Cys Ser Ala Arg Gly Ala Pro Ala
625                 630                 635                 640

Arg Arg Arg Gly Ala Arg Val Arg Asn Ala Thr Ser Arg Ser Arg Trp
                645                 650                 655

Trp Thr Ser Leu Arg Glu Ala Arg Trp Trp Cys Ala Ala Pro Ser
            660                 665                 670

Gly Thr Arg Met Thr Thr Ala Pro Thr Ala Thr Pro Trp Lys Val Thr
        675                 680                 685

Ala Pro Leu Gly Pro Thr Ala Leu Ser Trp Cys Thr Arg Arg Arg Asp
    690                 695                 700
```

```
Cys Pro Pro Gly Ser Phe Trp Leu Ile Pro Leu Leu Leu Leu
705                 710                 715                 720

Leu Pro Leu Leu Ala Leu Leu Leu Leu Cys Trp Lys Tyr Cys Ala
            725                 730                 735

Cys Cys Lys Ala Cys Leu Ala Leu Leu Pro Cys Cys Asn Arg Gly His
            740                 745                 750

Met Val Gly Phe Lys Glu Asp His Tyr Met Leu Arg Glu Asn Leu Met
            755                 760                 765

Ala Ser Asp His Leu Asp Thr Pro Met Leu Arg Ser Gly Asn Leu Lys
            770                 775                 780

Gly Arg Asp Val Val Arg Trp Lys Val Thr Asn Asn Met Gln Arg Pro
785                 790                 795                 800

Gly Phe Ala Thr His Ala Ala Ser Ile Asn Pro Thr Glu Leu Val Pro
            805                 810                 815

Tyr Gly Leu Ser Leu Arg Leu Ala Arg Leu Cys Thr Glu Asn Leu Leu
            820                 825                 830

Lys Pro Asp Thr Arg Glu Cys Ala Gln Leu Arg Gln Glu Val Glu Glu
            835                 840                 845

Asn Leu Asn Glu Val Tyr Arg Gln Ile Ser Gly Val His Lys Leu Gln
            850                 855                 860

Gln Thr Lys Phe Arg Gln Gln Pro Asn Ala Gly Lys Lys Gln Asp His
865                 870                 875                 880

Thr Ile Val Asp Thr Val Leu Met Ala Pro Arg Ser Ala Lys Pro Ala
            885                 890                 895

Leu Leu Lys Leu Thr Glu Lys Gln Val Glu Gln Arg Ala Phe His Asp
            900                 905                 910

Leu Lys Val Ala Pro Gly Tyr Tyr Thr Leu Thr Ala Asp Gln Asp Ala
            915                 920                 925

Arg Gly Met Val Glu Phe Gln Glu Gly Val Glu Leu Val Asp Val Arg
            930                 935                 940

Val Pro Leu Phe Ile Arg Pro Glu Asp Asp Glu Lys Gln Leu Leu
945                 950                 955                 960

Val Glu Ala Ile Asp Val Pro Ala Gly Thr Ala Thr Leu Gly Arg Arg
            965                 970                 975

Leu Val Asn Ile Thr Ile Ile Lys Glu Gln Ala Arg Asp Val Val Ser
            980                 985                 990

Phe Glu Gln Pro Glu Phe Ser Val Ser Arg Gly Asp Gln Val Ala Arg
            995                 1000                1005

Ile Pro Val Ile Arg Arg Val Leu Asp Gly Gly Lys Ser Gln Val Ser
            1010                1015                1020

Tyr Arg Thr Gln Asp Gly Thr Ala Gln Gly Asn Arg Asp Tyr Ile Pro
1025                1030                1035                1040

Val Glu Gly Glu Leu Leu Phe Gln Pro Gly Glu Ala Trp Lys Glu Leu
            1045                1050                1055

Gln Val Lys Leu Leu Glu Leu Gln Glu Val Asp Ser Leu Leu Arg Gly
            1060                1065                1070

Arg Gln Val Arg Arg Phe His Val Gln Leu Ser Asn Pro Lys Phe Gly
            1075                1080                1085

Ala His Leu Gly Gln Pro His Ser Thr Thr Ile Ile Ile Arg Asp Pro
            1090                1095                1100

Asp Glu Leu Asp Arg Ser Phe Thr Ser Gln Met Leu Ser Ser Gln Pro
1105                1110                1115                1120

Pro Pro His Gly Asp Leu Gly Ala Pro Gln Asn Pro Asn Ala Lys Ala
```

```
                    1125                1130                1135
Ala Gly Ser Arg Lys Ile His Phe Asn Trp Leu Pro Pro Ser Gly Lys
            1140                1145                1150

Pro Met Gly Tyr Arg Val Lys Tyr Trp Ile Gln Gly Asp Ser Glu Ser
        1155                1160                1165

Glu Ala His Leu Leu Asp Ser Lys Val Pro Ser Val Glu Leu Thr Asn
    1170                1175                1180

Leu Tyr Pro Tyr Cys Asp Tyr Glu Met Lys Val Cys Ala Tyr Gly Ala
1185                1190                1195                1200

Gln Gly Glu Gly Pro Tyr Ser Ser Leu Val Ser Cys Arg Thr His Gln
            1205                1210                1215

Glu Val Pro Ser Glu Pro Gly Arg Leu Ala Phe Asn Val Val Ser Ser
        1220                1225                1230

Thr Val Thr Gln Leu Ser Trp Ala Glu Pro Ala Glu Thr Asn Gly Glu
    1235                1240                1245

Ile Thr Ala Tyr Glu Val Cys Tyr Gly Leu Val Asn Asp Asp Asn Arg
1250                1255                1260

Pro Ile Gly Pro Met Lys Lys Val Leu Val Asp Asn Pro Lys Asn Arg
1265                1270                1275                1280

Met Leu Leu Ile Glu Asn Leu Arg Glu Ser Gln Pro Tyr Arg Tyr Thr
            1285                1290                1295

Val Lys Ala Arg Asn Gly Ala Gly Trp Gly Pro Glu Arg Glu Ala Ile
        1300                1305                1310

Ile Asn Leu Ala Thr Gln Pro Lys Arg Pro Met Ser Ile Pro Ile Ile
    1315                1320                1325

Pro Asp Ile Pro Ile Val Asp Ala Gln Ser Gly Glu Asp Tyr Asp Ser
1330                1335                1340

Phe Leu Met Tyr Ser Asp Asp Val Leu Arg Ser Pro Ser Gly Ser Gln
1345                1350                1355                1360

Arg Pro Ser Val Ser Asp Asp Thr Gly Cys Gly Trp Lys Phe Glu Pro
            1365                1370                1375

Leu Leu Gly Glu Glu Leu Asp Leu Arg Arg Val Thr Trp Arg Leu Pro
        1380                1385                1390

Pro Glu Leu Ile Pro Arg Leu Ser Ala Ser Ser Gly Arg Ser Ser Asp
    1395                1400                1405

Ala Glu Ala Pro His Gly Pro Pro Asp Asp Gly Gly Ala Gly Gly Lys
            1410                1415                1420

Gly Gly Ser Leu Pro Arg Ser Ala Thr Pro Gly Pro Pro Gly Glu His
1425                1430                1435                1440

Leu Val Asn Gly Arg Met Asp Phe Ala Phe Pro Gly Ser Thr Asn Ser
            1445                1450                1455

Leu His Arg Met Thr Thr Thr Ser Ala Ala Ala Tyr Gly Thr His Leu
        1460                1465                1470

Ser Pro His Val Pro His Arg Val Leu Ser Thr Ser Ser Thr Leu Thr
    1475                1480                1485

Arg Asp Tyr Asn Ser Leu Thr Arg Ser Glu His Ser His Ser Thr Thr
1490                1495                1500

Leu Pro Arg Asp Tyr Ser Thr Leu Thr Ser Val Ser Ser His Gly Leu
1505                1510                1515                1520

Pro Pro Ile Trp Glu His Gly Arg Ser Arg Leu Pro Leu Ser Trp Ala
            1525                1530                1535

Leu Gly Ser Arg Ser Arg Ala Gln Met Lys Gly Phe Pro Pro Ser Arg
        1540                1545                1550
```

Gly Pro Arg Asp Ser Ile Ile Leu Ala Gly Arg Pro Ala Ala Pro Ser
        1555                1560                1565

Trp Gly Pro Asp Ser Arg Leu Thr Ala Gly Val Pro Asp Thr Pro Thr
    1570                1575                1580

Arg Leu Val Phe Ser Ala Leu Gly Pro Thr Ser Leu Arg Val Ser Trp
1585                1590                1595                1600

Gln Glu Pro Arg Cys Glu Arg Pro Leu Gln Gly Tyr Ser Val Glu Tyr
                1605                1610                1615

Gln Leu Leu Asn Gly Gly Glu Leu His Arg Leu Asn Ile Pro Asn Pro
            1620                1625                1630

Ala Gln Thr Ser Val Val Glu Asp Leu Leu Pro Asn His Ser Tyr
        1635                1640                1645

Val Phe Arg Val Arg Ala Gln Ser Gln Glu Gly Trp Gly Arg Glu Arg
1650                1655                1660

Glu Gly Val Ile Thr Ile Glu Ser Gln Val His Pro Gln Ser Pro Leu
1665                1670                1675                1680

Cys Pro Leu Pro Gly Ser Ala Phe Thr Leu Ser Thr Pro Ser Ala Pro
                1685                1690                1695

Gly Pro Leu Val Phe Thr Ala Leu Ser Pro Asp Ser Leu Gln Leu Ser
            1700                1705                1710

Trp Glu Arg Pro Arg Arg Pro Asn Gly Asp Ile Val Gly Tyr Leu Val
        1715                1720                1725

Thr Cys Glu Met Ala Gln Gly Gly Gly Pro Ala Thr Ala Phe Arg Val
    1730                1735                1740

Asp Gly Asp Ser Pro Glu Ser Arg Leu Thr Val Pro Gly Leu Ser Glu
1745                1750                1755                1760

Asn Val Pro Tyr Lys Phe Lys Val Gln Ala Arg Thr Thr Glu Gly Phe
                1765                1770                1775

Gly Pro Glu Arg Glu Gly Ile Ile Thr Ile Glu Ser Gln Asp Gly Gly
            1780                1785                1790

Pro Phe Pro Gln Leu Gly Ser Arg Ala Gly Leu Phe Gln His Pro Leu
        1795                1800                1805

Gln Ser Glu Tyr Ser Ser Ile Ser Thr Thr His Thr Ser Ala Thr Glu
    1810                1815                1820

Pro Phe Leu Val Gly Pro Thr Leu Gly Ala Gln His Leu Glu Ala Gly
1825                1830                1835                1840

Gly Ser Leu Thr Arg His Val Thr Gln Glu Phe Val Ser Arg Thr Leu
                1845                1850                1855

Thr Thr Ser Gly Thr Leu Ser Thr His Met Asp Gln Gln Phe Phe Gln
            1860                1865                1870

Thr

<210> SEQ ID NO 7
<211> LENGTH: 5907
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 7
ggaccgtcga ggcagcggga ctgacccagc tgggctcact gtattaagaa gcggacccgc    60
gacccggagc gcccgggggac ccgatctggg agcctggacg ggtgcagcgc gcaggaatgc    120
agtccgcctg actcaccagc gcctccttcc tacctgcgcc gcccgtccat aaagcgctgc    180
tcgtcccgcc cgccgccgcc gccctgctgt cccgccgggc tcgcccgcgc gctcagctcg    240

```
acccaacgca gcccaagtcc gaggtagtct cactaaggag gaggaggatg gcagggccct    300
gttgcagccc atgggtgaag ctgctgctgc tggcacgaat gctgagtgcc agcctccctg    360
gagacctggc caaccgctgc aagaaggctc aggtgaagag ctgtaccgag tgcatccggg    420
tggacaagag ctgtgcctac tgcacagacg agctgttcaa ggagaggcgc tgcaacaccc    480
aggcggacgt tctggctgca ggctgcaggg gagagagcat cctggtcatg gagagcagcc    540
ttgaaatcac agagaacacc cagatcgtca ccagcctgca ccgcagccag gtatctcccc    600
aaggcctgca agtccggctg cggcggggtg aggagcgcac gtttgtgttc caggtctttg    660
agcccctgga gagcccgtg gatctgtata tcctcatgga cttctccaac tccatgtctg     720
acgatctgga caacctcaag cagatggggc agaacctggc caagatcctg cgccagctca    780
ccagcgacta caccattgga tttggaaagt tgtggacaa agtcagcgtc ccacagacag      840
acatgaggcc cgagaaactg aaggagccct ggcccaacag tgatccccg ttctccttca      900 agaacgttat cagcttaacg gagaatgtgg aagaattctg gaacaaactg caaggagaac    960
gcatctcagg caacctggac gctcctgaag ggggctttga tgccatcctg cagacagctg   1020
tgtgcacaag ggacattggc tggagggctg acagcaccca cctgctggtg ttctccaccg   1080
agtctgcctt ccactacgag gctgatggtg ccaacgttct ggccggcatc atgaaccgca   1140
atgatgagaa atgccacctg gacgcctcgg gcgcctacac ccaatacaag acacaggact   1200
acccatcagt gcccacgctg gttcgcctgc ttgccaagca taacatcatc cccatctttg   1260
ctgtcaccaa ctactcttac agctactatg agaagctcca taagtatttc cccgtctcct   1320
ctctgggcgt cctgcaggag gattcatcca acatcgtgga gctgctggag gaggccttct   1380
atcgaattcg ctccaacctg gacatccggg ctctggacag ccccagaggc ctgagaacag   1440
aggtcacctc cgatactctc cagaagacgg agactgggtc ctttcacatc aagcgggggg   1500
aagtgggcac atacaatgtg catctcccggg cagtggagga catagatggg acacatgtgt   1560
gccagctggc taaagaagac caagggggca acatccacct gaaaccctcc ttctctgatg   1620
gcctccggat ggacgcgagt gtgatctgtg acgtgtgccc ctgtgagctg caaaaggaag   1680
ttcgatcagc tcgctgtcac ttcagaggag acttcatgtg tggacactgt gtgtgcaatg   1740
agggctggag tggcaaaacc tgcaactgct ccaccggctc tctgagtgac acacagccct   1800
gcctgcgtga gggtgaggac aaaccgtgct cgggccacgg cgagtgccag tgcggacgct   1860
gtgtgtgcta tggtgaaggc cgctacgagg gtcacttctg cgagtatgac aacttccagt   1920
gtccccggac ctctggattc ctgtgcaatg accggggacg ctgttctatg ggagagtgtg   1980
tgtgtgagcc tggttggaca ggccgcagct gcgactgtcc cctcagcaat gccacctgca   2040
tcgatagcaa cggggggcatc tgcaacggcc gaggctactg tgagtgtggc cgttgtcact   2100
gcaaccagca gtcgctctac acggacacca cctgtgagat caactactct gcgatactgg   2160
gtctctgtga ggatctccgc tcctgcgtac agtgccaggc ctggggcacc ggggagaaga   2220
aagggcgcgc gtgtgacgat tgccccttta aagtcaagat ggtagacgag cttaagaaag   2280
aagaggtggt ggagtactgc tccttccggg atgaggatga cgactgcact tacagctaca   2340
acgtggaggg cgacgcagcc ctgggcccca acagcacagt cctggtccac aaaaagaaag   2400
actgcctccc ggctccttcc tggtggctca tccccctgct catcttcctc ctgttgctcc   2460
tggcgttgct tctgctgctc tgctggaaat actgtgcctg ctgcaaagcc tgcctggggc   2520
ttcttccttg ctgcaaccga ggtcacatgg tgggctttaa ggaagatcac tatatgcttc   2580
gggagaacct gatggcctct gaccacctgg acacgcccat gctacgaagc gggaacctca   2640
```

```
agggacgaga cacagtccgc tggaagatca ccaacaatgt gcagcgccct ggctttgcca    2700
cccatgccgc cagcaccagc cccacggagc tcgtacccta cgggctgtcc ctgcgccttg    2760
gccgcctctg cactgagaac cttatgaagc cgggcacccg agagtgtgac cagctacgcc    2820
aggaggtgga ggaaaatctg aatgaggtgt atagacaggt cagcggcgca cacaagctcc    2880
agcagacgaa gttccgacag cagcccaacg ccgggaaaaa gcagaccac accattgtgg     2940 acacagtgtt gctggcgccc cgctccgcca agcagatgct gctgaagctg acagagaagc    3000
aggtggagca ggggtccttc catgaactga aggtggcccc tggctactac actgtcacgg    3060
cagagcagga tgcccggggc atggtggagt tccaggaggg cgtggagctg gtggatgtgc    3120
gagtgcccct cttcatccgg cctgaggatg atgatgagaa gcagctgctg gtggaggcca    3180
ttgatgtccc tgtgagcact gccacccttg gtcgccgtct ggtaaacatc accattatca    3240
aggaacaagc tagtggggta gtgtccttcg agcagcctga atactcggtg agtcgtggag    3300
accaggtggc ccgcatccct gtcatccggc acatcctgga caatggcaag tcccaggtct    3360
cctatagcac acaggataat acagcacacg gacaccggga ttatgttccc gtggagggag    3420
agctgctgtt ccatcctggg gaaacctgga aggagttgca ggtgaagcta ctggagctgc    3480
aggaggttga ctccctcctg cgtggccgcc aggtccgccg cttccaagtc caactcagca    3540
accccaagtt cggagcccgc ctgggccagc ccagcacaac caccgttatt ctcgatgaaa    3600
cggacaggag tctcataaat caaacacttt catcgcctcc gccacccat ggagacctgg     3660 gcgcccaca gaaccccaat gccaaggctg ccggatccag aagatccat ttcaactggc      3720 tgccccctcc tggcaagcca atggggtaca gggtgaagta ctggatccag ggcgactctg    3780
aatctgaagc ccaccttcta gatagcaagg tgccctcagt ggaactcacc aacctgtatc    3840
cctattgcga ctacgaaatg aaggtgtgtg cctatggggc caagggtgag gggccctata    3900
gctcactggt gtcctgccgc acccaccagg aagtacccag tgagccaggg aggctggctt    3960
tcaatgtagt ctcttctacg gtgactcagc tgagctgggc agagccagct gagaccaatg    4020
gcgagatcac agcctacgag gtctgctatg actggtcaa tgaggacaac agacccattg     4080
gacctatgaa gaaggtgctc gtggacaacc ccaagaaccg gatgctgctc attgagaatc    4140
tgcgagattc ccagccatac cgatacacgg ttaaggcgcg caatggggca ggatggggac    4200
ccgagagaga ggctatcatc aacctggcta cacagcccaa gcggcccatg tccatcccta    4260
tcatcccaga catccccata gtggacgccc agggtggaga agactacgaa aacttcctta    4320
tgtacagtga tgacgtcctg cggtccccag ccagcagcca gaggcccagc gtttctgatg    4380
acactgagca cctggtgaat ggccggatgg actttgccta ccaggcagc gccaactccc      4440 tgcacagaat gactgcagcc aatgtggcct atggcacgca tctgagccca cacctgtccc    4500
accgagtgct gagcacgtcc tccacccta cccgggacta ccactctctg acacgcacag     4560
agcactccca ctcaggcaca cttcccaggg actactccac cctcacttcc ctttcctccc    4620
aagcctccct cctatctggg aagatggag gagcaggctt ccgctgtcct ggactcttgg      4680
gtccttgagc cgggctcaca tgaagggtgt gcccgcatcc aggggttcac cagactctat    4740
aatcctggcc gggcagtcag cagcaccctc ctggggtaca ggattcccgt ggggctgtgg    4800
gtgtgcctga cacaccact cggctggtgt tctctgccct ggggcgcacg tctttgaagg      4860
tgagctggca ggagccacag tgtgatcgga cgctgctggg ctacagtgtg aataccagc     4920 tactaacgtg cgtcgagatg catcggctca acatccctaa ccctggccaa acctcggtgg    4980
tggtagagga tctcctgcct aactactctc atgtgttccg ggtacgggca cagagccagg    5040
```

```
agggctgggg tcgagagcga gagggtgtca tcaccatcga gtcccaggtg caccccgcaga    5100 gccctctctg ccccctgcca ggctcagcct tcactctgag cacccccagc gccccaggac    5160
cactggtgtt cactgcccta agcccagact ccccgcagct cagctgggag cggccgagga    5220
gccgcaatgg agatatcctt ggctacctgg tgacctgtga gatggcccaa ggaggagcac    5280
cagccaggac cttccgggtg gacggagaca accctgagag ccggttgact gtacctggcc    5340
tcagtgagaa cgttccttac aagttcaagg ttcaggccag gacgaccgag ggctttgggc    5400
cagagcgtga gggtatcatc accatcgagt ctcaggttgg aggcccctcc ccacagctgg    5460
gcagcaattc tgggctcttc cagaacccag tgcaaagcga gttcagcagc gtgaccagca    5520
cgcacagcac cacgactgag cccttcctca tggatggtct aaccctgggg acccagcgcc    5580
tggaagcagg aggctcccte acccggcatg tgacccagga attcgtgacc cggaccttaa    5640
cggccagtgg ctctctcagc actcatatgg accaacagtt cttccaaacc tgaacctccc    5700
ccgcgcccca gccacctggg cccctccttg cctcctctcc tagcgccttc ttcctctgct    5760
gctctaccca cgagcttgct gaccacagag ccagcccctg tagtcagaga cagggtag    5820 gtgctgtcca ggaaccataa agtgggtaga ggtgatacaa ggtctttctg actgcatccc    5880
accctgggtc aatcccaca tgtaacc                                          5907
```

<210> SEQ ID NO 8
<211> LENGTH: 1466
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 8

```
Met Ala Gly Pro Cys Cys Ser Pro Trp Val Lys Leu Leu Leu Ala
 1               5                  10                  15

Arg Met Leu Ser Ala Ser Leu Pro Gly Asp Leu Ala Asn Arg Cys Lys
                20                  25                  30

Lys Ala Gln Val Lys Ser Cys Thr Glu Cys Ile Arg Val Asp Lys Ser
            35                  40                  45

Cys Ala Tyr Cys Thr Asp Glu Leu Phe Lys Glu Arg Arg Cys Asn Thr
        50                  55                  60

Gln Ala Asp Val Leu Ala Ala Gly Cys Arg Gly Glu Ser Ile Leu Val
 65                  70                  75                  80

Met Glu Ser Ser Leu Glu Ile Thr Glu Asn Thr Gln Ile Val Thr Ser
                85                  90                  95

Leu His Arg Ser Gln Val Ser Pro Gln Gly Leu Gln Val Arg Leu Arg
            100                 105                 110

Arg Gly Glu Glu Arg Thr Phe Val Phe Gln Val Phe Glu Pro Leu Glu
        115                 120                 125

Ser Pro Val Asp Leu Tyr Ile Leu Met Asp Phe Ser Asn Ser Met Ser
    130                 135                 140

Asp Asp Leu Asp Asn Leu Lys Gln Met Gly Gln Asn Leu Ala Lys Ile
145                 150                 155                 160

Leu Arg Gln Leu Thr Ser Asp Tyr Thr Ile Gly Phe Gly Lys Phe Val
                165                 170                 175

Asp Lys Val Ser Val Pro Gln Thr Asp Met Arg Pro Glu Lys Leu Lys
            180                 185                 190

Glu Pro Trp Pro Asn Ser Asp Pro Pro Phe Ser Phe Lys Asn Val Ile
        195                 200                 205
```

```
Ser Leu Thr Glu Asn Val Glu Glu Phe Trp Asn Lys Leu Gln Gly Glu
    210                 215                 220

Arg Ile Ser Gly Asn Leu Asp Ala Pro Glu Gly Phe Asp Ala Ile
225                 230                 235                 240

Leu Gln Thr Ala Val Cys Thr Arg Asp Ile Gly Trp Arg Ala Asp Ser
                    245                 250                 255

Thr His Leu Leu Val Phe Ser Thr Glu Ser Ala Phe His Tyr Glu Ala
                260                 265                 270

Asp Gly Ala Asn Val Leu Ala Gly Ile Met Asn Arg Asn Asp Glu Lys
            275                 280                 285

Cys His Leu Asp Ala Ser Gly Ala Tyr Thr Gln Tyr Lys Thr Gln Asp
    290                 295                 300

Tyr Pro Ser Val Pro Thr Leu Val Arg Leu Leu Ala Lys His Asn Ile
305                 310                 315                 320

Ile Pro Ile Phe Ala Val Thr Asn Tyr Ser Tyr Ser Tyr Tyr Glu Lys
                    325                 330                 335

Leu His Lys Tyr Phe Pro Val Ser Ser Leu Gly Val Leu Gln Glu Asp
                340                 345                 350

Ser Ser Asn Ile Val Glu Leu Glu Glu Ala Phe Tyr Arg Ile Arg
            355                 360                 365

Ser Asn Leu Asp Ile Arg Ala Leu Asp Ser Pro Arg Gly Leu Arg Thr
    370                 375                 380

Glu Val Thr Ser Asp Thr Leu Gln Lys Thr Glu Thr Gly Ser Phe His
385                 390                 395                 400

Ile Lys Arg Gly Glu Val Gly Thr Tyr Asn Val His Leu Arg Ala Val
                    405                 410                 415

Glu Asp Ile Asp Gly Thr His Val Cys Gln Leu Ala Lys Glu Asp Gln
                420                 425                 430

Gly Gly Asn Ile His Leu Lys Pro Ser Phe Ser Asp Gly Leu Arg Met
            435                 440                 445

Asp Ala Ser Val Ile Cys Asp Val Cys Pro Cys Glu Leu Gln Lys Glu
    450                 455                 460

Val Arg Ser Ala Arg Cys His Phe Arg Gly Asp Phe Met Cys Gly His
465                 470                 475                 480

Cys Val Cys Asn Glu Gly Trp Ser Gly Lys Thr Cys Asn Cys Ser Thr
                    485                 490                 495

Gly Ser Leu Ser Asp Thr Gln Pro Cys Leu Arg Glu Gly Glu Asp Lys
                500                 505                 510

Pro Cys Ser Gly His Gly Glu Cys Gln Cys Gly Arg Cys Val Cys Tyr
            515                 520                 525

Gly Glu Gly Arg Tyr Glu Gly His Phe Cys Glu Tyr Asp Asn Phe Gln
    530                 535                 540

Cys Pro Arg Thr Ser Gly Phe Leu Cys Asn Asp Arg Gly Arg Cys Ser
545                 550                 555                 560

Met Gly Glu Cys Val Cys Glu Pro Gly Trp Thr Gly Arg Ser Cys Asp
                    565                 570                 575

Cys Pro Leu Ser Asn Ala Thr Cys Ile Asp Ser Asn Gly Gly Ile Cys
                580                 585                 590

Asn Gly Arg Gly Tyr Cys Glu Cys Gly Arg Cys His Cys Asn Gln Gln
            595                 600                 605

Ser Leu Tyr Thr Asp Thr Thr Cys Glu Ile Asn Tyr Ser Ala Ile Leu
    610                 615                 620

Gly Leu Cys Glu Asp Leu Arg Ser Cys Val Gln Cys Gln Ala Trp Gly
```

-continued

```
            625                 630                 635                 640
Thr Gly Glu Lys Lys Gly Arg Ala Cys Asp Asp Cys Pro Phe Lys Val
                        645                 650                 655
Lys Met Val Asp Glu Leu Lys Lys Glu Glu Val Val Glu Tyr Cys Ser
                660                 665                 670
Phe Arg Asp Glu Asp Asp Cys Thr Tyr Ser Tyr Asn Val Glu Gly
            675                 680                 685
Asp Gly Ser Pro Gly Pro Asn Ser Thr Val Leu Val His Lys Lys Lys
        690                 695                 700
Asp Cys Leu Pro Ala Pro Ser Trp Trp Leu Ile Pro Leu Ile Phe
705                 710                 715                 720
Leu Leu Leu Leu Leu Ala Leu Leu Leu Leu Cys Trp Lys Tyr Cys
                        725                 730                 735
Ala Cys Cys Lys Ala Cys Leu Gly Leu Leu Pro Cys Cys Asn Arg Gly
                    740                 745                 750
His Met Val Gly Phe Lys Glu Asp His Tyr Met Leu Arg Glu Asn Leu
                755                 760                 765
Met Ala Ser Asp His Leu Asp Thr Pro Met Leu Arg Ser Gly Asn Leu
        770                 775                 780
Lys Gly Arg Asp Thr Val Arg Trp Lys Ile Thr Asn Asn Val Gln Arg
785                 790                 795                 800
Pro Gly Phe Ala Thr His Ala Ala Ser Thr Ser Pro Thr Glu Leu Val
                        805                 810                 815
Pro Tyr Gly Leu Ser Leu Arg Leu Gly Arg Leu Cys Thr Glu Asn Leu
                    820                 825                 830
Met Lys Pro Gly Thr Arg Glu Cys Asp Gln Leu Arg Gln Glu Val Glu
                835                 840                 845
Glu Asn Leu Asn Glu Val Tyr Arg Gln Val Ser Gly Ala His Lys Leu
        850                 855                 860
Gln Gln Thr Lys Phe Arg Gln Pro Asn Ala Gly Lys Lys Gln Asp
865                 870                 875                 880
His Thr Ile Val Asp Thr Val Leu Leu Ala Pro Arg Ser Ala Lys Gln
                        885                 890                 895
Met Leu Leu Lys Leu Thr Glu Lys Gln Val Glu Gln Gly Ser Phe His
                    900                 905                 910
Glu Leu Lys Val Ala Pro Gly Tyr Tyr Thr Val Thr Ala Glu Gln Asp
                915                 920                 925
Ala Arg Gly Met Val Glu Phe Gln Glu Gly Val Glu Leu Val Asp Val
        930                 935                 940
Arg Val Pro Leu Phe Ile Arg Pro Glu Asp Asp Glu Lys Gln Leu
945                 950                 955                 960
Leu Val Glu Ala Ile Asp Val Pro Val Ser Thr Ala Thr Leu Gly Arg
                        965                 970                 975
Arg Leu Val Asn Ile Thr Ile Lys Glu Gln Ala Ser Gly Val Val
                    980                 985                 990
Ser Phe Glu Gln Pro Glu Tyr Ser Val Ser Arg Gly Asp Gln Val Ala
                995                 1000                1005
Arg Ile Pro Val Ile Arg His Ile Leu Asp Asn Gly Lys Ser Gln Val
    1010                1015                1020
Ser Tyr Ser Thr Gln Asp Asn Thr Ala His Gly His Arg Asp Tyr Val
1025                1030                1035                1040
Pro Val Glu Gly Glu Leu Leu Phe His Pro Gly Glu Thr Trp Lys Glu
                        1045                1050                1055
```

-continued

Leu Gln Val Lys Leu Leu Glu Leu Gln Glu Val Asp Ser Leu Leu Arg
             1060                1065                1070

Gly Arg Gln Val Arg Arg Phe Gln Val Gln Leu Ser Asn Pro Lys Phe
         1075                1080                1085

Gly Ala Arg Leu Gly Gln Pro Ser Thr Thr Thr Val Ile Leu Asp Glu
     1090                1095                1100

Thr Asp Arg Ser Leu Ile Asn Gln Thr Leu Ser Ser Pro Pro Pro Pro
1105                1110                1115                1120

His Gly Asp Leu Gly Ala Pro Gln Asn Pro Asn Ala Lys Ala Ala Gly
             1125                1130                1135

Ser Arg Lys Ile His Phe Asn Trp Leu Pro Pro Gly Lys Pro Met
         1140                1145                1150

Gly Tyr Arg Val Lys Tyr Trp Ile Gln Gly Asp Ser Glu Ser Glu Ala
         1155                1160                1165

His Leu Leu Asp Ser Lys Val Pro Ser Val Glu Leu Thr Asn Leu Tyr
    1170                1175                1180

Pro Tyr Cys Asp Tyr Glu Met Lys Val Cys Ala Tyr Gly Ala Lys Gly
1185                1190                1195                1200

Glu Gly Pro Tyr Ser Ser Leu Val Ser Cys Arg Thr His Gln Glu Val
             1205                1210                1215

Pro Ser Glu Pro Gly Arg Leu Ala Phe Asn Val Val Ser Ser Thr Val
         1220                1225                1230

Thr Gln Leu Ser Trp Ala Glu Pro Ala Glu Thr Asn Gly Glu Ile Thr
         1235                1240                1245

Ala Tyr Glu Val Cys Tyr Gly Leu Val Asn Glu Asp Asn Arg Pro Ile
     1250                1255                1260

Gly Pro Met Lys Lys Val Leu Val Asp Asn Pro Lys Asn Arg Met Leu
1265                1270                1275                1280

Leu Ile Glu Asn Leu Arg Asp Ser Gln Pro Tyr Arg Tyr Thr Val Lys
             1285                1290                1295

Ala Arg Asn Gly Ala Gly Trp Gly Pro Glu Arg Glu Ala Ile Ile Asn
         1300                1305                1310

Leu Ala Thr Gln Pro Lys Arg Pro Met Ser Ile Pro Ile Ile Pro Asp
         1315                1320                1325

Ile Pro Ile Val Asp Ala Gln Gly Gly Glu Asp Tyr Glu Asn Phe Leu
    1330                1335                1340

Met Tyr Ser Asp Asp Val Leu Arg Ser Pro Ala Ser Ser Gln Arg Pro
1345                1350                1355                1360

Ser Val Ser Asp Asp Thr Glu His Leu Val Asn Gly Arg Met Asp Phe
             1365                1370                1375

Ala Tyr Pro Gly Ser Ala Asn Ser Leu His Arg Met Thr Ala Ala Asn
         1380                1385                1390

Val Ala Tyr Gly Thr His Leu Ser Pro His Leu Ser His Arg Val Leu
         1395                1400                1405

Ser Thr Ser Ser Thr Leu Thr Arg Asp Tyr His Ser Leu Thr Arg Thr
    1410                1415                1420

Glu His Ser His Ser Gly Thr Leu Pro Arg Asp Tyr Ser Thr Leu Thr
1425                1430                1435                1440

Ser Leu Ser Ser Gln Ala Ser Leu Leu Ser Gly Lys Met Gly Gly Ala
             1445                1450                1455

Gly Phe Arg Cys Pro Gly Leu Leu Gly Pro
         1460                1465

<210> SEQ ID NO 9

-continued

```
<211> LENGTH: 2205
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 9
atggcagggc cctgttgcag cccatgggtg aagctgctgc tgctggcacg aatgctgagt      60
gccagcctcc ctggagacct ggccaaccgc tgcaagaagg ctcaggtgaa gagctgtacc     120
gagtgcatcc gggtggacaa gagctgtgcc tactgcacag acgagctgtt caaggagagg     180
cgctgcaaca cccaggcgga cgttctggct gcaggctgca gggagagag catcctggtc      240 atggagagca gccttgaaat cacagagaac acccagatcg tcaccagcct gcaccgcagc     300
caggtatctc cccaaggcct gcaagtccgg ctgcggcggg gtgaggagcg cacgtttgtg     360
ttccaggtct ttgagccect ggagagcccc gtggatctgt atatcctcat ggacttctcc     420
aactccatgt ctgacgatct ggacaacctc aagcagatgg gcagaacct ggccaagatc      480 ctgcgccagc tcaccagcga ctacaccatt ggatttggaa agtttgtgga caaagtcagc     540
gtcccacaga cagacatgag gcccgagaaa ctgaaggagc cctggcccaa cagtgatccc     600
ccgttctcct tcaagaacgt tatcagctta acggagaatg tggaagaatt ctggaacaaa     660
ctgcaaggag aacgcatctc aggcaacctg gacgctcctg aagggggctt tgatgccatc     720
ctgcagacag ctgtgtgcac aagggacatt ggctggaggg ctgacagcac ccacctgctg     780
gtgttctcca ccgagtctgc cttccactac gaggctgatg tgccaacgt tctggccggc     840 atcatgaacc gcaatgatga aaatgccac ctggacgcct cgggcgccta cacccaatac     900
aagacacagg actacccatc agtgcccacg ctggttcgcc tgcttgccaa gcataacatc     960
atccccatct tgctgtcac aactactct tacagctact atgagaagct ccataagtat     1020
ttccccgtct cctctctggg cgtcctgcag gaggattcat ccaacatcgt ggagctgctg     1080
gaggaggcct tctatcgaat tcgctccaac ctggacatcc gggctctgga cagccccaga     1140
ggcctgagaa cagaggtcac ctccgatact ctccagaaga cggagactgg gtcctttcac     1200
atcaagcggg gggaagtggg cacatacaat gtgcatctcc gggcagtgga ggacatagat     1260
gggacacatg tgtgccagct ggctaaagaa gaccaagggg gcaacatcca cctgaaaccc     1320
tccttctctg atggcctccg gatggacgcg agtgtgatct gtgacgtgtg ccctgtgag     1380 ctgcaaaagg aagttcgatc agctcgctgt cacttcagag gagacttcat gtgtggacac     1440
tgtgtgtgca atgagggctg gagtggcaaa acctgcaact gctccaccgg ctctctgagt     1500
gacacacagc cctgcctgcg tgagggtgag gacaaaccgt gctcgggcca cggcgagtgc     1560
cagtgcggac gctgtgtgtg ctatggtgaa ggccgctacg agggtcactt ctgcgagtat     1620
gacaacttcc agtgtcccg gacctctgga ttcctgtgca atgaccgggg acgtgttct     1680 atgggagagt gtgtgtgtga gcctggttgg acaggccgca gctgcgactg tccctcagc     1740 aatgccacct gcatcgatag caacgggggc atctgcaacg gccgaggcta ctgtgagtgt     1800
ggccgttgtc actgcaacca gcagtcgctc tacacggaca ccacctgtga gatcaactac     1860
tctgcgatac tggtctctg tgaggatctc cgctcctgcg tacagtgcca ggcctggggc     1920
accggggaga agaagggcg cgcgtgtgac gattgcccct ttaaagtcaa gatggtagac     1980
gagcttaaga agaagaggt ggtggagtac tgctccttcc gggatgagga tgacgactgc     2040
acttacagct acaacgtgga gggcgacggc agccctgggc caacagcac agtcctggtc     2100 cacaaaaaga aagactgcct cccggctcct tcctggtggc tcatccccct gctcatcttc     2160
```

```
ctcctgttgc tcctggcgtt gcttctgctg ctctgctgga aatga              2205
```

<210> SEQ ID NO 10
<211> LENGTH: 734
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 10

```
Met Ala Gly Pro Cys Cys Ser Pro Trp Val Lys Leu Leu Leu Leu Ala
 1               5                  10                  15

Arg Met Leu Ser Ala Ser Leu Pro Gly Asp Leu Ala Asn Arg Cys Lys
            20                  25                  30

Lys Ala Gln Val Lys Ser Cys Thr Glu Cys Ile Arg Val Asp Lys Ser
        35                  40                  45

Cys Ala Tyr Cys Thr Asp Glu Leu Phe Lys Glu Arg Arg Cys Asn Thr
    50                  55                  60

Gln Ala Asp Val Leu Ala Ala Gly Cys Arg Gly Glu Ser Ile Leu Val
65                  70                  75                  80

Met Glu Ser Ser Leu Glu Ile Thr Glu Asn Thr Gln Ile Val Thr Ser
                85                  90                  95

Leu His Arg Ser Gln Val Ser Pro Gln Gly Leu Gln Val Arg Leu Arg
            100                 105                 110

Arg Gly Glu Glu Arg Thr Phe Val Phe Gln Val Phe Glu Pro Leu Glu
        115                 120                 125

Ser Pro Val Asp Leu Tyr Ile Leu Met Asp Phe Ser Asn Ser Met Ser
    130                 135                 140

Asp Asp Leu Asp Asn Leu Lys Gln Met Gly Gln Asn Leu Ala Lys Ile
145                 150                 155                 160

Leu Arg Gln Leu Thr Ser Asp Tyr Thr Ile Gly Phe Gly Lys Phe Val
                165                 170                 175

Asp Lys Val Ser Val Pro Gln Thr Asp Met Arg Pro Glu Lys Leu Lys
            180                 185                 190

Glu Pro Trp Pro Asn Ser Asp Pro Pro Phe Ser Phe Lys Asn Val Ile
        195                 200                 205

Ser Leu Thr Glu Asn Val Glu Glu Phe Trp Asn Lys Leu Gln Gly Glu
    210                 215                 220

Arg Ile Ser Gly Asn Leu Asp Ala Pro Glu Gly Gly Phe Asp Ala Ile
225                 230                 235                 240

Leu Gln Thr Ala Val Cys Thr Arg Asp Ile Gly Trp Arg Ala Asp Ser
                245                 250                 255

Thr His Leu Leu Val Phe Ser Thr Glu Ser Ala Phe His Tyr Glu Ala
            260                 265                 270

Asp Gly Ala Asn Val Leu Ala Gly Ile Met Asn Arg Asn Asp Glu Lys
        275                 280                 285

Cys His Leu Asp Ala Ser Gly Ala Tyr Thr Gln Tyr Lys Thr Gln Asp
    290                 295                 300

Tyr Pro Ser Val Pro Thr Leu Val Arg Leu Leu Ala Lys His Asn Ile
305                 310                 315                 320

Ile Pro Ile Phe Ala Val Thr Asn Tyr Ser Tyr Ser Tyr Tyr Glu Lys
                325                 330                 335

Leu His Thr Tyr Phe Pro Val Ser Ser Leu Gly Val Leu Gln Glu Asp
            340                 345                 350
```

```
Ser Ser Asn Ile Val Glu Leu Leu Glu Glu Ala Phe Tyr Arg Ile Arg
        355                 360                 365

Ser Asn Leu Asp Ile Arg Ala Leu Asp Ser Pro Arg Gly Leu Arg Thr
370                 375                 380

Glu Val Thr Ser Asp Thr Leu Gln Lys Thr Glu Thr Gly Ser Phe His
385                 390                 395                 400

Ile Lys Arg Gly Glu Val Gly Thr Tyr Asn Val His Leu Arg Ala Val
                405                 410                 415

Glu Asp Ile Asp Gly Thr His Val Cys Gln Leu Ala Lys Glu Asp Gln
            420                 425                 430

Gly Gly Asn Ile His Leu Lys Pro Ser Phe Ser Asp Gly Leu Arg Met
        435                 440                 445

Asp Ala Ser Val Ile Cys Asp Val Cys Pro Cys Glu Leu Gln Lys Glu
450                 455                 460

Val Arg Ser Ala Arg Cys His Phe Arg Gly Asp Phe Met Cys Gly His
465                 470                 475                 480

Cys Val Cys Asn Glu Gly Trp Ser Gly Lys Thr Cys Asn Cys Ser Thr
                485                 490                 495

Gly Ser Leu Ser Asp Thr Gln Pro Cys Leu Arg Glu Gly Glu Asp Lys
            500                 505                 510

Pro Cys Ser Gly His Gly Glu Cys Gln Cys Gly Arg Cys Val Cys Tyr
        515                 520                 525

Gly Glu Gly Arg Tyr Glu Gly His Phe Cys Glu Tyr Asp Asn Phe Gln
530                 535                 540

Cys Pro Arg Thr Ser Gly Phe Leu Cys Asn Asp Arg Gly Arg Cys Ser
545                 550                 555                 560

Met Gly Glu Cys Val Cys Glu Pro Gly Trp Thr Gly Arg Ser Cys Asp
                565                 570                 575

Cys Pro Leu Ser Asn Ala Thr Cys Ile Asp Ser Asn Gly Gly Ile Cys
            580                 585                 590

Asn Gly Arg Gly Tyr Cys Glu Cys Gly Arg Cys His Cys Asn Gln Gln
        595                 600                 605

Ser Leu Tyr Thr Asp Thr Thr Cys Glu Ile Asn Tyr Ser Ala Ile Leu
610                 615                 620

Gly Leu Cys Glu Asp Leu Arg Ser Cys Val Gln Cys Gln Ala Trp Gly
625                 630                 635                 640

Thr Gly Glu Lys Lys Gly Arg Ala Cys Asp Asp Cys Pro Phe Lys Val
                645                 650                 655

Lys Met Val Asp Glu Leu Lys Lys Glu Val Val Glu Tyr Cys Ser
            660                 665                 670

Phe Arg Asp Glu Asp Asp Cys Thr Tyr Ser Tyr Asn Val Glu Gly
675                 680                 685

Asp Gly Ser Pro Gly Pro Asn Ser Thr Val Leu Val His Lys Lys Lys
        690                 695                 700

Asp Cys Leu Pro Ala Pro Ser Trp Trp Leu Ile Pro Leu Leu Ile Phe
705                 710                 715                 720

Leu Leu Leu Leu Leu Ala Leu Leu Leu Leu Cys Trp Lys
                725                 730

<210> SEQ ID NO 11
<211> LENGTH: 3579
<212> TYPE: DNA
<213> ORGANISM: Artificial Sequence
<220> FEATURE:
<223> OTHER INFORMATION: Description of Artificial Sequence:/Note =
      Synthetic Construct
```

<400> SEQUENCE: 11

```
atgcctgcgc tctggctcag ctgctgcctc ggtgtcgcgc tcctgctgcc cgccagccag      60
gccacctcca ggagggaagt ctgtgattgc aatgggaagt ccaggcaatg tgtctttgat     120
caggagctcc atcgacaagc aggcagcggg ttccgttgcc tcaactgcaa tgacaataca     180
gcggggttc actgcgagcg tcgagggag gggttttacc agcatcagag caagagccgc      240
tgcctaccct gcaactgcca ctcaaagggt tccctcagtg ctggatgtga caactctgga     300
caatgcaggt gtaagccagg tgtgacagga caaagatgtg accagtgtca gccaggcttc     360
catatgctca ccgatgctgg atgcacccga gaccagggc aactagattc caagtgtgac      420
tgtgacccag ctggcatctc tggacccgt gattctggcc gatgtgtctg caaaccagcc      480
gtcactggag agcgctgtga taggtgccga ccacgtgact atcatctgga ccgggcaaac     540
cctgagggct gtacccagtg tttctgctat gggcattcag ccagctgcca cgcctctgcc     600
gacttcagtg tccacaaaat cacttcaact ttcagtcagg atgtggatgg ttggaaggcg     660
gttcagagaa acgggcacc tgcaaaactc cactggtcac agcgccatcg gacgtgttt       720
agttctgccc gaagatcaga ccccgtctat ttcgtggccc ctgccaaatt cctcggtaac     780
cagcaagtga gttacgggca gagcctgtct tttgactacc gcgtggacag aggaggtaga     840
cagccgtctg cctacgatgt gatcctggaa ggtgctggtc tacagatcag agctcctctg     900
atggctccag gcaagacact tccttgtggg atcacaaaga cttacacatt cagactgaat     960
gaacatccaa gcagtcactg gagtcccag ctgagttatt tcgaatatcg aaggttactg     1020
cggaacctca cagccctcct gatgatccga gctacgtacg agaatatag tacagggtac     1080
attgataacg tgaccctggt ttcagcccgc cctgtccttg gagccccagc cccttgggtt    1140
gaacgttgtg tatgcctgct ggggtacaag ggacaattct gccaggaatg tgcttctggt    1200
tacaaaagag attcggcaag attgggcgct tttggcgcct gtgttccctg taactgccaa    1260
ggggagggg cctgtgatcc agacacggga gattgctact cggggacga gaatcctgac      1320
attgagtgtg ctgactgtcc catcggtttc tacaatgacc cacatgaccc ccgcagctgc    1380
aagccatgtc cctgtcacaa tgggttcagc tgttcagtga tgcctgagac agaggaggtg    1440
gtgtgtaaca actgtccccc tgggtcaca ggtgcccgct gtgagctctg tgctgatggc     1500
ttcttgggg atccctttgg ggaacatggc ccagtgaggc cttgtcaacg ctgccaatgc    1560
aacaacaacg tggaccccaa tgcctctggg aactgtgacc agttgacagg cagatgcttg    1620
aaatgtatct acaacacggc cggtgtctac tgtgaccagt gcaaagcagg ttactttgga    1680
gacccattgg ctcccaaccc agcagacaag tgtcgagctt gcaactgcag ccccatgggt    1740
gcggagcctg gagagtgtcg aggtgatggc agctgtgttt gcaagccagg cttttggcgcc   1800
ttcaactgtg atcacgcagc cctaaccagt tgtcctgctt gctacaatca agtgaagatt    1860
cagatggacc agtttaccca gcagctccag agcctggagg ccctggtttc aaaggctcag    1920
ggtggtggtg gtggtggtac agtcccagtg cagctggaag gcaggatcga gcaggctgag    1980
caggcccttc aggacattct gggagaagct cagatttcag aagggcaat gagagccgtt     2040
gctgtccggc tggccaaggc aaggagccaa gagaacgact acaagacccg cctggatgac    2100
ctcaagatga ctgcagaaag gatccgggcc ctggcagtc agcatcagaa cagagttcag    2160
gatacgagca gactcatctc tcagatgcgc ctgagtctgg caggaagcga agctctcttg    2220
gaaaacacta atatccattc ttctgagcac tacgtgggc cgaatgattt taaaagtctg   2280
gctcaggagg ctacaagaaa ggcagacagc cacgctgagt cagctaacgc aatgaagcaa    2340
```

```
ctagcaaggg aaactgagga ctactccaaa caagcacttt cattggcccg caagctcttg    2400
agtggaggag gcggaagtgg ctcttgggac agctccgtgg tacaaggtct tatgggaaaa    2460
ttagagaaaa ccaagtccct gagccagcag ctgtcattgg agggcaccca agccgacatt    2520
gaagctgata ggtcgtatca gcacagtctc cgcctcctgg attctgcctc tcagcttcag    2580
ggagtcagtg atctgtcctt tcaggtggaa gcaaagagga tcagacaaaa ggctgattct    2640
ctctcaaacc tggtgaccag acaaacggat gcattcacgc gtgtgcgaaa caatctgggg    2700
aactgggaaa agaaaacacg gcagctttta cagactggaa aggataggag acagacttca    2760
gatcagctgc tttccgtgc  caaccttgct aaaaacagag cccaagaagc gctaagtatg    2820
ggcaatgcca ctttttatga agttgagaac atcctgaaga acctccgaga gtttgatctg    2880
caggttgaag acagaaaagc agaggctgaa gaggccatga gagactctc  ctctattagc    2940 cagaaggttg cggatgccag tgacaagacc cagcaagcag aaacggccct ggggagcgcc    3000
actgccgaca cccaacgggc aaagaacgca gctaggaggg ccctggagat cagcagcgag    3060
atagagctgg agatagggag tctgaacttg gaagctaatg tgacagcaga tggggccttg    3120
gccatggaga agggactgc  cactctgaag agcgagatga gagagatgat tgagctggcc    3180
agaaaggagc tggagtttga cacggataag gacacggtgc agctggtgat tactgaagcc    3240
cagcaagctg atgccagagc cacgagtgcc ggagttacca tccaagacac rctcaacaca    3300
ttggacggca tcctacacct catagaccag cctggcagtg tggatgaaga agggatgatg    3360
ctattagaac aagggctttt ccaagccaag acccagatca acagtcgact tcggcccttg    3420
atgtctgacc tggaggagag ggtgcgtcgg cagaggaacc acctccatct gctggagact    3480
agcatagatg gaattcttgc tgatgtgaag aacctggaga acattcgaga caacctgccc    3540
ccaggctgct acaatacccca agctcttgag caacagtga                         3579
```

<210> SEQ ID NO 12
<211> LENGTH: 1192
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 12

```
Met Pro Ala Leu Trp Leu Ser Cys Cys Leu Gly Val Ala Leu Leu Leu
 1               5                  10                  15

Pro Ala Ser Gln Ala Thr Ser Arg Arg Glu Val Cys Asp Cys Asn Gly
            20                  25                  30

Lys Ser Arg Gln Cys Val Phe Asp Gln Glu Leu His Arg Gln Ala Gly
        35                  40                  45

Ser Gly Phe Arg Cys Leu Asn Cys Asn Asp Asn Thr Ala Gly Val His
    50                  55                  60

Cys Glu Arg Ser Arg Glu Gly Phe Tyr Gln His Gln Ser Lys Ser Arg
65                  70                  75                  80

Cys Leu Pro Cys Asn Cys His Ser Lys Gly Ser Leu Ser Ala Gly Cys
                85                  90                  95

Asp Asn Ser Gly Gln Cys Arg Cys Lys Pro Gly Val Thr Gly Gln Arg
            100                 105                 110

Cys Asp Gln Cys Gln Pro Gly Phe His Met Leu Thr Asp Ala Gly Cys
        115                 120                 125

Thr Arg Asp Gln Gly Gln Leu Asp Ser Lys Cys Asp Cys Asp Pro Ala
    130                 135                 140
```

```
Gly Ile Ser Gly Pro Cys Asp Ser Gly Arg Cys Val Cys Lys Pro Ala
145                 150                 155                 160

Val Thr Gly Glu Arg Cys Asp Arg Cys Arg Pro Arg Asp Tyr His Leu
            165                 170                 175

Asp Arg Ala Asn Pro Glu Gly Cys Thr Gln Cys Phe Cys Tyr Gly His
            180                 185                 190

Ser Ala Ser Cys His Ala Ser Ala Asp Phe Ser Val His Lys Ile Thr
        195                 200                 205

Ser Thr Phe Ser Gln Asp Val Asp Gly Trp Lys Ala Val Gln Arg Asn
    210                 215                 220

Gly Ala Pro Ala Lys Leu His Trp Ser Gln Arg His Arg Asp Val Phe
225                 230                 235                 240

Ser Ser Ala Arg Arg Ser Asp Pro Val Tyr Phe Val Ala Pro Ala Lys
                245                 250                 255

Phe Leu Gly Asn Gln Gln Val Ser Tyr Gly Gln Ser Leu Ser Phe Asp
            260                 265                 270

Tyr Arg Val Asp Arg Gly Gly Arg Gln Pro Ser Ala Tyr Asp Val Ile
        275                 280                 285

Leu Glu Gly Ala Gly Leu Gln Ile Arg Ala Pro Leu Met Ala Pro Gly
    290                 295                 300

Lys Thr Leu Pro Cys Gly Ile Thr Lys Thr Tyr Thr Phe Arg Leu Asn
305                 310                 315                 320

Glu His Pro Ser Ser His Trp Ser Pro Gln Leu Ser Tyr Phe Glu Tyr
                325                 330                 335

Arg Arg Leu Leu Arg Asn Leu Thr Ala Leu Leu Met Ile Arg Ala Thr
            340                 345                 350

Tyr Gly Glu Tyr Ser Thr Gly Tyr Ile Asp Asn Val Thr Leu Val Ser
        355                 360                 365

Ala Arg Pro Val Leu Gly Ala Pro Ala Pro Trp Val Glu Arg Cys Val
    370                 375                 380

Cys Leu Leu Gly Tyr Lys Gly Gln Phe Cys Gln Glu Cys Ala Ser Gly
385                 390                 395                 400

Tyr Lys Arg Asp Ser Ala Arg Leu Gly Ala Phe Gly Ala Cys Val Pro
                405                 410                 415

Cys Asn Cys Gln Gly Glu Gly Ala Cys Asp Pro Asp Thr Gly Asp Cys
            420                 425                 430

Tyr Ser Gly Asp Glu Asn Pro Asp Ile Glu Cys Ala Asp Cys Pro Ile
        435                 440                 445

Gly Phe Tyr Asn Asp Pro His Asp Pro Arg Ser Cys Lys Pro Cys Pro
    450                 455                 460

Cys His Asn Gly Phe Ser Cys Ser Val Met Pro Glu Thr Glu Glu Val
465                 470                 475                 480

Val Cys Asn Asn Cys Pro Pro Gly Val Thr Gly Ala Arg Cys Glu Leu
                485                 490                 495

Cys Ala Asp Gly Phe Phe Gly Asp Pro Phe Gly Glu His Gly Pro Val
            500                 505                 510

Arg Pro Cys Gln Arg Cys Gln Cys Asn Asn Asn Val Asp Pro Asn Ala
        515                 520                 525

Ser Gly Asn Cys Asp Gln Leu Thr Gly Arg Cys Leu Lys Cys Ile Tyr
    530                 535                 540

Asn Thr Ala Gly Val Tyr Cys Asp Gln Cys Lys Ala Gly Tyr Phe Gly
545                 550                 555                 560

Asp Pro Leu Ala Pro Asn Pro Ala Asp Lys Cys Arg Ala Cys Asn Cys
```

```
                565                 570                 575
Ser Pro Met Gly Ala Glu Pro Gly Glu Cys Arg Gly Asp Gly Ser Cys
                580                 585                 590

Val Cys Lys Pro Gly Phe Gly Ala Phe Asn Cys Asp His Ala Ala Leu
            595                 600                 605

Thr Ser Cys Pro Ala Cys Tyr Asn Gln Val Lys Ile Gln Met Asp Gln
        610                 615                 620

Phe Thr Gln Gln Leu Gln Ser Leu Glu Ala Leu Val Ser Lys Ala Gln
625                 630                 635                 640

Gly Gly Gly Gly Gly Thr Val Pro Val Gln Leu Glu Gly Arg Ile
                645                 650                 655

Glu Gln Ala Glu Gln Ala Leu Gln Asp Ile Leu Gly Glu Ala Gln Ile
                660                 665                 670

Ser Glu Gly Ala Met Arg Ala Val Ala Val Arg Leu Ala Lys Ala Arg
            675                 680                 685

Ser Gln Glu Asn Asp Tyr Lys Thr Arg Leu Asp Asp Leu Lys Met Thr
        690                 695                 700

Ala Glu Arg Ile Arg Ala Leu Gly Ser Gln His Gln Asn Arg Val Gln
705                 710                 715                 720

Asp Thr Ser Arg Leu Ile Ser Gln Met Arg Leu Ser Leu Ala Gly Ser
                725                 730                 735

Glu Ala Leu Leu Glu Asn Thr Asn Ile His Ser Ser Glu His Tyr Val
                740                 745                 750

Gly Pro Asn Asp Phe Lys Ser Leu Ala Gln Glu Ala Thr Arg Lys Ala
            755                 760                 765

Asp Ser His Ala Glu Ser Ala Asn Ala Met Lys Gln Leu Ala Arg Glu
        770                 775                 780

Thr Glu Asp Tyr Ser Lys Gln Ala Leu Ser Leu Ala Arg Lys Leu Leu
785                 790                 795                 800

Ser Gly Gly Gly Gly Ser Gly Ser Trp Asp Ser Ser Val Val Gln Gly
                805                 810                 815

Leu Met Gly Lys Leu Glu Lys Thr Lys Ser Leu Ser Gln Gln Leu Ser
                820                 825                 830

Leu Glu Gly Thr Gln Ala Asp Ile Glu Ala Asp Arg Ser Tyr Gln His
            835                 840                 845

Ser Leu Arg Leu Leu Asp Ser Ala Ser Gln Leu Gln Gly Val Ser Asp
        850                 855                 860

Leu Ser Phe Gln Val Glu Ala Lys Arg Ile Arg Gln Lys Ala Asp Ser
865                 870                 875                 880

Leu Ser Asn Leu Val Thr Arg Gln Thr Asp Ala Phe Thr Arg Val Arg
                885                 890                 895

Asn Asn Leu Gly Asn Trp Glu Lys Glu Thr Arg Gln Leu Leu Gln Thr
                900                 905                 910

Gly Lys Asp Arg Arg Gln Thr Ser Asp Gln Leu Leu Ser Arg Ala Asn
            915                 920                 925

Leu Ala Lys Asn Arg Ala Gln Glu Ala Leu Ser Met Gly Asn Ala Thr
        930                 935                 940

Phe Tyr Glu Val Glu Asn Ile Leu Lys Asn Leu Arg Glu Phe Asp Leu
945                 950                 955                 960

Gln Val Glu Asp Arg Lys Ala Glu Ala Glu Ala Met Lys Arg Leu
                965                 970                 975

Ser Ser Ile Ser Gln Lys Val Ala Asp Ala Ser Asp Lys Thr Gln Gln
                980                 985                 990
```

-continued

| | | | | | | | | | | | | |
|---|---|---|---|---|---|---|---|---|---|---|---|---|
|Ala|Glu|Thr|Ala|Leu|Gly|Ser|Ala|Thr|Ala|Asp|Thr|Gln Arg Ala Lys|
| |995| | | |1000| | | |1005| | | |
|Asn|Ala|Ala|Arg|Glu|Ala|Leu|Glu|Ile|Ser|Ser|Glu|Ile Glu Leu Glu|
| |1010| | | |1015| | | |1020| | | |
|Ile|Gly|Ser|Leu|Asn|Leu|Glu|Ala|Asn|Val|Thr|Ala|Asp Gly Ala Leu|
|1025| | | |1030| | | |1035| | | |1040|
|Ala|Met|Glu|Lys|Gly|Thr|Ala|Thr|Leu|Lys|Ser|Glu|Met Arg Glu Met|
| | | |1045| | | |1050| | | |1055| |
|Ile|Glu|Leu|Ala|Arg|Lys|Glu|Leu|Glu|Phe|Asp|Thr|Asp Lys Asp Thr|
| | |1060| | | |1065| | | |1070| | |
|Val|Gln|Leu|Val|Ile|Thr|Glu|Ala|Gln|Gln|Ala|Asp|Ala Arg Ala Thr|
| |1075| | | |1080| | | |1085| | | |
|Ser|Ala|Gly|Val|Thr|Ile|Gln|Asp|Thr|Leu|Asn|Thr|Leu Asp Gly Ile|
| |1090| | | |1095| | | |1100| | | |
|Leu|His|Leu|Ile|Asp|Gln|Pro|Gly|Ser|Val|Asp|Glu|Glu Gly Met Met|
|1105| | | |1110| | | |1115| | | |1120|
|Leu|Leu|Glu|Gln|Gly|Leu|Phe|Gln|Ala|Lys|Thr|Gln|Ile Asn Ser Arg|
| | | |1125| | | |1130| | | |1135| |
|Leu|Arg|Pro|Leu|Met|Ser|Asp|Leu|Glu|Glu|Arg|Val|Arg Gln Arg|
| | | |1140| | | |1145| | | |1150| |
|Asn|His|Leu|His|Leu|Leu|Glu|Thr|Ser|Ile|Asp|Gly|Ile Leu Ala Asp|
| |1155| | | |1160| | | |1165| | | |
|Val|Lys|Asn|Leu|Glu|Asn|Ile|Arg|Asp|Asn|Leu|Pro|Pro Gly Cys Tyr|
| |1170| | | |1175| | | |1180| | | |
|Asn|Thr|Gln|Ala|Leu|Glu|Gln|Gln| | | | | |
|1185| | | |1190| | | | | | | | |

<210> SEQ ID NO 13
<211> LENGTH: 3582
<212> TYPE: DNA
<213> ORGANISM: Artificial Sequence
<220> FEATURE:
<223> OTHER INFORMATION: Description of Artificial Sequence:/Note = Synthetic Construct

<400> SEQUENCE: 13

```
atgcctgcgc tctggctggg ctgctgcctc tgcttctcgc tcctcctgcc cgcagcccgg      60
gccacctcca ggagggaagt ctgtgattgc aatgggaagt ccaggcagtg tatctttgat     120
cgggaacttc acagacaaac tggtaatgga ttccgctgcc tcaactgcaa tgacaacact     180
gatggcattc actgcgagaa gtgcaagaat ggcttttacc ggcacagaga aagggaccgc     240
tgtttgccct gcaattgtaa ctccaaaggt tctcttagtg ctcgatgtga caactctgga     300
cggtgcagct gtaaaccagg tgtgacagga gccagatgcg accgatgtct gccaggcttc     360
cacatgctca cggatgcggg tgcacccaa gaccagagac tgctagactc caagtgtgac     420
tgtgacccag ctggcatcgc agggccctgt gacgcgggcc gctgtgtctg caagccagct     480
gttactggag aacgctgtga taggtgtcga tcaggttact ataatctgga tgggggaac      540
cctgagggct gtacccagtg tttctgctat gggcattcag ccagctgccg cagctctgca     600
gaatacagtg tccataagat cacctctacc tttcatcaag atgttgatgg ctggaaggct     660
gtccaacgaa atgggtctcc tgcaaagctc aatggtcac agcgccatca agatgtgttt     720
agctcagccc aacgactaga ccctgtctat tttgtggctc ctgccaaatt tcttgggaat     780
caacaggtga gctatgggca agcctgtccc tttgactacc gtgtgacag aggaggcaga     840
cacccatctg cccatgatgt gattctggaa ggtgctggtc tacggatcac agctcccttg     900
```

```
atgccacttg gcaagacact gccttgtggg ctcaccaaga cttacacatt caggttaaat    960
gagcatccaa gcaataattg gagccccag ctgagttact ttgagtatcg aaggttactg    1020
cggaatctca cagccctccg catccgagct acatatggag aatacagtac tgggtacatt    1080
gacaatgtga ccctgatttc agcccgcct gtctctggag ccccagcacc ctgggttgaa    1140
cagtgtatat gtcctgttgg gtacaagggg caattctgcc aggattgtgc ttctggctac    1200
aagagagatt cagcgagact ggggccttt ggcacctgta ttccttgtaa ctgtcaaggg    1260 ggagggcct gtgatccaga cacaggagat tgttattcag gggatgagaa tcctgacatt    1320
gagtgtgctg actgcccaat tggtttctac aacgatccgc acgaccccg cagctgcaag    1380 ccatgtccct gtcataacgg gttcagctgc tcagtgatgc cggagacgga ggaggtggtg    1440
tgcaataact gccctcccgg ggtcaccggt gcccgctgtg agctctgtgc tgatggctac    1500
tttggggacc ccttttggtga acatggccca gtgaggcctt gtcagccctg tcaatgcaac    1560
aacaatgtgg accccagtgc ctctgggaat tgtgaccggc tgacaggcag gtgtttgaag    1620
tgtatccaca acacagccgg catctactgc gaccagtgca agcaggcta cttcggggac    1680 ccattggctc ccaacccagc agacaagtgt cgagcttgca actgtaaccc catgggctca    1740
gagcctgtag gatgtcgaag tgatggcacc tgtgttgca agccaggatt tggtggcccc    1800
aactgtgagc atggagcatt cagctgtcca gcttgctata atcaagtgaa gattcagatg    1860
gatcagttta tgcagcagct tcagagaatg gaggccctga tttcaaaggc tcagggtggt    1920
gatggagtag tacctgatac agagctgaaa ggcaggatgc agcaggctga gcaggccctt    1980
caggacattc tgagagatgc ccagatttca gaaggtgcta gcagatccct tggtctccag    2040
ttggccaagg tgaggagcca agagaacagc taccagagcc gcctggatga cctcaagatg    2100
actgtggaaa gagttcgggc tctgggaagt cagtaccaga accgagttcg ggatactcac    2160
aggctcatca ctcagatgca gctgagcctg cagaaagtg aagcttcctt gggaaacact    2220
aacattcctg cctcagacca ctacgtgggg ccaaatggct ttaaaagtct ggctcaggag    2280
gccacaagat tagcagaaag ccacgttgag tcagccagta acatggagca actgacaagg    2340
gaaactgagg actattccaa acaagccctc tcactggtgc gcaaggccct gcatgaagga    2400
gtcggaagcg gaagcggtag cccggacggt gctgtggtgc aagggcttgt ggaaaaattg    2460
gagaaaacca gtccctggcc ccagcagttg acaaggagg ccactcaagc ggaaattgaa    2520
gcagataggt cttatcagca cagtctccgc ctcctggatt cagtgtctcg gcttcaggga    2580
gtcagtgatc agtcctttca ggtggaagaa gcaaagagga tcaaacaaaa agcggattca    2640
ctctcaacgc tggtaaccag gcatatggat gagttcaagc gtacacaaaa gaatctggga    2700
aactggaaag aagaagcaca gcagctctta cagaatggaa aaagtgggag agagaaatca    2760
gatcagctgc tttcccgtgc caatcttgct aaaagcagag cacaagaagc actgagtatg    2820
ggcaatgcca ctttttatga agttgagagc atccttaaaa acctcagaga gtttgacctg    2880
caggtggaca acagaaaagc agaagctgaa gaagccatga agagactctc ctacatcagc    2940
cagaaggttt cagatgccag tgacaagacc cagcaagcag aaagagccct ggggagcgct    3000
gctgctgatg cacagagggc aaagaatggg gccggggagg ccctggaaat ctccagtgag    3060
attgaacagg agattgggag tctgaacttg gaagccaatg tgacagcaga tggagccttg    3120
gccatggaaa agggactggc ctctctgaag agtgagatga gggaagtgga aggagagctg    3180
gaaaggaagg agctggagtt tgacacgaat atggatgcag tacagatggt gattacagaa    3240
gcccagaagg ttgataccag agccaagaac gctgggggtta caatccaaga cacactcaac    3300
```

-continued

```
acattagacg gcctcctgca tctgatggac cagcctctca gtgtagatga agaggggctg    3360
gtcttactgg agcagaagct ttcccgagcc aagacccaga tcaacagcca actgcggccc    3420
atgatgtcag agctggaaga gagggcacgt cagcagaggg gccacctcca tttgctggag    3480
acaagcatag atgggattct ggctgatgtg aagaacttgg agaacattag ggacaacctg    3540
cccccaggct gctacaatac ccaggctctt gagcaacagt ga                      3582
```

<210> SEQ ID NO 14
<211> LENGTH: 1193
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 14

```
Met Pro Ala Leu Trp Leu Gly Cys Cys Leu Cys Phe Ser Leu Leu Leu
 1               5                  10                  15

Pro Ala Ala Arg Ala Thr Ser Arg Arg Glu Val Cys Asp Cys Asn Gly
            20                  25                  30

Lys Ser Arg Gln Cys Ile Phe Asp Arg Glu Leu His Arg Gln Thr Gly
        35                  40                  45

Asn Gly Phe Arg Cys Leu Asn Cys Asn Asp Asn Thr Asp Gly Ile His
    50                  55                  60

Cys Glu Lys Cys Lys Asn Gly Phe Tyr Arg His Arg Glu Arg Asp Arg
65                  70                  75                  80

Cys Leu Pro Cys Asn Cys Asn Ser Lys Gly Ser Leu Ser Ala Arg Cys
                85                  90                  95

Asp Asn Ser Gly Arg Cys Ser Cys Lys Pro Gly Val Thr Gly Ala Arg
            100                 105                 110

Cys Asp Arg Cys Leu Pro Gly Phe His Met Leu Thr Asp Ala Gly Cys
        115                 120                 125

Thr Gln Asp Gln Arg Leu Leu Asp Ser Lys Cys Asp Cys Asp Pro Ala
    130                 135                 140

Gly Ile Ala Gly Pro Cys Asp Ala Gly Arg Cys Val Cys Lys Pro Ala
145                 150                 155                 160

Val Thr Gly Glu Arg Cys Asp Arg Cys Arg Ser Gly Tyr Tyr Asn Leu
                165                 170                 175

Asp Gly Gly Asn Pro Glu Gly Cys Thr Gln Cys Phe Cys Tyr Gly His
            180                 185                 190

Ser Ala Ser Cys Arg Ser Ser Ala Glu Tyr Ser Val His Lys Ile Thr
        195                 200                 205

Ser Thr Phe His Gln Asp Val Asp Gly Trp Lys Ala Val Gln Arg Asn
    210                 215                 220

Gly Ser Pro Ala Lys Leu Gln Trp Ser Gln Arg His Gln Asp Val Phe
225                 230                 235                 240

Ser Ser Ala Gln Arg Leu Asp Pro Val Tyr Phe Val Ala Pro Ala Lys
                245                 250                 255

Phe Leu Gly Asn Gln Gln Val Ser Tyr Gly Gln Ser Leu Ser Phe Asp
            260                 265                 270

Tyr Arg Val Asp Arg Gly Gly Arg His Pro Ser Ala His Asp Val Ile
        275                 280                 285

Leu Glu Gly Ala Gly Leu Arg Ile Thr Ala Pro Leu Met Pro Leu Gly
    290                 295                 300

Lys Thr Leu Pro Cys Gly Leu Thr Lys Thr Tyr Thr Phe Arg Leu Asn
305                 310                 315                 320
```

```
Glu His Pro Ser Asn Asn Trp Ser Pro Gln Leu Ser Tyr Phe Glu Tyr
                325                 330                 335
Arg Arg Leu Leu Arg Asn Leu Thr Ala Leu Arg Ile Arg Ala Thr Tyr
                340                 345                 350
Gly Glu Tyr Ser Thr Gly Tyr Ile Asp Asn Val Thr Leu Ile Ser Ala
                355                 360                 365
Arg Pro Val Ser Gly Ala Pro Ala Pro Trp Val Glu Gln Cys Ile Cys
        370                 375                 380
Pro Val Gly Tyr Lys Gly Gln Phe Cys Gln Asp Cys Ala Ser Gly Tyr
385                 390                 395                 400
Lys Arg Asp Ser Ala Arg Leu Gly Pro Phe Gly Thr Cys Ile Pro Cys
                405                 410                 415
Asn Cys Gln Gly Gly Ala Cys Asp Pro Asp Thr Gly Asp Cys Tyr
                420                 425                 430
Ser Gly Asp Glu Asn Pro Asp Ile Glu Cys Ala Asp Cys Pro Ile Gly
                435                 440                 445
Phe Tyr Asn Asp Pro His Asp Pro Arg Ser Cys Lys Pro Cys Pro Cys
        450                 455                 460
His Asn Gly Phe Ser Cys Ser Val Met Pro Glu Thr Glu Val Val
465                 470                 475                 480
Cys Asn Asn Cys Pro Pro Gly Val Thr Gly Ala Arg Cys Glu Leu Cys
                485                 490                 495
Ala Asp Gly Tyr Phe Gly Asp Pro Phe Gly Glu His Gly Pro Val Arg
                500                 505                 510
Pro Cys Gln Pro Cys Gln Cys Asn Asn Asn Val Asp Pro Ser Ala Ser
        515                 520                 525
Gly Asn Cys Asp Arg Leu Thr Gly Arg Cys Leu Lys Cys Ile His Asn
530                 535                 540
Thr Ala Gly Ile Tyr Cys Asp Gln Cys Lys Ala Gly Tyr Phe Gly Asp
545                 550                 555                 560
Pro Leu Ala Pro Asn Pro Ala Asp Lys Cys Arg Ala Cys Asn Cys Asn
                565                 570                 575
Pro Met Gly Ser Glu Pro Val Gly Cys Arg Ser Asp Gly Thr Cys Val
                580                 585                 590
Cys Lys Pro Gly Phe Gly Gly Pro Asn Cys Glu His Gly Ala Phe Ser
        595                 600                 605
Cys Pro Ala Cys Tyr Asn Gln Val Lys Ile Gln Met Asp Gln Phe Met
        610                 615                 620
Gln Gln Leu Gln Arg Met Glu Ala Leu Ile Ser Lys Ala Gln Gly Gly
625                 630                 635                 640
Asp Gly Val Val Pro Asp Thr Glu Leu Glu Gly Arg Met Gln Gln Ala
                645                 650                 655
Glu Gln Ala Leu Gln Asp Ile Leu Arg Asp Ala Gln Ile Ser Glu Gly
                660                 665                 670
Ala Ser Arg Ser Leu Gly Leu Gln Leu Ala Lys Val Arg Ser Gln Glu
        675                 680                 685
Asn Ser Tyr Gln Ser Arg Leu Asp Asp Leu Lys Met Thr Val Glu Arg
        690                 695                 700
Val Arg Ala Leu Gly Ser Gln Tyr Gln Asn Arg Val Arg Asp Thr His
705                 710                 715                 720
Arg Leu Ile Thr Gln Met Gln Leu Ser Leu Ala Glu Ser Glu Ala Ser
                725                 730                 735
Leu Gly Asn Thr Asn Ile Pro Ala Ser Asp His Tyr Val Gly Pro Asn
```

-continued

```
                    740                 745                 750
Gly Phe Lys Ser Leu Ala Gln Glu Ala Thr Arg Leu Ala Glu Ser His
            755                 760                 765

Val Glu Ser Ala Ser Asn Met Glu Gln Leu Thr Arg Glu Thr Glu Asp
        770                 775                 780

Tyr Ser Lys Gln Ala Leu Ser Leu Val Arg Lys Ala Leu His Glu Gly
785                 790                 795                 800

Val Gly Ser Gly Ser Gly Ser Pro Asp Gly Ala Val Val Gln Gly Leu
                805                 810                 815

Val Glu Lys Leu Glu Lys Thr Lys Ser Leu Ala Gln Gln Leu Thr Arg
            820                 825                 830

Glu Ala Thr Gln Ala Glu Ile Glu Ala Asp Arg Ser Tyr Gln His Ser
        835                 840                 845

Leu Arg Leu Leu Asp Ser Val Ser Arg Leu Gln Gly Val Ser Asp Gln
    850                 855                 860

Ser Phe Gln Val Glu Glu Ala Lys Arg Ile Lys Gln Lys Ala Asp Ser
865                 870                 875                 880

Leu Ser Thr Leu Val Thr Arg His Met Asp Glu Phe Lys Arg Thr Gln
                885                 890                 895

Lys Asn Leu Gly Asn Trp Lys Glu Glu Ala Gln Gln Leu Leu Gln Asn
            900                 905                 910

Gly Lys Ser Gly Arg Glu Lys Ser Asp Gln Leu Leu Ser Arg Ala Asn
        915                 920                 925

Leu Ala Lys Ser Arg Ala Gln Glu Ala Leu Ser Met Gly Asn Ala Thr
    930                 935                 940

Phe Tyr Glu Val Glu Ser Ile Leu Lys Asn Leu Arg Glu Phe Asp Leu
945                 950                 955                 960

Gln Val Asp Asn Arg Lys Ala Glu Ala Glu Ala Met Lys Arg Leu
                965                 970                 975

Ser Tyr Ile Ser Gln Lys Val Ser Asp Ala Ser Asp Lys Thr Gln Gln
            980                 985                 990

Ala Glu Arg Ala Leu Gly Ser Ala Ala Asp Ala Gln Arg Ala Lys
        995                 1000                1005

Asn Gly Ala Gly Glu Ala Leu Glu Ile Ser Ser Glu Ile Glu Gln Glu
    1010                1015                1020

Ile Gly Ser Leu Asn Leu Glu Ala Asn Val Thr Ala Asp Gly Ala Leu
1025                1030                1035                1040

Ala Met Glu Lys Gly Leu Ala Ser Leu Lys Ser Glu Met Arg Glu Val
                1045                1050                1055

Glu Gly Glu Leu Glu Arg Lys Glu Leu Glu Phe Asp Thr Asn Met Asp
            1060                1065                1070

Ala Val Gln Met Val Ile Thr Glu Ala Gln Lys Val Asp Thr Arg Ala
        1075                1080                1085

Lys Asn Ala Gly Val Thr Ile Gln Asp Thr Leu Asn Thr Leu Asp Gly
    1090                1095                1100

Leu Leu His Leu Met Asp Gln Pro Leu Ser Val Asp Glu Glu Gly Leu
1105                1110                1115                1120

Val Leu Leu Glu Gln Lys Leu Ser Arg Ala Lys Thr Gln Ile Asn Ser
                1125                1130                1135

Gln Leu Arg Pro Met Met Ser Glu Leu Glu Glu Arg Ala Arg Gln Gln
            1140                1145                1150

Arg Gly His Leu His Leu Leu Glu Thr Ser Ile Asp Gly Ile Leu Ala
        1155                1160                1165
```

```
Asp Val Lys Asn Leu Glu Asn Ile Arg Asp Asn Leu Pro Pro Gly Cys
        1170                1175                1180

Tyr Asn Thr Gln Ala Leu Glu Gln Gln
1185                1190

<210> SEQ ID NO 15
<211> LENGTH: 1111
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 15

Met Pro Ala Leu Trp Leu Gly Cys Cys Leu Cys Phe Ser Leu Leu
 1               5                  10                  15

Pro Ala Ala Arg Ala Thr Ser Arg Arg Glu Val Cys Asp Cys Asn Gly
                20                  25                  30

Lys Ser Arg Gln Cys Ile Phe Asp Arg Glu Leu His Arg Gln Thr Gly
            35                  40                  45

Asn Gly Phe Arg Cys Leu Asn Cys Asn Asp Asn Thr Asp Gly Ile His
         50                  55                  60

Cys Glu Lys Cys Lys Asn Gly Phe Tyr Arg His Arg Glu Arg Asp Arg
 65                  70                  75                  80

Cys Leu Pro Cys Asn Cys Asn Ser Lys Gly Ser Leu Ser Ala Arg Cys
                85                  90                  95

Asp Asn Ser Gly Arg Cys Ser Cys Lys Pro Gly Val Thr Gly Ala Arg
                100                 105                 110

Cys Asp Arg Cys Leu Pro Gly Phe His Met Leu Thr Asp Ala Gly Cys
            115                 120                 125

Thr Gln Asp Gln Arg Leu Leu Asp Ser Lys Cys Asp Cys Asp Pro Ala
130                 135                 140

Gly Ile Ala Gly Pro Cys Asp Ala Gly Arg Cys Val Cys Lys Pro Ala
145                 150                 155                 160

Val Thr Gly Glu Arg Cys Asp Arg Cys Arg Ser Gly Tyr Tyr Asn Leu
                165                 170                 175

Asp Gly Gly Asn Pro Glu Gly Cys Thr Gln Cys Phe Cys Tyr Gly His
            180                 185                 190

Ser Ala Ser Cys Arg Ser Ser Ala Glu Tyr Ser Val His Lys Ile Thr
        195                 200                 205

Ser Thr Phe His Gln Asp Val Asp Gly Trp Lys Ala Val Gln Arg Asn
    210                 215                 220

Gly Ser Pro Ala Lys Leu Gln Trp Ser Gln Arg His Gln Asp Val Phe
225                 230                 235                 240

Ser Ser Ala Gln Arg Leu Asp Pro Val Tyr Phe Val Ala Pro Ala Lys
                245                 250                 255

Phe Leu Gly Asn Gln Gln Val Ser Tyr Gly Gln Ser Leu Ser Phe Asp
            260                 265                 270

Tyr Arg Val Asp Arg Gly Gly Arg His Pro Ser Ala His Asp Val Ile
        275                 280                 285

Leu Glu Gly Ala Gly Leu Arg Ile Thr Ala Pro Leu Met Pro Leu Gly
    290                 295                 300

Lys Thr Leu Pro Cys Gly Leu Thr Lys Thr Tyr Thr Phe Arg Leu Asn
305                 310                 315                 320

Glu His Pro Ser Asn Asn Trp Ser Pro Gln Leu Ser Tyr Phe Glu Tyr
                325                 330                 335
```

```
Arg Arg Leu Leu Arg Asn Leu Thr Ala Leu Arg Ile Arg Ala Thr Tyr
        340                 345                 350

Gly Glu Tyr Ser Thr Gly Tyr Ile Asp Asn Val Thr Leu Ile Ser Ala
        355                 360                 365

Arg Pro Val Ser Gly Ala Pro Ala Pro Trp Val Glu Gln Cys Ile Cys
        370                 375                 380

Pro Val Gly Tyr Lys Gly Gln Phe Cys Gln Asp Cys Ala Ser Gly Tyr
385                 390                 395                 400

Lys Arg Asp Ser Ala Arg Leu Gly Pro Phe Gly Thr Cys Ile Pro Cys
                405                 410                 415

Asn Cys Gln Gly Gly Ala Cys Asp Pro Asp Thr Gly Asp Cys Tyr
                420                 425                 430

Ser Gly Asp Glu Asn Pro Asp Ile Glu Cys Ala Asp Cys Pro Ile Gly
                435                 440                 445

Phe Tyr Asn Asp Pro His Asp Pro Arg Ser Cys Lys Pro Cys Pro Cys
        450                 455                 460

His Asn Gly Phe Ser Cys Ser Val Met Pro Glu Thr Glu Val Val
465                 470                 475                 480

Cys Asn Asn Cys Pro Pro Gly Val Thr Gly Ala Arg Cys Glu Leu Cys
                485                 490                 495

Ala Asp Gly Tyr Phe Gly Asp Pro Phe Gly Glu His Gly Pro Val Arg
        500                 505                 510

Pro Cys Gln Pro Cys Gln Cys Asn Asn Asn Val Asp Pro Ser Ala Ser
        515                 520                 525

Gly Asn Cys Asp Arg Leu Thr Gly Arg Cys Leu Lys Cys Ile His Asn
        530                 535                 540

Thr Ala Gly Ile Tyr Cys Asp Gln Cys Lys Ala Gly Tyr Phe Gly Asp
545                 550                 555                 560

Pro Leu Ala Pro Asn Pro Ala Asp Lys Cys Arg Ala Cys Asn Cys Asn
                565                 570                 575

Pro Met Gly Ser Glu Pro Val Gly Cys Arg Ser Asp Gly Thr Cys Val
                580                 585                 590

Cys Lys Pro Gly Phe Gly Gly Pro Asn Cys Glu His Gly Ala Phe Ser
        595                 600                 605

Cys Pro Ala Cys Tyr Asn Gln Val Lys Ile Gln Met Asp Gln Phe Met
        610                 615                 620

Gln Gln Leu Gln Arg Met Glu Ala Leu Ile Ser Lys Ala Gln Gly Gly
625                 630                 635                 640

Asp Gly Val Val Pro Asp Thr Glu Leu Glu Gly Arg Met Gln Gln Ala
                645                 650                 655

Glu Gln Ala Leu Gln Asp Ile Leu Arg Asp Ala Gln Ile Ser Glu Gly
                660                 665                 670

Ala Ser Arg Ser Leu Gly Leu Gln Leu Ala Lys Val Arg Ser Gln Glu
        675                 680                 685

Asn Ser Tyr Gln Ser Arg Leu Asp Asp Leu Lys Met Thr Val Glu Arg
        690                 695                 700

Val Arg Ala Leu Gly Ser Gln Tyr Gln Asn Arg Val Arg Asp Thr His
705                 710                 715                 720

Arg Leu Ile Thr Gln Met Gln Leu Ser Leu Ala Glu Ser Glu Ala Ser
                725                 730                 735

Leu Gly Asn Thr Asn Ile Pro Ala Ser Asp His Tyr Val Gly Pro Asn
                740                 745                 750

Gly Phe Lys Ser Leu Ala Gln Glu Ala Thr Arg Leu Ala Glu Ser His
        755                 760                 765
```

```
Val Glu Ser Ala Ser Asn Met Glu Gln Leu Thr Arg Glu Thr Glu Asp
    770                 775                 780

Tyr Ser Lys Gln Ala Leu Ser Leu Val Arg Lys Ala Leu His Glu Gly
785                 790                 795                 800

Val Gly Ser Gly Ser Gly Ser Pro Asp Gly Ala Val Gln Gly Leu
                805                 810                 815

Val Glu Lys Leu Glu Lys Thr Lys Ser Leu Ala Gln Gln Leu Thr Arg
            820                 825                 830

Glu Ala Thr Gln Ala Glu Ile Glu Ala Asp Arg Ser Tyr Gln His Ser
            835                 840                 845

Leu Arg Leu Leu Asp Ser Val Ser Arg Leu Gln Gly Val Ser Asp Gln
    850                 855                 860

Ser Phe Gln Val Glu Glu Ala Lys Arg Ile Lys Gln Lys Ala Asp Ser
865                 870                 875                 880

Leu Ser Thr Leu Val Thr Arg His Met Asp Glu Phe Lys Arg Thr Gln
                885                 890                 895

Lys Asn Leu Gly Asn Trp Lys Glu Glu Ala Gln Gln Leu Leu Gln Asn
                900                 905                 910

Gly Lys Ser Gly Arg Glu Lys Ser Asp Gln Leu Leu Ser Arg Ala Asn
        915                 920                 925

Leu Ala Lys Ser Arg Ala Gln Glu Ala Leu Ser Met Gly Asn Ala Thr
    930                 935                 940

Phe Tyr Glu Val Glu Ser Ile Leu Lys Asn Leu Arg Glu Phe Asp Leu
945                 950                 955                 960

Gln Val Asp Asn Arg Lys Ala Glu Ala Glu Ala Met Lys Arg Leu
                965                 970                 975

Ser Tyr Ile Ser Gln Lys Val Ser Asp Ala Ser Asp Lys Thr Gln Gln
            980                 985                 990

Ala Glu Arg Ala Leu Gly Ser Ala Ala Ala Asp Ala Gln Arg Ala Lys
        995                 1000                1005

Asn Gly Ala Gly Glu Ala Leu Glu Ile Ser Ser Glu Ile Glu Gln Glu
    1010                1015                1020

Ile Gly Ser Leu Asn Leu Glu Ala Asn Val Thr Ala Asp Gly Ala Leu
1025                1030                1035                1040

Ala Met Glu Lys Gly Leu Ala Ser Leu Lys Ser Glu Met Arg Glu Val
                1045                1050                1055

Glu Gly Glu Leu Glu Arg Lys Glu Leu Glu Phe Asp Thr Asn Met Asp
                1060                1065                1070

Ala Val Gln Met Val Ile Thr Glu Ala Gln Lys Val Asp Thr Arg Ala
        1075                1080                1085

Lys Asn Ala Gly Val Thr Ile Gln Asp Thr Leu Asn Thr Leu Asp Gly
    1090                1095                1100

Leu Leu His Leu Met Gly Met
1105                1110

<210> SEQ ID NO 16
<211> LENGTH: 5622
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 16
atggcagcgc cacgccccag cccatgggcc aggctgctcc tggcagcctt gatcagcgtc    60
```

-continued

```
agcctctctg ggaccttgaa ccgctgcaag aaggccccag tgaagagctg cacggagtgt    120
gtccgtgtgg ataaggactg cgcctactgc acagacgaga tgttcaggga ccggcgctgc    180
aacacccagg cggagctgct ggccgcgggc tgccagcggg agagcatcgt ggtcatggag    240
agcagcttcc aaatcacaga ggagacccag attgacacca ccctgcggcg cagccagatg    300 tcccccaag gcctgcgggt ccgtctgcgg cccggtgagg agcggcattt tgagctggag    360
gtgtttgagc cactggagag ccccgtggac ctgtacatcc tcatggactt ctccaactcc    420
atgtccgatg atctggacaa cctcaagaag atggggcaga acctggctcg ggtcctgagc    480
cagctcacca gcgactacac tattggattt ggcaagtttg tggacaaagt cagcgtcccg    540
cagacggaca tgaggcctga aagctgaag agccttggc ccaacagtga ccccccttc     600 tccttcaaga acgtcatcag cctgacagaa gatgtggatg agttccggaa taaactgcag    660
ggagagcgga tctcaggcaa cctggatgct cctgagggcg gcttcgatgc catcctgcag    720
acagctgtgt gcacgaggga cattggctgg cgccccgaca gcacccacct gctggtcttc    780
tccaccgagt cagccttcca ctatgaggct gatggcgcca acgtgctggc tggcatcatg    840
agccgcaacg atgaacggtg ccacctggac accacgggca cctacacccca gtacaggaca    900 caggactacc cgtcggtgcc caccctggtg cgcctgctcg ccaagcacaa catcatcccc    960
atctttgctg tcaccaacta ctcctatagc tactacgaga agcttcacac ctatttccct    1020
gtctcctcac tgggggtgct gcaggaggac tcgtccaaca tcgtggagct gctggaggag    1080
gccttcaatc ggatccgctc caacctggac atccgggccc tagacagccc ccgaggcctt    1140
cggacagagg tcacctccaa gatgttccag aagacgagga ctgggtcctt tcacatccgg    1200
cggggggaag tgggtatata ccaggtgcag ctgcgggccc ttgagcacgt ggatgggacg    1260
cacgtgtgcc agctgccgga ggaccagaag ggcaacatcc atctgaaacc ttccttctcc    1320
gacggcctca agatggacgc gggcatcatc tgtgatgtgt gcacctgcga gctgcaaaaa    1380
gaggtgcggt cagctcgctg cagcttcaac ggagacttcg tgtgcggaca gtgtgtgtgc    1440
agcgagggct ggagtggcca gacctgcaac tgctccaccg gctctctgag tgacattcag    1500
ccctgcctgc ggagggcga ggacaagccg tgctccggcc gtggggagtg ccagtgcggg    1560
cactgtgtgt gctacggcga aggccgctac gagggtcagt tctgcgagta tgacaacttc    1620
cagtgtcccc gcacttccgg gttcctctgc aatgaccgag gacgctgctc catgggccag    1680
tgtgtgtgtg agcctggttg gacaggccca agctgtgact gtcccctcag caatgccacc    1740
tgcatcgaca gcaatggggg catctgtaat ggacgtggcc actgtgagtg tggccgctgc    1800
cactgccacc agcagtcgct ctacacggac accatctgcg agatcaacta ctcggcgtcc    1860
acccgggcct ctgcgaggac ctacgctcct gcgtgcagtg ccaggcgtgg ggcaccggcg    1920
agaagaaggg gcgcacgtgt gaggaatgca acttcaaggt caagatggtg gacgagctta    1980
agagaggcga ggaggtggtg gtgcgctgct ccttccggga cgaggatgac gactgcacct    2040
acagctacac catggaaggt gacggcgccc ctgggcccaa cagcactgtc ctggtgcaca    2100
agaagaaggg actgccctcc gggctccttc tggtggctca tcccctgct cctcctcctc    2160 ctgccgctcc tggccctgct actgctgcta tgctggaagt actgtgcctg ctgcaaggcc    2220
tgcctggcac ttctcccgtg ctgcaaccga ggtcacatgg tgggctttaa ggaagaccac    2280
tacatgctgc gggagaacct gatggcctct gaccacttgg acacgccat gctgcgcagc    2340 gggaacctca agggccgtga cgtggtccgc tggaaggtca ccaacaacat gcagcggcct    2400
ggctttgcca ctcatgccgc cagcatcaac cccacagagc tggtgcccta cgggctgtcc    2460
```

```
ttgcgcctgg cccgcctttg caccgagaac ctgctgaagc ctgacactcg ggagtgcgcc    2520
cagctgcgcc aggaggtgga ggagaacctg aacgaggtct acaggcagat ctccggtgta    2580
cacaagctcc agcagaccaa gttccggcag cagcccaatg ccgggaaaaa gcaagaccac    2640
accattgtgg acacagtgct gatggcgccc cgctcggcca agccggccct gctgaagctt    2700
acagagaagc aggtggaaca gagggccttc cacgacctca agtggccccc cggctactac    2760
accctcactg cagaccagga cgcccggggc atggtggagt ccaggagggg cgtggagctg    2820
gtggacgtac gggtgcccct ctttatccgg cctgaggatg cgacgagaa gcagctgctg     2880 gtggaggcca tcgacgtgcc cgcaggcact gccaccctcg gccgccgcct ggtaaacatc    2940
accatcatca aggagcaagc cagagacgtg gtgtcctttg agcagcctga gttctcggtc    3000
agccgcgggg accaggtggc ccgcatccct gtcatccggc gtgtcctgga cggcgggaag    3060
tcccaggtct cctaccgcac acaggatggc accgcgcagg gcaaccggga ctacatcccc    3120
gtggagggtg agctgctgtt ccagcctggg gaggcctgga aagagctgca ggtgaagctc    3180
ctggagctgc aagaagttga ctccctcctg cggggccgcc aggtccgccg tttccacgtc    3240
cagctcagca accctaagtt tggggcccac ctgggccagc cccactccac caccatcatc    3300
atcagggacc cagatgaact ggaccggagc ttcacgagtc agatgttgtc atcacagcca    3360 cccccctcacg gcgacctggg cgccccgcag aaccccaatg ctaaggccgc tgggtccagg    3420
aagatccatt tcaactggct gccccccttct ggcaagccaa tggggtacag ggtaaagtac    3480
tggattcagg gtgactccga atccgaagcc cacctgctcg acagcaaggt gccctcagtg    3540
gagctcacca acctgtaccc gtattgcgac tatgagatga aggtgtgcgc ctacggggct    3600
cagggcgagg gaccctacag ctccctggtg tcctgccgca cccaccagga agtgcccagc    3660
gagccagggc gtctggcctt caatgtcgtc tcctccacgg tgacccagct gagctgggct    3720
gagccggctg agaccaacgg tgagatcaca gcctacgagg tctgctatgg cctggtcaac    3780
gatgacaacc gacctattgg gcccatgaag aaagtgctgg ttgacaaccc taagaaccgg    3840
atgctgctta ttgagaacct tcgggagtcc cagccctacc gctacacggt gaaggcgcgc    3900
aacgggcgcc gctgggggcc tgagcggag gccatcatca acctggccac ccagcccaag    3960
aggcccatgt ccatccccat catccctgac atccctatcg tggacgccca gagcggggag    4020
gactacgaca gcttccttat gtacagcgat gacgttctac gctctccatc gggcagccag    4080
aggcccagcg tctccgatga cactggctgc ggctggaagt tcgagcccct gctgggggag    4140
gagctggacc tgcggcgcgt cacgtggcgg ctgcccccgg agctcatccc gcgcctgtcg    4200
gccagcagcg ggcgctcctc cgacgccgag gcgccccacg ggccccccgga cgacggcggc    4260 gcgggcggga agggcggcag cctgcccgc agtgcgacac ccgggccccc cggagagcac    4320
ctggtgaatg gccggatgga ctttgccttc ccgggcagca ccaactccct gcacaggatg    4380
accacgacca gtgctgctgc ctatggcacc cacctgagcc cacacgtgcc ccaccgcgtg    4440
ctaagcacat cctccaccct cacacgggac tacaactcac tgacccgctc agaacactca    4500
cactcgacca cactgccgag ggactactcc accctcacct ccgtctcctc ccacggcctc    4560
cctcccatct gggaacacgg gaggagcagg cttccgctgt cctgggccct ggggtcccgg    4620
agtcgggctc agatgaaagg gttcccccct tccaggggcc cacgagactc tataatcctg    4680
gctgggaggc cagcagcgcc ctcctggggc ccagactctc gcctgactgc tggtgtgccc    4740
gacacgccca cccgcctggt gttctctgcc ctggggccca catctctcag agtgagctgg    4800
caggagccgc ggtgcgagcg gccgctgcag ggctacagtg tggagtacca gctgctgaac    4860
```

-continued

```
ggcggtgagc tgcatcggct caacatcccc aaccctgccc agacctcggt ggtggtggaa    4920
gacctcctgc ccaaccactc ctacgtgttc cgcgtgcggg cccagagcca ggaaggctgg    4980
ggccgagagc gtgagggtgt catcaccatt gaatcccagg tgcacccgca gagcccactg    5040
tgtcccctgc caggctccgc cttcactttg agcactccca gtgccccagg cccgctggtg    5100
ttcactgccc tgagcccaga ctcgctgcag ctgagctggg agcggccacg gaggcccaat    5160
ggggatatcg tcggctacct ggtgacctgt gagatggccc aaggaggagg tccagccacc    5220
gcattccggg tggatggaga cagccccgag agccggctga ccgtgccggg cctcagcgag    5280
aacgtgccct acaagttcaa ggtgcaggcc aggaccactg agggcttcgg ccagagcgc     5340 gagggcatca tcaccataga gtcccaggat ggaggtccct tcccgcagct gggcagccgt    5400
gccgggctct tccagcaccc gctgcaaagc gagtacagca gcatctccac cacccacacc    5460
agcgccaccg agcccttcct agtgggtccg accctggggg cccagcacct ggaggcaggc    5520
ggctccctca cccggcatgt gacccaggag tttgtgagcc ggacactgac caccagcgga    5580
acccttagca cccacatgga ccaacagttc ttccaaactt ga                       5622
```

<210> SEQ ID NO 17
<211> LENGTH: 1873
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 17

```
Met Ala Gly Pro Arg Pro Ser Pro Trp Ala Arg Leu Leu Leu Ala Ala
 1               5                  10                  15

Leu Ile Ser Val Ser Leu Ser Gly Thr Leu Asn Arg Cys Lys Lys Ala
             20                  25                  30

Pro Ile Lys Ser Cys Thr Glu Cys Val Arg Val Asp Lys Asp Cys Ala
         35                  40                  45

Tyr Cys Thr Asp Glu Met Phe Arg Asp Arg Arg Cys Asn Thr Gln Ala
     50                  55                  60

Glu Leu Leu Ala Ala Gly Cys Gln Arg Glu Ser Ile Val Val Met Glu
 65                  70                  75                  80

Ser Ser Phe Gln Ile Thr Glu Glu Thr Gln Ile Asp Thr Thr Leu Arg
                 85                  90                  95

Arg Ser Gln Met Ser Pro Gln Gly Leu Arg Val Arg Leu Arg Pro Gly
            100                 105                 110

Glu Glu Arg His Phe Glu Leu Glu Val Phe Glu Pro Leu Glu Ser Pro
        115                 120                 125

Val Asp Leu Tyr Ile Leu Met Asp Phe Ser Asn Ser Met Ser Asp Asp
    130                 135                 140

Leu Asp Asn Leu Lys Lys Met Gly Gln Asn Leu Ala Arg Val Leu Ser
145                 150                 155                 160

Gln Leu Thr Ser Asp Tyr Thr Ile Gly Phe Gly Lys Phe Val Asp Lys
                165                 170                 175

Val Ser Val Pro Gln Thr Asp Met Arg Pro Glu Lys Leu Lys Glu Pro
            180                 185                 190

Trp Pro Asn Ser Asp Pro Pro Phe Ser Phe Lys Asn Val Ile Ser Leu
        195                 200                 205

Thr Glu Asp Val Asp Glu Phe Arg Asn Lys Leu Gln Gly Glu Arg Ile
    210                 215                 220

Ser Gly Asn Leu Asp Ala Pro Glu Gly Gly Phe Asp Ala Ile Leu Gln
```

```
                225                 230                 235                 240
Thr Ala Val Cys Thr Arg Asp Ile Gly Trp Arg Pro Asp Ser Thr His
                    245                 250                 255
Leu Leu Val Phe Ser Thr Glu Ser Ala Phe His Tyr Glu Ala Asp Gly
                    260                 265                 270
Ala Asn Val Leu Ala Gly Ile Met Ser Arg Asn Asp Glu Arg Cys His
                    275                 280                 285
Leu Asp Thr Thr Gly Thr Tyr Thr Gln Tyr Arg Thr Gln Asp Tyr Pro
290                 295                 300
Ser Val Pro Thr Leu Val Arg Leu Leu Ala Lys His Asn Ile Ile Pro
305                 310                 315                 320
Ile Phe Ala Val Thr Asn Tyr Ser Tyr Ser Tyr Tyr Glu Lys Leu His
                    325                 330                 335
Thr Tyr Phe Pro Val Ser Ser Leu Gly Val Leu Gln Glu Asp Ser Ser
                    340                 345                 350
Asn Ile Val Glu Leu Leu Glu Glu Ala Phe Asn Arg Ile Arg Ser Asn
                    355                 360                 365
Leu Asp Ile Arg Ala Leu Asp Ser Pro Arg Gly Leu Arg Thr Glu Val
    370                 375                 380
Thr Ser Lys Met Phe Gln Lys Thr Arg Thr Gly Ser Phe His Ile Arg
385                 390                 395                 400
Arg Gly Glu Val Gly Ile Tyr Gln Val Gln Leu Arg Ala Leu Glu His
                    405                 410                 415
Val Asp Gly Thr His Val Cys Gln Leu Pro Glu Asp Gln Lys Gly Asn
                    420                 425                 430
Ile His Leu Lys Pro Ser Phe Ser Asp Gly Leu Lys Met Asp Ala Gly
                    435                 440                 445
Ile Ile Cys Asp Val Cys Thr Cys Glu Leu Gln Lys Glu Val Arg Ser
    450                 455                 460
Ala Arg Cys Ser Phe Asn Gly Asp Phe Val Cys Gly Gln Cys Val Cys
465                 470                 475                 480
Ser Glu Gly Trp Ser Gly Gln Thr Cys Asn Cys Ser Thr Gly Ser Leu
                    485                 490                 495
Ser Asp Ile Gln Pro Cys Leu Arg Glu Gly Glu Asp Lys Pro Cys Ser
                    500                 505                 510
Gly Arg Gly Glu Cys Gln Cys Gly His Cys Val Cys Tyr Gly Glu Gly
                    515                 520                 525
Arg Tyr Glu Gly Gln Phe Cys Glu Tyr Asp Asn Phe Gln Cys Pro Arg
    530                 535                 540
Thr Ser Gly Phe Leu Cys Asn Asp Arg Gly Arg Cys Ser Met Gly Gln
545                 550                 555                 560
Cys Val Cys Glu Pro Gly Trp Thr Gly Pro Ser Cys Asp Cys Pro Leu
                    565                 570                 575
Ser Asn Ala Thr Cys Ile Asp Ser Asn Gly Gly Ile Cys Asn Gly Arg
                    580                 585                 590
Gly His Cys Glu Cys Gly Arg Cys His Cys His Gln Gln Ser Leu Tyr
                    595                 600                 605
Thr Asp Thr Ile Cys Glu Ile Asn Tyr Ser Ala Ser Thr Arg Ala Ser
    610                 615                 620
Ala Arg Thr Tyr Ala Pro Ala Cys Ser Ala Arg Gly Ala Pro Ala
625                 630                 635                 640
Arg Arg Arg Gly Ala Arg Val Arg Asn Ala Thr Ser Arg Ser Arg Trp
                    645                 650                 655
```

-continued

Trp Thr Ser Leu Arg Glu Ala Arg Arg Trp Cys Ala Ala Pro Ser
            660                 665                 670

Gly Thr Arg Met Thr Thr Ala Pro Thr Ala Thr Pro Trp Lys Val Thr
        675                 680                 685

Ala Pro Leu Gly Pro Thr Ala Leu Ser Trp Cys Thr Arg Arg Arg Asp
690                 695                 700

Cys Pro Pro Gly Ser Phe Trp Trp Leu Ile Pro Leu Leu Leu Leu
705                 710                 715                 720

Leu Pro Leu Leu Ala Leu Leu Leu Leu Cys Trp Lys Tyr Cys Ala
                725                 730                 735

Cys Cys Lys Ala Cys Leu Ala Leu Leu Pro Cys Cys Asn Arg Gly His
            740                 745                 750

Met Val Gly Phe Lys Glu Asp His Tyr Met Leu Arg Glu Asn Leu Met
        755                 760                 765

Ala Ser Asp His Leu Asp Thr Pro Met Leu Arg Ser Gly Asn Leu Lys
770                 775                 780

Gly Arg Asp Val Val Arg Trp Lys Val Thr Asn Asn Met Gln Arg Pro
785                 790                 795                 800

Gly Phe Ala Thr His Ala Ala Ser Ile Asn Pro Thr Glu Leu Val Pro
                805                 810                 815

Tyr Gly Leu Ser Leu Arg Leu Ala Arg Leu Cys Thr Glu Asn Leu Leu
            820                 825                 830

Lys Pro Asp Thr Arg Glu Cys Ala Gln Leu Arg Gln Glu Val Glu Glu
        835                 840                 845

Asn Leu Asn Glu Val Tyr Arg Gln Ile Ser Gly Val His Lys Leu Gln
850                 855                 860

Gln Thr Lys Phe Arg Gln Gln Pro Asn Ala Gly Lys Lys Gln Asp His
865                 870                 875                 880

Thr Ile Val Asp Thr Val Leu Met Ala Pro Arg Ser Ala Lys Pro Ala
                885                 890                 895

Leu Leu Lys Leu Thr Glu Lys Gln Val Glu Gln Arg Ala Phe His Asp
            900                 905                 910

Leu Lys Val Ala Pro Gly Tyr Tyr Thr Leu Thr Ala Asp Gln Asp Ala
        915                 920                 925

Arg Gly Met Val Glu Phe Gln Glu Gly Val Glu Leu Val Asp Val Arg
930                 935                 940

Val Pro Leu Phe Ile Arg Pro Glu Asp Asp Asp Glu Lys Gln Leu Leu
945                 950                 955                 960

Val Glu Ala Ile Asp Val Pro Ala Gly Thr Ala Thr Leu Gly Arg Arg
                965                 970                 975

Leu Val Asn Ile Thr Ile Ile Lys Glu Gln Ala Arg Asp Val Val Ser
            980                 985                 990

Phe Glu Gln Pro Glu Phe Ser Val Ser Arg Gly Asp Gln Val Ala Arg
        995                 1000                1005

Ile Pro Val Ile Arg Arg Val Leu Asp Gly Gly Lys Ser Gln Val Ser
        1010                1015                1020

Tyr Arg Thr Gln Asp Gly Thr Ala Gln Gly Asn Arg Asp Tyr Ile Pro
1025                1030                1035                1040

Val Glu Gly Glu Leu Leu Phe Gln Pro Gly Glu Ala Trp Lys Glu Leu
                1045                1050                1055

Gln Val Lys Leu Leu Glu Leu Gln Glu Val Asp Ser Leu Leu Arg Gly
            1060                1065                1070

Arg Gln Val Arg Arg Phe His Val Gln Leu Ser Asn Pro Lys Phe Gly
        1075                1080                1085

```
Ala His Leu Gly Gln Pro His Ser Thr Thr Ile Ile Ile Arg Asp Pro
    1090                1095                1100

Asp Glu Leu Asp Arg Ser Phe Thr Ser Gln Met Leu Ser Ser Gln Pro
1105                1110                1115                1120

Pro Pro His Gly Asp Leu Gly Ala Pro Gln Asn Pro Asn Ala Lys Ala
            1125                1130                1135

Ala Gly Ser Arg Lys Ile His Phe Asn Trp Leu Pro Pro Ser Gly Lys
        1140                1145                1150

Pro Met Gly Tyr Arg Val Lys Tyr Trp Ile Gln Gly Asp Ser Glu Ser
            1155                1160                1165

Glu Ala His Leu Leu Asp Ser Lys Val Pro Ser Val Glu Leu Thr Asn
        1170                1175                1180

Leu Tyr Pro Tyr Cys Asp Tyr Glu Met Lys Val Cys Ala Tyr Gly Ala
1185                1190                1195                1200

Gln Gly Glu Gly Pro Tyr Ser Ser Leu Val Ser Cys Arg Thr His Gln
            1205                1210                1215

Glu Val Pro Ser Glu Pro Gly Arg Leu Ala Phe Asn Val Val Ser Ser
            1220                1225                1230

Thr Val Thr Gln Leu Ser Trp Ala Glu Pro Ala Glu Thr Asn Gly Glu
        1235                1240                1245

Ile Thr Ala Tyr Glu Val Cys Tyr Gly Leu Val Asn Asp Asp Asn Arg
        1250                1255                1260

Pro Ile Gly Pro Met Lys Lys Val Leu Val Asp Asn Pro Lys Asn Arg
1265                1270                1275                1280

Met Leu Leu Ile Glu Asn Leu Arg Glu Ser Gln Pro Tyr Arg Tyr Thr
            1285                1290                1295

Val Lys Ala Arg Asn Gly Ala Gly Trp Gly Pro Glu Arg Glu Ala Ile
            1300                1305                1310

Ile Asn Leu Ala Thr Gln Pro Lys Arg Pro Met Ser Ile Pro Ile Ile
        1315                1320                1325

Pro Asp Ile Pro Ile Val Asp Ala Gln Ser Gly Glu Asp Tyr Asp Ser
    1330                1335                1340

Phe Leu Met Tyr Ser Asp Asp Val Leu Arg Ser Pro Ser Gly Ser Gln
1345                1350                1355                1360

Arg Pro Ser Val Ser Asp Asp Thr Gly Cys Gly Trp Lys Phe Glu Pro
            1365                1370                1375

Leu Leu Gly Glu Glu Leu Asp Leu Arg Arg Val Thr Trp Arg Leu Pro
            1380                1385                1390

Pro Glu Leu Ile Pro Arg Leu Ser Ala Ser Ser Gly Arg Ser Ser Asp
    1395                1400                1405

Ala Glu Ala Pro His Gly Pro Pro Asp Asp Gly Ala Gly Gly Lys
        1410                1415                1420

Gly Gly Ser Leu Pro Arg Ser Ala Thr Pro Gly Pro Pro Gly Glu His
1425                1430                1435                1440

Leu Val Asn Gly Arg Met Asp Phe Ala Phe Pro Gly Ser Thr Asn Ser
            1445                1450                1455

Leu His Arg Met Thr Thr Thr Ser Ala Ala Ala Tyr Gly Thr His Leu
        1460                1465                1470

Ser Pro His Val Pro His Arg Val Leu Ser Thr Ser Ser Thr Leu Thr
        1475                1480                1485

Arg Asp Tyr Asn Ser Leu Thr Arg Ser Glu His Ser His Ser Thr Thr
    1490                1495                1500

Leu Pro Arg Asp Tyr Ser Thr Leu Thr Ser Val Ser Ser His Gly Leu
```

```
                1505                1510                1515                1520
Pro Pro Ile Trp Glu His Gly Arg Ser Arg Leu Pro Leu Ser Trp Ala
                    1525                1530                1535
Leu Gly Ser Arg Ser Arg Ala Gln Met Lys Gly Phe Pro Pro Ser Arg
                1540                1545                1550
Gly Pro Arg Asp Ser Ile Ile Leu Ala Gly Arg Pro Ala Ala Pro Ser
            1555                1560                1565
Trp Gly Pro Asp Ser Arg Leu Thr Ala Gly Val Pro Asp Thr Pro Thr
        1570                1575                1580
Arg Leu Val Phe Ser Ala Leu Gly Pro Thr Ser Leu Arg Val Ser Trp
1585                1590                1595                1600
Gln Glu Pro Arg Cys Glu Arg Pro Leu Gln Gly Tyr Ser Val Glu Tyr
                1605                1610                1615
Gln Leu Leu Asn Gly Gly Glu Leu His Arg Leu Asn Ile Pro Asn Pro
                    1620                1625                1630
Ala Gln Thr Ser Val Val Glu Asp Leu Leu Pro Asn His Ser Tyr
                1635                1640                1645
Val Phe Arg Val Arg Ala Gln Ser Gln Glu Gly Trp Gly Arg Glu Arg
            1650                1655                1660
Glu Gly Val Ile Thr Ile Glu Ser Gln Val His Pro Gln Ser Pro Leu
1665                1670                1675                1680
Cys Pro Leu Pro Gly Ser Ala Phe Thr Leu Ser Thr Pro Ser Ala Pro
                1685                1690                1695
Gly Pro Leu Val Phe Thr Ala Leu Ser Pro Asp Ser Leu Gln Leu Ser
                    1700                1705                1710
Trp Glu Arg Pro Arg Arg Pro Asn Gly Asp Ile Val Gly Tyr Leu Val
                1715                1720                1725
Thr Cys Glu Met Ala Gln Gly Gly Gly Pro Ala Thr Ala Phe Arg Val
            1730                1735                1740
Asp Gly Asp Ser Pro Glu Ser Arg Leu Thr Val Pro Gly Leu Ser Glu
1745                1750                1755                1760
Asn Val Pro Tyr Lys Phe Lys Val Gln Ala Arg Thr Thr Glu Gly Phe
                1765                1770                1775
Gly Pro Glu Arg Glu Gly Ile Ile Thr Ile Glu Ser Gln Asp Gly Gly
                    1780                1785                1790
Pro Phe Pro Gln Leu Gly Ser Arg Ala Gly Leu Phe Gln His Pro Leu
                1795                1800                1805
Gln Ser Glu Tyr Ser Ser Ile Ser Thr Thr His Thr Ser Ala Thr Glu
            1810                1815                1820
Pro Phe Leu Val Gly Pro Thr Leu Gly Ala Gln His Leu Glu Ala Gly
1825                1830                1835                1840
Gly Ser Leu Thr Arg His Val Thr Gln Glu Phe Val Ser Arg Thr Leu
                    1845                1850                1855
Thr Thr Ser Gly Thr Leu Ser Thr His Met Asp Gln Gln Phe Phe Gln
                1860                1865                1870
Thr

<210> SEQ ID NO 18
<211> LENGTH: 5622
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 18
```

-continued

```
atggcagggc cacgccccag cccatgggcc aggctgctcc tggcagcctt gatcagcgtc    60
agcctctctg ggaccttgaa ccgctgcaag aaggcccgaa taaagagctg cacggagtgt   120
gtccgtgtgg ataaggactg cgcctactgc acagacgaga tgttcaggga ccggcgctgc   180
aacacccagg cggagctgct ggccgcgggc tgccagcggg agagcatcgt ggtcatggag   240
agcagcttcc aaatcacaga ggagacccag attgacacca ccctgcggcg cagccagatg   300
tcccccaag gcctgcgggt ccgtctgcgg cccggtgagg agcggcattt tgagctggag   360
gtgtttgagc cactggagag ccccgtggac ctgtacatcc tcatggactt ctccaactcc   420
atgtccgatg atctggacaa cctcaagaag atggggcaga acctggctcg ggtcctgagc   480
cagctcacca gcgactacac tattggattt ggcaagtttg tggacaaagt cagcgtcccg   540
cagacggaca tgaggcctga aagctgaag agccttggc ccaacagtga ccccccttc     600
tccttcaaga acgtcatcag cctgacagaa gatgtggatg agttccggaa taaactgcag   660
ggagagcgga tctcaggcaa cctggatgct cctgagggcg gcttcgatgc catcctgcag   720
acagctgtgt gcacgaggga cattggctgg cgcccggaca gcacccacct gctggtcttc   780
tccaccgagt cagccttcca ctatgaggct gatggcgcca acgtgctggc tggcatcatg   840
agccgcaacg atgaacggtg ccacctggac accacgggca cctacaccca gtacaggaca   900
caggactacc cgtcggtgcc caccctggtg cgcctgctcg ccaagcacaa catcatcccc   960
atctttgctg tcaccaacta ctcctatagc tactacgaga agcttcacac ctatttccct  1020
gtctcctcac tgggggtgct gcaggaggac tcgtccaaca tcgtggagct gctggaggag  1080
gccttcaatc ggatccgctc caacctggac atccgggccc tagacagccc ccgaggcctt  1140
cggacagagg tcacctccaa gatgttccag aagacgagga ctgggtcctt tcacatccgg  1200
cggggggaag tgggtatata ccaggtgcag ctgcgggccc ttgagcacgt ggatgggacg  1260
cacgtgtgcc agctgccgga ggaccagaag ggcaacatcc atctgaaacc ttccttctcc  1320
gacggcctca agatggacgc gggcatcatc tgtgatgtgt gcacctgcga gctgcaaaaa  1380
gaggtgcggt cagctcgctg cagcttcaac ggagacttcg tgtgcggaca gtgtgtgtgc  1440
agcgagggct ggagtggcca gacctgcaac tgctccaccg gctctctgag tgacattcag  1500
ccctgcctgc ggaagggcga ggacaagccg tgctccggcc gtggggagtg ccagtgcggg  1560
cactgtgtgt gctacggcga aggccgctac gagggtcagt tctgcgagta tgacaacttc  1620
cagtgtcccc gcacttccgg gttcctctgc aatgaccgag acgctgctc catgggccag  1680
tgtgtgtgtg agcctggttg gacaggccca agctgtgact gtccctcag caatgccacc  1740
tgcatcgaca gcaatggggg catctgtaat ggacgtggcc actgtgagtg tggccgctgc  1800
cactgccacc agcagtcgct ctacacggac accatctgcg agatcaacta ctcggcgtcc  1860
accgggcct ctgcgaggac ctacgctcct gcgtgcagtg ccaggcgtgg ggcaccggcg  1920
agaagaaggg gcgcacgtgt gaggaatgca acttcaaggt caagatggtg gacgagctta  1980
agagaggcga ggaggtggtg gtgcgctgct ccttccggga cgaggatgac gactgcacct  2040
acagctacac catggaaggt gacggcgccc ctggcccaa cagcactgtc ctggtgcaca  2100
agaagaaggg actgccctcc gggctccttc tggtggctca tccccctgct cctcctcctc  2160
ctgccgctcc tggccctgct actgctgcta tgctggaagt actgtgcctg ctgcaaggcc  2220
tgcctggcac ttctcccgtg ctgcaaccga ggtcacatgg tgggctttaa ggaagaccac  2280
tacatgctgc gggagaacct gatggcctct gaccacttgg acacgccat gctgcgcagc  2340
gggaacctca agggccgtga cgtggtccgc tggaaggtca ccaacaacat gcagcggcct  2400
```

```
ggctttgcca ctcatgccgc cagcatcaac cccacagagc tggtgcccta cgggctgtcc    2460
ttgcgcctgg cccgccttgg caccgagaac ctgctgaagc ctgacactcg ggagtgcgcc    2520
cagctgcgcc aggaggtgga ggagaacctg aacgaggtct acaggcagat ctccggtgta    2580
cacaagctcc agcagaccaa gttccggcag cagcccaatg ccgggaaaaa gcaagaccac    2640
accattgtgg acacagtgct gatggcgccc cgctcggcca agccggccct gctgaagctt    2700
acagagaagc aggtggaaca gagggccttc cacgacctca aggtggcccc cggctactac    2760
accctcactg cagaccagga cgcccggggc atggtggagt ccaggagggg cgtggagctg    2820
gtggacgtac gggtgcccct ctttatccgg cctgaggatg acgacgagaa gcagctgctg    2880
gtggaggcca tcgacgtgcc cgcaggcact gccaccctcg gccgccgcct ggtaaacatc    2940
accatcatca aggagcaagc cagagacgtg gtgtcctttg agcagcctga gttctcggtc    3000
agccgcgggg accaggtggc ccgcatcct gtcatccggc gtgtcctgga cggcgggaag    3060
tcccaggtct cctaccgcac acaggatggc accgcgcagg gcaacgggga ctacatcccc    3120
gtggagggtg agctgctgtt ccagcctggg gaggcctgga agagctgca ggtgaagctc    3180 ctggagctgc aagaagttga ctccctcctg cggggccgcc aggtccgccg tttccacgtc    3240
cagctcagca ccctaagtt tggggcccac ctgggccagc cccactccac caccatcatc    3300
atcagggacc cagatgaact ggaccggagc ttcacgagtc agatgttgtc atcacagcca    3360 cccctcacg gcgacctggg cgccccgcag aaccccaatg ctaaggccgc tgggtccagg    3420
aagatccatt tcaactggct gccccttct ggcaagccaa tggggtacag ggtaaagtac    3480
tggattcagg gtgactccga atccgaagcc cacctgctcg acagcaaggt gccctcagtg    3540
gagctcacca acctgtaccc gtattgcgac tatgagatga aggtgtgcgc ctacggggct    3600
cagggcgagg gaccctacag ctccctggtg tcctgccgca cccaccagga agtgcccagc    3660
gagccagggc gtctggcctt caatgtcgtc tcctccacgg tgacccagct gagctgggct    3720
gagccggctg agaccaacgg tgagatcaca gcctacgagg tctgctatgg cctggtcaac    3780
gatgacaacc gacctattgg gcccatgaag aaagtgctgg ttgacaaccc taagaaccgg    3840
atgctgctta ttgagaacct tcgggagtcc cagccctacc gctacacggt gaaggcgcgc    3900
aacggggccg gctgggggcc tgagcgggag gccatcatca acctggccac ccagcccaag    3960
aggcccatgt ccatccccat catccctgac atccctatcg tggacgccca gagcggggag    4020
gactacgaca gcttccttat gtacagcgat gacgttctac gctctccatc gggcagccag    4080
aggcccagcg tctccgatga cactggctgc ggctggaagt tcgagcccct gctggggag    4140 gagctggacc tgcggcgcgt cacgtggcgg ctgccccgg agctcatccc gcgcctgtcg    4200
gccagcagcg ggcgctcctc cgacgccgag gcgcccacg ggccccggga cgacggcggc    4260 gcggcggga agggcggcag cctgcccgc agtgcgacac ccgggccccc cggagagcac    4320
ctggtgaatg gccggatgga ctttgccttc ccgggcagca ccaactccct gcacaggatg    4380
accacgacca gtgctgctgc ctatggcacc cacctgagcc acacgtgcc ccaccgcgtg    4440 ctaagcacat cctccaccct cacacgggac tacaactcac tgacccgctc agaacactca    4500
cactcgacca cactgccgag ggactactcc accctcacct ccgtctcctc ccacggcctc    4560
cctcccatct gggaacacgg gaggagcagg cttccgctgt cctgggccct ggggtcccgg    4620
agtcgggctc agatgaaagg gttccccct tccagggggcc cacgagactc tataatcctg    4680
gctgggaggc cagcagcgcc ctcctggggc ccagactctc gcctgactgc tggtgtgccc    4740
gacacgccca cccgcctggt gttctctgcc ctggggccca catctctcag agtgagctgg    4800
```

```
caggagccgc ggtgcgagcg gccgctgcag ggctacagtg tggagtacca gctgctgaac    4860
ggcggtgagc tgcatcggct caacatcccc aaccctgccc agacctcggt ggtggtggaa    4920
gacctcctgc ccaaccactc ctacgtgttc cgcgtgcggg cccagagcca ggaaggctgg    4980
ggccgagagc gtgagggtgt catcaccatt gaatcccagg tgcacccgca gagcccactg    5040
tgtcccctgc caggctccgc cttcactttg agcactccca gtgccccagg cccgctggtg    5100
ttcactgccc tgagcccaga ctcgctgcag ctgagctggg agcggccacg gaggcccaat    5160
ggggatatcg tcggctacct ggtgacctgt gagatggccc aaggaggagg tccagccacc    5220
gcattccggg tggatggaga cagccccgag agccggctga ccgtgccggg cctcagcgag    5280
aacgtgccct acaagttcaa ggtgcaggcc aggaccactg agggcttcgg gccagagcgc    5340
gagggcatca tcaccataga gtcccaggat ggaggtccct ccccgcagct gggcagccgt    5400
gccgggctct ccagcacccc gctgcaaagc gagtacagca gcatctccac cacccacacc    5460
agcgccaccg agcccttcct agtgggtccg accctggggg cccagcacct ggaggcaggc    5520
ggctccctca cccggcatgt gacccaggag tttgtgagcc ggacactgac caccagcgga    5580
acccttagca cccacatgga ccaacagttc ttccaaactt ga                      5622
```

<210> SEQ ID NO 19
<211> LENGTH: 5622
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 19

```
atggcagggc cacggcccag cccatgggcc aggctgctcc tggcagcctt gatcagcgtc      60
agcctctctg ggaccttgaa ccgctgcaag aaggccccaa taaagagctg cacggagtgt     120
gtccgtgtgg ataaggactg cgcctactgc acagacgaga tgttcaggga ccggcgctgc     180
aacacccagg cggagctgct ggccgcgggc tgccagcggg agagcatcgt ggtcatggag     240
agcagcttcc aaatcacaga ggagacccag attgacacca ccctgcggcg cagccagatg     300
tccccccaag gcctgcgggt ccgtctgcgg cccggtgagg agcggcattt tgagctggag     360
gtgtttgagc cactggagag ccccgtggac ctgtacatcc tcatggactt ctccaactcc     420
atgtccgatg atctggacaa cctcaagaag atggggcaga acctggctcg ggtcctgagc     480
cagctcacca cgcgactaca tattggattt ggcaagtttg tggacaaagt cagcgtcccg     540
cagacggaca tgaggcctga aagctgaag gagccttggc ccaacagtga ccccccttc      600 tccttcaaga acgtcatcag cctgacagaa gatgtgatg agttccggaa taaactgcag     660
ggagagcgga tctcaggcaa cctggatgct cctgagggcg gcttcgatgc catcctgcag     720
acagctgtgt gcacgaggga cattggctgg cgcccggaca gcacccacct gctggtcttc     780
tccaccgagt cagccttcca ctatgaggct gatggcgcca acgtgctggc tggcatcatg     840
agccgcaacg atgaacggtg ccacctggac accacgggca cctacaccca gtacaggaca     900
caggactacc cgtcggtgcc cacccctggtg cgcctgctcg ccaagcacaa catcatcccc     960
atctttgctg tcaccaacta ctcctatagc tactacgaga agcttcacac ctatttccct    1020
gtctcctcac tgggggtgct gcaggaggac tcgtccaaca tcgtggagct gctggaggag    1080
gccttcaatc ggatccgctc caacctggac atccggggcc tagacagccc ccgaggcctt    1140
cggacagagg tcacctccaa gatgttccag aagacgagga ctgggtcctt tcacatccgg    1200
```

```
cgggggggaag tgggtatata ccaggtgcag ctgcgggccc ttgagcacgt ggatgggacg    1260
cacgtgtgcc agctgccgga ggaccagaag ggcaacatcc atctgaaacc ttccttctcc    1320
gacggcctca agatggacgc gggcatcatc tgtgatgtgt gcacctgcga gctgcaaaaa    1380
gaggtgcggt cagctcgctg cagcttcaac ggagacttcg tgtgcggaca gtgtgtgtgc    1440
agcgagggct ggagtggcca gacctgcaac tgctccaccg gctctctgag tgacattcag    1500
ccctgcctgc gggagggcga ggacaagccg tgctccggcc gtggggagtg ccagtgcggg    1560
cactgtgtgt gctacggcga aggccgctac gagggtcagt tctgcgagta tgacaacttc    1620
cagtgtcccc gcacttccgg gttcctctgc aatgaccgag gacgctgctc catgggccag    1680
tgtgtgtgtg agcctggttg gacaggccca agctgtgact gtccctcag  caatgccacc     1740 tgcatcgaca gcaatggggg catctgtaat ggacgtggcc actgtgagtg tggccgctgc    1800
cactgccacc agcagtcgct ctacacggac accatctgcg agatcaacta ctcggcgtcc    1860
acccgggcct ctgcgaggac ctacgctcct gcgtgcagtg ccaggcgtgg ggcaccggcg    1920
agaagaaggg gcgcacgtgt gaggaatgca acttcaaggt caagatggtg gacgagctta    1980
agagaggcga ggaggtggtg gtgcgctgct ccttccggga cgaggatgac gactgcacct    2040
acagctacac catggaaggt gacggcgccc ctgggcccaa cagcactgtc ctggtgcaca    2100
agaagaaggg actgccctcc gggctccttc tggtggctca tccccctgct cctcctcctc    2160
ctgccgctcc tggccctgct actgctgcta tgctggaagt actgtgcctg ctgcaaggcc    2220
tgcctggcac ttctcccgtg ctgcaaccga ggtcacatgg tgggctttaa ggaagaccac    2280
tacatgctgc gggagaacct gatggcctct gaccacttgg acacgccat  gctgcgcagc     2340 gggaacctca agggccgtga cgtggtccgc tggaaggtca ccaacaacat gcagcggcct    2400
ggctttgcca ctcatgccgc cagcatcaac cccacagagc tggtgcccta cgggctgtcc    2460
ttgcgcctgg cccgcctttg caccgagaac ctgctgaagc ctgacactcg ggagtgcgcc    2520
cagctgcgcc aggaggtgga ggagaacctg aacgaggtct acaggcagat ctccggtgta    2580
cacaagctcc agcagaccaa gttccggcag cagcccaatg ccgggaaaaa gcaagaccac    2640
accattgtgg acacagtgct gatggcgccc cgctcggcca agccggccct gctgaagctt    2700
acagagaagc aggtggaaca gagggccttc cacgacctca aggtggcccc cggctactac    2760
accctcactg cagaccagga cgcccggggc atggtggagt tccaggaggg cgtggagctg    2820
gtggacgtac gggtgcccct ctttatccgg cctgaggatg acgacgagaa gcagctgctg    2880
gtggaggcca tcgacgtgcc cgcaggcact gccaccctcg gccgccgcct ggtaaacatc    2940
accatcatca aggagcaagc cagagacgtg gtgtcctttg agcagcctga gttctcggtc    3000
agccgcgggg accaggtggc ccgcatccct gtcatccggc gtgtcctgga cggcgggaag    3060
tcccaggtct cctaccgcac acaggatggc accgcgcagg gcaaccggga ctacatcccc    3120
gtggagggtg agctgctgtt ccagcctggg gaggcctgga agagctgca  ggtgaagctc     3180 ctggagctgc aagaagttga ctccctcctg cggggccgcc aggtccgccg tttccacgtc    3240
cagctcagca cccctaagtt tggggcccac ctgggccagc cccactccac caccatcatc    3300
atcagggacc cagatgaact ggaccggagc ttcacgagtc agatgttgtc atcacagcca    3360
ccccctcacg gcgacctggg cgcccgcag  aaccccaatg ctaaggccgc tgggtccagg     3420
aagatccatt tcaactggct gccccttct  ggcaagccaa tggggtacag ggtaaagtac     3480
tggattcagg gtgactccga atccgaagcc cacctgctcg acagcaaggt gccctcagtg    3540
gagctcacca acctgtaccc gtattgcgac tatgagatga aggtgtgcgc ctacgggggct    3600
```

```
cagggcgagg gaccctacag ctccctggtg tcctgccgca cccaccagga agtgcccagc    3660
gagccagggc gtctggcctt caatgtcgtc tcctccacgg tgacccagct gagctgggct    3720
gagccggctg agaccaacgg tgagatcaca gcctacgagg tctgctatgg cctggtcaac    3780
gatgacaacc gacctattgg gcccatgaag aaagtgctgg ttgacaaccc taagaaccgg    3840
atgctgctta ttgagaacct tcgggagtcc cagccctacc gctacacggt gaaggcgcgc    3900
aacggggccg gctgggggcc tgagcgggag gccatcatca acctggccac ccagcccaag    3960
aggcccatgt ccatccccat catccctgac atccctatcg tggacgccca gagcggggag    4020
gactacgaca gcttccttat gtacagcgat gacgttctac gctctccatc gggcagccag    4080
aggcccagcg tctccgatga cactggctgc ggctggaagt tcgagcccct gctgggggag    4140
gagctggacc tgcggcgcgt cacgtggcgg ctgccccccgg agctcatccc gcgcctgtcg    4200
gccagcagcg ggcgctcctc cgacgccgag gcgcccacg  ggccccccgga cgacggcggc    4260 gcgggcggga agggcggcag cctgcccgc  agtgcgacac ccgggccccc cggagagcac    4320
ctggtgaatg gccggatgga cttttgccttc ccgggcagca ccaactccct gcacaggatg    4380
accacgacca gtgctgctgc ctatggcacc cacctgagcc acacgtgcc  ccaccgcgtg    4440 ctaagcacat cctccaccct cacacgggac tacaactcac tgacccgctc agaacactca    4500
cactcgacca cactgccgag ggactactcc accctcacct ccgtctcctc ccacggcctc    4560
cctcccatct gggaacacgg gaggagcagg cttccgctgt cctgggccct ggggtcccgg    4620
agtcgggctc agatgaaagg gttccccccct tccagggggcc cacgagactc tataatcctg    4680
gctgggaggc cagcagcgcc ctcctggggc ccagactctc gcctgactgc tggtgtgccc    4740
gacacgccca cccgcctggt gttctctgcc ctggggccca catctctcag agtgagctgg    4800
caggagccgc ggtgcgagcg gccgctgcag ggctacagtg tggagtacca gctgctgaac    4860
ggcggtgagc tgcatcggct caacatcccc aaccctgccc agacctcggt ggtggtggaa    4920
gacctcctgc ccaaccactc ctacgtgttc cgcgtgcggg cccagagcca ggaaggctgg    4980
ggccgagagc gtgagggtgt catcaccatt gaatcccagg tgcacccgca gagcccactg    5040 tgtccctgc caggctccgc cttcactttg agcactccca gtgccccagg cccgctggtg    5100
ttcactgccc tgagcccaga ctcgctgcag ctgagctggg agcggccacg gaggcccaat    5160
ggggatatcg tcggctacct ggtgacctgt gagatggccc aagaggagg  tccagccacc    5220 gcattccggg tggatggaga cagccccgag agccggctga ccgtgccggg cctcagcgag    5280
aacgtgccct acaagttcaa ggtgcaggcc aggaccactg agggcttcgg ccagagcgc   5340 gagggcatca tcaccataga gtcccaggat ggaggtccct tcccgcagct gggcagccgt    5400
gccgggctct tccagcaccc gctgcaaagc gagtacagca gcatctccac cacccacacc    5460
agcgccaccg agcccttcct agtgggtccg accctggggg cccagcacct ggaggcaggc    5520
ggctccctca cccggcatgt gacccaggag tttgtgagcc ggacactgac caccagcgga    5580
acccttagca cccacatgga ccaacagttc ttccaaactt ga                      5622
```

<210> SEQ ID NO 20
<211> LENGTH: 8972
<212> TYPE: DNA
<213> ORGANISM: Artificial Sequence
<220> FEATURE:
<223> OTHER INFORMATION: Description of Artificial Sequence:/Note =
    Synthetic Construct

<400> SEQUENCE: 20

```
gtccaagggt agccaaggat ggctgcagct tcatatgatc agttgttaaa gcaagttgag      60
```

```
gcactgaaga tggagaactc aaatcttcga caagagctag aagataattc caatcatctt      120
acaaaactgg aaactgaggc atctaatatg aaggaagtac ttaaacaact acaaggaagt      180
attgaagatg aagctatggc ttcttctgga cagattgatt tattagagcg tcttaaagag      240
cttaacttag atagcagtaa tttccctgga gtaaaactgc ggtcaaaaat gtccctccgt      300
tcttatggaa gccgggaagg atctgtatca agccgttctg gagagtgcag tcctgttcct      360
atgggttcat ttccaagaag agggtttgta aatggaagca gagaaagtac tggatattta      420
gaagaacttg agaaagagag gtcattgctt cttgctgatc ttgacaaaga agaaaaggaa      480
aaagactggt attacgctca acttcagaat ctcactaaaa gaatagatag tcttcctttta     540 actgaaaatt tttccttaca aacagatatg accagaaggc aattggaata tgaagcaagg      600
caaatcagag ttgcgatgga agaacaacta ggtacctgcc aggatatgga aaaacgagca      660
cagcgaagaa tagccagaat tcagcaaatc gaaaaggaca tacttcgtat acgacagctt      720
ttacagtccc aagcaacaga agcagagagg tcatctcaga acaagcatga aaccggctca      780
catgatgctg agcggcagaa tgaaggtcaa ggagtgggag aaatcaacat ggcaacttct      840
ggtaatggtc agggttcaac tacacgaatg gaccatgaaa cagccagtgt tttgagttct      900
agtagcacac actctgcacc tcgaaggctg acaagtcatc tgggaaccaa ggtggaaatg      960
gtgtattcat tgttgtcaat gcttggtact catgataagg atgatatgtc gcgaactttg     1020
ctagctatgt ctagctccca agacagctgt atatccatgc gacagtctgg atgtcttcct     1080
ctcctcatcc agcttttaca tggcaatgac aaagactctg tattgttggg aaattcccgg     1140
ggcagtaaag aggctcgggc cagggccagt gcagcactcc acaacatcat tcactcacag     1200
cctgatgaca agagaggcag gcgtgaaatc cgagtccttc atcttttgga acagatacgc     1260
gcttactgtg aaacctgttg ggagtggcag gaagctcatg aaccaggcat ggaccaggac     1320
aaaaatccaa tgccagctcc tgttgaacat cagatctgtc ctgctgtgtg tgttctaatg     1380
aaactttcat ttgatgaaga gcatagacat gcaatgaatg aactaggggg actacaggcc     1440
attgcagaat tattgcaagt ggactgtgaa atgtacgggc ttactaatga ccactacagt     1500
attacactaa gacgatatgc tggaatggct ttgacaaact tgacttttgg agatgtagcc     1560
aacaaggcta cgctatgctc tatgaaaggc tgcatgagag cacttgtggc ccaactaaaa     1620
tctgaaagtg aagacttaca gcaggttatt gcaagtgttt tgaggaattt gtcttggcga     1680
gcagatgtaa atagtaaaaa gacgttgcga gaagttggaa gtgtgaaagc attgatggaa     1740
tgtgctttag aagttaaaaa ggaatcaacc ctcaaaagcg tattgagtgc cttatggaat     1800
ttgtcagcac attgcactga gaataaagct gatatatgtg ctgtagatgg tgcacttgca     1860
tttttggttg gcactcttac ttaccggagc cagacaaaca ctttagccat tattgaaagt     1920
ggaggtggga tattacggaa tgtgtccagc ttgatagcta caaatgagga ccacaggcaa     1980
atcctaagag agaacaactg tctacaaact ttattacaac acttaaaatc tcatagtttg     2040
acaatagtca gtaatgcatg tggaactttg tggaatctct cagcaagaaa tcctaaagac     2100
caggaagcat tatgggacat gggggcagtt agcatgctca agaacctcat tcattcaaag     2160
cacaaaatga ttgctatggg aagtgctgca gctttaagga atctcatggc aaataggcct     2220
gcgaagtaca aggatgccaa tattatgtct cctggctcaa gcttgccatc tcttcatgtt     2280
aggaaacaaa aagccctaga agcagaatta gatgctcagc acttatcaga aacttttgac     2340
aatatagaca atttaagtcc caaggcatct catcgtagta agcagagaca caagcaaagt     2400
ctctatggtg attatgtttt tgacaccaat cgacatgatg ataataggtc agacaatttt     2460
```

```
aatactggca acatgactgt cctttcacca tatttgaata ctacagtgtt acccagctcc   2520
tcttcatcaa gaggaagctt agatagttct cgttctgaaa agatagaag tttggagaga    2580 gaacgcggaa ttggtctagg caactaccat ccagcaacag aaaatccagg aacttcttca   2640
aagcgaggtt tgcagatctc caccactgca gcccagattg ccaaagtcat ggaagaagtg   2700
tcagccattc atacctctca ggaagacaga agttctgggt ctaccactga attacattgt   2760
gtgacagatg agagaaatgc acttagaaga agctctgctg cccatacaca ttcaaacact   2820
tacaatttca ctaagtcgga aaattcaaat aggacatgtt ctatgcctta tgccaaatta   2880
gaatacaaga gatcttcaaa tgatagttta aatagtgtca gtagtagtga tggttatggt   2940
aaaagaggtc aaatgaaacc ctcgattgaa tcctattctg aagatgatga agtaagttt    3000 tgcagttatg gtcaataccc agccgaccta gcccataaaa tacatagtgc aaatcatatg   3060
gatgataatg atggagaact agatacacca ataaattata gtcttaaata ttcagatgag   3120
cagttgaact ctgaaggca aagtccttca cagaatgaaa gatgggcaag acccaaacac    3180
ataatagaag atgaaataaa acaaagtgag caaagacaat caaggaatca agtacaact    3240 tatcctgttt atactgagag cactgatgat aaacacctca gttccaacc acattttgga    3300 cagcaggaat gtgtttctcc atacaggtca cggggagcca atggttcaga aacaaatcga   3360
gtgggttcta atcatggaat taatcaaaat gtaagccagt cttttgtgtca agaagatgac  3420 tatgaagatg ataagcctac caattatagt gaacgttact ctgaagaaga acagcatgaa   3480
gaagaagaga gaccaacaaa ttatagcata aaatataatg aagagaaacg tcatgtggat   3540
cagcctattg attatagttt aaaatatgcc acagatattc cttcatcaca gaaacagtca   3600
ttttcattct caaagagttc atctggacaa agcagtaaaa ccgaacatat gtcttcaagc   3660
agtgagaata cgtccacacc ttcatctaat gccaagaggc agaatcagct ccatccaagt   3720
tctgcacaga gtagaagtgg tcagcctcaa aaggctgcca cttgcaaagt tcttctatt    3780 aaccaagaaa caatacagac ttattgtgta gaagatactc caatatgttt ttcaagatgt   3840
agttcattat catctttgtc atcagctgaa gatgaaatag gatgtaatca gacgacacag   3900
gaagcagatt ctgctaatac cctgcaaata gcagaaataa aagaaaagat tggaactagg   3960
tcagctgaag atcctgtgag cgaagttcca gcagtgtcac agcaccctag aaccaaatcc   4020
agcagactgc agggttctag tttatcttca gaatcagcca ggcacaaagc tgttgaattt   4080
tcttcaggag cgaaatctcc ctccaaaagt ggtgctcaga cacccaaaag tccacctgaa   4140
cactatgttc aggagacccc actcatgttt agcagatgta cttctgtcag ttcacttgat   4200
agttttgaga gtcgttcgat tgccagctcc gttcagagtg aaccatgcag tggaatggta   4260
agtggcatta taagccccag tgatcttcca gatagccctg gacaaaccat gccaccaagc   4320
agaagtaaaa cacctccacc acctcctcaa acagctcaaa ccaagcgaga agtacctaaa   4380
aataaagcac ctactgctga aaagagagag agtggaccta gcaagctgc agtaaatgct    4440 gcagttcaga gggtccaggt tcttccagat gctgatactt tattacattt tgccacggaa   4500
agtactccag atggattttc ttgttcatcc agcctgagtg ctctgagcct cgatgagcca   4560
tttatacaga aagatgtgga attaagaata atgcctccag ttcaggaaaa tgacaatggg   4620
aatgaaacag aatcagagca gcctaaagaa tcaaatgaaa accaagagaa agaggcagaa   4680
aaaactattg attctgaaaa ggacctatta gatgattcag atgatgatga tattgaaata   4740
ctagaagaat gtattatttc tgccatgcca acaaagtcat cacgtaaagc aaaaaagcca   4800
gcccagactg cttcaaaatt acctccacct gtggcaagga aaccaagtca gctgcctgtg   4860
```

```
tacaaacttc taccatcaca aaacaggttg caacccccaaa agcatgttag ttttacaccg    4920
ggggatgata tgccacgggt gtattgtgtt gaagggacac ctataaactt ttccacagct    4980
acatctctaa gtgatctaac aatcgaatcc cctccaaatg agttagctgc tggagaagga    5040
gttagaggag gagcacagtc aggtgaattt gaaaaacgag ataccattcc tacagaaggc    5100
agaagtacag atgaggctca aggaggaaaa acctcatctg taaccatacc tgaattggat    5160
gacaataaag cagaggaagg tgatattctt gcagaatgca ttaattctgc tatgcccaaa    5220
gggaaaagtc acaagccttt ccgtgtgaaa aagataatgg accaggtcca gcaagcatct    5280
gcgtcgtctt ctgcacccaa caaaaatcag ttagatggta agaaaaagaa accaacttca    5340
ccagtaaaac ctataccaca aaatactgaa tataggacac gtgtaagaaa aaatgcagac    5400
tcaaaaaata atttaaatgc tgagagagtt ttctcagaca caaagattc aaagaaacag    5460 aatttgaaaa ataattccaa ggacttcaat gataagctcc caaataatga agatagagtc    5520
agaggaagtt ttgcttttga ttcacctcat cattacacgc ctattgaagg aactccttac    5580 tgttttcac gaaatgattc tttgagttct ctagattttg atgatgatga tgttgacctt    5640
tccagggaaa aggctgaatt aagaaaggca aagaaaata aggaatcaga ggctaaagtt    5700
accagccaca cagaactaac ctccaaccaa caatcagcta ataagacaca agctattgca    5760
aagcagccaa taaatcgagg tcagcctaaa cccatacttc agaaacaatc cacttttccc    5820
cagtcatcca aagacatacc agacagaggg gcagcaactg atgaaaagtt acagaatttt    5880
gctattgaaa atactccagt ttgcttttct cataattcct ctctgagttc tctcagtgac    5940
attgaccaag aaaacaacaa taaagaaaat gaacctatca aagagactga gcccctgac    6000 tcacaggag aaccaagtaa acctcaagca tcaggctatg ctcctaaatc atttcatgtt    6060
gaagataccc cagtttgttt ctcaagaaac agttctctca gttctcttag tattgactct    6120
gaagatgacc tgttgcagga atgtataagc tccgcaatgc caaaaaagaa aaagccttca    6180
agactcaagg gtgataatga aaaacatagt cccagaaata tgggtggcat attaggtgaa    6240
gatctgacac ttgatttgaa agatatacag agaccagatt cagaacatgg tctatcccct    6300
gattcagaaa attttgattg gaaagctatt caggaaggtg caaattccat agtaagtagt    6360
ttacatcaag ctgctgctgc tgcatgttta tctagacaag cttcgtctga ttcagattcc    6420
atcctttccc tgaaatcagg aatctctctg ggatcaccat ttcatcttac acctgatcaa    6480
gaagaaaaac cctttacaag taataaaggc ccacgaattc taaaaccagg ggagaaaagt    6540
acattggaaa ctaaaaagat agaatctgaa agtaaaggaa tcaaaggagg aaaaaaagtt    6600
tataaaagtt tgattactgg aaaagttcga tctaattcag aaatttcagg ccaaatgaaa    6660
cagccccttc aagcaaacat gccttcaatc tctcgaggca ggacaatgat tcatattcca    6720
ggagttcgaa atagctcctc aagtacaagt cctgtttcta aaaaaggccc accccttaag    6780
actccagcct ccaaaagccc tagtgaaggt caaacagcca ccacttctcc tagaggagcc    6840
aagccatctg tgaaatcaga attaagccct gttgccaggc agacatccca aataggtggg    6900
tcaagtaaag cacttctag atcaggatct agagattcga ccccttcaag acctgcccag    6960
caaccattaa gtagacctat acagtctcct ggccgaaact caatttcccc tggtagaaat    7020
ggaataagtc ctcctaacaa attatctcaa cttccaagga catcatcccc tagtactgct    7080
tcaactaagt cctcaggttc tggaaaaatg tcatatacat ctccaggtag acagatgagc    7140
caacagaacc ttaccaaaca aacaggttta tccaagaatg ccagtagtat tccaagaagt    7200
gagtctgcct ccaaaggact aaatcagatg aataatggta atggagccaa taaaaaggta    7260
```

```
gaactttcta gaatgtcttc aactaaatca agtggaagtg aatctgatag atcagaaaga    7320
cctgtattag tacgccagtc aactttcatc aaagaagctc caagcccaac cttaagaaga    7380
aaattggagg aatctgcttc atttgaatct ctttctccat catctagacc agcttctccc    7440
actaggtccc aggcacaaac tccagtttta agtccttccc ttcctgatat gtctctatcc    7500
acacattcgt ctgttcaggc tggtggatgg cgaaaactcc cacctaatct cagtcccact    7560
atagagtata atgatggaag accagcaaag cgccatgata ttgcacggtc tcattctgaa    7620
agtccttcta gacttccaat caataggtca ggaacctgga acgtgagca cagcaaacat    7680 tcatcatccc ttcctcgagt aagcacttgg agaagaactg gaagttcatc ttcaattctt    7740
tctgcttcat cagaatccag tgaaaaagca aaagtgagg atgaaaaaca tgtgaactct    7800
atttcaggaa ccaaacaaag taagaaaaac caagtatccg caaaaggaac atggagaaaa    7860
ataaaagaaa atgaatttc tcccacaaat agtacttctc agaccgtttc ctcaggtgct    7920
acaaatggtg ctgaatcaaa gactctaatt tatcaaatgg cacctgctgt ttctaaaaca    7980
gaggatgttt gggtgagaat tgaggactgt cccattaaca atcctagatc tggaagatct    8040
cccacaggta atactccccc ggtgattgac agtgtttcag aaaaggcaaa tccaaacatt    8100
aaagattcaa aagataatca ggcaaaacaa aatgtgggta atggcagtgt tcccatgcgt    8160
accgtgggtt tggaaaatcg cctgaactcc tttattcagg tggatgcccc tgaccaaaaa    8220
ggaactgaga taaaccagg acaaaataat cctgtccctg tatcagagac taatgaaagt    8280
tctatagtgg aacgtacccc attcagttct agcagctcaa gcaaacacag ttcacctagt    8340
gggactgttg ctgccagagt gactccttt aattacaacc caagccctag gaaaagcagc    8400
gcagatagca cttcagctcg gccatctcag atcccaactc cagtgaataa caacacaaag    8460
aagcgagatt ccaaaactga cagcacagaa tccagtggaa cccaaagtcc taagcgccat    8520
tctgggtctt accttgtgac atctgtttaa aagagaggaa gaatgaaact aagaaaattc    8580
tatgttaatt acaactgcta tatagacatt ttgtttcaaa tgaaacttta aaagactgaa    8640
aaattttgta aataggtttg attcttgtta gagggtttt gttctggaag ccatatttga    8700
tagtatactt tgtcttcact ggtcttattt tgggaggcac tcttgatggt taggaaaaaa    8760
atagtaaagc caagtatgtt tgtacagtat gttttacatg tatttaaagt agcacccatc    8820
ccaacttcct ttaattattg cttgtcttaa aataatgaac actacagata gaaaatatga    8880
tatattgctg ttatcaatca tttctagatt ataaactgac taaacttaca tcagggaaaa    8940
attggtattt atgcaaaaaa aaatgttttt gt                                  8972

<210> SEQ ID NO 21
<211> LENGTH: 2843
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 21

Met Ala Ala Ala Ser Tyr Asp Gln Leu Leu Lys Gln Val Glu Ala Leu
1               5                   10                  15

Lys Met Glu Asn Ser Asn Leu Arg Gln Glu Leu Glu Asp Asn Ser Asn
            20                  25                  30

His Leu Thr Lys Leu Glu Thr Glu Ala Ser Asn Met Lys Glu Val Leu
        35                  40                  45

Lys Gln Leu Gln Gly Ser Ile Glu Asp Glu Ala Met Ala Ser Ser Gly
```

```
                50                  55                  60
Gln Ile Asp Leu Leu Glu Arg Leu Lys Glu Leu Asn Leu Asp Ser Ser
 65                  70                  75                  80

Asn Phe Pro Gly Val Lys Leu Arg Ser Lys Met Ser Leu Arg Ser Tyr
                 85                  90                  95

Gly Ser Arg Glu Gly Ser Val Ser Ser Arg Ser Gly Glu Cys Ser Pro
                100                 105                 110

Val Pro Met Gly Ser Phe Pro Arg Arg Gly Phe Val Asn Gly Ser Arg
                115                 120                 125

Glu Ser Thr Gly Tyr Leu Glu Glu Leu Glu Lys Glu Arg Ser Leu Leu
                130                 135                 140

Leu Ala Asp Leu Asp Lys Glu Glu Lys Glu Lys Asp Trp Tyr Tyr Ala
145                 150                 155                 160

Gln Leu Gln Asn Leu Thr Lys Arg Ile Asp Ser Leu Pro Leu Thr Glu
                165                 170                 175

Asn Phe Ser Leu Gln Thr Asp Met Thr Arg Arg Gln Leu Glu Tyr Glu
                180                 185                 190

Ala Arg Gln Ile Arg Val Ala Met Glu Glu Gln Leu Gly Thr Cys Gln
                195                 200                 205

Asp Met Glu Lys Arg Ala Gln Arg Arg Ile Ala Arg Ile Gln Gln Ile
                210                 215                 220

Glu Lys Asp Ile Leu Arg Ile Arg Gln Leu Leu Gln Ser Gln Ala Thr
225                 230                 235                 240

Glu Ala Glu Arg Ser Ser Gln Asn Lys His Glu Thr Gly Ser His Asp
                245                 250                 255

Ala Glu Arg Gln Asn Glu Gly Gln Gly Val Gly Glu Ile Asn Met Ala
                260                 265                 270

Thr Ser Gly Asn Gly Gln Gly Ser Thr Thr Arg Met Asp His Glu Thr
                275                 280                 285

Ala Ser Val Leu Ser Ser Ser Thr His Ser Ala Pro Arg Arg Leu
                290                 295                 300

Thr Ser His Leu Gly Thr Lys Val Glu Met Val Tyr Ser Leu Leu Ser
305                 310                 315                 320

Met Leu Gly Thr His Asp Lys Asp Asp Met Ser Arg Thr Leu Leu Ala
                325                 330                 335

Met Ser Ser Ser Gln Asp Ser Cys Ile Ser Met Arg Gln Ser Gly Cys
                340                 345                 350

Leu Pro Leu Leu Ile Gln Leu Leu His Gly Asn Asp Lys Asp Ser Val
                355                 360                 365

Leu Leu Gly Asn Ser Arg Gly Ser Lys Glu Ala Arg Ala Arg Ala Ser
                370                 375                 380

Ala Ala Leu His Asn Ile Ile His Ser Gln Pro Asp Asp Lys Arg Gly
385                 390                 395                 400

Arg Arg Glu Ile Arg Val Leu His Leu Leu Glu Gln Ile Arg Ala Tyr
                405                 410                 415

Cys Glu Thr Cys Trp Glu Trp Gln Glu Ala His Glu Pro Gly Met Asp
                420                 425                 430

Gln Asp Lys Asn Pro Met Pro Ala Pro Val Glu His Gln Ile Cys Pro
                435                 440                 445

Ala Val Cys Val Leu Met Lys Leu Ser Phe Asp Glu Glu His Arg His
                450                 455                 460

Ala Met Asn Glu Leu Gly Gly Leu Gln Ala Ile Ala Glu Leu Leu Gln
465                 470                 475                 480
```

```
Val Asp Cys Glu Met Tyr Gly Leu Thr Asn Asp His Tyr Ser Ile Thr
                485                 490                 495

Leu Arg Arg Tyr Ala Gly Met Ala Leu Thr Asn Leu Thr Phe Gly Asp
            500                 505                 510

Val Ala Asn Lys Ala Thr Leu Cys Ser Met Lys Gly Cys Met Arg Ala
        515                 520                 525

Leu Val Ala Gln Leu Lys Ser Glu Ser Glu Asp Leu Gln Gln Val Ile
    530                 535                 540

Ala Ser Val Leu Arg Asn Leu Ser Trp Arg Ala Asp Val Asn Ser Lys
545                 550                 555                 560

Lys Thr Leu Arg Glu Val Gly Ser Val Lys Ala Leu Met Glu Cys Ala
                565                 570                 575

Leu Glu Val Lys Lys Glu Ser Thr Leu Lys Ser Val Leu Ser Ala Leu
            580                 585                 590

Trp Asn Leu Ser Ala His Cys Thr Glu Asn Lys Ala Asp Ile Cys Ala
        595                 600                 605

Val Asp Gly Ala Leu Ala Phe Leu Val Gly Thr Leu Thr Tyr Arg Ser
    610                 615                 620

Gln Thr Asn Thr Leu Ala Ile Ile Glu Ser Gly Gly Gly Ile Leu Arg
625                 630                 635                 640

Asn Val Ser Ser Leu Ile Ala Thr Asn Glu Asp His Arg Gln Ile Leu
                645                 650                 655

Arg Glu Asn Asn Cys Leu Gln Thr Leu Leu Gln His Leu Lys Ser His
            660                 665                 670

Ser Leu Thr Ile Val Ser Asn Ala Cys Gly Thr Leu Trp Asn Leu Ser
        675                 680                 685

Ala Arg Asn Pro Lys Asp Gln Glu Ala Leu Trp Asp Met Gly Ala Val
    690                 695                 700

Ser Met Leu Lys Asn Leu Ile His Ser Lys His Lys Met Ile Ala Met
705                 710                 715                 720

Gly Ser Ala Ala Ala Leu Arg Asn Leu Met Ala Asn Arg Pro Ala Lys
                725                 730                 735

Tyr Lys Asp Ala Asn Ile Met Ser Pro Gly Ser Ser Leu Pro Ser Leu
            740                 745                 750

His Val Arg Lys Gln Lys Ala Leu Glu Ala Glu Leu Asp Ala Gln His
        755                 760                 765

Leu Ser Glu Thr Phe Asp Asn Ile Asp Asn Leu Ser Pro Lys Ala Ser
    770                 775                 780

His Arg Ser Lys Gln Arg His Lys Gln Ser Leu Tyr Gly Asp Tyr Val
785                 790                 795                 800

Phe Asp Thr Asn Arg His Asp Asp Asn Arg Ser Asp Asn Phe Asn Thr
                805                 810                 815

Gly Asn Met Thr Val Leu Ser Pro Tyr Leu Asn Thr Thr Val Leu Pro
            820                 825                 830

Ser Ser Ser Ser Ser Arg Gly Ser Leu Asp Ser Ser Arg Ser Glu Lys
        835                 840                 845

Asp Arg Ser Leu Glu Arg Glu Arg Gly Ile Gly Leu Gly Asn Tyr His
    850                 855                 860

Pro Ala Thr Glu Asn Pro Gly Thr Ser Ser Lys Arg Gly Leu Gln Ile
865                 870                 875                 880

Ser Thr Thr Ala Ala Gln Ile Ala Lys Val Met Glu Glu Val Ser Ala
                885                 890                 895

Ile His Thr Ser Gln Glu Asp Arg Ser Ser Gly Ser Thr Thr Glu Leu
            900                 905                 910
```

```
His Cys Val Thr Asp Glu Arg Asn Ala Leu Arg Arg Ser Ser Ala Ala
            915                 920                 925

His Thr His Ser Asn Thr Tyr Asn Phe Thr Lys Ser Glu Asn Ser Asn
            930                 935                 940

Arg Thr Cys Ser Met Pro Tyr Ala Lys Leu Glu Tyr Lys Arg Ser Ser
945                 950                 955                 960

Asn Asp Ser Leu Asn Ser Val Ser Ser Asp Gly Tyr Gly Lys Arg
            965                 970                 975

Gly Gln Met Lys Pro Ser Ile Glu Ser Tyr Ser Glu Asp Glu Ser
            980                 985                 990

Lys Phe Cys Ser Tyr Gly Gln Tyr Pro Ala Asp Leu Ala His Lys Ile
            995                 1000                1005

His Ser Ala Asn His Met Asp Asp Asn Asp Gly Glu Leu Asp Thr Pro
            1010                1015                1020

Ile Asn Tyr Ser Leu Lys Tyr Ser Asp Glu Gln Leu Asn Ser Gly Arg
1025                1030                1035                1040

Gln Ser Pro Ser Gln Asn Glu Arg Trp Ala Arg Pro Lys His Ile Ile
            1045                1050                1055

Glu Asp Glu Ile Lys Gln Ser Glu Gln Arg Gln Ser Arg Asn Gln Ser
            1060                1065                1070

Thr Thr Tyr Pro Val Tyr Thr Glu Ser Thr Asp Lys His Leu Lys
            1075                1080                1085

Phe Gln Pro His Phe Gly Gln Gln Glu Cys Val Ser Pro Tyr Arg Ser
            1090                1095                1100

Arg Gly Ala Asn Gly Ser Glu Thr Asn Arg Val Gly Ser Asn His Gly
1105                1110                1115                1120

Ile Asn Gln Asn Val Ser Gln Ser Leu Cys Gln Glu Asp Asp Tyr Glu
            1125                1130                1135

Asp Asp Lys Pro Thr Asn Tyr Ser Glu Arg Tyr Ser Glu Glu Gln
            1140                1145                1150

His Glu Glu Glu Arg Pro Thr Asn Tyr Ser Ile Lys Tyr Asn Glu
            1155                1160                1165

Glu Lys Arg His Val Asp Gln Pro Ile Asp Tyr Ser Leu Lys Tyr Ala
            1170                1175                1180

Thr Asp Ile Pro Ser Ser Gln Lys Gln Ser Phe Ser Phe Ser Lys Ser
1185                1190                1195                1200

Ser Ser Gly Gln Ser Ser Lys Thr Glu His Met Ser Ser Ser Glu
            1205                1210                1215

Asn Thr Ser Thr Pro Ser Ser Asn Ala Lys Arg Gln Asn Gln Leu His
            1220                1225                1230

Pro Ser Ser Ala Gln Ser Arg Ser Gly Gln Pro Gln Lys Ala Ala Thr
            1235                1240                1245

Cys Lys Val Ser Ser Ile Asn Gln Glu Thr Ile Gln Thr Tyr Cys Val
            1250                1255                1260

Glu Asp Thr Pro Ile Cys Phe Ser Arg Cys Ser Ser Leu Ser Ser Leu
1265                1270                1275                1280

Ser Ser Ala Glu Asp Glu Ile Gly Cys Asn Gln Thr Thr Gln Glu Ala
            1285                1290                1295

Asp Ser Ala Asn Thr Leu Gln Ile Ala Glu Ile Lys Glu Lys Ile Gly
            1300                1305                1310

Thr Arg Ser Ala Glu Asp Pro Val Ser Glu Val Pro Ala Val Ser Gln
            1315                1320                1325

His Pro Arg Thr Lys Ser Ser Arg Leu Gln Gly Ser Ser Leu Ser Ser
```

```
              1330          1335          1340
Glu Ser Ala Arg His Lys Ala Val Glu Phe Ser Ser Gly Ala Lys Ser
1345              1350              1355              1360

Pro Ser Lys Ser Gly Ala Gln Thr Pro Lys Ser Pro Glu His Tyr
              1365              1370              1375

Val Gln Glu Thr Pro Leu Met Phe Ser Arg Cys Thr Ser Val Ser Ser
              1380              1385              1390

Leu Asp Ser Phe Glu Ser Arg Ser Ile Ala Ser Val Gln Ser Glu
          1395              1400              1405

Pro Cys Ser Gly Met Val Ser Gly Ile Ile Ser Pro Ser Asp Leu Pro
    1410              1415              1420

Asp Ser Pro Gly Gln Thr Met Pro Pro Ser Arg Ser Lys Thr Pro Pro
1425              1430              1435              1440

Pro Pro Pro Gln Thr Ala Gln Thr Lys Arg Glu Val Pro Lys Asn Lys
              1445              1450              1455

Ala Pro Thr Ala Glu Lys Arg Glu Ser Gly Pro Lys Gln Ala Ala Val
              1460              1465              1470

Asn Ala Ala Val Gln Arg Val Gln Val Leu Pro Asp Ala Asp Thr Leu
          1475              1480              1485

Leu His Phe Ala Thr Glu Ser Thr Pro Asp Gly Phe Ser Cys Ser Ser
    1490              1495              1500

Ser Leu Ser Ala Leu Ser Leu Asp Glu Pro Phe Ile Gln Lys Asp Val
1505              1510              1515              1520

Glu Leu Arg Ile Met Pro Pro Val Gln Glu Asn Asp Asn Gly Asn Glu
              1525              1530              1535

Thr Glu Ser Glu Gln Pro Lys Glu Ser Asn Glu Asn Gln Glu Lys Glu
              1540              1545              1550

Ala Glu Lys Thr Ile Asp Ser Glu Lys Asp Leu Leu Asp Asp Ser Asp
          1555              1560              1565

Asp Asp Asp Ile Glu Ile Leu Glu Glu Cys Ile Ile Ser Ala Met Pro
    1570              1575              1580

Thr Lys Ser Ser Arg Lys Ala Lys Lys Pro Ala Gln Thr Ala Ser Lys
1585              1590              1595              1600

Leu Pro Pro Pro Val Ala Arg Lys Pro Ser Gln Leu Pro Val Tyr Lys
              1605              1610              1615

Leu Leu Pro Ser Gln Asn Arg Leu Gln Pro Gln Lys His Val Ser Phe
          1620              1625              1630

Thr Pro Gly Asp Asp Met Pro Arg Val Tyr Cys Val Glu Gly Thr Pro
    1635              1640              1645

Ile Asn Phe Ser Thr Ala Thr Ser Leu Ser Asp Leu Thr Ile Glu Ser
1650              1655              1660

Pro Pro Asn Glu Leu Ala Ala Gly Glu Gly Val Arg Gly Gly Ala Gln
1665              1670              1675              1680

Ser Gly Glu Phe Glu Lys Arg Asp Thr Ile Pro Thr Glu Gly Arg Ser
          1685              1690              1695

Thr Asp Glu Ala Gln Gly Gly Lys Thr Ser Ser Val Thr Ile Pro Glu
              1700              1705              1710

Leu Asp Asp Asn Lys Ala Glu Glu Gly Asp Ile Leu Ala Glu Cys Ile
          1715              1720              1725

Asn Ser Ala Met Pro Lys Gly Lys Ser His Lys Pro Phe Arg Val Lys
    1730              1735              1740

Lys Ile Met Asp Gln Val Gln Gln Ala Ser Ala Ser Ser Ser Ala Pro
1745              1750              1755              1760
```

-continued

```
Asn Lys Asn Gln Leu Asp Gly Lys Lys Lys Pro Thr Ser Pro Val
            1765                1770                1775
Lys Pro Ile Pro Gln Asn Thr Glu Tyr Arg Thr Arg Val Arg Lys Asn
        1780                1785                1790
Ala Asp Ser Lys Asn Asn Leu Asn Ala Glu Arg Val Phe Ser Asp Asn
        1795                1800                1805
Lys Asp Ser Lys Gln Asn Leu Lys Asn Asn Ser Lys Asp Phe Asn
    1810                1815                1820
Asp Lys Leu Pro Asn Asn Glu Asp Arg Val Arg Gly Ser Phe Ala Phe
1825                1830                1835                1840
Asp Ser Pro His His Tyr Thr Pro Ile Glu Gly Thr Pro Tyr Cys Phe
            1845                1850                1855
Ser Arg Asn Asp Ser Leu Ser Ser Leu Asp Phe Asp Asp Asp Val
        1860                1865                1870
Asp Leu Ser Arg Glu Lys Ala Glu Leu Arg Lys Ala Lys Glu Asn Lys
        1875                1880                1885
Glu Ser Glu Ala Lys Val Thr Ser His Thr Glu Leu Thr Ser Asn Gln
        1890                1895                1900
Gln Ser Ala Asn Lys Thr Gln Ala Ile Ala Lys Gln Pro Ile Asn Arg
1905                1910                1915                1920
Gly Gln Pro Lys Pro Ile Leu Gln Lys Gln Ser Thr Phe Pro Gln Ser
            1925                1930                1935
Ser Lys Asp Ile Pro Asp Arg Gly Ala Ala Thr Asp Glu Lys Leu Gln
            1940                1945                1950
Asn Phe Ala Ile Glu Asn Thr Pro Val Cys Phe Ser His Asn Ser Ser
        1955                1960                1965
Leu Ser Ser Leu Ser Asp Ile Asp Gln Glu Asn Asn Asn Lys Glu Asn
    1970                1975                1980
Glu Pro Ile Lys Glu Thr Glu Pro Pro Asp Ser Gln Gly Glu Pro Ser
1985                1990                1995                2000
Lys Pro Gln Ala Ser Gly Tyr Ala Pro Lys Ser Phe His Val Glu Asp
            2005                2010                2015
Thr Pro Val Cys Phe Ser Arg Asn Ser Ser Leu Ser Ser Leu Ser Ile
            2020                2025                2030
Asp Ser Glu Asp Asp Leu Leu Gln Glu Cys Ile Ser Ser Ala Met Pro
        2035                2040                2045
Lys Lys Lys Lys Pro Ser Arg Leu Lys Gly Asp Asn Glu Lys His Ser
    2050                2055                2060
Pro Arg Asn Met Gly Gly Ile Leu Gly Glu Asp Leu Thr Leu Asp Leu
2065                2070                2075                2080
Lys Asp Ile Gln Arg Pro Asp Ser Glu His Gly Leu Ser Pro Asp Ser
            2085                2090                2095
Glu Asn Phe Asp Trp Lys Ala Ile Gln Glu Gly Ala Asn Ser Ile Val
            2100                2105                2110
Ser Ser Leu His Gln Ala Ala Ala Ala Cys Leu Ser Arg Gln Ala
        2115                2120                2125
Ser Ser Asp Ser Asp Ser Ile Leu Ser Leu Lys Ser Gly Ile Ser Leu
        2130                2135                2140
Gly Ser Pro Phe His Leu Thr Pro Asp Gln Glu Glu Lys Pro Phe Thr
2145                2150                2155                2160
Ser Asn Lys Gly Pro Arg Ile Leu Lys Pro Gly Glu Lys Ser Thr Leu
            2165                2170                2175
Glu Thr Lys Lys Ile Glu Ser Glu Ser Lys Gly Ile Lys Gly Gly Lys
            2180                2185                2190
```

```
Lys Val Tyr Lys Ser Leu Ile Thr Gly Lys Val Arg Ser Asn Ser Glu
            2195                2200                2205

Ile Ser Gly Gln Met Lys Gln Pro Leu Gln Ala Asn Met Pro Ser Ile
    2210                2215                2220

Ser Arg Gly Arg Thr Met Ile His Ile Pro Gly Val Arg Asn Ser Ser
2225                2230                2235                2240

Ser Ser Thr Ser Pro Val Ser Lys Lys Gly Pro Pro Leu Lys Thr Pro
            2245                2250                2255

Ala Ser Lys Ser Pro Ser Glu Gly Gln Thr Ala Thr Thr Ser Pro Arg
    2260                2265                2270

Gly Ala Lys Pro Ser Val Lys Ser Glu Leu Ser Pro Val Ala Arg Gln
        2275                2280                2285

Thr Ser Gln Ile Gly Gly Ser Ser Lys Ala Pro Ser Arg Ser Gly Ser
    2290                2295                2300

Arg Asp Ser Thr Pro Ser Arg Pro Ala Gln Gln Pro Leu Ser Arg Pro
2305                2310                2315                2320

Ile Gln Ser Pro Gly Arg Asn Ser Ile Ser Pro Gly Arg Asn Gly Ile
            2325                2330                2335

Ser Pro Pro Asn Lys Leu Ser Gln Leu Pro Arg Thr Ser Ser Pro Ser
        2340                2345                2350

Thr Ala Ser Thr Lys Ser Gly Ser Gly Lys Met Ser Tyr Thr Ser
        2355                2360                2365

Pro Gly Arg Gln Met Ser Gln Gln Asn Leu Thr Lys Gln Thr Gly Leu
    2370                2375                2380

Ser Lys Asn Ala Ser Ser Ile Pro Arg Ser Glu Ser Ala Ser Lys Gly
2385                2390                2395                2400

Leu Asn Gln Met Asn Asn Gly Asn Gly Ala Asn Lys Lys Val Glu Leu
            2405                2410                2415

Ser Arg Met Ser Ser Thr Lys Ser Ser Gly Ser Glu Ser Asp Arg Ser
        2420                2425                2430

Glu Arg Pro Val Leu Val Arg Gln Ser Thr Phe Ile Lys Glu Ala Pro
    2435                2440                2445

Ser Pro Thr Leu Arg Arg Lys Leu Glu Glu Ser Ala Ser Phe Glu Ser
    2450                2455                2460

Leu Ser Pro Ser Ser Arg Pro Ala Ser Pro Thr Arg Ser Gln Ala Gln
2465                2470                2475                2480

Thr Pro Val Leu Ser Pro Ser Leu Pro Asp Met Ser Leu Ser Thr His
            2485                2490                2495

Ser Ser Val Gln Ala Gly Gly Trp Arg Lys Leu Pro Pro Asn Leu Ser
        2500                2505                2510

Pro Thr Ile Glu Tyr Asn Asp Gly Arg Pro Ala Lys Arg His Asp Ile
            2515                2520                2525

Ala Arg Ser His Ser Glu Ser Pro Ser Arg Leu Pro Ile Asn Arg Ser
    2530                2535                2540

Gly Thr Trp Lys Arg Glu His Ser Lys His Ser Ser Ser Leu Pro Arg
2545                2550                2555                2560

Val Ser Thr Trp Arg Arg Thr Gly Ser Ser Ser Ser Ile Leu Ser Ala
            2565                2570                2575

Ser Ser Glu Ser Ser Glu Lys Ala Lys Ser Glu Asp Glu Lys His Val
        2580                2585                2590

Asn Ser Ile Ser Gly Thr Lys Gln Ser Lys Glu Asn Gln Val Ser Ala
            2595                2600                2605

Lys Gly Thr Trp Arg Lys Ile Lys Glu Asn Glu Phe Ser Pro Thr Asn
```

```
                  2610                  2615                 2620
Ser Thr Ser Gln Thr Val Ser Ser Gly Ala Thr Asn Gly Ala Glu Ser
2625                2630                2635                2640

Lys Thr Leu Ile Tyr Gln Met Ala Pro Ala Val Ser Lys Thr Glu Asp
              2645                2650                2655

Val Trp Val Arg Ile Glu Asp Cys Pro Ile Asn Asn Pro Arg Ser Gly
              2660                2665                2670

Arg Ser Pro Thr Gly Asn Thr Pro Pro Val Ile Asp Ser Val Ser Glu
              2675                2680                2685

Lys Ala Asn Pro Asn Ile Lys Asp Ser Lys Asn Gln Ala Lys Gln
        2690                2695                2700

Asn Val Gly Asn Gly Ser Val Pro Met Arg Thr Val Gly Leu Glu Asn
2705                2710                2715                2720

Arg Leu Asn Ser Phe Ile Gln Val Asp Ala Pro Asp Gln Lys Gly Thr
              2725                2730                2735

Glu Ile Lys Pro Gly Gln Asn Asn Pro Val Pro Val Ser Glu Thr Asn
              2740                2745                2750

Glu Ser Ser Ile Val Glu Arg Thr Pro Phe Ser Ser Ser Ser Ser
        2755                2760                2765

Lys His Ser Ser Pro Ser Gly Thr Val Ala Ala Arg Val Thr Pro Phe
         2770                2775                2780

Asn Tyr Asn Pro Ser Pro Arg Lys Ser Ser Ala Asp Ser Thr Ser Ala
2785                2790                2795                2800

Arg Pro Ser Gln Ile Pro Thr Pro Val Asn Asn Asn Thr Lys Lys Arg
              2805                2810                2815

Asp Ser Lys Thr Asp Ser Thr Glu Ser Ser Gly Thr Gln Ser Pro Lys
              2820                2825                2830

Arg His Ser Gly Ser Tyr Leu Val Thr Ser Val
              2835                2840

<210> SEQ ID NO 22
<211> LENGTH: 3625
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 22
ggccaccgga gcggcccggc gacgatcgct gacagcttcc cctgcccttc ccgtcggtcg    60
ggccgccagc cgccgcagcc ctcggcctgc acgcagccac cggccccgct cccggagccc   120
agcgccgccg aggccgcagc cgcccggcca gtaaggcggc gccgcccgcg gccaccgcgg   180
gccctgccgt tccctccgcc gcgctgcgcc atggcgcggc gctgactggc ctggcccggc   240
cccgccgcgc tcccgctcgc cccgacccgc actcgggccc gccgggctc cggcctgccg   300 ccgcctcttc cttctccagc cggcaggccc cgccgcttag gagggagagc ccacccgcgc   360
caggaggccg aacgcggact cgccacccgg cttcagaatg gcagaagatg atccatattt   420
gggaaggcct gaacaaatgt tcatttggga tccttctttg actcatacaa tatttaatcc   480
agaagtattt caaccacaga tggcactgcc aacagatggc ccataccttc aaatattaga   540
gcaacctaaa cagagaggat ttcgtttccg ttatgtatgt gaaggcccat ccatggtgg   600 actacctggt gcctctagtg aaaagaacaa gaagtcttac cctcaggtca aatctgcaa   660 ctatgtggga ccagcaaagg ttattgttca gttggtcaca aatggaaaaa atatccacct   720
gcatgcccac agcctggtgg aaaacactg tgaggatggg atctgcactg taactgctgg   780
```

```
acccaaggac atggtggtcg gcttcgcaaa cctgggtata cttcatgtga caaagaaaaa    840
agtatttgaa acactggaag cacgaatgac agaggcgtgt ataagggct ataatcctgg     900 actcttggtg cacccctgacc ttgcctattt gcaagcagaa ggtggagggg accggcagct   960
gggagatcgg gaaaaagagc taatccgcca agcagctctg cagcagacca aggagatgga  1020
cctcagcgtg gtgcggctca tgtttacagc ttttcttccg atagcactg gcagcttcac   1080 aaggcgcctg gaacccgtgg tatcagacgc catctatgac agtaaagccc ccaatgcatc  1140
caacttgaaa attgtaagaa tggacaggac agctggatgt gtgactggag ggaggaaat   1200 ttatcttctt tgtgacaaag ttcagaaaga tgacatccag attcgatttt atgaagagga  1260
agaaaatggt ggagtctggg aaggatttgg agatttttcc cccacagatg ttcatagaca  1320
atttgccatt gtcttcaaaa ctccaaagta taaagatatt aatattacaa aaccagcctc  1380
tgtgtttgtc cagcttcgga ggaaatctga cttggaaact agtgaaccaa aacctttcct  1440
ctactatcct gaaatcaaag ataaagaaga agtgcagagg aaacgtcaga agctcatgcc  1500 caattttcg gatagtttcg gcggtggtag tggtgccgga gctggaggcg gaggcatgtt  1560
tggtagtggc ggtggaggag ggggcactgg aagtacaggt ccagggtata gcttcccaca  1620
ctatggattt cctacttatg gtgggattac tttccatcct ggaactacta aatctaatgc  1680
tgggatgaag catggaacca tggacactga atctaaaaag gaccctgaag ttgtgacaa   1740 aagtgatgac aaaaacactg taaacctctt tgggaaagtt attgaaacca cagagcaaga  1800
tcaggagccc agcgaggcca ccgttgggaa tggtgaggtc actctaacgt atgcaacagg  1860
aacaaaagaa gagagtgctg gagttcagga taacctcttt ctagagaagg ctatgcagct  1920
tgcaaagagg catgccaatg ccctttcga ctacgcggtg acaggagacg tgaagatgct  1980
gctggccgtc cagcgccatc tcactgctgt gcaggatgag aatgggaca gtgtcttaca  2040 cttagcaatc atccaccttc attctcaact tgtgagggat ctactagaag tcacatctgg  2100
tttgatttct gatgacatta tcaacatgag aaatgatctg taccagacgc ccttgcactt  2160
ggcagtgatc actaagcagg aagatgtggt ggaggatttg ctgagggctg ggccgacct   2220 gagccttctg gaccgcttgg gtaactctgt tttgcaccta gctgccaaag aaggacatga  2280
taaagttctc agtatcttac tcaagcacaa aaaggcagca ctacttcttg accaccccaa  2340 cgggacggt ctgaatgcca ttcatctagc catgatgagc aatagcctgc catgtttgct   2400
gctgctggtg gccgctgggg ctgacgtcaa tgctcaggag cagaagtccg gcgcacagc   2460 actgcacctg gctgtggagc acgacaacat ctcattggca ggctgcctgc tcctggaggg  2520
tgatgcccat gtggacagta ctacctacga tggaaccaca cccctgcata tagcagctgg  2580
gagagggtcc accaggctgg cagctcttct caaagcagca ggagcagatc ccctggtgga  2640
gaactttgag cctctctatg acctggatga ctcttgggaa aatgcaggag aggatgaagg  2700
agttgtgcct ggaaccacgc ctctagatat ggccaccagc tggcaggtat ttgacatatt  2760
aaatgggaaa ccatatgagc cagagtttac atctgatgat ttactagcac aaggagacat  2820
gaaacagctg gctgaagatg tgaagctgca gctgtataag ttactagaaa ttcctgatcc  2880
agacaaaaac tgggctactc tggcgcagaa attaggtctg gggatactta ataatgcctt  2940
ccggctgagt cctgctcctt ccaaaacact tatgacaaac tatgaggtct ctgggggtac  3000
agtcagagag ctggtggagg ccctgagaca aatgggctac accgaagcaa ttgaagtgat  3060
ccaggcagcc tccagcccag tgaagaccac ctctcaggcc cactcgctgc ctctctcgcc  3120
tgcctccaca aggcagcaaa tagacgagct ccgagacagt gacagtgtct gcgacacggg  3180
```

-continued

```
cgtggagaca tccttccgca aactcagctt taccgagtct ctgaccagtg gtgcctcact    3240
gctaactctc aacaaaatgc cccatgatta tgggcaggaa ggacctctag aaggcaaaat    3300
ttagcctgct gacaatttcc cacaccgtgt aaaccaaagc cctaaaattc cactgcgttg    3360
tccacaagac agaagctgaa gtgcatccaa aggtgctcag agagccggcc cgcctgaatc    3420
attctcgatt taactcgaga ccttttcaac ttggcttcct ttcttggttc ataaatgaat    3480
tttagtttgg ttcacttaca gatagtatct agcaatcaca acactggctg agcggatgca    3540
tctggggatg aggttgctta ctaagctttg ccagctgctg ctggatcaca gctgctttct    3600
gttgtcattg ctgttgtccc tctgc                                          3625
```

<210> SEQ ID NO 23
<211> LENGTH: 968
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 23

```
Met Ala Glu Asp Asp Pro Tyr Leu Gly Arg Pro Glu Gln Met Phe His
  1               5                  10                  15

Leu Asp Pro Ser Leu Thr His Thr Ile Phe Asn Pro Glu Val Phe Gln
             20                  25                  30

Pro Gln Met Ala Leu Pro Thr Asp Gly Pro Tyr Leu Gln Ile Leu Glu
         35                  40                  45

Gln Pro Lys Gln Arg Gly Phe Arg Phe Arg Tyr Val Cys Glu Gly Pro
     50                  55                  60

Ser His Gly Gly Leu Pro Gly Ala Ser Ser Glu Lys Asn Lys Lys Ser
 65                  70                  75                  80

Tyr Pro Gln Val Lys Ile Cys Asn Tyr Val Gly Pro Ala Lys Val Ile
                 85                  90                  95

Val Gln Leu Val Thr Asn Gly Lys Asn Ile His Leu His Ala His Ser
            100                 105                 110

Leu Val Gly Lys His Cys Glu Asp Gly Ile Cys Thr Val Thr Ala Gly
        115                 120                 125

Pro Lys Asp Met Val Val Gly Phe Ala Asn Leu Gly Ile Leu His Val
    130                 135                 140

Thr Lys Lys Lys Val Phe Glu Thr Leu Glu Ala Arg Met Thr Glu Ala
145                 150                 155                 160

Cys Ile Arg Gly Tyr Asn Pro Gly Leu Leu Val His Pro Asp Leu Ala
                165                 170                 175

Tyr Leu Gln Ala Glu Gly Gly Gly Asp Arg Gln Leu Gly Asp Arg Glu
            180                 185                 190

Lys Glu Leu Ile Arg Gln Ala Ala Leu Gln Gln Thr Lys Glu Met Asp
        195                 200                 205

Leu Ser Val Val Arg Leu Met Phe Thr Ala Phe Leu Pro Asp Ser Thr
    210                 215                 220

Gly Ser Phe Thr Arg Arg Leu Glu Pro Val Val Ser Asp Ala Ile Tyr
225                 230                 235                 240

Asp Ser Lys Ala Pro Asn Ala Ser Asn Leu Lys Ile Val Arg Met Asp
                245                 250                 255

Arg Thr Ala Gly Cys Val Thr Gly Gly Glu Glu Ile Tyr Leu Leu Cys
            260                 265                 270

Asp Lys Val Gln Lys Asp Asp Ile Gln Ile Arg Phe Tyr Glu Glu Glu
```

```
                275                 280                 285
Glu Asn Gly Gly Val Trp Glu Gly Phe Gly Asp Phe Ser Pro Thr Asp
290                 295                 300

Val His Arg Gln Phe Ala Ile Val Phe Lys Thr Pro Lys Tyr Lys Asp
305                 310                 315                 320

Ile Asn Ile Thr Lys Pro Ala Ser Val Phe Val Gln Leu Arg Arg Lys
            325                 330                 335

Ser Asp Leu Glu Thr Ser Glu Pro Lys Pro Phe Leu Tyr Tyr Pro Glu
        340                 345                 350

Ile Lys Asp Lys Glu Glu Val Gln Arg Lys Arg Gln Lys Leu Met Pro
    355                 360                 365

Asn Phe Ser Asp Ser Phe Gly Gly Ser Gly Ala Gly Ala Gly Gly
370                 375                 380

Gly Gly Met Phe Gly Ser Gly Gly Gly Gly Thr Gly Ser Thr
385                 390                 395                 400

Gly Pro Gly Tyr Ser Phe Pro His Tyr Gly Phe Pro Thr Tyr Gly Gly
                405                 410                 415

Ile Thr Phe His Pro Gly Thr Thr Lys Ser Asn Ala Gly Met Lys His
            420                 425                 430

Gly Thr Met Asp Thr Glu Ser Lys Lys Asp Pro Glu Gly Cys Asp Lys
        435                 440                 445

Ser Asp Asp Lys Asn Thr Val Asn Leu Phe Gly Lys Val Ile Glu Thr
450                 455                 460

Thr Glu Gln Asp Gln Glu Pro Ser Glu Ala Thr Val Gly Asn Gly Glu
465                 470                 475                 480

Val Thr Leu Thr Tyr Ala Thr Gly Thr Lys Glu Glu Ser Ala Gly Val
                485                 490                 495

Gln Asp Asn Leu Phe Leu Glu Lys Ala Met Gln Leu Ala Lys Arg His
            500                 505                 510

Ala Asn Ala Leu Phe Asp Tyr Ala Val Thr Gly Asp Val Lys Met Leu
        515                 520                 525

Leu Ala Val Gln Arg His Leu Thr Ala Val Gln Asp Glu Asn Gly Asp
    530                 535                 540

Ser Val Leu His Leu Ala Ile Ile His Leu His Ser Gln Leu Val Arg
545                 550                 555                 560

Asp Leu Leu Glu Val Thr Ser Gly Leu Ile Ser Asp Asp Ile Ile Asn
                565                 570                 575

Met Arg Asn Asp Leu Tyr Gln Thr Pro Leu His Leu Ala Val Ile Thr
            580                 585                 590

Lys Gln Glu Asp Val Val Glu Asp Leu Leu Arg Ala Gly Ala Asp Leu
        595                 600                 605

Ser Leu Leu Asp Arg Leu Gly Asn Ser Val Leu His Leu Ala Ala Lys
    610                 615                 620

Glu Gly His Asp Lys Val Leu Ser Ile Leu Leu Lys His Lys Lys Ala
625                 630                 635                 640

Ala Leu Leu Leu Asp His Pro Asn Gly Asp Gly Leu Asn Ala Ile His
                645                 650                 655

Leu Ala Met Met Ser Asn Ser Leu Pro Cys Leu Leu Leu Val Ala
            660                 665                 670

Ala Gly Ala Asp Val Asn Ala Gln Glu Gln Lys Ser Gly Arg Thr Ala
        675                 680                 685

Leu His Leu Ala Val Glu His Asp Asn Ile Ser Leu Ala Gly Cys Leu
    690                 695                 700
```

Leu Leu Glu Gly Asp Ala His Val Asp Ser Thr Thr Tyr Asp Gly Thr
705                 710                 715                 720

Thr Pro Leu His Ile Ala Ala Gly Arg Gly Ser Thr Arg Leu Ala Ala
            725                 730                 735

Leu Leu Lys Ala Ala Gly Ala Asp Pro Leu Val Glu Asn Phe Glu Pro
        740                 745                 750

Leu Tyr Asp Leu Asp Asp Ser Trp Glu Asn Ala Gly Glu Asp Glu Gly
    755                 760                 765

Val Val Pro Gly Thr Thr Pro Leu Asp Met Ala Thr Ser Trp Gln Val
770                 775                 780

Phe Asp Ile Leu Asn Gly Lys Pro Tyr Glu Pro Glu Phe Thr Ser Asp
785                 790                 795                 800

Asp Leu Leu Ala Gln Gly Asp Met Lys Gln Leu Ala Glu Asp Val Lys
            805                 810                 815

Leu Gln Leu Tyr Lys Leu Leu Glu Ile Pro Asp Pro Asp Lys Asn Trp
        820                 825                 830

Ala Thr Leu Ala Gln Lys Leu Gly Leu Gly Ile Leu Asn Asn Ala Phe
    835                 840                 845

Arg Leu Ser Pro Ala Pro Ser Lys Thr Leu Met Asp Asn Tyr Glu Val
850                 855                 860

Ser Gly Gly Thr Val Arg Glu Leu Val Glu Ala Leu Arg Gln Met Gly
865                 870                 875                 880

Tyr Thr Glu Ala Ile Glu Val Ile Gln Ala Ala Ser Ser Pro Val Lys
            885                 890                 895

Thr Thr Ser Gln Ala His Ser Leu Pro Leu Ser Pro Ala Ser Thr Arg
        900                 905                 910

Gln Gln Ile Asp Glu Leu Arg Asp Ser Asp Ser Val Cys Asp Thr Gly
    915                 920                 925

Val Glu Thr Ser Phe Arg Lys Leu Ser Phe Thr Glu Ser Leu Thr Ser
930                 935                 940

Gly Ala Ser Leu Leu Thr Leu Asn Lys Met Pro His Asp Tyr Gly Gln
945                 950                 955                 960

Glu Gly Pro Leu Glu Gly Lys Ile
            965

<210> SEQ ID NO 24
<211> LENGTH: 306
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 24
gagtttagtt tgtcagtgta tcaaaaaatg aagtttaatg tggctatggg aactggagtt      60
ttagattggc taagaaacag tgatgatgat gaagacagcc aggaaaatgc tgataaaaat     120
gaagatggtg gggagaagaa catggaagac tcagggcatg aaacaggcat tgattcacag     180
tcccaaggct catttcaggc ccctcagccc tcacagtcct cacagtctgt tcataatcag     240
ccatatcaca tctgtagagg ttttacttgc tttaaaaaac cacctccccc tgaacctgaa     300
acataa                                                                306

<210> SEQ ID NO 25
<211> LENGTH: 101
<212> TYPE: PRT
<213> ORGANISM: Artificial Sequence
<220> FEATURE:

<223> OTHER INFORMATION: Description of Artificial Sequence:/Note =
      Synthetic Construct

<400> SEQUENCE: 25

Glu Phe Ser Leu Ser Val Tyr Gln Lys Met Lys Phe Asn Val Ala Met
1               5                   10                  15

Gly Thr Gly Val Leu Asp Trp Leu Arg Asn Ser Asp Asp Glu Asp
            20                  25                  30

Ser Gln Glu Asn Ala Asp Lys Asn Glu Asp Gly Gly Lys Asn Met
        35                  40                  45

Glu Asp Ser Gly His Glu Thr Gly Ile Asp Ser Gln Ser Gln Gly Ser
50                  55                  60

Phe Gln Ala Pro Gln Pro Ser Gln Ser Ser Gln Ser Val His Asn Gln
65                  70                  75                  80

Pro Tyr His Ile Cys Arg Gly Phe Thr Cys Phe Lys Lys Pro Pro Pro
                85                  90                  95

Pro Glu Pro Glu Thr
            100

<210> SEQ ID NO 26
<211> LENGTH: 480
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 26
ttccggtttt tctcagggga cgttgaaatt attttttgtaa cgggagtcgg gagaggacgg      60
ggcgtgcccc gcgtgcgcgc gcgtcgtcct ccccggcgct cctccacagc tcgctggctc     120
ccgccgcgga aaggcgtcat gccgcccaaa acccccccgaa aaacggccgc caccgccgcc    180
gctgccgccg cggaaccccc ggcaccgccg ccgccgcccc ctcctgagga ggacccagag     240
caggacagcg gcccggagga cctgcctctc gtcagggaa gtattacaaa tggaagatga      300
tctggtgatt tcatttcagt taatgctatg tgtccttgac tatttttatta aactctcacc    360 tcccatgttg ctcaaagaac catataaaac agctgttata cccattaatg gttcacctcg     420
aacacccagg cgaggtcaga acaggagtgc acggatagca aaacaactag aaaatgatac     480

<210> SEQ ID NO 27
<211> LENGTH: 53
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 27

Met Pro Pro Lys Thr Pro Arg Lys Thr Ala Ala Thr Ala Ala Ala
1               5                   10                  15

Ala Ala Glu Pro Pro Ala Pro Pro Pro Pro Pro Glu Glu Asp
            20                  25                  30

Pro Glu Gln Asp Ser Gly Pro Glu Asp Leu Pro Leu Val Arg Gly Ser
        35                  40                  45

Ile Thr Asn Gly Arg
    50

<210> SEQ ID NO 28
<211> LENGTH: 297
<212> TYPE: DNA

<213> ORGANISM: Artificial Sequence
<220> FEATURE:
<223> OTHER INFORMATION: Description of Artificial Sequence:/Note = Synthetic Construct

<400> SEQUENCE: 28

```
atgcatggag atacacctac attgcatgaa tatatgttag atttgcaacc agagacaact    60
gatctctact gttatgagca attaaatgac agctcagagg aggaggatga aatagatggt   120
ccagctggac aagcagaacc ggacagagcc cattacaata ttgtaacctt ttgttgcaag   180
tgtgactcta cgcttcggtt gtgcgtacaa agcacacacg tagacatttg tactttggaa   240
gacctgttaa tgggcacact aggaattgtg tgccccatct gttctcagaa accatag     297
```

<210> SEQ ID NO 29
<211> LENGTH: 98
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 29

```
Met His Gly Asp Thr Pro Thr Leu His Glu Tyr Met Leu Asp Leu Gln
  1               5                  10                  15
Pro Glu Thr Thr Asp Leu Tyr Cys Tyr Glu Gln Leu Asn Asp Ser Ser
                 20                  25                  30
Glu Glu Glu Asp Glu Ile Asp Gly Pro Ala Gly Gln Ala Glu Pro Asp
             35                  40                  45
Arg Ala His Tyr Asn Ile Val Thr Phe Cys Cys Lys Cys Asp Ser Thr
         50                  55                  60
Leu Arg Leu Cys Val Gln Ser Thr His Val Asp Ile Cys Thr Leu Glu
     65                  70                  75                  80
Asp Leu Leu Met Gly Thr Leu Gly Ile Val Cys Pro Ile Cys Ser Gln
                 85                  90                  95
Lys Pro
```

<210> SEQ ID NO 30
<211> LENGTH: 1303
<212> TYPE: DNA
<213> ORGANISM: Artificial Sequence
<220> FEATURE:
<223> OTHER INFORMATION: Description of Artificial Sequence:/Note = Synthetic Construct

<400> SEQUENCE: 30

```
gtccaggagc aggtagctgc tgggctccgg ggacactttg cgttcgggct gggagcgtgc    60
tttccacgac ggtgacacgc ttccctggat tggcagccag actgccttcc gggtcactgc   120
catggaggag ccgcagtcag atcctagcgt cgagcccccct ctgagtcagg aaacattttc   180
agacctatgg aaactacttc ctgaaaacaa cgttctgtcc cccttgccgt cccaagcaat   240
ggatgatttg atgctgtccc ggacgatat tgaacaatgg ttcactgaag acccaggtcc   300
agatgaagct cccagaatgc cagaggctgc tccccccgtg gcccctgcac cagcgactcc   360
tacaccggcg gcccctgcac cagcccctc ctggcccctg tcatcttctg tcccttccca   420
gaaaacctac cagggcagct acggtttccg tctgggcttc ttgcattctg ggacagccaa   480
gtctgtgact tgcacgtact cccctgccct caacaagatg ttttgccaac tggccaagac   540
ctgccctgtg cagctgtggg ttgattccac accccccgccc ggcaccccgcg tccgcgccat   600
ggccatctac aagcagtcac agcacatgac ggaggttgtg aggcgctgcc cccaccatga   660
```

```
gcgctgctca gatagcgatg gtctggcccc tcctcagcat cttatccgag tggaaggaaa    720
tttgcgtgtg gagtatttgg atgacagaaa cacttttcga catagtgtgg tggtgcccta    780
tgagccgcct gaggttggct ctgactgtac caccatccac tacaaactac agtgtaacag    840
ttcctgcatg ggcggcatga accggaggcc catcctcacc atcatcacac tggaagactc    900
cagtggtaat ctactgggac ggaacagctt tgaggtgcgt gtttgtgcct gtcctgggag    960
agaccggcgc acagaggaag agaatctccg caagaaaggg gagcctcacc acgagctgcc   1020
cccagggagc actaagcgag cactgcccaa caacaccagc tcctctcccc agccaaagaa   1080
gaaaccactg gatggagaat atttcaccct tcagatccgt gggcgtgagc gcttcgagat   1140
gttccgagag ctgaatgagg ccttggaact caaggatgcc caggctggga aggagccagg   1200
ggggagcagg gctcactcca gccacctgaa gtccaaaaag ggtcagtcta cctcccgcca   1260
taaaaaactc atgttcaaga cagaagggcc tgactcagac tga                     1303
```

<210> SEQ ID NO 31
<211> LENGTH: 393
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 31

```
Met Glu Glu Pro Gln Ser Asp Pro Ser Val Glu Pro Pro Leu Ser Gln
 1               5                  10                  15

Glu Thr Phe Ser Asp Leu Trp Lys Leu Leu Pro Glu Asn Asn Val Leu
             20                  25                  30

Ser Pro Leu Pro Ser Gln Ala Met Asp Asp Leu Met Leu Ser Pro Asp
         35                  40                  45

Asp Ile Glu Gln Trp Phe Thr Glu Asp Pro Gly Pro Asp Glu Ala Pro
     50                  55                  60

Arg Met Pro Glu Ala Ala Pro Pro Val Ala Pro Ala Pro Ala Thr Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
```

```
                        245                 250                 255
Leu Glu Asp Ser Ser Gly Asn Leu Leu Gly Arg Asn Ser Phe Glu Val
                260                 265                 270

Arg Val Cys Ala Cys Pro Gly Arg Asp Arg Arg Thr Glu Glu Glu Asn
            275                 280                 285

Leu Arg Lys Lys Gly Glu Pro His His Glu Leu Pro Pro Gly Ser Thr
        290                 295                 300

Lys Arg Ala Leu Pro Asn Asn Thr Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390
```

<210> SEQ ID NO 32
<211> LENGTH: 1208
<212> TYPE: DNA
<213> ORGANISM: Artificial Sequence
<220> FEATURE:
<223> OTHER INFORMATION: Description of Artificial Sequence:/Note = Synthetic Construct

<400> SEQUENCE: 32

```
ggtgtcacgc ttctccgaag actggatgac tgccatggag gagtcacagt cggatatcag     60
cctcgagctc cctctgagcc aggagacatt ttcaggctta tggaaactac ttcctcagaa    120
agatatcctg ccatcacctc actgcatgga cgatctgttg ctgccccagg atgttgagga    180
gttttttgaa ggcccaagtg aagccctccg agtgtcagga gctcctgcag cacaggaccc    240
tgtcaccgag acccctgggc cagcggcccc tgccccagcc actccatggc ccctgtcatc    300
ttttgtccct tctcaaaaaa cttaccaggg caactatggc ttccacctgg gcttcctgca    360
gtctgggaca gccaagtctg ttatgtgcac gtactctcct ccctcaata agctattctg    420
ccagctggcg aagacgtgcc ctgtgcagtt gtgggtcagc gccacacctc agctgggag    480
ccgtgtccgc gccatggcca tctacaagaa gtcacagcac atgacggagg tcgtgagacg    540
ctgccccac catgagcgct gctccgatgg tgatggcctg ctcctcccc agcatcttat    600
ccgggtggaa ggaaatttgt atcccgagta tctggaagac aggcagactt ttcgccacag    660
cgtggtggta ccttatgagc cacccgaggc cggctctgag tataccacca tccactacaa    720
gtacatgtgt aatagctcct gcatgggggg catgaaccgc cgacctatcc ttaccatcat    780
cacactggaa gactccagtg gaaccttctc tggacgggac agctttgagg ttcgtgtttg    840
tgcctgccct gggagagacc gccgtacaga agaagaaaat ttccgcaaaa aggaagtcct    900
ttgccctgaa ctgccccag ggagcgcaaa gagagcgctg cccacctgca caagcgcctc    960
tccccgcaa aagaaaaaac cacttgatgg agagtatttc accctcaaga tccgcgggcg   1020
taaacgcttc gagatgttcc gggagctgaa tgaggcctta gagttaaagg atgcccatgc   1080
tacagaggag tctggagaca gcagggctca ctccagctac ctgaagacca gaagggccta   1140
gtctacttcc cgccataaaa aaacaatggt caagaaagtg gggcctgact cagactgact   1200
```

```
gcctctgc                                                            1208
```

<210> SEQ ID NO 33
<211> LENGTH: 390
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 33

```
Met Thr Ala Met Glu Glu Ser Gln Ser Asp Ile Ser Leu Glu Leu Pro
 1               5                  10                  15

Leu Ser Gln Glu Thr Phe Ser Gly Leu Trp Lys Leu Leu Pro Pro Glu
            20                  25                  30

Asp Ile Leu Pro Ser Pro His Cys Met Asp Asp Leu Leu Leu Pro Gln
        35                  40                  45

Asp Val Glu Glu Phe Phe Glu Gly Pro Ser Glu Ala Leu Arg Val Ser
    50                  55                  60

Gly Ala Pro Ala Ala Gln Asp Pro Val Thr Glu Thr Pro Gly Pro Ala
65                  70                  75                  80

Ala Pro Ala Pro Ala Thr Pro Trp Pro Leu Ser Ser Phe Val Pro Ser
                85                  90                  95

Gln Lys Thr Tyr Gln Gly Asn Tyr Gly Phe His Leu Gly Phe Leu Gln
            100                 105                 110

Ser Gly Thr Ala Lys Ser Val Met Cys Thr Tyr Ser Pro Pro Leu Asn
        115                 120                 125

Lys Leu Phe Cys Gln Leu Ala Lys Thr Cys Pro Val Gln Leu Trp Val
    130                 135                 140

Ser Ala Thr Pro Pro Ala Gly Ser Arg Val Arg Ala Met Ala Ile Tyr
145                 150                 155                 160

Lys Lys Ser Gln His Met Thr Glu Val Val Arg Arg Cys Pro His His
                165                 170                 175

Glu Arg Cys Ser Asp Gly Asp Gly Leu Ala Pro Pro Gln His Leu Ile
            180                 185                 190

Arg Val Glu Gly Asn Leu Tyr Pro Glu Tyr Leu Glu Asp Arg Gln Thr
        195                 200                 205

Phe Arg His Ser Val Val Val Pro Tyr Glu Pro Pro Glu Ala Gly Ser
    210                 215                 220

Glu Tyr Thr Thr Ile His Tyr Lys Tyr Met Cys Asn Ser Ser Cys Met
225                 230                 235                 240

Gly Gly Met Asn Arg Arg Pro Ile Leu Thr Ile Ile Thr Leu Glu Asp
                245                 250                 255

Ser Ser Gly Asn Leu Leu Gly Arg Asp Ser Phe Glu Val Arg Val Cys
            260                 265                 270

Ala Cys Pro Gly Arg Asp Arg Arg Thr Glu Glu Glu Asn Phe Arg Lys
        275                 280                 285

Lys Glu Val Leu Cys Pro Glu Leu Pro Pro Gly Ser Ala Lys Arg Ala
    290                 295                 300

Leu Pro Thr Cys Thr Ser Ala Ser Pro Pro Gln Lys Lys Lys Pro Leu
305                 310                 315                 320

Asp Gly Glu Tyr Phe Thr Leu Lys Ile Arg Gly Arg Lys Arg Phe Glu
                325                 330                 335

Met Phe Arg Glu Leu Asn Glu Ala Leu Glu Leu Lys Asp Ala His Ala
            340                 345                 350

Thr Glu Glu Ser Gly Asp Ser Arg Ala His Ser Ser Tyr Leu Lys Thr
```

```
            355                 360                 365
Lys Lys Gly Gln Ser Thr Ser Arg His Lys Thr Met Val Lys Lys
    370                 375                 380

Val Gly Pro Asp Ser Asp
385                 390

<210> SEQ ID NO 34
<211> LENGTH: 2121
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 34
ctgctcgcgg ccgccaccgc cgggccccgg ccgtccctgg ctcccctcct gcctcgagaa      60
gggcagggct tctcagaggc ttggcgggaa aaaagaacgg agggagggat cgcgctgagt     120
ataaaagccg gttttcgggg ctttatctaa ctcgctgtag taattccagc gagaggcaga     180
gggagcgagc gggcggccgg ctagggtgga agagccgggc gagcagagct gcgctgcggg     240
cgtcctggga agggagatcc ggagcgaata ggggcttcg cctctggccc agccctcccg      300
cttgatcccc caggccagcg gtccgcaacc cttgccgcat ccacgaaact ttgcccatag     360 cagcgggcg gcactttgca ctggaactta caacacccga gcaaggacgc gactctcccg      420
acgcggggag gctattctgc ccatttgggg acacttcccc gccgctgcca ggacccgctt     480
ctctgaaagg ctctccttgc agctgcttag acgctggatt tttttcgggt agtggaaaac     540
cagcagcctc ccgcgacgat gccctcaac gttagcttca ccaacaggaa ctatgacctc      600
gactacgact cggtgcagcc gtatttctac tgcgacgagg aggagaactt ctaccagcag     660
cagcagcaga gcgagctgca gccccggcg cccagcgagg atatctggaa gaaattcgag      720
ctgctgccca ccccgccct gtcccctagc cgccgctccg gctctgctc gcctcctac       780 gttgcggtca caccctcctc ccttcgggga caacgacg cggtggcgg gagcttctcc        840 acggccgacc agctggagat ggtgaccgag ctgctgggag agacatggt gaaccagagt     900 ttcatctgcg acccggacga cgagaccttc atcaaaaaca tcatcatcca ggactgtatg     960
tggagcggct tctcggccgc cgccaagctc gtctcagaga agctggcctc ctaccaggct    1020
gcgcgcaaag acagcggcag cccgaacccc gcccgcggcc acagcgtctg ctccacctcc    1080
agcttgtacc tgcaggatct gagcgccgcc gcctcagagt gcatcgaccc ctcggtggtc    1140
ttcccctacc ctctcaacga cagcagctcg cccaagtcct gcgcctcgca agactccagc    1200
gccttctctc cgtcctcgga ttctctgctc tcctcgacgg agtcctcccc gcagggcagc    1260
cccgagcccc tggtgctcca tgaggagaca ccgcccacca ccagcagcga ctctgaggag    1320
gaacaagaag atgaggaaga aatcgatgtt gtttctgtgg aaaagaggca ggctcctggc    1380
aaaaggtcag agtctggatc accttctgct ggaggccaca gcaaacctcc tcacagccca    1440
ctggtcctca gaggtgcca cgtctccaca catcagcaca actacgcagc gcctccctcc    1500
actcggaagg actatcctgc tgccaagagg gtcaagttgg acagtgtcag agtcctgaga    1560
cagatcagca caaccgaaa atgcaccagc cccaggtcct cggacaccga ggagaatgtc    1620
aagaggcgaa cacacaacgt cttggagcgc agaggagga acgagctaaa acggagcttt    1680
tttgcccctg cgtgaccagat cccggagttg gaaaacaatg aaaaggcccc caaggtagtt    1740
atccttaaaa aagccacagc atacatcctg tccgtccaag cagaggagca aaagctcatt    1800
tctgaagagg acttgttgcg gaaacgacga gaacagttga acacaaaact gaacagcta     1860
```

```
cggaactctt gtgcgtaagg aaaagtaagg aaaacgattc cttctaacag aaatgtcctg  1920
agcaatcacc tatgaacttg tttcaaatgc atgatcaaat gcaacctcac aaccttggct  1980
gagtcttgag actgaaagat ttagccataa tgtaaactgc ctcaaattgg actttgggca  2040
taaaagaact ttttttatgct taccatcttt ttttttttctt taacagattt gtatttaaga  2100
attgttttta aaaattttta a                                            2121
```

<210> SEQ ID NO 35
<211> LENGTH: 439
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 35

```
Met Pro Leu Asn Val Ser Phe Thr Asn Arg Asn Tyr Asp Leu Asp Tyr
 1               5                  10                  15

Asp Ser Val Gln Pro Tyr Phe Tyr Cys Asp Glu Glu Glu Asn Phe Tyr
             20                  25                  30

Gln Gln Gln Gln Ser Glu Leu Gln Pro Pro Ala Pro Ser Glu Asp
         35                  40                  45

Ile Trp Lys Lys Phe Glu Leu Leu Pro Thr Pro Pro Leu Ser Pro Ser
 50                  55                  60

Arg Arg Ser Gly Leu Cys Ser Pro Ser Tyr Val Ala Val Thr Pro Phe
 65                  70                  75                  80

Ser Leu Arg Gly Asp Asn Asp Gly Gly Gly Ser Phe Ser Thr Ala
                 85                  90                  95

Asp Gln Leu Glu Met Val Thr Glu Leu Leu Gly Gly Asp Met Val Asn
                100                 105                 110

Gln Ser Phe Ile Cys Asp Pro Asp Asp Glu Thr Phe Ile Lys Asn Ile
            115                 120                 125

Ile Ile Gln Asp Cys Met Trp Ser Gly Phe Ser Ala Ala Ala Lys Leu
130                 135                 140

Val Ser Glu Lys Leu Ala Ser Tyr Gln Ala Ala Arg Lys Asp Ser Gly
145                 150                 155                 160

Ser Pro Asn Pro Ala Arg Gly His Ser Val Cys Ser Thr Ser Ser Leu
                165                 170                 175

Tyr Leu Gln Asp Leu Ser Ala Ala Ser Glu Cys Ile Asp Pro Ser
            180                 185                 190

Val Val Phe Pro Tyr Pro Leu Asn Asp Ser Ser Ser Pro Lys Ser Cys
            195                 200                 205

Ala Ser Gln Asp Ser Ser Ala Phe Ser Pro Ser Ser Asp Ser Leu Leu
        210                 215                 220

Ser Ser Thr Glu Ser Ser Pro Gln Gly Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Ala
            260                 265                 270

Pro Gly Lys Arg Ser Glu Ser Gly Ser Pro Ser Ala Gly Gly His Ser
        275                 280                 285

Lys Pro Pro His Ser Pro Leu Val Leu Lys Arg Cys His Val Ser Thr
    290                 295                 300

His Gln His Asn Tyr Ala Ala Pro Pro Ser Thr Arg Lys Asp Tyr Pro
```

```
                305                 310                 315                 320
Ala Ala Lys Arg Val Lys Leu Asp Ser Val Arg Val Leu Arg Gln Ile
                325                 330                 335

Ser Asn Asn Arg Lys Cys Thr Ser Pro Arg Ser Ser Asp Thr Glu Glu
                340                 345                 350

Asn Val Lys Arg Arg Thr His Asn Val Leu Glu Arg Gln Arg Arg Asn
                355                 360                 365

Glu Leu Lys Arg Ser Phe Phe Ala Leu Arg Asp Gln Ile Pro Glu Leu
            370                 375                 380

Glu Asn Asn Glu Lys Ala Pro Lys Val Val Ile Leu Lys Lys Ala Thr
385                 390                 395                 400

Ala Tyr Ile Leu Ser Val Gln Ala Glu Glu Gln Lys Leu Ile Ser Glu
                405                 410                 415

Glu Asp Leu Leu Arg Lys Arg Arg Glu Gln Leu Lys His Lys Leu Glu
                420                 425                 430

Gln Leu Arg Asn Ser Cys Ala
            435

<210> SEQ ID NO 36
<211> LENGTH: 403
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 36

Met Thr Ala Ile Ile Lys Glu Ile Val Ser Arg Asn Lys Arg Arg Tyr
 1               5                  10                  15

Gln Glu Asp Gly Phe Asp Leu Asp Leu Thr Tyr Ile Tyr Pro Asn Ile
                20                  25                  30

Ile Ala Met Gly Phe Pro Ala Glu Arg Leu Glu Gly Val Tyr Arg Asn
                35                  40                  45

Asn Ile Asp Asp Val Val Arg Phe Leu Asp Ser Lys His Lys Asn His
            50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
                100                 105                 110

Ser Glu Asp Asp Asn His Val Ala Ala Ile His Cys Lys Ala Gly Lys
            115                 120                 125

Gly Arg Thr Gly Val Met Ile Cys Ala Tyr Leu Leu His Arg Gly Lys
            130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
                180                 185                 190

Leu Leu Phe His Lys Met Met Phe Glu Thr Ile Pro Met Phe Ser Gly
            195                 200                 205

Gly Thr Cys Asn Pro Gln Phe Val Val Cys Gln Leu Lys Val Lys Ile
            210                 215                 220

Tyr Ser Ser Asn Ser Gly Pro Thr Arg Arg Glu Asp Lys Phe Met Tyr
```

-continued

```
              225                 230                 235                 240
Phe Glu Phe Pro Gln Pro Leu Pro Val Cys Gly Asp Ile Lys Val Glu
                    245                 250                 255

Phe Phe His Lys Gln Asn Lys Met Leu Lys Lys Asp Lys Met Phe His
                260                 265                 270

Phe Trp Val Asn Thr Phe Phe Ile Pro Gly Pro Glu Glu Thr Ser Glu
            275                 280                 285

Lys Val Glu Asn Gly Ser Leu Cys Asp Gln Glu Ile Asp Ser Ile Cys
        290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
                340                 345                 350

Glu Pro Ser Asn Pro Glu Ala Ser Ser Thr Ser Val Thr Pro Asp
                355                 360                 365

Val Ser Asp Asn Glu Pro Asp His Tyr Arg Tyr Ser Asp Thr Thr Asp
        370                 375                 380

Ser Asp Pro Glu Asn Glu Pro Phe Asp Glu Asp Gln His Thr Gln Ile
385                 390                 395                 400

Thr Lys Val

<210> SEQ ID NO 37
<211> LENGTH: 5775
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 37
tcctaggcgg cggccgcggc ggcggaggca gcagcggcgg cggcagtggc ggcggcgaag      60
gtggcggcgg ctcggccagt actcccggcc cccgccattt cggactggga gcagcgcgg     120 cgcaggcact gaaggcggcg gcggggccag aggctcagcg gctcccaggt gcgggagaga    180
ggcctgctga aaatgactga atataaactt gtggtagttg gagcttgtgg cgtaggcaag    240
agtgccttga cgatacagct aattcagaat cattttgtgg acgaatatga tccaacaata    300
gaggattcct acaggaagca agtagtaatt gatggagaaa cctgtctctt ggatattctc    360
gacacagcag gtcaagagga gtacagtgca atgagggacc agtacatgag gactggggag    420
ggctttcttt gtgtatttgc cataaataat actaaatcat ttgaagatat tcaccattat    480
agagaacaaa ttaaaagagt taaggactct gaagatgtac ctatggtcct agtaggaaat    540
aaatgtgatt tgccttctag aacagtagac acaaaacagg ctcaggactt agcaagaagt    600
tatggaattc cttttattga acatcagca aagacaagac agggtgttga tgatgccttc    660
tatacattag ttcgagaaat tcgaaaacat aaagaaaaga tgagcaaaga tggtaaaaag    720
aagaaaaaga agtcaaagac aaagtgtgta attatgtaaa tacaatttgt acttttttct    780
taaggcatac tagtacaagt ggtaatttt gtacattaca ctaaattatt agcatttgtt    840
ttagcattac ctaatttttt tcctgctcca tgcagactgt tagcttttac cttaaatgct    900
tattttaaaa tgacagtgga agttttttt tcctcgaagt gccagtattc ccagagtttt    960 ggttttgaa ctagcaatgc ctgtgaaaaa gaaactgaat acctaagatt tctgtcttgg   1020 ggttttggt gcatgcagtt gattacttct tatttttctt accaagtgtg aatgttggtg   1080
```

```
tgaaacaaat taatgaagct tttgaatcat ccctattctg tgttttatct agtcacataa   1140
atggattaat tactaatttc agttgagacc ttctaattgg ttttttactga aacattgagg   1200 gacacaaatt tatgggcttc ctgatgatga ttcttctagg catcatgtcc tatagtttgt   1260
catccctgat gaatgtaaag ttacactgtt cacaaaggtt ttgtctcctt tccactgcta   1320
ttagtcatgg tcactctccc caaaatatta tattttttct ataaaaagaa aaaatggaa    1380 aaaaattaca aggcaatgga aactattata aggccatttc cttttcacat tagataaatt   1440
actataaaga ctcctaatag cttttttcctg ttaaggcaga cccagtatga atggggattat 1500 tatagcaacc attttggggc tatatttaca tgctactaaa ttttttataat aattgaaaag  1560 attttaacaa gtataaaaaa attctcatag gaattaaatg tagtctccct gtgtcagact   1620
gctctttcat agtataactt taaatctttt cttcaacttg agtctttgaa gatagtttta   1680
attctgcttg tgacattaaa agattatttg ggccagttat agcttattag gtgttgaaga   1740
gaccaaggtt gcaagccagg ccctgtgtga accttgagct ttcatagaga gtttcacagc   1800
atggactgtg tgccccacgg tcatccgagt ggttgtacga tgcattggtt agtcaaaaat   1860
ggggagggac tagggcagtt tggatagctc aacaagatac aatctcactc tgtggtggtc   1920
ctgctgacaa atcaagagca ttgcttttgt ttcttaagaa aacaaactct tttttaaaaa   1980
ttacttttaa atattaactc aaaagttgag attttggggt ggtggtgtgc caagacatta   2040
attttttttt taaacaatga agtgaaaaag tttacaatc tctaggtttg gctagttctc    2100
ttaacactgg ttaaattaac attgcataaa cactttcaa gtctgatcca tatttaataa    2160
tgctttaaaa taaaataaa aacaatcctt ttgataaatt taaaatgtta cttatttttaa   2220 aataaatgaa gtgagatggc atggtgaggt gaaagtatca ctggactagg ttgttggtga   2280
cttaggttct agataggtgt cttttaggac tctgattttg aggacatcac ttactatcca   2340
tttcttcatg ttaaaagaag tcatctcaaa ctcttagttt ttttttttta cactatgtga   2400
tttatattcc atttacataa ggatacactt atttgtcaag ctcagcacaa tctgtaaatt   2460
tttaacctat gttacaccat cttcagtgcc agtcttgggc aaaattgtgc aagaggtgaa   2520
gtttatattt gaatatccat tctcgttttta ggactcttct tccatattag tgtcatcttg   2580
cctccctacc ttccacatgc cccatgactt gatgcagttt taatacttgt aattccccta   2640
accataagat ttactgctgc tgtggatatc tccatgaagt tttcccactg agtcacatca   2700
gaaatgccct acatcttatt ttcctcaggg ctcaagagaa tctgacagat accataaagg   2760
gatttgacct aatcactaat tttcaggtgg tggctgatgc tttgaacatc tctttgctgc   2820
ccaatccatt agcgacagta ggatttttca accctggtat gaatagacag aaccctatcc   2880
agtggaagga gaatttaata aagatagtgc agaaagaatt ccttaggtaa tctataacta   2940
ggactactcc tggtaacagt aatacattcc attgttttag taaccagaaa tcttcatgca   3000
atgaaaaata ctttaattca tgaagcttac ttttttttttt ttggtgtcag agtctcgctc   3060
ttgtcaccca ggctggaatg cagtggcgcc atctcagctc actgcaacct tccatcttcc   3120
caggttcaag cgattctcgt gcctcggcct cctgagtagc tgggattaca ggcgtgtgca   3180
ctacactcaa ctaattttg tatttttagg agagacgggg tttcacctgt tggccaggct    3240
ggtctcgaac tcctgacctc aagtgattca cccaccttgg cctcataaac ctgttttgca   3300
gaactcattt attcagcaaa tatttattga gtgcctacca gatgccagtc accgcacaag   3360
gcactgggta tatggtatcc ccaaacaaga gacataatcc cggtccttag gtactgctag   3420
tgtggtctgt aatatcttac taaggccttt ggtatacgac ccagagataa cacgatgcgt   3480
```

```
attttagttt tgcaaagaag gggtttggtc tctgtgccag ctctataatt gttttgctac   3540
gattccactg aaactcttcg atcaagctac tttatgtaaa tcacttcatt gttttaaagg   3600
aataaacttg attatattgt tttttttattt ggcataactg tgattctttt aggacaatta  3660
ctgtacacat taaggtgtat gtcagatatt catattgacc caaatgtgta atattccagt   3720
tttctctgca taagtaatta aaatatactt aaaaattaat agttttatct gggtacaaat   3780
aaacagtgcc tgaactagtt cacagacaag ggaaacttct atgtaaaaat cactatgatt   3840
tctgaattgc tatgtgaaac tacagatctt tggaacactg tttaggtagg gtgttaagac   3900
ttgacacagt acctcgtttc tacacagaga agaaatggc catacttcag gaactgcagt    3960
gcttatgagg ggatatttag gcctcttgaa tttttgatgt agatgggcat tttttttaagg  4020 tagtggttaa ttacctttat gtgaactttg aatggtttaa caaagatttt gttttttgtag  4080 agattttaaa gggggagaat tctagaaata aatgttacct aattattaca gccttaaaga   4140
caaaaatcct tgttgaagtt ttttttaaaaa aagactaaat tacatagact taggcattaa   4200
catgtttgtg gaagaatata gcagacgtat attgtatcat ttgagtgaat gttcccaagt   4260
aggcattcta ggctctatttt aactgagtca cactgcatag gaatttagaa cctaactttt   4320
ataggttatc aaaactgttg tcaccattgc acaattttgt cctaatatat acatagaaac   4380
tttgtggggc atgttaagtt acagtttgca caagttcatc tcatttgtat tccattgatt   4440 ttttttttttc ttctaaacat tttttcttca aaacagtata tataactttt tttaggggat   4500
tttttttaga cagcaaaaaa ctatctgaag atttccattt gtcaaaagt aatgatttct    4560 tgataattgt gtagtgaatg tttttttagaa cccagcagtt accttgaaag ctgaatttat   4620
atttagtaac ttctgtgtta atactggata gcatgaattc tgcattgaga aactgaatag   4680
ctgtcataaa atgctttctt tcctaaagaa agatactcac atgagttctt gaagaatagt   4740
cataactaga ttaagatctg tgttttagtt taatagtttg aagtgcctgt ttgggataat   4800
gataggtaat ttagatgaat ttaggggaaa aaaaagttat ctgcagttat gttgagggcc   4860
catctctccc cccacacccc cacagagcta actgggttac agtgttttat ccgaaagttt   4920
ccaattccac tgtcttgtgt tttcatgttg aaaatacttt tgcattttttc ctttgagtgc   4980 caatttctta ctagtactat ttcttaatgt aacatgttta cctggcctgt cttttaacta   5040
tttttgtata gtgtaaactg aaacatgcac attttgtaca ttgtgctttc ttttgtgggt   5100
catatgcagt gtgatccagt tgttttccat catttggttg cgctgaccta ggaatgttgg   5160
tcatatcaaa cattaaaaat gaccactctt ttaatgaaat taactttttaa atgtttatag   5220 gagtatgtgc tgtgaagtga tctaaaattt gtaatatttt tgtcatgaac tgtactactc   5280
ctaattattg taatgtaata aaaatagtta cagtgactat gagtgtgtat ttattcatgc   5340
aaatttgaac tgtttgcccc gaaatggata tggatacttt ataagccata gacactatag   5400
tataccagtg aatcttttat gcagcttgtt agaagtatcc ttttattttc taaaaggtgc   5460
tgtggatatt atgtaaaggc gtgtttgctt aaacaatttt ccatatttag aagtagatgc   5520
aaaacaaatc tgcctttatg acaaaaaaat aggataacat tatttatttta tttcctttta   5580 tcaataaggt aattgataca caacaggtga cttggttttta ggcccaaagg tagcagcagc  5640
aacattaata atggaaataa ttgaatagtt agttatgtat gttaatgcca gtcaccagca   5700
ggctatttca aggtcagaag taatgactcc atacatatta tttatttcta taactacatt   5760
taaatcatta ccagg                                                    5775
```

```
<210> SEQ ID NO 38
<211> LENGTH: 188
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 38

Met Thr Glu Tyr Lys Leu Val Val Gly Ala Cys Gly Val Gly Lys
 1               5                  10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Ile Asp Gly
                35                  40                  45

Glu Thr Cys Leu Leu Asp Ile Leu Asp Thr Ala Gly Gln Glu Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
                115                 120                 125

Gln Ala Gln Asp Leu Ala Arg Ser Tyr Gly Ile Pro Phe Ile Glu Thr
                130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
                180                 185

<210> SEQ ID NO 39
<211> LENGTH: 5711
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 39
agctcgctga gacttcctgg accccgcacc aggctgtggg gtttctcaga taactgggcc        60
cctgcgctca ggaggccttc accctctgct ctgggtaaag ttcattggaa cagaaagaaa       120
tggatttatc tgctcttcgc gttgaagaag tacaaaatgt cattaatgct atgcagaaaa       180
tcttagagtg tcccatctgt ctggagttga tcaaggaacc tgtctccaca agtgtgacc        240 acatattttg caaattttgc atgctgaaac ttctcaacca gaagaaaggg ccttcacagt       300 gtccttatg taagaatgat ataaccaaaa ggagcctaca agaaagtacg agatttagtc        360
aacttgttga gagctattg aaaatcattt gtgcttttca gcttgacaca ggtttggagt        420
atgcaaacag ctataatttt gcaaaaaagg aaaataactc tcctgaacat ctaaagatg        480 aagtttctat catccaaagt atgggctaca gaaaccgtgc caaagactt ctacagagtg        540 aacccgaaaa tccttccttg caggaaacca gtctcagtgt ccaactctct aaccttggaa       600
ctgtgagaac tctgaggaca aagcagcgga tacaacctca aaagacgtct gtctacattg       660
aattgggatc tgattcttct gaagataccg ttaataaggc aacttattgc agtgtgggag       720
```

```
atcaagaatt gttacaaatc acccctcaag gaaccaggga tgaaatcagt ttggattctg    780
caaaaaaggc tgcttgtgaa ttttctgaga cggatgtaac aaatactgaa catcatcaac    840
ccagtaataa tgatttgaac accactgaga agcgtgcagc tgagaggcat ccagaaaagt    900
atcagggtag ttctgtttca aacttgcatg tggagccatg tggcacaaat actcatgcca    960
gctcattaca gcatgagaac agcagtttat tactcactaa agacagaatg aatgtagaaa   1020
aggctgaatt ctgtaataaa agcaaacagc ctggcttagc aaggagccaa cataacagat   1080
gggctggaag taaggaaaca tgtaatgata ggcggactcc cagcacagaa aaaaaggtag   1140
atctgaatgc tgatcccctg tgtgagagaa aagaatggaa taagcagaaa ctgccatgct   1200
cagagaatcc tagagatact gaagatgttc cttggataac actaaatagc agcattcaga   1260
aagttaatga gtggttttcc agaagtgatg aactgttagg ttctgatgac tcacatgatg   1320
gggagtctga atcaaatgcc aaagtagctg atgtattgga cgttctaaat gaggtagatg   1380
aatattctgg ttcttcagag aaaatagact tactggccag tgatcctcat gaggctttaa   1440
tatgtaaaag tgaaagagtt cactccaaat cagtagagag taatattgaa gacaaaatat   1500
ttgggaaaac ctatcggaag aaggcaagcc tccccaactt aagccatgta actgaaaatc   1560
taattatagg agcatttgtt actgagccac agataataca agagcgtccc ctcacaaata   1620
aattaaagcg taaaggagaa cctacatcag gccttcatcc tgaggatttt atcaagaaag   1680
cagatttggc agttcaaaag actcctgaaa tgataaatca gggaactaac caaacggagc   1740
agaatggtca agtgatgaat attactaata gtggtcatga gaataaaaca aaaggtgatt   1800
ctattcagaa tgagaaaaat cctaacccaa tagaatcact cgaaaaagaa tctgctttca   1860
aaacgaaagc tgaacctata agcagcagta taagcaatat ggaactcgaa ttaaatatcc   1920
acaattcaaa agcacctaaa aagaataggc tgaggaggaa gtcttctacc aggcatattc   1980
atgcgcttga actagtagtc agtagaaatc taagcccacc taattgtact gaattgcaaa   2040
ttgatagttg ttctagcagt gaagagataa agaaaaaaaa gtacaaccaa atgccagtca   2100
ggcacagcag aaacctacaa ctcatggaag gtaaagaacc tgcaactgga gccaagaaga   2160
gtaacaagcc aaatgaacag acaagtaaaa gacatgacag cgatactttc ccagagctga   2220
agttaacaaa tgcacctggt tctttttacta agtgttcaaa taccagtgaa cttaaagaat   2280
ttgtcaatcc tagccttcca agagaagaaa aagaagagaa actagaaaca gttaaagtgt   2340
ctaataatgc tgaagaccc aaagatctca tgttaagtgg agaaagggtt ttgcaaactg   2400
aaagatctgt agagagtagc agtatttcat tggtacctgg tactgattat ggcactcagg   2460
aaagtatctc gttactggaa gttagcactc tagggaaggc aaaaacagaa ccaaataaat   2520
gtgtgagtca gtgtgcagca tttgaaaacc ccaagggact aattcatggt tgttccaaag   2580
ataatagaaa tgacacagaa ggctttaagt atccattggg acatgaagtt aaccacagtc   2640
gggaaacaag catagaaatg gaagaaagtg aacttgatgc tcagtatttg cagaatacat   2700
tcaaggtttc aaagcgccag tcatttgctc cgttttcaaa tccaggaaat gcagaagagg   2760
aatgtgcaac attctctgcc cactctgggt ccttaaagaa acaaagtcca aaagtcactt   2820
ttgaatgtga acaaaaggaa gaaatcaag gaaagaatga gtctaatatc aagcctgtac   2880
agacagttaa tatcactgca ggcttcctg tggttggtca gaaagataag ccagttgata   2940
atgccaaatg tagtatcaaa ggaggctcta ggttttgtct atcatctcag ttcagaggca   3000
acgaaactgg actcattact ccaaataaac atggactttt acaaaaccca tatcgtatac   3060
caccactttt tcccatcaag tcatttgtta aaactaaatg taagaaaaat ctgctagagg   3120
```

```
aaaactttga ggaacattca atgtcacctg aaagagaaat gggaaatgag aacattccaa   3180
gtacagtgag cacaattagc cgtaataaca ttagagaaaa tgttttaaa gaagccagct    3240 caagcaatat taatgaagta ggttccagta ctaatgaagt gggctccagt attaatgaaa   3300
taggttccag tgatgaaaac attcaagcag aactaggtag aaacagaggg ccaaaattga   3360
atgctatgct tagattaggg gttttgcaac ctgaggtcta taaacaaagt cttcctggaa   3420
gtaattgtaa gcatcctgaa ataaaaaagc aagaatatga agaagtagtt cagactgtta   3480
atacagattt ctctccatat ctgatttcag ataacttaga acagcctatg gaagtagtc    3540 atgcatctca ggtttgttct gagacacctg atgacctgtt agatgatggt gaaataaagg   3600
aagatactag ttttgctgaa aatgacatta aggaaagttc tgctgttttt agcaaaagcg   3660
tccagaaagg agagcttagc aggagtccta gcccctttcac ccatacacat ttggctcagg  3720
gttaccgaag aggggccaag aaattagagt cctcagaaga gaacttatct agtgaggatg   3780
aagagcttcc ctgcttccaa cacttgttat ttggtaaagt aaacaatata ccttctcagt   3840
ctactaggca tagcaccgtt gctaccgagt gtctgtctaa aacacagag gagaatttat    3900 tatcattgaa gaatagctta aatgactgca gtaaccaggg aatattggca aaggcatctc   3960
aggaacatca ccttagtgag gaaacaaaat gttctgctag cttgttttct tcacagtgca   4020
gtgaattgga agacttgact gcaaatacaa acacccagga tcctttcttg attggttctt   4080
ccaaacaaat gaggcatcag tctgaaagcc agggagttgg tctgagtgac aaggaattgg   4140
tttcagatga tgaagaaaga ggaacgggct tggaagaaaa taatcaagaa gagcaaagca   4200
tggattcaaa cttaggtgaa gcagcatctg ggtgtgagag tgaaacaagc gtctctgaag   4260
actgctcagg gctatcctct cagagtgaca ttttaaccac tcagcagagg gataccatgc   4320
aacataacct gataaagctc cagcaggaaa tggctgaact agaagctgtg ttagaacagc   4380
atgggagcca gccttctaac agctaccctt ccatcataag tgactcttct gcccttgagg   4440
acctgcgaaa tccagaacaa agcacatcag aaaaagcagt attaacttca cagaaaagta   4500
gtgaataccc tataagccag aatccagaag gcctttctgc tgacaagttt gaggtgtctg   4560
cagatagttc taccagtaaa aataaagaac caggagtgga aaggtcatcc ccttctaaat   4620
gcccatcatt agatgatagg tggtacatgc acagttgctc tgggagtctt cagaatagaa   4680
actacccatc tcaagaggag ctcattaagg ttgttgatgt ggaggagcaa cagctggaag   4740
agtctgggcc acacgatttg acggaaacat cttacttgcc aaggcaagat ctagagggaa   4800
ccccttacct ggaatctgga atcagcctct tctctgatga ccctgaatct gatccttctg   4860
aagacagagc cccagagtca gctcgtgttg gcaacatacc atcttcaacc tctgcattga   4920
aagttcccca attgaaagtt gcagaatctg cccagagtcc agctgctgct catactactg   4980
atactgctgg gtataatgca atggaagaaa gtgtgagcag ggagaagcca gaattgacag   5040
cttcaacaga aagggtcaac aaaagaatgt ccatggtggt gtctggcctg accccagaag   5100
aatttatgct cgtgtacaag tttgccagaa aacaccacat cactttaact aatctaatta   5160
ctgaagagac tactcatgtt gttatgaaaa cagatgctga gtttgtgtgt aacggacac    5220 tgaaatattt tctaggaatt gcgggaggaa aatgggtagt tagctatttc tgggtgaccc   5280
agtctattaa agaagaaaa atgctgaatg agcatgattt tgaagtcaga ggagatgtgg    5340
tcaatggaag aaaccaccaa ggtccaaagc gagcaagaga atcccaggac agaaagatct   5400 tcaggggct agaaatctgt tgctatgggc ccttcaccaa catgcccaca gatcaactgg     5460
aatggatggt acagctgtgt ggtgcttctg tggtgaagga gctttcatca ttcacccttg   5520
```

```
gcacaggtgt ccacccaatt gtggttgtgc agccagatgc ctggacagag gacaatggct   5580
tccatgcaat tgggcagatg tgtgaggcac ctgtggtgac ccgagagtgg gtgttggaca   5640
gtgtagcact ctaccagtgc caggagctgg acacctacct gatacccag atcccccaca   5700 gccactactg a                                                       5711
```

<210> SEQ ID NO 40
<211> LENGTH: 1863
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 40

```
Met Asp Leu Ser Ala Leu Arg Val Glu Glu Val Gln Asn Val Ile Asn
 1               5                  10                  15

Ala Met Gln Lys Ile Leu Glu Cys Pro Ile Cys Leu Glu Leu Ile Lys
             20                  25                  30

Glu Pro Val Ser Thr Lys Cys Asp His Ile Phe Cys Lys Phe Cys Met
         35                  40                  45

Leu Lys Leu Leu Asn Gln Lys Lys Gly Pro Ser Gln Cys Pro Leu Cys
     50                  55                  60

Lys Asn Asp Ile Thr Lys Arg Ser Leu Gln Glu Ser Thr Arg Phe Ser
 65                  70                  75                  80

Gln Leu Val Glu Glu Leu Leu Lys Ile Ile Cys Ala Phe Gln Leu Asp
                 85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
        275                 280                 285

Ser Leu Leu Leu Thr Lys Asp Arg Met Asn Val Glu Lys Ala Glu Phe
    290                 295                 300

Cys Asn Lys Ser Lys Gln Pro Gly Leu Ala Arg Ser Gln His Asn Arg
305                 310                 315                 320
```

-continued

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
                340                 345                 350

Trp Asn Lys Gln Lys Leu Pro Cys Ser Glu Asn Pro Arg Asp Thr Glu
                355                 360                 365

Asp Val Pro Trp Ile Thr Leu Asn Ser Ser Ile Gln Lys Val Asn Glu
            370                 375                 380

Trp Phe Ser Arg Ser Asp Glu Leu Leu Gly Ser Asp Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
                420                 425                 430

Ala Ser Asp Pro His Glu Ala Leu Ile Cys Lys Ser Glu Arg Val His
                435                 440                 445

Ser Lys Ser Val Glu Ser Asn Ile Glu Asp Lys Ile Phe Gly Lys Thr
                450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Arg Pro Thr Ser Gly Leu
                500                 505                 510

His Pro Glu Asp Phe Ile Lys Lys Ala Asp Leu Ala Val Gln Lys Thr
                515                 520                 525

Pro Glu Met Ile Asn Gln Gly Thr Asn Gln Thr Glu Gln Asn Gly Gln
                530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
                580                 585                 590

Asn Met Glu Leu Glu Leu Asn Ile His Asn Ser Lys Ala Pro Lys Lys
                595                 600                 605

Asn Arg Leu Arg Arg Lys Ser Ser Thr Arg His Ile His Ala Leu Glu
                610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655

Gln Met Pro Val Arg His Ser Arg Asn Leu Gln Leu Met Glu Gly Lys
                660                 665                 670

Glu Pro Ala Thr Gly Ala Lys Lys Ser Asn Lys Pro Asn Glu Gln Thr
                675                 680                 685

Ser Lys Arg His Asp Ser Asp Thr Phe Pro Glu Leu Lys Leu Thr Asn
                690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
                740                 745                 750

```
Ser Gly Glu Arg Val Leu Gln Thr Glu Arg Val Glu Ser Ser Ser
        755                 760                 765

Ile Ser Leu Val Pro Gly Thr Asp Tyr Gly Thr Gln Glu Ser Ile Ser
        770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                    805                 810                 815

Gly Cys Ser Lys Asp Asn Arg Asn Asp Thr Glu Gly Phe Lys Tyr Pro
                820                 825                 830

Leu Gly His Glu Val Asn His Ser Arg Glu Thr Ser Ile Glu Met Glu
        835                 840                 845

Glu Ser Glu Leu Asp Ala Gln Tyr Leu Gln Asn Thr Phe Lys Val Ser
    850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                    885                 890                 895

Pro Lys Val Thr Phe Glu Cys Glu Gln Lys Glu Glu Asn Gln Gly Lys
                900                 905                 910

Asn Glu Ser Asn Ile Lys Pro Val Gln Thr Val Asn Ile Thr Ala Gly
            915                 920                 925

Phe Pro Val Val Gly Gln Lys Asp Lys Pro Val Asp Asn Ala Lys Cys
        930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                    965                 970                 975

Pro Tyr Arg Ile Pro Pro Leu Phe Pro Ile Lys Ser Phe Val Lys Thr
                980                 985                 990

Lys Cys Lys Lys Asn Leu Leu Glu Glu Asn Phe Glu Glu His Ser Met
            995                 1000                1005

Ser Pro Glu Arg Glu Met Gly Asn Glu Asn Ile Pro Ser Thr Val Ser
    1010                1015                1020

Thr Ile Ser Arg Asn Asn Ile Arg Glu Asn Val Phe Lys Glu Ala Ser
1025                1030                1035                1040

Ser Ser Asn Ile Asn Glu Val Gly Ser Ser Thr Asn Glu Val Gly Ser
                1045                1050                1055

Ser Ile Asn Glu Ile Gly Ser Ser Asp Glu Asn Ile Gln Ala Glu Leu
            1060                1065                1070

Gly Arg Asn Arg Gly Pro Lys Leu Asn Ala Met Leu Arg Leu Gly Val
            1075                1080                1085

Leu Gln Pro Glu Val Tyr Lys Gln Ser Leu Pro Gly Ser Asn Cys Lys
    1090                1095                1100

His Pro Glu Ile Lys Lys Gln Glu Tyr Glu Glu Val Val Gln Thr Val
1105                1110                1115                1120

Asn Thr Asp Phe Ser Pro Tyr Leu Ile Ser Asp Asn Leu Glu Gln Pro
                1125                1130                1135

Met Gly Ser Ser His Ala Ser Gln Val Cys Ser Glu Thr Pro Asp Asp
                1140                1145                1150

Leu Leu Asp Asp Gly Glu Ile Lys Glu Asp Thr Ser Phe Ala Glu Asn
            1155                1160                1165

Asp Ile Lys Glu Ser Ser Ala Val Phe Ser Lys Ser Val Gln Lys Gly
```

```
               1170           1175          1180
Glu Leu Ser Arg Ser Pro Ser Pro Phe Thr His Thr His Leu Ala Gln
1185            1190          1195          1200

Gly Tyr Arg Arg Gly Ala Lys Lys Leu Glu Ser Ser Glu Glu Asn Leu
            1205           1210          1215

Ser Ser Glu Asp Glu Glu Leu Pro Cys Phe Gln His Leu Leu Phe Gly
            1220           1225          1230

Lys Val Asn Asn Ile Pro Ser Gln Ser Thr Arg His Ser Thr Val Ala
            1235           1240          1245

Thr Glu Cys Leu Ser Lys Asn Thr Glu Glu Asn Leu Leu Ser Leu Lys
            1250           1255          1260

Asn Ser Leu Asn Asp Cys Ser Asn Gln Val Ile Leu Ala Lys Ala Ser
1265            1270          1275          1280

Gln Glu His His Leu Ser Glu Thr Lys Cys Ser Ala Ser Leu Phe
            1285           1290          1295

Ser Ser Gln Cys Ser Glu Leu Glu Asp Leu Thr Ala Asn Thr Asn Thr
            1300           1305          1310

Gln Asp Pro Phe Leu Ile Gly Ser Ser Lys Gln Met Arg His Gln Ser
            1315           1320          1325

Glu Ser Gln Gly Val Gly Leu Ser Asp Lys Glu Leu Val Ser Asp Asp
            1330           1335          1340

Glu Glu Arg Gly Thr Gly Leu Glu Glu Asn Asn Gln Glu Glu Gln Ser
1345            1350          1355          1360

Met Asp Ser Asn Leu Gly Glu Ala Ala Ser Gly Cys Glu Ser Glu Thr
            1365           1370          1375

Ser Val Ser Glu Asp Cys Ser Gly Leu Ser Ser Gln Ser Asp Ile Leu
            1380           1385          1390

Thr Thr Gln Gln Arg Asp Thr Met Gln His Asn Leu Ile Lys Leu Gln
            1395           1400          1405

Gln Glu Met Ala Glu Leu Glu Ala Val Leu Glu Gln His Gly Ser Gln
            1410           1415          1420

Pro Ser Asn Ser Tyr Pro Ser Ile Ile Ser Asp Ser Ser Ala Leu Glu
1425            1430          1435          1440

Asp Leu Arg Asn Pro Glu Gln Ser Thr Ser Glu Lys Ala Val Leu Thr
            1445           1450          1455

Ser Gln Lys Ser Ser Glu Tyr Pro Ile Ser Gln Asn Pro Glu Gly Leu
            1460           1465          1470

Ser Ala Asp Lys Phe Glu Val Ser Ala Asp Ser Ser Thr Ser Lys Asn
            1475           1480          1485

Lys Glu Pro Gly Val Glu Arg Ser Ser Pro Ser Lys Cys Pro Ser Leu
            1490           1495          1500

Asp Asp Arg Trp Tyr Met His Ser Cys Ser Gly Ser Leu Gln Asn Arg
1505            1510          1515          1520

Asn Tyr Pro Ser Gln Glu Glu Leu Ile Lys Val Val Asp Val Glu Glu
            1525           1530          1535

Gln Gln Leu Glu Glu Ser Gly Pro His Asp Leu Thr Glu Thr Ser Tyr
            1540           1545          1550

Leu Pro Arg Gln Asp Leu Glu Gly Thr Pro Tyr Leu Glu Ser Gly Ile
            1555           1560          1565

Ser Leu Phe Ser Asp Asp Pro Glu Ser Asp Pro Ser Glu Asp Arg Ala
            1570           1575          1580

Pro Glu Ser Ala Arg Val Gly Asn Ile Pro Ser Ser Thr Ser Ala Leu
1585            1590          1595          1600
```

-continued

```
Lys Val Pro Gln Leu Lys Val Ala Glu Ser Ala Gln Ser Pro Ala Ala
            1605                1610                1615

Ala His Thr Thr Asp Thr Ala Gly Tyr Asn Ala Met Glu Glu Ser Val
        1620                1625                1630

Ser Arg Glu Lys Pro Glu Leu Thr Ala Ser Thr Glu Arg Val Asn Lys
    1635                1640                1645

Arg Met Ser Met Val Val Ser Gly Leu Thr Pro Glu Glu Phe Met Leu
1650                1655                1660

Val Tyr Lys Phe Ala Arg Lys His His Ile Thr Leu Thr Asn Leu Ile
1665                1670                1675                1680

Thr Glu Glu Thr Thr His Val Val Met Lys Thr Asp Ala Glu Phe Val
            1685                1690                1695

Cys Glu Arg Thr Leu Lys Tyr Phe Leu Gly Ile Ala Gly Gly Lys Trp
        1700                1705                1710

Val Val Ser Tyr Phe Trp Val Thr Gln Ser Ile Lys Glu Arg Lys Met
    1715                1720                1725

Leu Asn Glu His Asp Phe Glu Val Arg Gly Asp Val Val Asn Gly Arg
        1730                1735                1740

Asn His Gln Gly Pro Lys Arg Ala Arg Glu Ser Gln Asp Arg Lys Ile
1745                1750                1755                1760

Phe Arg Gly Leu Glu Ile Cys Cys Tyr Gly Pro Phe Thr Asn Met Pro
            1765                1770                1775

Thr Asp Gln Leu Glu Trp Met Val Gln Leu Cys Gly Ala Ser Val Val
        1780                1785                1790

Lys Glu Leu Ser Ser Phe Thr Leu Gly Thr Gly Val His Pro Ile Val
    1795                1800                1805

Val Val Gln Pro Asp Ala Trp Thr Glu Asp Asn Gly Phe His Ala Ile
1810                1815                1820

Gly Gln Met Cys Glu Ala Pro Val Val Thr Arg Glu Trp Val Leu Asp
1825                1830                1835                1840

Ser Val Ala Leu Tyr Gln Cys Gln Glu Leu Asp Thr Tyr Leu Ile Pro
            1845                1850                1855

Gln Ile Pro His Ser His Tyr
        1860
```

<210> SEQ ID NO 41
<211> LENGTH: 10987
<212> TYPE: DNA
<213> ORGANISM: Artificial Sequence
<220> FEATURE:
<223> OTHER INFORMATION: Description of Artificial Sequence:/Note = Synthetic Construct

<400> SEQUENCE: 41

```
ggtggcgcga gcttctgaaa ctaggcggca gaggcggagc cgctgtggca ctgctgcgcc      60
tctgctcgcg ctcgggtgtc ttttgcggcg gtgggtcgcc gccggagaa gcgtgagggg     120 acagatttgt gaccggcgcg gttttttgtca gcttactccg gccaaaaaag aactgcacct    180
ctggagcgga cttatttacc aagcattgga ggaatatcgt aggtaaaaat gcctattgga    240
tccaaagaga ggccaacatt ttttgaaatt tttaagacac gctgcaacaa agcagattta    300
ggaccaataa gtcttaattg gtttgaagaa ctttcttcag aagctccacc ctataattct    360
gaacctgcag aagaatctga acataaaaac aacaattacg aaccaaacct atttaaaact    420
ccacaaagga aaccatctta taatcagctg gcttcaactc aataatatt caaagagcaa    480 gggctgactc tgccgctgta ccaatctcct gtaaagaat tagataaatt caaattagac    540
```

```
ttaggaagga atgttcccaa tagtagacat aaaagtcttc gcacagtgaa aactaaaatg    600
gatcaagcag atgatgtttc ctgtccactt ctaaattctt gtcttagtga aagtcctgtt    660
gttctacaat gtacacatgt aacaccacaa agagataagt cagtggtatg tgggagtttg    720
tttcatacac caaagtttgt gaagggtcgt cagacaccaa acatatttc tgaaagtcta    780 ggagctgagg tggatcctga tatgtcttgg tcaagttctt tagctacacc acccacccctt   840 agttctactg tgctcatagt cagaaatgaa gaagcatctg aaactgtatt tcctcatgat    900
actactgcta atgtgaaaag ctattttccc aatcatgatg aaagtctgaa gaaaaatgat    960
agatttatcg cttctgtgac agacagtgaa aacacaaatc aaagagaagc tgcaagtcat   1020
ggatttggaa aaacatcagg gaattcattt aaagtaaata gctgcaaaga ccacattgga   1080
aagtcaatgc caaatgtcct agaagatgaa gtatatgaaa cagttgtaga tacctctgaa   1140
gaagatagtt tttcattatg tttttctaaa tgtagaacaa aaaatctaca aaaagtaaga   1200
actagcaaga ctaggaaaaa aattttccat gaagcaaacg ctgatgaatg tgaaaaatct   1260
aaaaaccaag tgaaagaaaa atactcattt gtatctgaag tggaaccaaa tgatactgat   1320
ccattagatt caaatgtagc acatcagaag ccctttgaga gtggaagtga caaaatctcc   1380
aaggaagttg taccgtcttt ggcctgtgaa tggtctcaac taacccttc aggtctaaat   1440 ggagcccaga tggagaaaat acccctattg catatttctt catgtgacca aaatatttca   1500 gaaaagacc tattagacac agagaacaaa agaaagaaag attttcttac ttcagagaat   1560
tctttgccac gtatttctag cctaccaaaa tcagagaagc cattaaatga ggaaacagtg   1620
gtaaataaga gagatgaaga gcagcatctt gaatctcata cagactgcat tcttgcagta   1680
aagcaggcaa tatctggaac ttctccagtg gcttcttcat ttcagggtat caaaaagtct   1740
atattcagaa taagagaatc acctaaagag actttcaatg caagttttc aggtcatatg   1800 actgatccaa actttaaaaa agaaactgaa gcctctgaaa gtggactgga atacatact    1860 gtttgctcac agaaggagga ctccttatgt ccaaatttaa ttgataatgg aagctggcca   1920
gccaccacca cacagaattc tgtagctttg aagaatgcag gtttaatatc cactttgaaa   1980
aagaaaacaa ataagtttat ttatgctata catgatgaaa catttataa aggaaaaaaa   2040 ataccgaaag accaaaaatc agaactaatt aactgttcag cccagtttga agcaaatgct   2100
tttgaagcac cacttacatt tgcaaatgct gattcaggtt tattgcattc ttctgtgaaa   2160
agaagctgtt cacagaatga ttctgaagaa ccaactttgt ccttaactag ctcttttggg   2220
acaattctga ggaaatgttc tagaaatgaa acatgttcta ataatacagt aatctctcag   2280
gatcttgatt ataagaagc aaaatgtaat aaggaaaaac tacagttatt tattaccccca   2340 gaagctgatt ctctgtcatg cctgcaggaa ggacagtgtg aaaatgatcc aaaaagcaaa   2400
aaagtttcag atataaaaga agaggtcttg gctgcagcat gtcacccagt acaacattca   2460
aaagtggaat acagtgatac tgactttcaa tcccagaaaa gtcttttata tgatcatgaa   2520
aatgccagca ctcttatttt aactcctact tccaaggatg ttctgtcaaa cctagtcatg   2580
atttctagag gcaagaatc atacaaaatg tcagacaagc tcaaggtaa caattatgaa   2640 tctgatgttg aattaaccaa aaatattccc atggaaaaga tcaagatgt atgtgcttta   2700 aatgaaaatt ataaaacgt tgagctgttg ccacctgaaa aatacatgag agtagcatca   2760
ccttcaagaa aggtacaatt caaccaaaac acaaatctaa gagtaatcca aaaaaatcaa   2820
gaagaaacta cttcaatttc aaaaataact gtcaatccag actctgaaga acttttctca   2880
gacaatgaga ataattttgt cttccaagta gctaatgaaa ggaataatct tgctttagga   2940
```

```
aatactaagg aacttcatga aacagacttg acttgtgtaa acgaacccat tttcaagaac    3000
tctaccatgg ttttatatgg agacacaggt gataaacaag caacccaagt gtcaattaaa    3060
aaagatttgg tttatgttct tgcagaggag aacaaaaata gtgtaaagca gcatataaaa    3120
atgactctag gtcaagattt aaaatcggac atctccttga atatagataa aataccagaa    3180
aaaaataatg attacatgaa caaatgggca ggactcttag gtccaatttc aaatcacagt    3240
tttggaggta gcttcagaac agcttcaaat aaggaaatca agctctctga acataacatt    3300
aagaagagca aaatgttctt caaagatatt gaagaacaat atcctactag tttagcttgt    3360
gttgaaattg taaataccct tggcattagat aatcaaaaga aactgagcaa gcctcagtca    3420
attaatactg tatctgcaca tttacagagt agtgtagttg tttctgattg taaaaatagt    3480
catataaccc ctcagatgtt attttccaag caggatttta attcaaacca taatttaaca    3540
cctagccaaa aggcagaaat tacagaactt tctactatat tagaagaatc aggaagtcag    3600
tttgaattta ctcagtttag aaaaccaagc tacatattgc agaagagtac atttgaagtg    3660
cctgaaaacc agatgactat cttaaagacc acttctgagg aatgcagaga tgctgatctt    3720
catgtcataa tgaatgcccc atcgattggt caggtagaca gcagcaagca atttgaaggt    3780
acagttgaaa ttaaacggaa gtttgctggc ctgttgaaaa atgactgtaa caaaagtgct    3840
tctggttatt taacagatga aaatgaagtg gggtttaggg gcttttattc tgctcatggc    3900
acaaaactga atgtttctac tgaagctctg caaaaagctg tgaaactgtt tagtgatatt    3960
gagaatatta gtgaggaaac ttctgcagag gtacatccaa taagtttatc ttcaagtaaa    4020
tgtcatgatt ctgttgtttc aatgtttaag atagaaaatc ataatgataa aactgtaagt    4080
gaaaaaaata taaatgcca actgatatta caaaataata ttgaaatgac tactggcact    4140
tttgttgaag aaattactga aaattacaag agaaatactg aaaatgaaga taacaaatat    4200
actgctgcca gtagaaattc tcataactta gaatttgatg gcagtgattc aagtaaaaat    4260
gatactgttt gtattcataa agatgaaacg gacttgctat ttactgatca gcacaacata    4320
tgtcttaaat tatctggcca gtttatgaag gagggaaaca ctcagattaa agaagatttg    4380
tcagatttaa ctttttttgga agttgcgaaa gctcaagaag catgtcatgg taatacttca    4440
aataaagaac agttaactgc tactaaaacg gagcaaaata taaaagattt tgagacttct    4500
gatacatttt ttcagactgc aagtgggaaa aatattagtg tcgccaaaga gtcatttaat    4560
aaaattgtaa atttctttga tcagaaacca gaagaattgc ataacttttc cttaaattct    4620
gaattacatt ctgacataag aaagaacaaa atggacattc aagttatga ggaaacagac    4680
atagttaaac acaaaatact gaaagaaagt gtcccagttg gtactggaaa tcaactagtg    4740
accttccagg gacaacccga acgtgatgaa aagatcaaag aacctactct gttgggtttt    4800
catacagcta gcgggaaaaa agttaaaatt gcaaggaat cttttggacaa agtgaaaaac    4860
cttttttgatg aaaagagca aggtactagt gaaatcacca gttttagcca tcaatgggca    4920
aagaccctaa agtacagaga ggcctgtaaa gaccttgaat tagcatgtga gaccattgag    4980
atcacagctg ccccaaagtg taagaaatg cagaattctc tcaataatga taaaaacctt    5040
gtttctattg agactgtggt gccacctaag ctcttaagtg ataatttatg tagacaaact    5100
gaaaatctca aaacatcaaa aagtatctttt ttgaaagtta agtacatga aaatgtagaa    5160
aaagaaacag caaaaagtcc tgcaacttgt tacacaaatc agtcccctta ttcagtcatt    5220
gaaaattcag ccttagcttt ttacacaagt tgtagtagaa aaacttctgt gagtcagact    5280
tcattacttg aagcaaaaaa atggcttaga gaaggaatat ttgatggtca accagaaaga    5340
```

```
ataaatactg cagattatgt aggaaattat ttgtatgaaa ataattcaaa cagtactata   5400
gctgaaaatg acaaaaatca tctctccgaa aaacaagata cttatttaag taacagtagc   5460
atgtctaaca gctattccta ccattctgat gaggtatata atgattcagg atatctctca   5520
aaaaataaac ttgattctgg tattgagcca gtattgaaga atgttgaaga tcaaaaaaac   5580
actagttttt ccaaagtaat atccaatgta aaagatgcaa atgcataccc acaaactgta   5640
aatgaagata tttgcgttga ggaacttgtg actagctctt caccctgcaa aaataaaaat   5700
gcagccatta aattgtccat atctaatagt aataattttg aggtagggcc acctgcattt   5760
aggatagcca gtggtaaaat cgtttgtgtt tcacatgaaa caattaaaaa agtgaaagac   5820
atatttacag acagtttcag taaagtaatt aaggaaaaca acgagaataa atcaaaaatt   5880
tgccaaacga aaattatggc aggttgttac gaggcattgg atgattcaga ggatattctt   5940
cataactctc tagataatga tgaatgtagc acgcattcac ataaggtttt tgctgacatt   6000
cagagtgaag aaattttaca acataaccaa aatatgtctg gattggagaa agtttctaaa   6060
atatcacctt gtgatgttag tttggaaact tcagatatat gtaaatgtag tataggaag    6120 cttcataagt cagtctcatc tgcaaatact tgtgggattt ttagcacagc aagtggaaaa   6180
tctgtccagg tatcagatgc ttcattacaa aacgcaagac aagtgttttc tgaaatagaa   6240
gatagtacca agcaagtctt ttccaaagta ttgtttaaaa gtaacgaaca ttcagaccag   6300
ctcacaagag aagaaaatac tgctatacgt actccagaac atttaatatc ccaaaaaggc   6360
ttttcatata atgtggtaaa ttcatctgct ttctctggat ttagtacagc aagtggaaag   6420
caagtttcca ttttagaaag ttccttacac aaagttaagg gagtgttaga ggaatttgat   6480
ttaatcagaa ctgagcatag tcttcactat tcacctacgt ctagacaaaa tgtatcaaaa   6540
atacttcctc gtgttgataa gagaaaccca gagcactgtg taaactcaga aatggaaaaa   6600
acctgcagta aagaatttaa attatcaaat aacttaaatg ttgaaggtgg ttcttcagaa   6660
aataatcact ctattaaagt ttctccatat ctctctcaat ttcaacaaga caaacaacag   6720
ttggtattag aaccaaagt ctcacttgtt gagaacattc atgttttggg aaaagaacag   6780
gcttcaccta aaaacgtaaa aatggaaatt ggtaaaactg aaacttttc tgatgttcct   6840 gtgaaaacaa atatagaagt ttgttctact tactccaaag attcagaaaa ctactttgaa   6900
acagaagcag tagaaattgc taaagctttt atggaagatg atgaactgac agattctaaa   6960
ctgccaagtc atgccacaca ttctcttttt acatgtcccg aaaatgagga atggttttg    7020 tcaaattcaa gaattggaaa aagaagagga gagccccta tcttagtggg agaaccctca    7080
atcaaaagaa acttattaaa tgaatttgac aggataatag aaaatcaaga aaatcctta    7140 aaggcttcaa aaagcactcc agatggcaca ataaagatc gaagattgtt tatgcatcat   7200
gtttctttag agccgattac ctgtgtaccc tttcgcacaa ctaaggaacg tcaagagata   7260
cagaatccaa attttaccgc acctggtcaa gaatttctgt ctaaatctca tttgtatgaa   7320
catctgactt tggaaaaatc ttcaagcaat ttagcagttt caggacatcc attttatcaa   7380
gtttctgcta caagaaatga aaaaatgaga cacttgatta ctacaggcag accaaccaaa   7440
gtctttgttc cacctttaa aactaaatca cattttcaca gagttgaaca gtgtgttagg   7500
aatattaact tggaggaaaa cagacaaaag caaaacattg atggacatgg ctctgatgat   7560
agtaaaaata agattaatga caatgagatt catcagttta caaaaacaa ctccaatcaa   7620 gcagcagctg taactttcac aaagtgtgaa gaagaacctt tagatttaat tacaagtctt   7680
cagaatgcca gagatataca ggatatgcga attaagaaga acaaaggca acgcgtcttt   7740
```

```
ccacagccag gcagtctgta tcttgcaaaa acatccactc tgcctcgaat ctctctgaaa    7800
gcagcagtag gaggccaagt tccctctgcg tgttctcata acagctgta tacgtatggc     7860 gtttctaaac attgcataaa aattaacagc aaaaatgcag agtcttttca gtttcacact    7920
gaagattatt ttggtaagga aagtttatgg actggaaaag gaatacagtt ggctgatggt    7980
ggatggctca taccctccaa tgatggaaag gctggaaaag aagaattta tagggctctg     8040 tgtgacactc caggtgtgga tccaaagctt atttctagaa tttgggttta taatcactat    8100
agatggatca tatggaaact ggcagctatg gaatgtgcct ttcctaagga atttgctaat    8160
agatgcctaa gcccagaaag ggtgcttctt caactaaaat acagatatga tacgaaaatt    8220
gatagaagca gaagatcggc tataaaaaag ataatggaaa gggatgacac agctgcaaaa    8280
acacttgttc tctgtgtttc tgacataatt tcattgagcg caaatatatc tgaaacttct    8340
agcaataaaa ctagtagtgc agatacccaa aaagtggcca ttattgaact tacagatggg    8400
tggtatgctg ttaaggccca gttagatcct cccctcttag ctgtcttaaa gaatggcaga    8460
ctgacagttg gtcagaagat tattcttcat ggagcagaac tggtgggctc tcctgatgcc    8520
tgtacacctc ttgaagcccc agaatctctt atgttaaaga tttctgctaa cagtactcgg    8580
cctgctcgct ggtataccaa acttggattc tttcctgacc ctagaccttt tcctctgccc    8640
ttatcatcgc ttttcagtga tggaggaaat gttggttgtg ttgatgtaat tattcaaaga    8700 gcataccta tacagtggat ggagaagaca tcatctggat tatacatatt tcgcaatgaa     8760
agagaggaag aaaaggaagc agcaaaatat gtggaggccc aacaaaagag actagaagcc    8820
ttattcacta aaattcagga ggaatttgaa gaacatgaag aaaacacaac aaaaccatat    8880
ttaccatcac gtgcactaac aagacagcaa gttcgtgctt tgcaagatgg tgcagagctt    8940
tatgaagcag tgaagaatgc agcagaccca gcttaccttg agggttattt cagtgaagag    9000
cagttaagag ccttgaataa tcacaggcaa atgttgaatg ataagaaaca agctcagatc    9060
cagttggaaa ttaggaaggc catggaatct gctgaacaaa aggaacaagg tttatcaagg    9120
gatgtcacaa ccgtgtggaa gttgcgtatt gtaagctatt caaaaaaaga aaaagattca    9180
gttatactga gtatttggcg tccatcatca gatttatatt ctctgttaac agaaggaaag    9240
agatacagaa tttatcatct tgcaacttca aaatctaaaa gtaaatctga aagagctaac    9300
atacagttag cagcgacaaa aaaaactcag tatcaacaac taccggtttc agatgaaatt    9360
ttatttcaga tttaccagcc acgggagccc cttcacttca gcaaattttt agatccagac    9420
tttcagccat cttgttctga ggtggaccta ataggatttg tcgtttctgt tgtgaaaaaa    9480
acaggacttg ccccttttcgt ctatttgtca gacgaatgtt acaatttact ggcaataaag   9540
ttttggatag accttaatga ggacattatt aagcctcata tgttaattgc tgcaagcaac    9600
ctccagtggc gaccagaatc caaatcaggc cttcttactt tatttgctgg agattttttct  9660 gtgttttctg ctagtccaaa agagggccac tttcaagaga cattcaacaa aatgaaaaat    9720
actgttgaga atattgacat actttgcaat gaagcagaaa acaagcttat gcatatactg    9780
catgcaaatg atcccaagtg gtccacccca actaaagact gtacttcagg gccgtacact    9840
gctcaaatca ttcctggtac aggaaacaag cttctgatgt cttctcctaa ttgtgagata    9900
tattatcaaa gtcctttatc actttgtatg gccaaaagga agtctgtttc cacacctgtc    9960
tcagcccaga tgacttcaaa gtcttgtaaa ggggagaaag agattgatga ccaaaagaac   10020
tgcaaaaaga gaagagcctt ggatttcttg agtagactgc ctttacctcc acctgttagt   10080
cccatttgta catttgtttc tccggctgca cagaaggcat ttcagccacc aaggagttgt   10140
```

-continued

```
ggcaccaaat acgaaacacc cataaagaaa aagaactga attctcctca gatgactcca  10200
tttaaaaaat tcaatgaaat ttctcttttg gaaagtaatt caatagctga cgaagaactt  10260
gcattgataa atacccaagc tcttttgtct ggttcaacag gagaaaaaca atttatatct  10320
gtcagtgaat ccactaggac tgctcccacc agttcagaag attatctcag actgaaacga  10380
cgttgtacta catctctgat caaagaacag gagagttccc aggccagtac ggaagaatgt  10440
gagaaaaata agcaggacac aattacaact aaaaaatata tctaagcatt tgcaaaggcg  10500
acaataaatt attgacgctt aacctttcca gtttataaga ctggaatata atttcaaacc  10560
acacattagt acttatgttg cacaatgaga aaagaaatta gtttcaaatt tacctcagcg  10620
tttgtgtatc gggcaaaaat cgttttgccc gattccgtat tggtatactt ttgcttcagt  10680
tgcatatctt aaaactaaat gtaatttatt aactaatcaa gaaaaacatc tttggctgag  10740
ctcggtggct catgcctgta atcccaacac tttgagaagc tgaggtggga ggagtgcttg  10800
aggccaggag ttcaagacca gcctgggcaa catagggaga ccccccatctt tacgaagaaa  10860
aaaaaaaagg ggaaaagaaa atcttttaaa tctttggatt tgatcactac aagtattatt  10920
ttacaatcaa caaaatggtc atccaaactc aaacttgaga aaatatcttg ctttcaaatt  10980
gacacta                                                            10987
```

<210> SEQ ID NO 42
<211> LENGTH: 3418
<212> TYPE: PRT
<213> ORGANISM: Artificial Sequence
<220> FEATURE:
<223> OTHER INFORMATION: Description of Artificial Sequence:/Note = Synthetic Construct

<400> SEQUENCE: 42

```
Met Pro Ile Gly Ser Lys Glu Arg Pro Thr Phe Phe Glu Ile Phe Lys
  1               5                  10                  15
Thr Arg Cys Asn Lys Ala Asp Leu Gly Pro Ile Ser Leu Asn Trp Phe
             20                  25                  30
Glu Glu Leu Ser Ser Glu Ala Pro Pro Tyr Asn Ser Glu Pro Ala Glu
         35                  40                  45
Glu Ser Glu His Lys Asn Asn Asn Tyr Glu Pro Asn Leu Phe Lys Thr
     50                  55                  60
Pro Gln Arg Lys Pro Ser Tyr Asn Gln Leu Ala Ser Thr Pro Ile Ile
 65                  70                  75                  80
Phe Lys Glu Gln Gly Leu Thr Leu Pro Leu Tyr Gln Ser Pro Val Lys
                 85                  90                  95
Glu Leu Asp Lys Phe Lys Leu Asp Leu Gly Arg Asn Val Pro Asn Ser
            100                 105                 110
Arg His Lys Ser Leu Arg Thr Val Lys Thr Lys Met Asp Gln Ala Asp
        115                 120                 125
Asp Val Ser Cys Pro Leu Leu Asn Ser Cys Leu Ser Glu Ser Pro Val
    130                 135                 140
Val Leu Gln Cys Thr His Val Thr Pro Gln Arg Asp Lys Ser Val Val
145                 150                 155                 160
Cys Gly Ser Leu Phe His Thr Pro Lys Phe Val Lys Gly Arg Gln Thr
                165                 170                 175
Pro Lys His Ile Ser Glu Ser Leu Gly Ala Glu Val Asp Pro Asp Met
            180                 185                 190
Ser Trp Ser Ser Ser Leu Ala Thr Pro Pro Thr Leu Ser Ser Thr Val
        195                 200                 205
```

```
Leu Ile Val Arg Asn Glu Glu Ala Ser Glu Thr Val Phe Pro His Asp
210                 215                 220

Thr Thr Ala Asn Val Lys Ser Tyr Phe Ser Asn His Asp Glu Ser Leu
225                 230                 235                 240

Lys Lys Asn Asp Arg Phe Ile Ala Ser Val Thr Asp Ser Glu Asn Thr
                245                 250                 255

Asn Gln Arg Glu Ala Ala Ser His Gly Phe Gly Lys Thr Ser Gly Asn
            260                 265                 270

Ser Phe Lys Val Asn Ser Cys Lys Asp His Ile Gly Lys Ser Met Pro
        275                 280                 285

Asn Val Leu Glu Asp Glu Val Tyr Glu Thr Val Val Asp Thr Ser Glu
    290                 295                 300

Glu Asp Ser Phe Ser Leu Cys Phe Ser Lys Cys Arg Thr Lys Asn Leu
305                 310                 315                 320

Gln Lys Val Arg Thr Ser Lys Thr Arg Lys Lys Ile Phe His Glu Ala
                325                 330                 335

Asn Ala Asp Glu Cys Glu Lys Ser Lys Asn Gln Val Lys Glu Lys Tyr
            340                 345                 350

Ser Phe Val Ser Glu Val Glu Pro Asn Asp Thr Asp Pro Leu Asp Ser
        355                 360                 365

Asn Val Ala His Gln Lys Pro Phe Glu Ser Gly Ser Asp Lys Ile Ser
    370                 375                 380

Lys Glu Val Val Pro Ser Leu Ala Cys Glu Trp Ser Gln Leu Thr Leu
385                 390                 395                 400

Ser Gly Leu Asn Gly Ala Gln Met Glu Lys Ile Pro Leu Leu His Ile
                405                 410                 415

Ser Ser Cys Asp Gln Asn Ile Ser Glu Lys Asp Leu Leu Asp Thr Glu
            420                 425                 430

Asn Lys Arg Lys Lys Asp Phe Leu Thr Ser Glu Asn Ser Leu Pro Arg
        435                 440                 445

Ile Ser Ser Leu Pro Lys Ser Glu Lys Pro Leu Asn Glu Glu Thr Val
    450                 455                 460

Val Asn Lys Arg Asp Glu Glu Gln His Leu Glu Ser His Thr Asp Cys
465                 470                 475                 480

Ile Leu Ala Val Lys Gln Ala Ile Ser Gly Thr Ser Pro Val Ala Ser
                485                 490                 495

Ser Phe Gln Gly Ile Lys Lys Ser Ile Phe Arg Ile Arg Glu Ser Pro
            500                 505                 510

Lys Glu Thr Phe Asn Ala Ser Phe Ser Gly His Met Thr Asp Pro Asn
        515                 520                 525

Phe Lys Lys Glu Thr Glu Ala Ser Glu Ser Gly Leu Glu Ile His Thr
    530                 535                 540

Val Cys Ser Gln Lys Glu Asp Ser Leu Cys Pro Asn Leu Ile Asp Asn
545                 550                 555                 560

Gly Ser Trp Pro Ala Thr Thr Thr Gln Asn Ser Val Ala Leu Lys Asn
                565                 570                 575

Ala Gly Leu Ile Ser Thr Leu Lys Lys Lys Thr Asn Lys Phe Ile Tyr
            580                 585                 590

Ala Ile His Asp Glu Thr Phe Tyr Lys Gly Lys Lys Ile Pro Lys Asp
        595                 600                 605

Gln Lys Ser Glu Leu Ile Asn Cys Ser Ala Gln Phe Glu Ala Asn Ala
    610                 615                 620

Phe Glu Ala Pro Leu Thr Phe Ala Asn Ala Asp Ser Gly Leu Leu His
625                 630                 635                 640
```

-continued

```
Ser Ser Val Lys Arg Ser Cys Ser Gln Asn Asp Ser Glu Glu Pro Thr
            645                 650                 655

Leu Ser Leu Thr Ser Ser Phe Gly Thr Ile Leu Arg Lys Cys Ser Arg
            660                 665                 670

Asn Glu Thr Cys Ser Asn Asn Thr Val Ile Ser Gln Asp Leu Asp Tyr
            675                 680                 685

Lys Glu Ala Lys Cys Asn Lys Glu Lys Leu Gln Leu Phe Ile Thr Pro
            690                 695                 700

Glu Ala Asp Ser Leu Ser Cys Leu Gln Glu Gly Gln Cys Glu Asn Asp
705                 710                 715                 720

Pro Lys Ser Lys Val Ser Asp Ile Lys Glu Val Leu Ala Ala
            725                 730                 735

Ala Cys His Pro Val Gln His Ser Lys Val Glu Tyr Ser Asp Thr Asp
            740                 745                 750

Phe Gln Ser Gln Lys Ser Leu Leu Tyr Asp His Glu Asn Ala Ser Thr
            755                 760                 765

Leu Ile Leu Thr Pro Thr Ser Lys Asp Val Leu Ser Asn Leu Val Met
            770                 775                 780

Ile Ser Arg Gly Lys Glu Ser Tyr Lys Met Ser Asp Lys Leu Lys Gly
785                 790                 795                 800

Asn Asn Tyr Glu Ser Asp Val Glu Leu Thr Lys Asn Ile Pro Met Glu
            805                 810                 815

Lys Asn Gln Asp Val Cys Ala Leu Asn Glu Asn Tyr Lys Asn Val Glu
            820                 825                 830

Leu Leu Pro Pro Glu Lys Tyr Met Arg Val Ala Ser Pro Ser Arg Lys
            835                 840                 845

Val Gln Phe Asn Gln Asn Thr Asn Leu Arg Val Ile Gln Lys Asn Gln
            850                 855                 860

Glu Glu Thr Thr Ser Ile Ser Lys Ile Thr Val Asn Pro Asp Ser Glu
865                 870                 875                 880

Glu Leu Phe Ser Asp Asn Glu Asn Asn Phe Val Phe Gln Val Ala Asn
            885                 890                 895

Glu Arg Asn Asn Leu Ala Leu Gly Asn Thr Lys Glu Leu His Glu Thr
            900                 905                 910

Asp Leu Thr Cys Val Asn Glu Pro Ile Phe Lys Asn Ser Thr Met Val
            915                 920                 925

Leu Tyr Gly Asp Thr Gly Asp Lys Gln Ala Thr Gln Val Ser Ile Lys
            930                 935                 940

Lys Asp Leu Val Tyr Val Leu Ala Glu Glu Asn Lys Asn Ser Val Lys
945                 950                 955                 960

Gln His Ile Lys Met Thr Leu Gly Gln Asp Leu Lys Ser Asp Ile Ser
            965                 970                 975

Leu Asn Ile Asp Lys Ile Pro Glu Lys Asn Asn Asp Tyr Met Asn Lys
            980                 985                 990

Trp Ala Gly Leu Leu Gly Pro Ile Ser Asn His Ser Phe Gly Gly Ser
            995                 1000                1005

Phe Arg Thr Ala Ser Asn Lys Glu Ile Lys Leu Ser Glu His Asn Ile
            1010                1015                1020

Lys Lys Ser Lys Met Phe Phe Lys Asp Ile Glu Glu Gln Tyr Pro Thr
1025                1030                1035                1040

Ser Leu Ala Cys Val Glu Ile Val Asn Thr Leu Ala Leu Asp Asn Gln
            1045                1050                1055

Lys Lys Leu Ser Lys Pro Gln Ser Ile Asn Thr Val Ser Ala His Leu
```

```
                   1060                1065                1070
Gln Ser Ser Val Val Ser Asp Cys Lys Asn Ser His Ile Thr Pro
            1075                1080                1085
Gln Met Leu Phe Ser Lys Gln Asp Phe Asn Ser Asn His Asn Leu Thr
            1090                1095                1100
Pro Ser Gln Lys Ala Glu Ile Thr Glu Leu Ser Thr Ile Leu Glu Glu
1105                1110                1115                1120
Ser Gly Ser Gln Phe Glu Phe Thr Gln Phe Arg Lys Pro Ser Tyr Ile
            1125                1130                1135
Leu Gln Lys Ser Thr Phe Glu Val Pro Glu Asn Gln Met Thr Ile Leu
            1140                1145                1150
Lys Thr Thr Ser Glu Glu Cys Arg Asp Ala Asp Leu His Val Ile Met
            1155                1160                1165
Asn Ala Pro Ser Ile Gly Gln Val Asp Ser Ser Lys Gln Phe Glu Gly
            1170                1175                1180
Thr Val Glu Ile Lys Arg Lys Phe Ala Gly Leu Leu Lys Asn Asp Cys
1185                1190                1195                1200
Asn Lys Ser Ala Ser Gly Tyr Leu Thr Asp Glu Asn Glu Val Gly Phe
            1205                1210                1215
Arg Gly Phe Tyr Ser Ala His Gly Thr Lys Leu Asn Val Ser Thr Glu
            1220                1225                1230
Ala Leu Gln Lys Ala Val Lys Leu Phe Ser Asp Ile Glu Asn Ile Ser
            1235                1240                1245
Glu Glu Thr Ser Ala Glu Val His Pro Ile Ser Leu Ser Ser Ser Lys
            1250                1255                1260
Cys His Asp Ser Val Val Ser Met Phe Lys Ile Glu Asn His Asn Asp
1265                1270                1275                1280
Lys Thr Val Ser Glu Lys Asn Asn Lys Cys Gln Leu Ile Leu Gln Asn
            1285                1290                1295
Asn Ile Glu Met Thr Thr Gly Thr Phe Val Glu Glu Ile Thr Glu Asn
            1300                1305                1310
Tyr Lys Arg Asn Thr Glu Asn Glu Asp Asn Lys Tyr Thr Ala Ala Ser
            1315                1320                1325
Arg Asn Ser His Asn Leu Glu Phe Asp Gly Ser Asp Ser Ser Lys Asn
            1330                1335                1340
Asp Thr Val Cys Ile His Lys Asp Glu Thr Asp Leu Leu Phe Thr Asp
1345                1350                1355                1360
Gln His Asn Ile Cys Leu Lys Leu Ser Gly Gln Phe Met Lys Glu Gly
            1365                1370                1375
Asn Thr Gln Ile Lys Glu Asp Leu Ser Asp Leu Thr Phe Leu Glu Val
            1380                1385                1390
Ala Lys Ala Gln Glu Ala Cys His Gly Asn Thr Ser Asn Lys Glu Gln
            1395                1400                1405
Leu Thr Ala Thr Lys Thr Glu Gln Asn Ile Lys Asp Phe Glu Thr Ser
            1410                1415                1420
Asp Thr Phe Phe Gln Thr Ala Ser Gly Lys Asn Ile Ser Val Ala Lys
1425                1430                1435                1440
Glu Ser Phe Asn Lys Ile Val Asn Phe Phe Asp Gln Lys Pro Glu Glu
            1445                1450                1455
Leu His Asn Phe Ser Leu Asn Ser Glu Leu His Ser Asp Ile Arg Lys
            1460                1465                1470
Asn Lys Met Asp Ile Leu Ser Tyr Glu Glu Thr Asp Ile Val Lys His
            1475                1480                1485
```

-continued

```
Lys Ile Leu Lys Glu Ser Val Pro Val Gly Thr Gly Asn Gln Leu Val
    1490                1495                1500

Thr Phe Gln Gly Gln Pro Glu Arg Asp Glu Lys Ile Lys Glu Pro Thr
1505                1510                1515                1520

Leu Leu Gly Phe His Thr Ala Ser Gly Lys Lys Val Lys Ile Ala Lys
                1525                1530                1535

Glu Ser Leu Asp Lys Val Lys Asn Leu Phe Asp Glu Lys Glu Gln Gly
                1540                1545                1550

Thr Ser Glu Ile Thr Ser Phe Ser His Gln Trp Ala Lys Thr Leu Lys
            1555                1560                1565

Tyr Arg Glu Ala Cys Lys Asp Leu Glu Leu Ala Cys Glu Thr Ile Glu
        1570                1575                1580

Ile Thr Ala Ala Pro Lys Cys Lys Glu Met Gln Asn Ser Leu Asn Asn
1585                1590                1595                1600

Asp Lys Asn Leu Val Ser Ile Glu Thr Val Val Pro Pro Lys Leu Leu
                1605                1610                1615

Ser Asp Asn Leu Cys Arg Gln Thr Glu Asn Leu Lys Thr Ser Lys Ser
                1620                1625                1630

Ile Phe Leu Lys Val Lys Val His Glu Asn Val Glu Lys Glu Thr Ala
            1635                1640                1645

Lys Ser Pro Ala Thr Cys Tyr Thr Asn Gln Ser Pro Tyr Ser Val Ile
        1650                1655                1660

Glu Asn Ser Ala Leu Ala Phe Tyr Thr Ser Cys Ser Arg Lys Thr Ser
1665                1670                1675                1680

Val Ser Gln Thr Ser Leu Leu Glu Ala Lys Lys Trp Leu Arg Glu Gly
                1685                1690                1695

Ile Phe Asp Gly Gln Pro Glu Arg Ile Asn Thr Ala Asp Tyr Val Gly
                1700                1705                1710

Asn Tyr Leu Tyr Glu Asn Asn Ser Asn Ser Thr Ile Ala Glu Asn Asp
            1715                1720                1725

Lys Asn His Leu Ser Glu Lys Gln Asp Thr Tyr Leu Ser Asn Ser Ser
        1730                1735                1740

Met Ser Asn Ser Tyr Ser Tyr His Ser Asp Glu Val Tyr Asn Asp Ser
1745                1750                1755                1760

Gly Tyr Leu Ser Lys Asn Lys Leu Asp Ser Gly Ile Glu Pro Val Leu
                1765                1770                1775

Lys Asn Val Glu Asp Gln Lys Asn Thr Ser Phe Ser Lys Val Ile Ser
            1780                1785                1790

Asn Val Lys Asp Ala Asn Ala Tyr Pro Gln Thr Val Asn Glu Asp Ile
        1795                1800                1805

Cys Val Glu Glu Leu Val Thr Ser Ser Ser Pro Cys Lys Asn Lys Asn
    1810                1815                1820

Ala Ala Ile Lys Leu Ser Ile Ser Asn Ser Asn Asn Phe Glu Val Gly
1825                1830                1835                1840

Pro Pro Ala Phe Arg Ile Ala Ser Gly Lys Ile Val Cys Val Ser His
                1845                1850                1855

Glu Thr Ile Lys Lys Val Lys Asp Ile Phe Thr Asp Ser Phe Ser Lys
            1860                1865                1870

Val Ile Lys Glu Asn Asn Glu Asn Lys Ser Lys Ile Cys Gln Thr Lys
        1875                1880                1885

Ile Met Ala Gly Cys Tyr Glu Ala Leu Asp Asp Ser Glu Asp Ile Leu
    1890                1895                1900

His Asn Ser Leu Asp Asn Asp Glu Cys Ser Thr His Ser His Lys Val
1905                1910                1915                1920
```

-continued

Phe Ala Asp Ile Gln Ser Glu Glu Ile Leu Gln His Asn Gln Asn Met
              1925                1930                1935

Ser Gly Leu Glu Lys Val Ser Lys Ile Ser Pro Cys Asp Val Ser Leu
         1940                1945                1950

Glu Thr Ser Asp Ile Cys Lys Cys Ser Ile Gly Lys Leu His Lys Ser
         1955                1960                1965

Val Ser Ser Ala Asn Thr Cys Gly Ile Phe Ser Thr Ala Ser Gly Lys
         1970                1975                1980

Ser Val Gln Val Ser Asp Ala Ser Leu Gln Asn Ala Arg Gln Val Phe
1985                1990                1995                2000

Ser Glu Ile Glu Asp Ser Thr Lys Gln Val Phe Ser Lys Val Leu Phe
              2005                2010                2015

Lys Ser Asn Glu His Ser Asp Gln Leu Thr Arg Glu Glu Asn Thr Ala
              2020                2025                2030

Ile Arg Thr Pro Glu His Leu Ile Ser Gln Lys Gly Phe Ser Tyr Asn
              2035                2040                2045

Val Val Asn Ser Ser Ala Phe Ser Gly Phe Ser Thr Ala Ser Gly Lys
              2050                2055                2060

Gln Val Ser Ile Leu Glu Ser Ser Leu His Lys Val Lys Gly Val Leu
2065                2070                2075                2080

Glu Glu Phe Asp Leu Ile Arg Thr Glu His Ser Leu His Tyr Ser Pro
              2085                2090                2095

Thr Ser Arg Gln Asn Val Ser Lys Ile Leu Pro Arg Val Asp Lys Arg
              2100                2105                2110

Asn Pro Glu His Cys Val Asn Ser Glu Met Glu Lys Thr Cys Ser Lys
              2115                2120                2125

Glu Phe Lys Leu Ser Asn Asn Leu Asn Val Glu Gly Gly Ser Ser Glu
              2130                2135                2140

Asn Asn His Ser Ile Lys Val Ser Pro Tyr Leu Ser Gln Phe Gln Gln
2145                2150                2155                2160

Asp Lys Gln Gln Leu Val Leu Gly Thr Lys Val Ser Leu Val Glu Asn
              2165                2170                2175

Ile His Val Leu Gly Lys Glu Gln Ala Ser Pro Lys Asn Val Lys Met
              2180                2185                2190

Glu Ile Gly Lys Thr Glu Thr Phe Ser Asp Val Pro Val Lys Thr Asn
              2195                2200                2205

Ile Glu Val Cys Ser Thr Tyr Ser Lys Asp Ser Glu Asn Tyr Phe Glu
              2210                2215                2220

Thr Glu Ala Val Glu Ile Ala Lys Ala Phe Met Glu Asp Asp Glu Leu
2225                2230                2235                2240

Thr Asp Ser Lys Leu Pro Ser His Ala Thr His Ser Leu Phe Thr Cys
              2245                2250                2255

Pro Glu Asn Glu Glu Met Val Leu Ser Asn Ser Arg Ile Gly Lys Arg
              2260                2265                2270

Arg Gly Glu Pro Leu Ile Leu Val Gly Glu Pro Ser Ile Lys Arg Asn
              2275                2280                2285

Leu Leu Asn Glu Phe Asp Arg Ile Ile Glu Asn Gln Glu Lys Ser Leu
              2290                2295                2300

Lys Ala Ser Lys Ser Thr Pro Asp Gly Thr Ile Lys Asp Arg Arg Leu
2305                2310                2315                2320

Phe Met His His Val Ser Leu Glu Pro Ile Thr Cys Val Pro Phe Arg
              2325                2330                2335

Thr Thr Lys Glu Arg Gln Glu Ile Gln Asn Pro Asn Phe Thr Ala Pro

-continued

```
            2340            2345            2350
Gly Gln Glu Phe Leu Ser Lys Ser His Leu Tyr Glu His Leu Thr Leu
            2355            2360            2365
Glu Lys Ser Ser Ser Asn Leu Ala Val Ser Gly His Pro Phe Tyr Gln
            2370            2375            2380
Val Ser Ala Thr Arg Asn Glu Lys Met Arg His Leu Ile Thr Thr Gly
2385            2390            2395            2400
Arg Pro Thr Lys Val Phe Val Pro Pro Phe Lys Thr Lys Ser His Phe
            2405            2410            2415
His Arg Val Glu Gln Cys Val Arg Asn Ile Asn Leu Glu Glu Asn Arg
            2420            2425            2430
Gln Lys Gln Asn Ile Asp Gly His Gly Ser Asp Asp Ser Lys Asn Lys
            2435            2440            2445
Ile Asn Asp Asn Glu Ile His Gln Phe Asn Lys Asn Asn Ser Asn Gln
            2450            2455            2460
Ala Ala Ala Val Thr Phe Thr Lys Cys Glu Glu Glu Pro Leu Asp Leu
2465            2470            2475            2480
Ile Thr Ser Leu Gln Asn Ala Arg Asp Ile Gln Asp Met Arg Ile Lys
            2485            2490            2495
Lys Lys Gln Arg Gln Arg Val Phe Pro Gln Pro Gly Ser Leu Tyr Leu
            2500            2505            2510
Ala Lys Thr Ser Thr Leu Pro Arg Ile Ser Leu Lys Ala Ala Val Gly
            2515            2520            2525
Gly Gln Val Pro Ser Ala Cys Ser His Lys Gln Leu Tyr Thr Tyr Gly
            2530            2535            2540
Val Ser Lys His Cys Ile Lys Ile Asn Ser Lys Asn Ala Glu Ser Phe
2545            2550            2555            2560
Gln Phe His Thr Glu Asp Tyr Phe Gly Lys Glu Ser Leu Trp Thr Gly
            2565            2570            2575
Lys Gly Ile Gln Leu Ala Asp Gly Gly Trp Leu Ile Pro Ser Asn Asp
            2580            2585            2590
Gly Lys Ala Gly Lys Glu Glu Phe Tyr Arg Ala Leu Cys Asp Thr Pro
            2595            2600            2605
Gly Val Asp Pro Lys Leu Ile Ser Arg Ile Trp Val Tyr Asn His Tyr
            2610            2615            2620
Arg Trp Ile Ile Trp Lys Leu Ala Ala Met Glu Cys Ala Phe Pro Lys
2625            2630            2635            2640
Glu Phe Ala Asn Arg Cys Leu Ser Pro Glu Arg Val Leu Leu Gln Leu
            2645            2650            2655
Lys Tyr Arg Tyr Asp Thr Glu Ile Asp Arg Ser Arg Arg Ser Ala Ile
            2660            2665            2670
Lys Lys Ile Met Glu Arg Asp Asp Thr Ala Ala Lys Thr Leu Val Leu
            2675            2680            2685
Cys Val Ser Asp Ile Ile Ser Leu Ser Ala Asn Ile Ser Glu Thr Ser
            2690            2695            2700
Ser Asn Lys Thr Ser Ser Ala Asp Thr Gln Lys Val Ala Ile Ile Glu
2705            2710            2715            2720
Leu Thr Asp Gly Trp Tyr Ala Val Lys Ala Gln Leu Asp Pro Pro Leu
            2725            2730            2735
Leu Ala Val Leu Lys Asn Gly Arg Leu Thr Val Gly Gln Lys Ile Ile
            2740            2745            2750
Leu His Gly Ala Glu Leu Val Gly Ser Pro Asp Ala Cys Thr Pro Leu
            2755            2760            2765
```

-continued

Glu Ala Pro Glu Ser Leu Met Leu Lys Ile Ser Ala Asn Ser Thr Arg
    2770                2775                2780

Pro Ala Arg Trp Tyr Thr Lys Leu Gly Phe Phe Pro Asp Pro Arg Pro
2785                2790                2795                2800

Phe Pro Leu Pro Leu Ser Ser Leu Phe Ser Asp Gly Gly Asn Val Gly
            2805                2810                2815

Cys Val Asp Val Ile Ile Gln Arg Ala Tyr Pro Ile Gln Trp Met Glu
            2820                2825                2830

Lys Thr Ser Ser Gly Leu Tyr Ile Phe Arg Asn Glu Arg Glu Glu Glu
            2835                2840                2845

Lys Glu Ala Ala Lys Tyr Val Glu Ala Gln Gln Lys Arg Leu Glu Ala
            2850                2855                2860

Leu Phe Thr Lys Ile Gln Glu Glu Phe Glu Glu His Glu Glu Asn Thr
2865                2870                2875                2880

Thr Lys Pro Tyr Leu Pro Ser Arg Ala Leu Thr Arg Gln Gln Val Arg
            2885                2890                2895

Ala Leu Gln Asp Gly Ala Glu Leu Tyr Glu Ala Val Lys Asn Ala Ala
            2900                2905                2910

Asp Pro Ala Tyr Leu Glu Gly Tyr Phe Ser Glu Glu Gln Leu Arg Ala
            2915                2920                2925

Leu Asn Asn His Arg Gln Met Leu Asn Asp Lys Lys Gln Ala Gln Ile
            2930                2935                2940

Gln Leu Glu Ile Arg Lys Ala Met Glu Ser Ala Glu Gln Lys Glu Gln
2945                2950                2955                2960

Gly Leu Ser Arg Asp Val Thr Thr Val Trp Lys Leu Arg Ile Val Ser
            2965                2970                2975

Tyr Ser Lys Lys Glu Lys Asp Ser Val Ile Leu Ser Ile Trp Arg Pro
            2980                2985                2990

Ser Ser Asp Leu Tyr Ser Leu Leu Thr Glu Gly Lys Arg Tyr Arg Ile
            2995                3000                3005

Tyr His Leu Ala Thr Ser Lys Ser Lys Ser Lys Ser Glu Arg Ala Asn
            3010                3015                3020

Ile Gln Leu Ala Ala Thr Lys Lys Thr Gln Tyr Gln Gln Leu Pro Val
3025                3030                3035                3040

Ser Asp Glu Ile Leu Phe Gln Ile Tyr Gln Pro Arg Glu Pro Leu His
            3045                3050                3055

Phe Ser Lys Phe Leu Asp Pro Asp Phe Gln Pro Ser Cys Ser Glu Val
            3060                3065                3070

Asp Leu Ile Gly Phe Val Val Ser Val Val Lys Lys Thr Gly Leu Ala
            3075                3080                3085

Pro Phe Val Tyr Leu Ser Asp Glu Cys Tyr Asn Leu Leu Ala Ile Lys
            3090                3095                3100

Phe Trp Ile Asp Leu Asn Glu Asp Ile Ile Lys Pro His Met Leu Ile
3105                3110                3115                3120

Ala Ala Ser Asn Leu Gln Trp Arg Pro Glu Ser Lys Ser Gly Leu Leu
            3125                3130                3135

Thr Leu Phe Ala Gly Asp Phe Ser Val Phe Ser Ala Ser Pro Lys Glu
            3140                3145                3150

Gly His Phe Gln Glu Thr Phe Asn Lys Met Lys Asn Thr Val Glu Asn
            3155                3160                3165

Ile Asp Ile Leu Cys Asn Glu Ala Glu Asn Lys Leu Met His Ile Leu
            3170                3175                3180

His Ala Asn Asp Pro Lys Trp Ser Thr Pro Thr Lys Asp Cys Thr Ser
3185                3190                3195                3200

```
Gly Pro Tyr Thr Ala Gln Ile Ile Pro Gly Thr Gly Asn Lys Leu Leu
            3205                3210                3215

Met Ser Ser Pro Asn Cys Glu Ile Tyr Tyr Gln Ser Pro Leu Ser Leu
            3220                3225                3230

Cys Met Ala Lys Arg Lys Ser Val Ser Thr Pro Val Ser Ala Gln Met
            3235                3240                3245

Thr Ser Lys Ser Cys Lys Gly Glu Lys Glu Ile Asp Asp Gln Lys Asn
            3250                3255                3260

Cys Lys Lys Arg Arg Ala Leu Asp Phe Leu Ser Arg Leu Pro Leu Pro
3265                3270                3275                3280

Pro Pro Val Ser Pro Ile Cys Thr Phe Val Ser Pro Ala Ala Gln Lys
            3285                3290                3295

Ala Phe Gln Pro Pro Arg Ser Cys Gly Thr Lys Tyr Glu Thr Pro Ile
            3300                3305                3310

Lys Lys Lys Glu Leu Asn Ser Pro Gln Met Thr Pro Phe Lys Lys Phe
            3315                3320                3325

Asn Glu Ile Ser Leu Leu Glu Ser Asn Ser Ile Ala Asp Glu Glu Leu
            3330                3335                3340

Ala Leu Ile Asn Thr Gln Ala Leu Leu Ser Gly Ser Thr Gly Glu Lys
3345                3350                3355                3360

Gln Phe Ile Ser Val Ser Glu Ser Thr Arg Thr Ala Pro Thr Ser Ser
            3365                3370                3375

Glu Asp Tyr Leu Arg Leu Lys Arg Arg Cys Thr Thr Ser Leu Ile Lys
            3380                3385                3390

Glu Gln Glu Ser Ser Gln Ala Ser Thr Glu Glu Cys Glu Lys Asn Lys
            3395                3400                3405

Gln Asp Thr Ile Thr Thr Lys Lys Tyr Ile
            3410                3415

<210> SEQ ID NO 43
<211> LENGTH: 149
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 43

Leu Leu Gly Ile Cys Leu Thr Ser Thr Val Gln Leu Val Thr Gln Leu
 1               5                  10                  15

Met Pro Tyr Gly Cys Leu Leu Asp His Val Arg Glu His Arg Gly Arg
            20                  25                  30

Leu Gly Ser Gln Asp Leu Leu Asn Trp Cys Val Gln Ile Ala Lys Gly
        35                  40                  45

Met Ser Tyr Leu Glu Glu Val Arg Leu Val His Arg Asp Leu Ala Ala
    50                  55                  60

Arg Asn Val Leu Val Lys Ser Pro Asn His Val Lys Ile Thr Asp Phe
65                  70                  75                  80

Gly Leu Ala Arg Leu Leu Asp Ile Asp Glu Thr Glu Tyr His Ala Asp
                85                  90                  95

Gly Gly Lys Val Pro Ile Lys Trp Met Ala Leu Glu Ser Ile Leu Arg
            100                 105                 110

Arg Arg Phe Thr His Gln Ser Asp Val Trp Ser Tyr Gly Val Thr Val
        115                 120                 125

Trp Glu Leu Met Thr Phe Gly Ala Lys Pro Tyr Asp Gly Ile Pro Ala
    130                 135                 140
```

Arg Glu Ile Pro Asp
145

<210> SEQ ID NO 44
<211> LENGTH: 36
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 44

Lys Tyr Thr Met Arg Arg Leu Leu Gln Glu Thr Glu Leu Val Glu Pro
  1               5                  10                  15

Leu Thr Pro Ser Gly Ala Met Pro Asn Gln Ala Gln Met Arg Ile Leu
             20                  25                  30

Lys Glu Thr Glu
         35

<210> SEQ ID NO 45
<211> LENGTH: 4530
<212> TYPE: DNA
<213> ORGANISM: Artificial Sequence
<220> FEATURE:
<223> OTHER INFORMATION: Description of Artificial Sequence:/Note =
      Synthetic Construct

<400> SEQUENCE: 45

| | | | | | | |
|---|---|---|---|---|---|---|
| aattctcgag | ctcgtcgacc | ggtcgacgag | ctcgagggtc | gacgagctcg | agggcgcgcg | 60 |
| cccggccccc | acccctcgca | gcacccgcg | ccccgcgccc | tcccagccgg | gtccagccgg | 120 |
| agccatgggg | ccggagccgc | agtgagcacc | atggagctgg | cggccttgtg | ccgctggggg | 180 |
| ctcctcctcg | ccctcttgcc | ccccggagcc | gcgagcaccc | aagtgtgcac | cggcacagac | 240 |
| atgaagctgc | ggctccctgc | cagtcccgag | acccacctgg | acatgctccg | ccacctctac | 300 |
| cagggctgcc | aggtggtgca | gggaaacctg | gaactcacct | acctgcccac | caatgccagc | 360 |
| ctgtccttcc | tgcaggatat | ccaggaggtg | cagggctacg | tgctcatcgc | tcacaaccaa | 420 |
| gtgaggcagg | tcccactgca | gaggctgcgg | attgtgcgag | gcacccagct | ctttgaggac | 480 |
| aactatgccc | tggccgtgct | agacaatgga | gaccgctga | acaataccac | ccctgtcaca | 540 |
| ggggcctccc | aggaggcct | gcgggagctg | cagcttcgaa | gcctcacaga | gatcttgaaa | 600 |
| ggaggggtct | tgatccagcg | gaaccccag | ctctgctacc | aggacacgat | tttgtggaag | 660 |
| gacatcttcc | acaagaacaa | ccagctggct | ctcacactga | tagacaccaa | ccgctctcgg | 720 |
| gcctgccacc | cctgttctcc | gatgtgtaag | ggctcccgct | gctggggaga | gagttctgag | 780 |
| gattgtcaga | gcctgacgcg | cactgtctgt | gccggtggct | gtgcccgctg | caaggggcca | 840 |
| ctgcccactg | actgctgcca | tgagcagtgt | gctgccggct | gcacgggccc | caagcactct | 900 |
| gactgcctgg | cctgcctcca | cttcaaccac | agtggcatct | gtgagctgca | ctgcccagcc | 960 |
| ctggtcacct | acaacacaga | cacgtttgag | tccatgccca | atcccgaggg | ccggtataca | 1020 |
| ttcggcgcca | gctgtgtgac | tgcctgtccc | tacaactacc | tttctacgga | cgtgggatcc | 1080 |
| tgcaccctcg | tctgcccct | gcacaaccaa | gaggtgacag | cagaggatgg | aacacagcgg | 1140 |
| tgtgagaagt | gcagcaagcc | ctgtgcccga | gtgtgctatg | gtctgggcat | ggagcacttg | 1200 |
| cgagaggtga | gggcagttac | cagtgccaat | atccaggagt | tgctggctg | caagaagatc | 1260 |
| tttgggagcc | tggcatttct | gccggagagc | tttgatgggg | acccagcctc | caacactgcc | 1320 |
| ccgctccagc | cagagcagct | ccaagtgttt | gagactctgg | aagagatcac | aggttaccta | 1380 |

```
tacatctcag catggccgga cagcctgcct gacctcagcg tcttccagaa cctgcaagta   1440
atccggggac gaattctgca caatggcgcc tactcgctga ccctgcaagg gctgggcatc   1500
agctggctgg ggctgcgctc actgagggaa ctgggcagtg gactggccct catccaccat   1560
aacacccacc tctgcttcgt gcacacggtg ccctgggacc agctctttcg gaacccgcac   1620
caagctctgc tccacactgc caaccggcca gaggacgagt gtgtgggcga gggcctggcc   1680
tgccaccagc tgtgcgcccg agggcactgc tggggtccag ggcccaccca gtgtgtcaac   1740
tgcagccagt tccttcgggg ccaggagtgc gtggaggaat gccgagtact gcaggggctc   1800
cccagggagt atgtgaatgc caggcactgt ttgccgtgcc accctgagtg tcagcccag    1860 aatggctcag tgacctgttt tggaccggag gctgaccagt gtgtggcctg tgcccactat   1920
aaggacccct ccttctgcgt ggcccgctgc cccagcggtg tgaaacctga cctctcctac   1980
atgcccatct ggaagtttcc agatgaggag ggcgcatgcc agccttgccc catcaactgc   2040
acccactcct gtgtggacct ggatgacaag ggctgccccg ccgagcagag agccagccct   2100
ctgacgtcca tcgtctctgc ggtggttggc attctgctgg tcgtggtctt ggggtggtc    2160 tttgggatcc tcatcaagcg acggcagcag aagatccgga agtacacgat gcggagactg   2220
ctgcaggaaa cggagctggt ggagccgctg acacctagcg gagcgatgcc caaccaggcg   2280
cagatgcgga tcctgaaaga gacggagctg aggaaggtga ggtgcttgg atctggcgct    2340 tttggcacag tctacaaggg catctggatc cctgatgggg agaatgtgaa aattccagtg   2400
gccatcaaag tgttgaggga aaacacatcc cccaaagcca caaagaaat cttagacgaa    2460 gcatacgtga tggctggtgt gggctcccca tatgtctccc gccttctggg catctgcctg   2520
acatccacgt gcagctggt gacacagctt atgccctatg ctgcctctt agaccatgtc     2580 cgggaaaacc gcggacgcct gggctcccag gacctgctga actggtgtat gcagattgcc   2640
aaggggatga gctacctgga ggatgtgcgg ctcgtacaca gggacttggc cgctcggaac   2700
gtgctggtca agagtcccaa ccatgtcaaa attacagact cgggctggc tcggctgctg    2760 gacattgacg agacagagta ccatgcagat gggggcaagg tgcccatcaa gtggatggcg   2820
ctggagtcca ttctccgccg gcggttcacc caccagagtg atgtgtggag ttatggtgtg   2880
actgtgtggg agctgatgac ttttggggcc aaaccttacg atgggatccc agcccgggag   2940
atccctgacc tgctggaaaa gggggagcgg ctgccccagc cccccatctg caccattgat   3000
gtctacatga tcatggtcaa atgttggatg attgactctg aatgtcggcc aagattccgg   3060
gagttggtgt ctgaattctc ccgcatggcc agggaccccc agcgctttgt ggtcatccag   3120
aatgaggact gggcccagc cagtcccttg acagcacct tctaccgctc actgctggag      3180
gacgatgaca tgggggacct ggtggatgct gaggagtatc tggtaccca gcagggcttc    3240 ttctgtccag accctgcccc gggcgctggg ggcatggtcc accacaggca ccgcagctca   3300
tctaccagga gtggcggtgg ggacctgaca ctagggctgg agccctctga agaggaggcc   3360
cccaggtctc cactggcacc ctccgaaggg ctggctccg atgtatttga tggtgacctg   3420
ggaatggggg cagccaaggg gctgcaaagc ctccccacac atgaccccag ccctctacag   3480
cggtacagtg aggaccccac agtacccctg ccctctgaga ctgatggcta cgttgccccc   3540
ctgacctgca gccccagcc tgaatatgtg aaccagccaa atgttcggcc ccagccccct   3600
tcgccccgag agggccctct gcctgctgcc cgacctgctg gtgccactct ggaaagggcc   3660
aagactctct cccagggaa gaatgggtc gtcaaagacg ttttttgcctt tgggggtgcc    3720 gtggagaacc ccgagtactt gacaccccag ggaggagctg cccctcagcc ccaccctcct   3780
```

```
cctgccttca gcccagcctt cgacaacctc tattactggg accaggaccc accagagcgg    3840
ggggctccac ccagcacctt caaagggaca cctacggcag agaacccaga gtacctgggt    3900
ctggacgtgc cagtgtgaac cagaaggcca agtccgcaga agccctgatg tgtcctcagg    3960
gagcagggaa ggcctgactt ctgctggcat caagaggtgg gagggccctc cgaccacttc    4020
caggggaacc tgccatgcca ggaacctgtc ctaaggaacc ttccttcctg cttgagttcc    4080
cagatggctg gaaggggtcc agcctcgttg gaagaggaac agcactgggg agtctttgtg    4140
gattctgagg ccctgcccaa tgagactcta gggtccagtg gatgccacag cccagcttgg    4200 cccttttcctt ccagatcctg ggtactgaaa gccttaggga agctggcctg agaggggaag   4260
cggccctaag ggagtgtcta agaacaaaag cgacccattc agagactgtc cctgaaacct    4320
agtactgccc cccatgagga aggaacagca atggtgtcag tatccaggct ttgtacagag    4380
tgcttttctg tttagttttt acttttttg ttttgttttt ttaaagacga aataaagacc     4440
caggggagaa tgggtgttgt atggggaggc aagtgtgggg ggtccttctc cacacccact    4500
ttgtccattt gcaaatatat tttggaaaac                                     4530
```

US 8,613,907 B2

COMPOSITIONS THAT INHIBIT PROLIFERATION OF CANCER CELLS

This application claims benefit of U.S. Provisional Application No. 60/365,078 filed on Mar. 15, 2002, entitled "Compositions that inhibit proliferation of cancer cells," which application is herein incorporated by reference in its entirety and is also a continuation-in-part and claims priority to international application PCT/US01/32127 filed on Oct. 12, 2001, entitled "Compositions that inhibit proliferation of cancer cells," which application is herein incorporated by reference in its entirety which claims benefit of U. S. Provisional Application No. 60/239,705 filed on Oct. 12, 2000 entitled, "Agents promoting apoptosis in cancer cells via interruption of oncogene-induced integrin signaling", and which application is herein incorporated by reference in its entirety, and U.S. Provisional Application No. 60/242,812 filed on Oct. 24, 2000 entitled, "Agents promoting apoptosis in cancer cells via interruption of oncogene-induced integrin signaling" which is herein incorporated by reference in its entirety.

I. BACKGROUND OF THE INVENTION

In cancer cells multiple oncogenic lesions cooperate in malignant transformation. Such cooperation permits survival and proliferation of tumor cells in absence of contact with extra-cellular matrix (ECM), suggesting that tumor cell survival and proliferation have become independent of the engagement of integrin signaling by ECM.

Carcinogenesis is caused by multiple cooperating genetic lesions leading to a progressive deregulation of cellular signaling and cell cycle restriction point control. The mutations involved result in oncogene activation or loss of tumor-suppressor gene function. Typically, single oncogenes are insufficient to cause malignant transformation because they simultaneously induce signals stimulating and inhibiting cell growth. As a result cell proliferation remains restricted. In contrast, cooperating oncogenic lesions act in concert to disable such inhibitory signals while reinforcing the growth-promoting stimuli. The co-operation of oncogenic lesions involves integration of multiple signals converging on the regulation of cell cycle-dependent kinase complexes (Lloyd et al., 1997; Perez-Roger et al., 1999; Roper et al., 2001; Sewing et al., 1997).

Disclosed herein are compositions and methods that show survival of various transformed cell types requires cell-autonomous (autocrine) integrin signaling activity. This activity is induced by cooperating oncogenic lesions and involves induction of integrin receptor and ligand components such as integrin alpha6 and integrin beta4, and laminin5-gamma2 chains. Blocking of integrin or the laminin ligand function induces rapid apoptosis of the transformed cells, even when growing in presence of ECM. In contrast, normal cells remain viable when exposed to the same treatment.

The disclosed compositions and methods are related to the cooperation of oncogenic lesions controlling the ability of transformed cells to proliferate in the absence of contact with the extra-cellular matrix (ECM). As taught herein, oncogenes cooperate to promote a cell-autonomous (autocrine) integrin signaling loop that proves essential for the survival of various transformed cell types. As this signaling loop is not established in corresponding normal cells, the signaling components of this loop constitute attractive targets for cancer therapy.

II. SUMMARY OF THE INVENTION

In accordance with the purposes of this invention, as embodied and broadly described herein, this invention, in one aspect, relates to compositions and methods related to integrin mediated cancer cell growth.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

III. BRIEF DESCRIPTION OF THE DRAWINGS

The accompanying drawings, which are incorporated in and constitute a part of this specification, illustrate several embodiments of the invention and together with the description, serve to explain the principles of the invention.

Figure 1D:
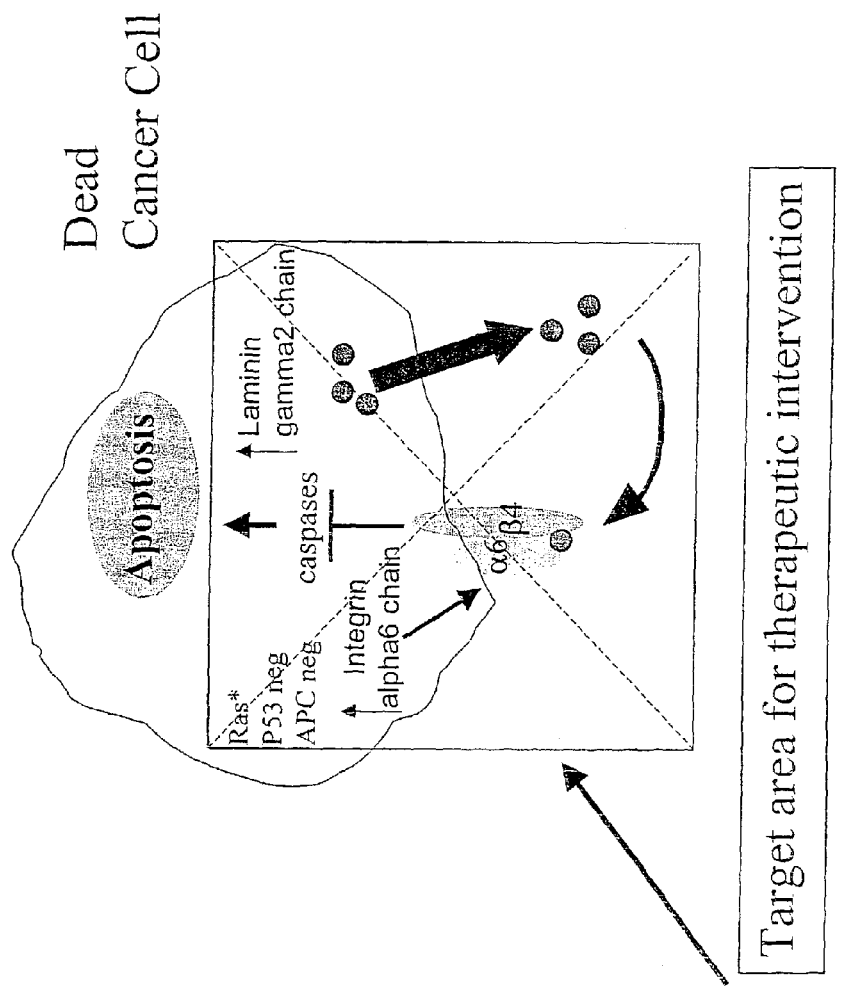

FIG. 1 shows a series of schematics representative of the disclosed relationships and compositions. In normal cells integrin receptors signal to suppress programmed cell death (apoptosis) when engaged by appropriate extra-cellular matrix (ECM) ligands. When receptor-ligand interaction is lost, the cells undergo apoptosis due to the lack of survival signals (FIG. 1-. Panel 1). In cancer cells multiple oncogenic lesions cooperate to cause malignant transformation. Such cooperation permits survival and proliferation of tumor cells independent of integrin receptor-ECM interactions. This property has been termed anchorage-independence (Panel 2). We have discovered the mechanistic basis of anchorage-independence. The transformed cells replace the requirement for ECM-dependent signaling with a surrogate integrin signaling loop on which they rely for survival. In colonic epithelial cells, activation of Ras in combination with APC (adenomatous polyposis coli) or p53 mutations leads to induction of integrin receptor and ligand components such as integrin alpha6 and laminin gamma2 chains. As a consequence, laminin-dependent activation of alpha6/beta4 integrin receptors signals to inhibit caspase activity and thus to suppress apoptosis (Panel 3). Ablation of integrin alpha6, laminin ligand function or alpha6/beta4 integrin receptor function induces apoptosis of the transformed cells, even when growing in the presence of ECM. In contrast, non-transformed control cells remain viable when exposed to the same treatment, indicating that the dependence of the transformed cells on autocrine integrin signaling may be a particular feature of the cancer cell phenotype. The essential role of alpha6 integrin extends to various transformed cell types including mesenchymal and SW480 human colon carcinoma cells. Thus inhibition of laminin/alpha6 integrin-mediated signaling is an important method to induce cancer cell-specific death in a variety of cell types (Panel 4).

Figure 2:
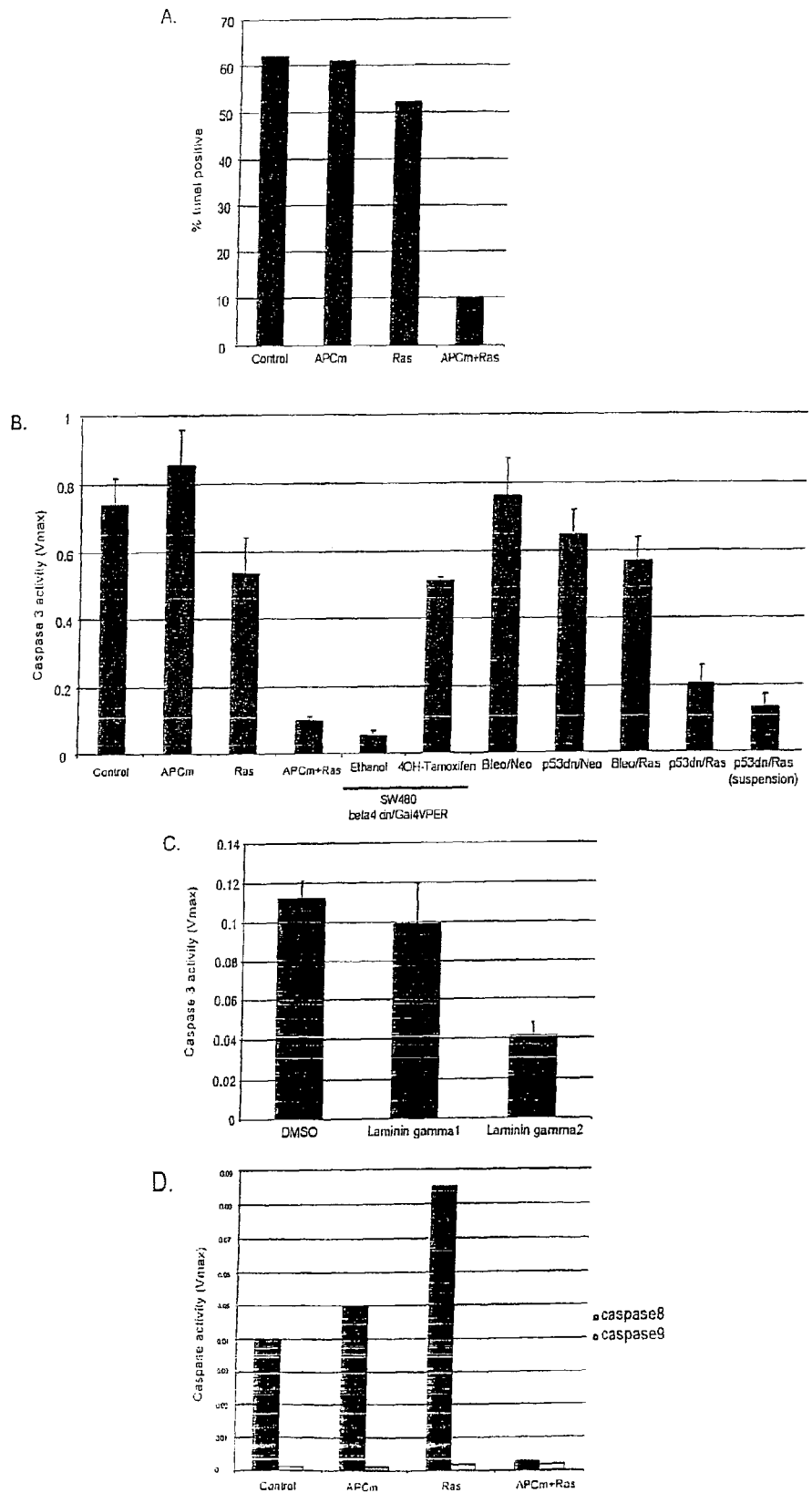

FIG. 2 shows that oncogene cooperation protects cells from apoptosis. FIG. 2A shows control, APCm, Ras, APCm+Ras cells that were detached from collagen IV substrates with Trypsin/EDTA and kept in suspension at $2 \times 10^5$ cells/ml in RPMI 10% FCS for 12 h at 39° C. Subsequently TUNEL analysis was performed on poly-lysine treated slides. The percentage of tunel-positive cells was determined by immunofluorescence microscopy. FIG. 2B shows control, APCm, Ras, APCm Ras, SW480 cells were detached and maintained in suspension as described in (A). SW480 beta4 dn/Gal4VPER cells, express a 4OH-tamoxifen-inducible dominant-negative form of the beta4 integrin. Cells were pelleted and protein extracts were prepared in 300 µl of 50 mM Tris-HCl, pH 7.4; 1% NP40; 0.25% sodium deoxycholate; 150 mM NaCl; 1 mM EGTA. 200 µl of extracts were incubated for 10 min with 2 µl of Caspase 3 fluorometric Substrate (Upstate Biotechnology). Vmax of caspase activity was determined by measuring the fluorescence at 460 nm after excitation at 380 nm for 1 h. FIG. 2C shows laminin gamma1 and gamma2-specific peptides were added to APCmin+Ras cells at the concentration of 100 µg/ml. Caspase activity was measured as in (B). FIG. 2D shows caspase 8 and caspase 9 activities were measured as in (B) using caspase 8 and caspase 9-specific fluorimetric substrates (Upstate Biotechnologies).

Figure 3:
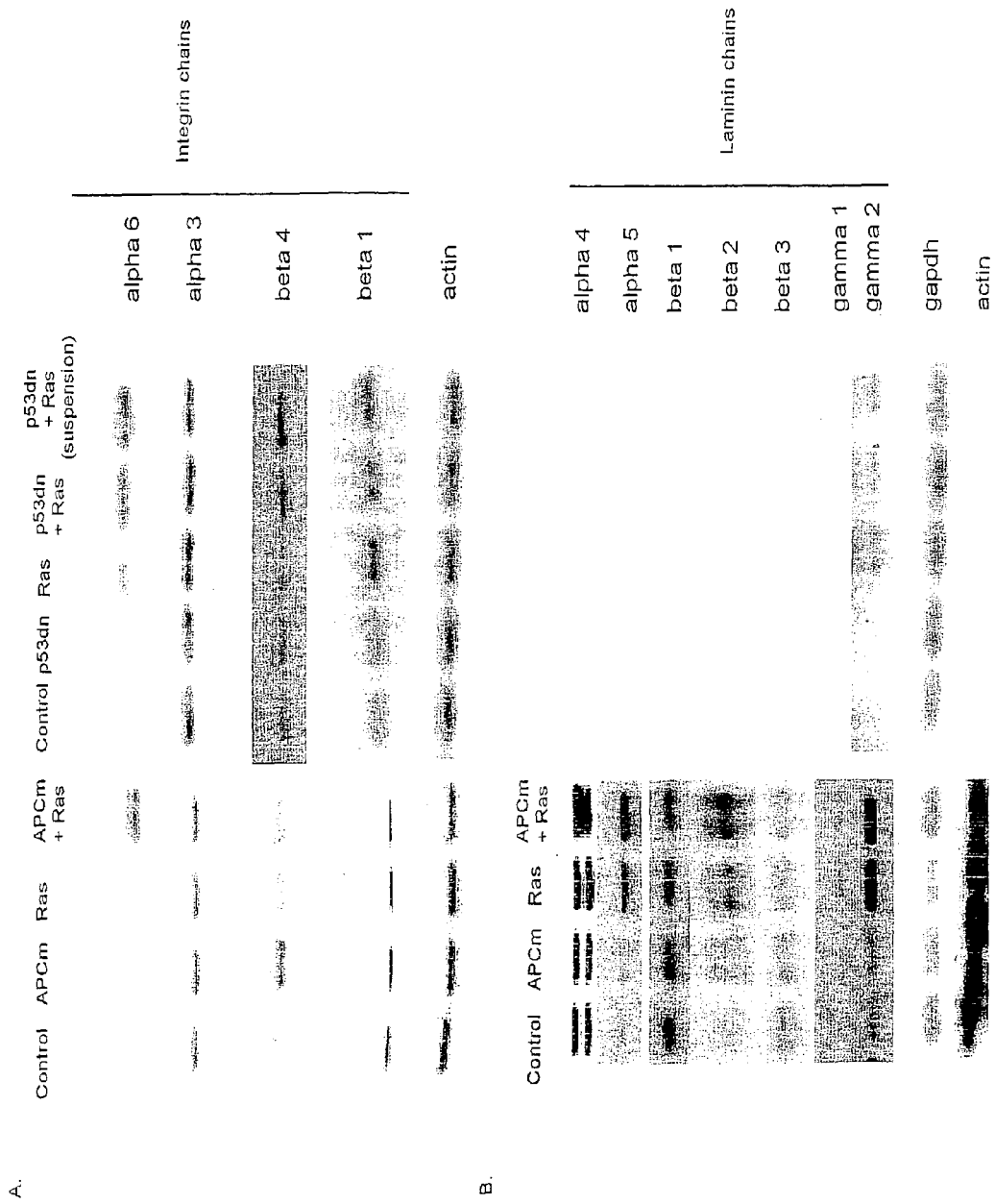

FIG. 3 shows alterations of integrin and laminin expression profiles in malignant cell transformation. FIG. 3A shows integrin expression and FIG. 3B shows laminin expression. The indicated cell populations were cultured on collagen IV-coated dishes at 39° C. in RPMI 10% FCS. Total RNA was extracted from $10^6$ cells for each sample and used for RT-PCR (laminins, alpha4, gamma2 and GAPDH) or RNase protection. For RT-PCR, cDNA was subjected to 28 cycles (linear range) of PCR amplification. PCR products were analyzed on a 2% agarose gel. For RNase protection, 10 µg of total RNA was used per reaction. Products were resolved on a 4.5% polyacrylamide/10M urea gel.

Figure 4:
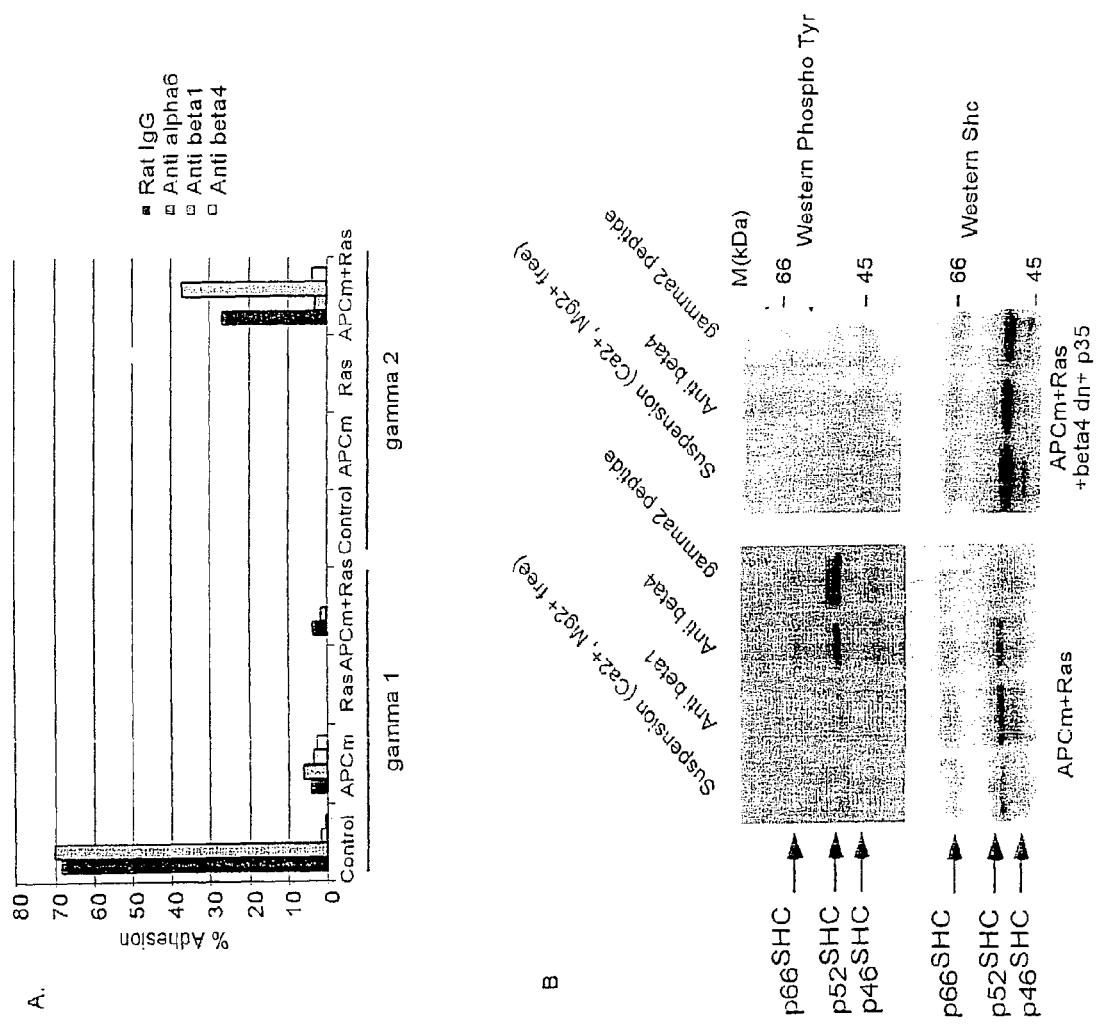

FIG. 4 shows alpha6/beta4 integrin is engaged by the laminin gamma2 chain to activate Shc (a src homology domain containing protein). FIG. 4A shows cells detached from collagen IV coated dishes with 3 mM EDTA (in PBS) were incubated on ice with the indicated antibodies for 1 h. Cells were then plated on 96well dishes coated with gamma1 or gamma2-specific peptides and were permitted to attach for 30 min in RPMI medium at 39° C. After incubation, wells were washed with RPMI. The percentage of attached cells per well was measured by hexoaminidase activity after lysis of the cells in the well and incubation with the substrate p-nitrophenol-N-acetyl-β-D-glucosaminide for 5 h at 37° C. FIG. 4B shows cells indicated were detached as in (A) and resuspended at $10^7$ cells/ml in PBS. After 1 h of incubation on ice, cells were pelleted by centrifugation 5 min at 900 rpm and resuspended in RPMI containing the phosphatase inhibitor pervanadate at 10 µM. The cells were incubated with beta1 and beta4 integrin antibodies as well as the laminin gamma2-specific peptide for 40 min. Protein extracts were prepared and subjected to an immuno-precipitation with an anti-Shc antibody. Phospho-tyrosine was detected with a phopho-tyrosine-specific antibody in IP-western-blots (upper panels). The levels of Shc protein were monitored with a Shc-specific antibody reusing the same membrane (lower panels).

Figure 5:
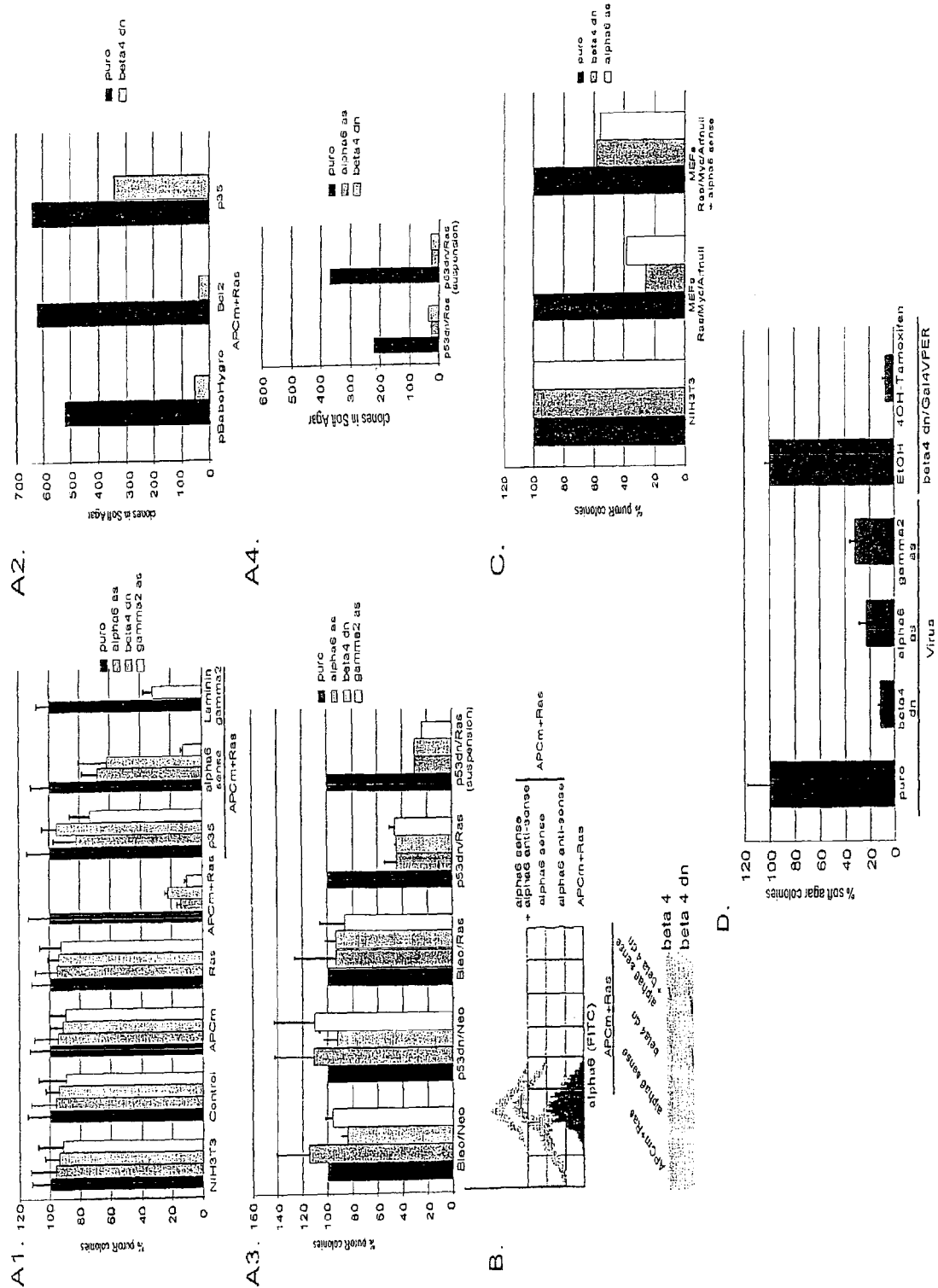

FIG. 5 shows integrin alpha6/beta4 and Laminin gamma2 chain expression is essential for survival of transformed cells. FIG. 5A1 shows the indicated cell populations were infected at an MOI of 2 with recombinant retroviruses expressing anti-sense RNA for alpha6 integrin, the gamma2 laminin chain or a beta4 integrin dominant-negative mutant together with a puromycin resistance gene. After 2 weeks of selection with puromycin on coliagen4-coated dishes, colonies were stained with Giemsa and counted. APCm+Ras alpha6 and APCm+Ras p35 cells express the alpha6 integrin chain and the anti-apoptotic baculovirus p35, respectively. APCm+Ras cells were also plated on dishes pre-coated with a laminin gamma2-specific peptide. FIG. 5A2 shows APCm+Ras hygro, APCm+Ras Bcl2 and APCm+Ras p35 cells express the hygromycin resistance marker, and the anti-apoptotic proteins Bcl2 or p35, respectively. The cells were infected at an MOI of 2 with retroviruses carrying the beta4 integrin dominant-negative mutant and a puromycin resistance gene, or the puromycin resistance gene alone. Cells ($10^5$) were maintained in soft agar at 39° C. for two weeks after which macroscopically visible colonies were counted. FIG. 5A3 shows the indicated cell populations were infected at an MOI of 2 with recombinant retroviruses, drug-selected and maintained as described in A1. FIG. 5A4 shows the indicated cell populations were infected at an MOI of 2 with recombinant retroviruses expressing anti-sense RNA for alpha6 integrin, the beta4 integrin dominant-negative mutant or the puromycin resistance marker. Cells ($10^5$) were maintained in soft agar and evaluated as described in A2. FIG. 5B shows the effect of the alpha6 anti-sense RNA expression on the cell surface expression of alpha6 integrin was monitored by FACS analysis using an anti-alpha6 rat monoclonal antibody and a FITC conjugated goat anti-rat antiserum as the secondary antibody (upper panel). Expression of the beta4 dominant-negative mutant was confirmed by RNAse protection. A probe overlapping the c-terminal end of the beta4 dominant negative mRNA was used to measure beta4 integrin and beta4 dn expression in the same sample (lower panel). FIG. 5C shows arf null mouse embryo fibroblasts (MEFs) that were infected with retroviruses expressing the oncogenes Myc and Ras. Cells were then additionally infected with a retroviruses expressing anti-sense RNA for alpha6 integrin or the beta4 integrin dominant-negative mutant as shown in (A). MEFS Ras/Myc/Arfnull+alpha6 sense express the alpha6 integrin chain. FIG. 5D shows SW480 human colon carcinoma cells that were infected as described in (A) using VSV pseudotyped viruses. Infected cells were selected with puromycin in soft agar. Clones were counted 2 weeks after selection. SW480 beta4 dn/Gal4VPER cells, express a 4OH-tamoxifen-inducible dominant-negative form of the beta4 integrin. The cells ($10^5$) were maintained in soft agar for 2 weeks in presence or absence of 4OH-tamoxifen.

Figure 6:
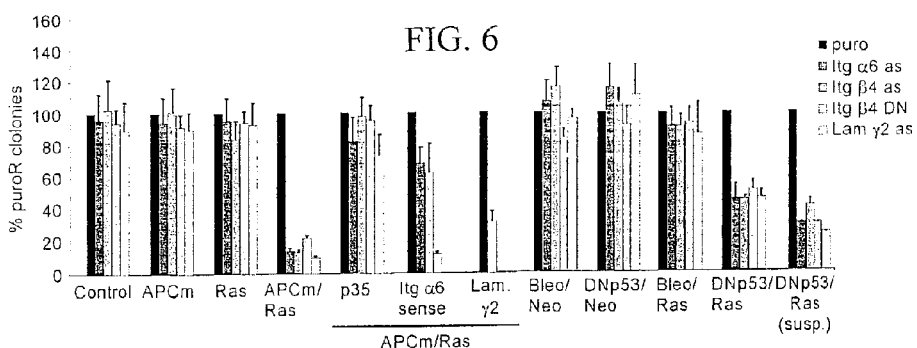
Figure 6:
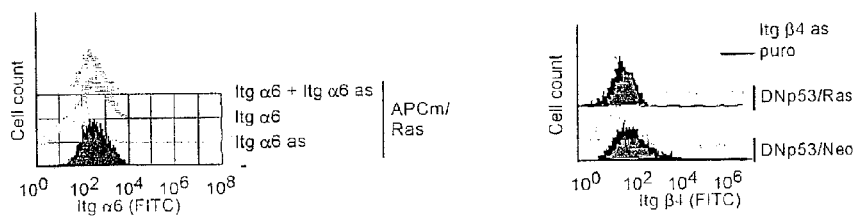
Figure 6:
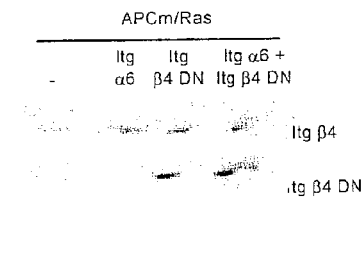
Figure 6:
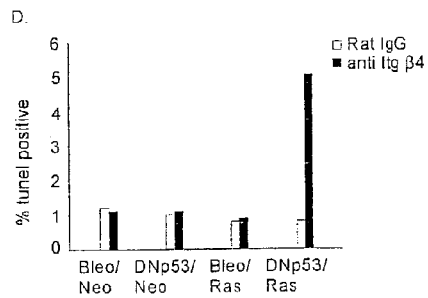
Figure 6:
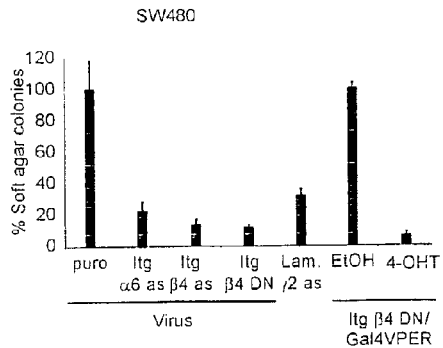
Figure 6:
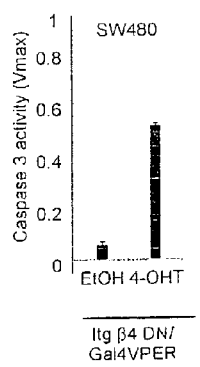
Figure 6:
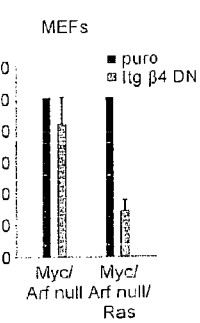
Figure 7:
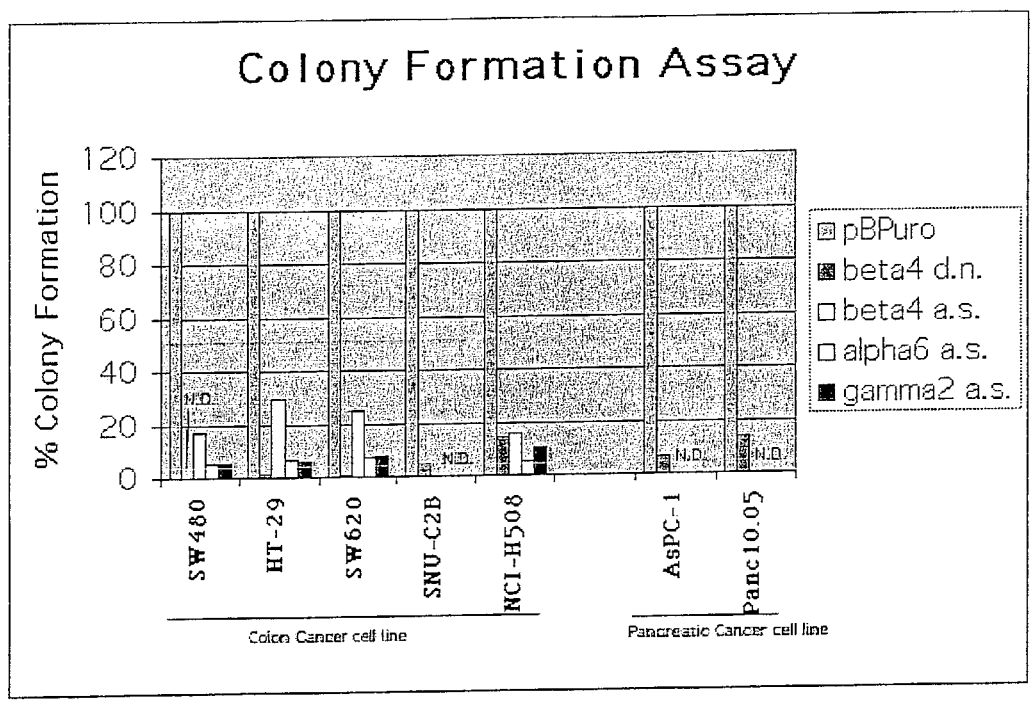

FIG. 6 shows integrin alpha6/beta4 and Laminin gamma2 chain expression is essential for survival of transformed cells. A. Colony formation. Cell populations indicated were infected at an MOI of 1 with recombinant retroviruses encoding anti-sense RNA for alpha6 integrin (Itg α6 as), beta4 integrin (Itg β4 as), the gamma2 laminin chain (Lam γ2 as) or a beta4 integrin dominant-negative mutant (Itg β4 dn) together with a puromycin resistance gene, or the puromycin resistance gene alone (puro). 24 h post infection cells were plated into medium containing 2.5 µg/ml puromycin on collagen IV-coated dishes. After 2 weeks in selection colonies were stained with Giemsa and counted. At least 200 colonies/plate were counted for all viruses after infection of control cells and at least 3-5 independent experiments for each virus were carried out. APCm/Ras alpha6 and APCm/Ras p35 cells were polyclonal pools infected with retroviruses encoding the alpha6 integrin polypetide chain or stably transfected with an expression plasmid encoding the anti-apoptotic baculovirus protein p35, respectively. APCm/Ras cells were also plated on dishes pre-coated with the laminin gamma2-specific peptide. B. Anti-sense RNA mediates decreased cell surface expression of integrins alpha6 (left panel) and beta4 (right panel). Integrin expression on the indicated cell populations was monitored by FACS analysis using an anti-alpha6 or anti-beta4 rat monoclonal antibodies and a FITC conjugated goat anti-rat antiserum as the secondary antibody. C. Expression of the beta4 dominant-negative mutant was confirmed by RNAse protection. A probe overlapping the C-terminal end of the beta4 dominant negative mRNA was used to measure beta4 integrin and beta4 dn expression in the same samples. D. Integrin beta4-specific antibodies selectively induce apoptosis in transformed DNp53/Ras cells. Cell lines indicated were detached from collagen IV substrates with PBS/3 mM EDTA, and incubated with 0.5 µg/ml of Rat IgG or anti-beta4 integrin (346-11A, Pharmingen). Cells were then plated on collagen IV-coated chamber slides (Nalge Nunc) and cultured for 24 h in RPMI supplemented with 10% FCS and 1× ITS-A. The percentage of tunel positive cells was determined by immunofluorescence microscopy. Three independent fields with at least 200 cells were counted per sample. E. Colony outgrowth of SW480 human colon carcinoma cells is inhibited by constructs targeting integrin and laminin expression. Cells were infected as described in (A) using VSV pseudotyped viruses. Infected cells were plated into soft agar containing puromycin. Colonies were counted 2 weeks after selection. SW480 beta4 DN/Gal4VPER cells, express 4OH-tamoxifen-inducible dominant-negative beta4 integrin. The cells ($10^5$) were maintained in soft agar for 2 weeks in presence or absence of 4OH-tamoxifen. F. Inducible integrin beta4-DN mutant leads to caspase 3 activation in SW480 cells. SW480-beta4 DN/Gal4VPER cells were detached from the culture dishes and maintained in suspension in presence or absence of 4OH-Tamoxifen for 24 h. Caspase 3 activity was determined as described in FIG. 1B. G. Integrin beta4-DN mutant inhibits colony outgrowth of transformed mouse embryo fibroblasts (MEFs). Myc/p19Arf-/- and Ras+Myc/p19Arf-/- MEFs were infected with retroviruses expressing the puromycin resistance gene alone or together with the beta4 integrin dominant-negative mutant. Cells were then plated onto tissue culture dishes and processed as described in (A).

IV. DETAILED DESCRIPTION

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods, specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

B. Compositions and Methods

Disclosed are compositions and methods related to integrins and integrin signaling. It is shown herein that integrin alpha6, integrin beta4, and laminin5, through at least up regulation of the beta and gamma chains of laminin5, are upregulated in cancer cells. Integrin alpha6 and integrin beta4 interact to form the integrin receptor, A6B4. The integrin receptor A6B4 specifically interacts with laminin5 and laminin5 specifically interacts with A6B4. Furthermore, it is shown that interference with the production or function of alpha6, beta4, or the laminin gamma2 chain not only prevents proliferation of the cancer cells, dependent on the upregulation of alpha6, beta4, and the laminin gamma2 chain, but that this kills the cancer cells as well. Alpha6 and beta4 signaling occur through the integrin receptor A6B4. Thus, interference with the formation of A6B4, will interfere with the function of A6B4, for example, the signaling of A6B4. Thus, disclosed are compositions and methods that interfere with the function of alpha6, beta4, laminin5, the laminin gamma2 chain, or A6B4. Also disclosed are compositions and methods that interfere with the function of molecules involved with the signal transduction that is connected to either alpha6, beta4, laminin5, the laminin gamma2 chain, or A6B4. Also disclosed are methods for reducing the proliferation of cancer cells, as well as methods of killing cancer cells that involve using the compositions disclosed herein that interfere, reduce, or eliminate the function or the alpha6, beta4, laminin5, the laminin gamma2 chain, or A6B4 function.

Disclosed herein is a relationship between two types of molecules in a cancer cell. The first type of molecule is an integrin receptor, composed of integrins, and the second type of molecule is a ligand that interacts with the integrin receptor, through the integrins. There are specificities that exist between the integrin receptors and their ligands. One aspect, disclosed herein is that when a cell goes from a non-cancerous state to a cancerous state, there is a co-upregulation of both the ligand (or parts of the ligand, such as subunits) and the cognate integrin receptor. The co-upregulation of both types of molecules creates an autocrine loop situation, wherein the signaling pathways controlled by the integrin receptor become autonomously activated, rather than exogenously activated, as would normally occur. The upregulation of both types of molecules creates a more fully transformed cellular phenotype in which cancer cell survival depends on the autocrine loop. Now therapeutic activities can target both points in the autocrine loop. Specific examples, of this co-upregulation in cancer cells are disclosed herein. For example, laminin 5 (both the beta and gamma2 chains are upregulated) and integrin receptor alpha6beta4; laminin 10/11 and the integrin receptors alpha6beta1 and alpha3beta1.

As the Examples herein indicate which integrins, which integrin receptor, and which integrin ligand are involved in conferring cancer cells ability to grow in the absence of extra cellular matrix (ECM), also disclosed are methods using these integrins, integrin receptors and ligands to identify molecules that interact with them and/or interfere with their function.

1. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed, while specific reference of each various individual and collective permutation of these compounds may not be explicitly disclosed, each is specifically contemplated and described herein. For example, if a particular beta4 or alpha6 is disclosed and discussed and a number of modifications that can be made to a number of molecules including the modifications to beta4 or alpha6 are discussed, specifically contemplated is each and every combination and permutation of these modifications and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

a) Integrins and Their Ligands

For proper embryonic development, tissue homeostasis, and wound healing, cell proliferation must be tightly regulated, both in space and over time. In particular, a cell must be able to sense its relationship to other cells and the extracellular matrix (ECM) and convert these positional cues into biochemical signals affecting the regulation of proliferation. Because of their ability to couple the recognition of positional cues to the activation of intracellular signaling pathways, adhesion receptors, such as integrins and cadherins, are likely to be necessary to achieve this goal.

The integrins mediate cell adhesion primarily by binding to distinct, although overlapping, subsets of ECM proteins. Normal cells require contact with serum-derived ECM components for proliferation, differentiation and survival (e.g. Clark and Brugge, 1995; Lin and Bissell, 1993; Parise el al., 2000), a phenomenon called anchorage-dependence. This involves signaling through integrin receptors (Hynes, 1992). Fibronectin and laminin as well as other ECM proteins are known to act as ligands for integrin receptors (Akiyama et al., 1990). Integrins are transmembrane proteins forming alpha-beta chain heterodimers. Alpha and beta chain integrins are members of distinct gene families. The ligand binding specificity of the hetero dimers is determined by specific combinations of alpha and beta chain gene family members (Hynes, 1992). Ligand binding triggers signaling of integrin receptors through the cytoplasmic tail of the beta chain via interaction with various signaling components.

Integrins activate common as well as subgroup-specific signaling pathways (Clark and Brugge, 1995; Giancotti and Ruoslahti, 1999). In particular, while most integrins activate focal adhesion kinase (FAK), the $\alpha1\beta1$, $\alpha5\beta1$, $\alpha v\beta3$ and $\alpha6\beta4$ integrins are coupled to the Ras-extracellular signal-regulated kinase (ERK) signaling pathway by Shc (Mainiero el al., 1997; Mainiero et al., 1995; Wary et al., 1996). Shc is an SH2-PTB domain adapter protein expressed in three forms, p46, p52 and p66, two of which (p46 and p52) link various tyrosine kinases to Ras by recruiting the Grb2/SOS complex to the plasma membrane (Pawson and Scott, 1997). Upon activation by SOS, Ras stimulates a kinase cascade culminating in the activation of the mitogen-activated protein kinase (MAPK) ERK (Marshall, 1995). ERK phosphorylates ternary complex transcription factors, such as Elk-1 and Sap-1/2, and promotes transcription of the immediate-early gene Fos (Treisman, 1996). In primary endothelial cells and keratinocytes, mitogens and Shc-linked integrins cooperate, in a synergic fashion, to promote transcription from the Fos promoter. Accordingly, ligation of integrins linked to Shc enables these cells to progress through G1 in response to mitogens, whereas ligation of other integrins results in growth arrest, even in the presence of mitogens (Mainiero et al., 1997; Wary et al., 1996). Shc is like a binary switch controlling cell cycle progression in response to the ECM. Moreover, integrin receptors have been shown to induce intracellular signaling leading to AKT activation supporting cell survival (Lee and Juliano, 2000).

In contrast with normal cells, cancer cells generally are able to survive and proliferate in the absence of anchorage to ECM (Giancotti and Mainiero, 1994), suggesting that tumor cell survival and proliferation have become independent of the engagement of integrin signaling through ECM.

Proliferation in the absence of anchorage to ECM of secondary rat embryo fibroblasts requires the cooperation of Ras and Myc or Ras and adenovirus E1a oncogenes (Land et al., 1983; Ruley, 1983). Similarly, murine colonic epithelial cells require both activated Ras and mutation of the adenomous polyposis coli gene (APCmin) (D'Abaco et al., 1996) in order to proliferate in suspension.

Integrins are a large family of cell surface receptor molecules that function to mediate interactions between cells and between cells and the extracellular matrix. Integrin receptors are heterodimers composed of two subunits, an alpha integrin and a beta integrin. The heterodimer forms, is expressed on the cell surface, and acts to transmit signals obtained from interactions with the extracellular matrix or other cells, through the cellular membrane and into the cytosol of the cell. The signal transduction that takes place occurs because of ligand interactions with the receptor. Integrin receptors can have a number of ligands, including collagens, fibronectins, and laminins.

There are currently at least 18 different alpha integrins and at least 8 different beta integrins that have been shown to form at least 24 different alphabeta heterodimers. Certain integrins, such as beta1, interact in a number of different heterodimers, but many subunits only form a single heterodimer, either because of structural constraints on their interactions, or cellular expression patterns that provide only a limited number of potential dimer partners. Disclosed herein are specific relationships that occur between a subset of integrins, integrin receptors, and their ligands. The disclosed relationships, revolve around the alpha6beta4 receptor, formed by the alpha6 and beta4 integrins. Of particular interest is the relationship between the ligand for the alpha6beta4 receptor, laminin5. The laminins are made up of 3 chains, an alpha chain, a beta chain, and a gamma chain. The specificity of the interaction between laminin5 and alpha6beta4 receptor is controlled by the gamma chain. Laminin5 contains a gamma2 chain which only interacts with the alpha6beta4 integrin receptor.

Integrin alpha6 has seven amino-terminal repeating segments that may fold into a seven unit beta-propeller, five n-terminal FG-GAP domains and three divalent cation sites. The transmembrane domain is followed by a short cytoplasmic tail, that is alternatively spliced in A and B forms. The alpha6 integrin chain also shows alternative splicing between repeat units III and IV, resulting in the presence or absence of Exon X2. Integrin alpha6 is processed into a heavy and a light chain that are disulphide linked. A representative allele of the human alpha6 cDNA is set forth in SEQ ID NO:1. It is understood that the disclosed functional domains as well as the others contained within alpha6 are considered separately disclosed as discreet fragments of the alpha6 protein as well as the nucleic acid that encodes them.

Integrin beta4 contains a MIDAS-like motif and four cysteine-rich repeats, three EGF-like domains in the N-terminal extracellular domain, a trans-membrane region and a long cytoplasmic tail containing two pairs of fibronectin Type III repeats. The latter are connected by a variable segment that may undergo alternative splicing. Integrin beta4 also undergoes proteolytic processing in its cytoplasmic tail, causing the 200 kD mature form to be converted to 165 and 130 kD fragments. A representative allele of the human beta4 cDNA is set forth in SEQ ID NO:5. It is understood that the disclosed functional domains as well as the others contained within beta4 are considered separately disclosed as discreet fragments of the beta4 protein as well as the nucleic acid that encodes them.

Laminin5 is composed of the laminin chains alpha3, beta3 and gamma2. Laminin5 can may contain either the shorter laminin alpha3A chain or the longer alpha3B chain. Laminin5 can also be trimmed by proteolytic processing of the N-terminal portion of its alpha3A chain and the N-terminal portion of the gamma2 chain. The Laminin gamma2 chain contains at least six laminin EGF-like domains (Domains III and V) with an embedded laminin B domain (Domain IV) within the N-terminal half. The c-terminal tail contains a coiled-coil domain. The N-terminal processed portion of the gamma2 chain is sufficient to bind to and activate the integrin alpha6/beta4 receptor. A representative allele of the human laminin5-gamma2 cDNA is set forth in SEQ ID NO:13. It is understood that the disclosed functional domains as well as the others contained within the laminin5 protein and laminin5-gamma2 protein are considered separately disclosed as discreet fragments of the laminin5 protein and laminin5-gamma2 protein as well as and the nucleic acid that encodes them.

Disclosed are compositions and methods for inhibiting integrin signaling, for example, integrin signaling dependent on alpha6 and beta4 integrins. For example, compositions and methods that inhibit integrin receptor signaling from, for example, the alpha6beta4 integrin receptor are disclosed. It is also understood that the integrin receptor signaling can be affected by, for example, interfering with a molecule, such as a ligand for the integrin receptor, or a downstream signaling molecule of the integrin receptor in a way that prevents the integrin receptor signal from being fully propagated. It is understood that the compositions and methods for inhibition of integrin signaling and function can be any composition or method that ultimately inhibits the cell proliferation in which the integrin is expressed, by for example killing the cell. It is understood that the compositions and methods typically can fall into three basic non-limiting classes of function regulators, which are discussed herein.

b) Classes of Integrin Regulators (1) Production Regulators

Production regulators is a broad class of integrin function regulators that are directed at the production of the target integrin, by for example, preventing mRNA synthesis or expression of the target integrin, or by causing mRNA degradation of the target integrin which inhibits the translation of the target integrin. While production regulators, can be any type of molecule targeting any point in the integrin production pathway, typically these types of compositions will target either the mRNA expression or the protein expression of the integrin. For example, if beta4 integrin, alpha6 integrin, or the gamma2 subunit of laminin5, which has been shown herein to be upregulated in cancer cells and which causes the cancer cell to be able to live in the absence of the ECM, was the target integrin, a typical production regulator of beta4 integrin, alpha6 integrin, or the gamma2 subunit of laminin5 would be for example, an antisense molecule that targeted the mRNA of beta4 integrin, alpha6 integrin, or the gamma2 subunit of laminin5. It is also understood that a production regulator could also target any molecule that is disclosed herein, or is within the signaling chain associated with a target integrin or integrin receptor. For example, the inhibition of the production of the ligand for a target integrin receptor is one way of inhibiting integrin function of that receptor. Thus, production regulators can either inhibit or enhance integrin production.

(2) Integrin to Integrin Regulators

Another type of integrin function regulator is an integrin-integrin regulator. This type of function regulator, typically prevents integrins from interacting to form a functional integrin receptor. For example, an integrin to integrin regulator could be a composition that would interact with beta4 in a way that would prevent beta4 from interacting with alpha6 to form the alpha6beta4 integrin receptor or it could be a composition that would interact with alpha6 in a way that would prevent alpha6 from interacting with beta4 to form the alpha6beta4 integrin receptor. It is also contemplated that the function regulators of the integrin to integrin interaction can affect the signaling pathways dependent on integrin receptors containing alph6 or beta4 integrins. It is not required that an integrin to integrin regulator prevent an integrin from interacting with all of the possible integrin partners it could interact with, just that it prevent the interaction of the target integrin with another specific integrin. For example, the integrin alpha6 interacts with beta1 integrin and beta4 integrin. In certain embodiments. the compositions interfere with alpha6-beta4 interactions but do not interfere with alpha6-beta1 interactions.

(3) Integrin to Other Molecule Regulators

The third class of function regulators are the integrin to other molecule regulators. These compositions are designed to specifically interfere with molecules such as small molecule ligands or other proteins that interact with the integrin or integrin receptor. For example, an integrin to other molecule regulator might target a ligand for a particular integrin receptor, such as the alpha6beta4 receptor. The ligand for the alpha6beta4 receptor is laminin5 or the laminin gamma2 chain. Compositions that interact with laminin5 such that laminin5 or the laminin gamma2 chain interactions with alpha6beta4 are inhibited or reduced are specifically contemplated herein. Likewise, there are other molecules, such as She molecules, that also interact with integrins, such as the alpha6beta4 receptor. Compositions that specifically interact with the She molecules such that they prevent the appropriate interactions between the She molecule and the alpha6beta4 receptor are disclosed.

c) Integrin Regulator Examples

Just as there are different general classes of molecules that can regulate (such as by inhibition) the function of the disclosed integrins and integrin receptors, so to there are many different types of molecules that perform that regulation. For example, any molecule that can perform the regulation of for example, the disclosed integrins, integrin receptors, or signaling pathways produced by the disclosed integrins and integrin receptors are contemplated. For example, antibodies or small molecules which inhibit the disclosed compositions are herein disclosed. Also disclosed are, for example, functional nucleic acids, such as ribozymes or antisense molecules that can inhibit the disclosed integrin function in a variety of ways. A non-limiting list of exemplary molecules is discussed herein.

(1) Antibodies

Antibodies can be used to regulate, for example, the function of the disclosed integrins and integrin receptors, molecules that interact with the disclosed integrin receptors, and molecules in the signaling pathways of the disclosed integrin receptors.

As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

Antibodies can be either polyclonal or monoclonal. Polyclonal antibodies, typically are derived from the serum of an animal that has been immunogenically challenged, and monoclonal antibodies are derived as discussed herein.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

As used herein, the term "antibody or fragments thereof" encompasses chimeric antibodies and hybrid antibodies, with dual or multiple antigen or epitope specificities, and fragments, such as F(ab')2, Fab', Fab and the like, including hybrid fragments. Thus, fragments of the antibodies that retain the ability to bind their specific antigens are provided. For example, fragments of antibodies which maintain integrin receptor binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference. Single chain divalent antibodies are also provided.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992)).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody (Sims et al., J. Immunol., 151:2296 (1993) and Chothia et al., J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see, WO 94/04679, published Mar. 3, 1994).

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA, 90:2551-255 (1993); Jakobovits et al., Nature, 362:255-258 (1993); Bruggemann et al., Year in Immuno., 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cote et al. and Boerner et al. are also available for the preparation of human monoclonal antibodies (Cole et al., Monoclonal Antibodies and Cancer Therapy, Alan R. Liss, p. 77 (1985); Boerner et al., J. Immunol., 147(1):86-95 (1991)).

The present invention further provides a hybridoma cell that produces the monoclonal antibody of the invention. The term "monoclonal antibody" as used herein refers to an antibody obtained from a substantially homogeneous population of antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired activity (See, U.S. Pat. No. 4,816,567 and Morrison et al., Proc. Natl. Acad. Sci. USA, 81:6851-6855 (1984)).

Monoclonal antibodies of the invention may be prepared using hybridoma methods, such as those described by Kohler and Milstein, Nature, 256:495 (1975) or Harlow and Lane. Antibodies, A Laboratory Manual. Cold Spring Harbor Publications, New York, (1988). In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro. Preferably, the immunizing agent comprises an intergin receptor. Traditionally, the generation of monoclonal antibodies has depended on the availability of purified protein or peptides for use as the immunogen. More recently DNA based immunizations have shown promise as a way to elicit strong immune responses and generate monoclonal antibodies. In this approach, DNA-based immunization can be used, wherein DNA encoding a portion of the integrin receptor expressed as a fusion protein with human IgG1 is injected into the host animal according to methods known in the art (e.g., Kilpatrick K E, et al. Gene gun delivered DNA-based immunizations mediate rapid production of murine monoclonal antibodies to the Flt-3 receptor. Hybridoma. December 1998;17(6):569-76; Kilpatrick K E et al. High-affinity monoclonal antibodies to PED/PEA-15 generated using 5 microg of DNA. Hybridoma. August 2000;19(4):297-302, which are incorporated herein by referenced in full for the methods of antibody production).

An alternate approach to immunizations with either purified protein or DNA is to use antigen expressed in baculovirus. The advantages to this system include ease of generation, high levels of expression, and post-translational modifications that are highly similar to those seen in mammalian systems. Use of this system involves expressing domains of intergin receptor antibody as fusion proteins. The antigen is produced by inserting a gene fragment in-frame between the signal sequence and the mature protein domain of the intergin receptor antibody nucleotide sequence. This results in the display of the foreign proteins on the surface of the virion. This method allows immunization with whole virus, eliminating the need for purification of target antigens.

Generally, peripheral blood lymphocytes ("PBLs") are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, "Monoclonal Antibodies: Principles and Practice" Academic Press, (1986) pp. 59-103). Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, J. Immunol., 133:3001 (1984); Brodeur et al., "Monoclonal Antibody Production Techniques and Applications" Marcel Dekker, Inc., New York, (1987) pp. 51-63).

The culture medium in which the hybridoma cells are cultured can then be assayed for the presence of monoclonal antibodies directed against an intergin receptor. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below or in Harlow and Lane "Antibodies, A Laboratory Manual" Cold Spring Harbor Publications, New York, (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, protein G, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Optionally, such a non-immunoglobulin polypeptide is substituted for the constant domains of an antibody of the invention or substituted for the variable domains of one antigen-combining site of an antibody of the invention to create a chimeric bivalent antibody comprising one antigen-combining site having specificity for an intergin receptor and another antigen-combining site having specificity for a different antigen.

In vitro methods are also suitable for preparing monovalent antibodies. Digestion of antibodies to produce fiagments thereof, particularly, Fab fragments, can be accomplished using routine techniques known in the art. For instance, digestion can be performed using papain. Examples of papain digestion are described in WO 94/29348 published Dec. 22, 1994, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group.

Antibody fragments originally were produced as pairs of Fab' fragments which have hinge cysteines between them. Other chemical couplings of antibody fragments are also known.

An isolated immunogenically specific paratope or fragment of the antibody is also provided. A specific immunogenic epitope of the antibody can be isolated from the whole antibody by chemical or mechanical disruption of the molecule. The purified fragments thus obtained are tested to determine their immunogenicity and specificity by the methods taught herein. Immunoreactive paratopes of the antibody, optionally, are synthesized directly. An immunoreactive fragment is defined as an amino acid sequence of at least about two to five consecutive amino acids derived from the antibody amino acid sequence.

One method of producing proteins comprising the antibodies of the present invention is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the antibody of the present invention, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fiagment thereof. (Grant G A (1992) Synthetic Peptides: A User Guide. W. H. Freeman and Co., N.Y. (1992); Bodansky M and Trost B., Ed. (1993) Principles of Peptide Synthesis. Springer-Verlag Inc., NY. Alternatively, the peptide or polypeptide is independently synthesized in vivo as described above. Once isolated, these independent peptides or polypeptides may be linked to form an antibody or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini M et al. (1992) FEBS Lett. 307:97-101; Clark-Lewis I et al., J.Biol.Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

The invention also provides fragments of antibodies which have bioactivity. The polypeptide fragments of the present invention can be recombinant proteins obtained by cloning nucleic acids encoding the polypeptide in an expression system capable of producing the polypeptide fragments thereof, such as an adenovirus or baculoviius exprcssion system. For example, one can determine the active domain of an antibody from a specific hybridoma that can cause a biological effect associated with the interaction of the antibody with an intergin receptor. For example, amino acids found to not contribute to either the activity or the binding specificity or affinity of the antibody can be deleted without a loss in the respective activity. For example, in various embodiments, amino or carboxy-terminal amino acids are sequentially removed from either the native or the modified non-immunoglobulin molecule or the immunoglobulin molecule and the respective activity assayed in one of many available assays. In another example, a fragment of an antibody comprises a modified antibody wherein at least one amino acid has been substituted for the naturally occurring amino acid at a specific position, and a portion of either amino terminal or carboxy terminal amino acids, or even an internal region of the antibody, has been replaced with a polypeptide fragment or other moiety, such as biotin, which can facilitate in the purification of the modified antibody. For example, a modified antibody can be fused to a maltose binding protein, through either peptide chemistry or cloning the respective nucleic acids encoding the two polypeptide fragments into an expression vector such that the expression of the coding region results in a hybrid polypeptide. The hybrid polypeptide can be affinity purified by passing it over an amylose affinity solid support, and the modified antibody receptor can then be separated from the maltose binding region by cleaving the hybrid polypeptide with the specific protease factor Xa. (See, for example, New England Biolabs Product Catalog, 1996, pg. 164.). Similar purification procedures are available for isolating hybrid proteins from eukaryotic cells as well.

The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller M J et al. Nucl. Acids Res. 10:6487-500 (1982).

A variety of immunoassay formats may be used to select antibodies that selectively bind with a particular protein, variant, or fragment. For example, solid-phase ELISA immunoassays are routinely used to select antibodies selectively immunoreactive with a protein, protein variant, or fragment thereof. See Harlow and Lane. Antibodies, A Laboratory Manual. Cold Spring Harbor Publications, New York, (1988), for a description of immunoassay formats and conditions that could be used to determine selective binding. The binding affinity of a monoclonal antibody can, for example, be determined by the Scatchard analysis of Munson et al., Anal. Biochem., 107:220 (1980).

Also provided is an antibody reagent kit comprising containers of the monoclonal antibody or fragment thereof of the invention and one or more reagents for detecting binding of the antibody or fragment thereof to an intergin receptor molecule. The reagents can include, for example, fluorescent tags, enzymatic tags, or other tags. The reagents can also include secondary or tertiary antibodies or reagents for enzymatic reactions, wherein the enzymatic reactions produce a product that can be visualized. Also provided is the production of antibodies in transgenic animals, for example, antibodies secreted in milk of a mammal.

(2) Antibody Conjugates

The antibodies for the integrin receptor or fragments thereof or the specific substrate analogs can be used to identify and/or inactivate cancer cells in vitro or in vivo. As discussed herein, it is understood that the disclosed antibodies can be conjugated to a variety of molecules which can aid in the antibodies ability to inhibit or kill the cancer cell. For example, the antibody can be coupled to a label which is detectable but which does not interfere with binding to the integrin receptors or fragments thereof. Although described primarily with reference to radioisotopes, especially indium ("In"), which is useful for diagnostic purposes, and yttrium ("Y"), which is cytotoxic, other substances which harm or inactivate cancer cells can be substituted for the radioisotope. The antibodies or substrate analogs may be unlabeled or labeled with a therapeutic agent. These agents can be coupled either directly or indirectly to the disclosed antibodies or substrate analogs. One example of indirect coupling is by use of a spacer moiety. These spacer moieties, in turn, can be either insoluble or soluble (Diener, et al., Science, 231:148, 1986) and can be selected to enable drug release from the antibodies or substrate analogs at the target site. Examples of therapeutic agents which can be coupled to the disclosed antibodies or analogs are drugs, radioisotopes, lectins, and toxins or agents which will covalently attach the antibody or substrate analog to the target or surrounding moelcules.

(a) Radioisotope Conjugation

Certain isotypes may be more preferable than others depending on such factors as cellular distribution as well as isotype stability and emission. In general, alpha and beta particle-emitting radioisotopes are preferred in immunotherapy. Preferred are short range, high energy alpha emitters such as $^{212}$Bi. Non-limiting examples of radioisotopes which can be bound to the disclosed antibodies for therapeutic purposes are . $^{125}$I, $^{131}$I, $^{90}$Y, $^{67}$Cu, $^{212}$Bi, $^{211}$At, $^{212}$Pb, $^{47}$Sc, $^{109}$Pd, and $^{188}$Re.

The radioisotopes are preferred since they are small and well characterized, and can be used as diagnostics and followed after administration using standard non-invasive radioimaging techniques.

As radioisotopes decay, they emit characteristic photons or particles or both. Photons, commonly referred to as gamma rays, are penetrating. If their energy level is high enough, they can travel through the body and be detected by diagnostic instrumentation. Radioisotopes that emit photons can be attached to an antibody or substrate analog and used for diagnostic imaging. This application is termed radioimmunoscintigraphy (RIS). The shorter the distance between the antigen and the target, the shorter the required range of emission of the radioisotope. Auger electrons have a very short path length (5-10 nm) and need to be internalized to be cytotoxic (Adelstein, et al., Nucl. Med. Biol. 14:165-169 (1987)). Only antibodies or analogs that are internalized after binding to a cell should be considered for radioisotopes that emit Auger electrons. Alpha particles need to be close to a cell (within 3-4 cell diameters) to be effective (Vriesendorp, et al., Radioimmunoglobulin therapy. In: High Dose Cancer Therapy. Armitage, et al. (eds). (Williams & Wilkins, Baltimore, Md. 1992) pp. 84-123). Both Auger electrons and alpha emitters have high selectivity because their short-range emission will not irradiate neighboring normal cells.

The radiometals $^{111}$In and $^{90}$Y are, respectively, pure γ- and pure β-emitters. Iodine-125, the most commonly used emitter of Auger electrons, has a half-life of 60 days and frequently is released by the immunoconjugate in vivo (dehalogenation) (Vriesendorp, et al., 1992). The most commonly considered alpha emitters for clinical use, astatine-211 and bismuth-212, have short half-lives (7.2 h and 1.0 h, respectively) and decay into radioactive isotopes, that may not be retained by the immunoconjugate after the first alpha emission (Wilbur, Antibiot. Immunoconjug. Radiopharm. 4:85-97 (1991)). The use of an immunoconjugate radiolabeled with $^{111}$In has been proposed to predict the behavior of the poorly imageable $^{90}$Y-labeled immunoconjugate (Korngold, et al., Cancer Res. 20:1488-1494 (1960); Welt, et al., J. Clin. Oncol. 12:1561-1571 (1994); Breitz, et al., J. Nucl. Med. 33:1099-1112 (1992); Vriesendorp, et al., Cancer Res. (suppl) 55:5888s-5892s (1995)). Previous studies using stable radiometal chelation have demonstrated similar biodistributions for radioimmunoconjugates labeled with $^{111}$In and $^{90}$Y (Welt, et al., J. Clin. Oncol. 12:1561-1571 (1994); Breitz, et al., J. Nucl. Med. 33:1099-1112 (1992)).

For diagnostic administration, the immunoconjugate would be radiolabeled with a pure gamma-emitting radioisotope like indium-111 ($^{111}$In) or technetium-99m ($^{99m}$Tc). Both of these isotopes emit gamma rays within the appropriate energy range for imaging, (100-250 keV). Energies below this range are not penetrating enough to reach an external imaging device. Higher energy levels are difficult to collimate and provide diagnostic images with poor resolution. The short-half life of $^{99m}$Tc restricts its use to immunoconjugates with rapid tumor uptake. The use of $^{111}$In-labeled immunoconjugate has been proposed to predict the in vivo behavior of an immunoconjugate radiolabeled with $^{90}$Y, a pure beta-emitter, since they have similar half-lives and comparable chelation chemistry (Vriesendorp, et al., Cancer. Res. (suppl) 55:5888s-5892s (1995); Vriesendorp, et al., Radioimmunoglobulin therapy. 1992); DeNardo, et al., J. Nucl. Med. 36:829-836 (1995); Leichner, et al., Int. J. Radiat. Oncol. Biol. Phys. 14:1033-1042 (1988)). An advantage of using two separate radioisotopes, one for imaging and one for therapy, is that it allows for outpatient treatment. The low amount of radioactivity used diagnostically does not represent a radiation hazard, while the radiation emitted by a therapeutic pure beta-emitter will largely be absorbed in the vicinity of the targeted cells. This treatment scheme is dependent on similar pharmacokinetics for both radiolabeled reagents and requires a stable means of attaching both radioactive compounds to the antibody.

Some radioisotopes can be attached directly to the antibody; others require an indirect form of attachment. The radioisotopes $^{125}$I, $^{131}$I, $^{99m}$Tc, $^{186}$Re and $^{188}$Re can be covalently bound to proteins (including antibodies) through amino acid functional groups. For radioactive iodine it is usually through the phenolic group found on tyrosine. There are numerous methods to accomplish this: chloramine-T (Greenwood, et al. *Biochem J.* 89: 114-123 (1963)); and Iodogen (Salacinski, et al. *Anal. Biochem.* 117: 136-146 (1981)). Tc and Re can be covalently bound through the sulfhydryl group of cysteine (Griffiths, et al. *Cancer Res.* 51: 4594-4602 (1991)). The problem with most of the techniques is that the body has efficient methods to break these covalent bonds, releasing the radioisotopes back into the circulatory system. Generally, these methods are acceptable for imaging purposes ($^{99m}$Tc), but not for therapeutic purposes.

(b) Toxin/Agent Conjugation

Toxins are poisonous substances produced by plants, animals, or microorganisms that, in sufficient dose, are often lethal. Diphtheria toxin is a substance produced by Corynebacterium diphtheria which can be used therapeutically. This toxin consists of an alpha and beta subunit which under proper conditions can be separated. Lectins are proteins, usually isolated from plant material, which bind to specific sugar moieties. Many lectins are also able to agglutinate cells and stimulate lymphocytes. However, ricin is a toxic lectin which has been used immunotherapeutically. This is accomplished by binding the alpha-peptide chain of ricin, which is responsible for toxicity, to the antibody molecule to enable site specific delivery of the toxic effect. Other therapeutic agents which can be coupled to the disclosed antibodies are known, or can be easily ascertained, by those of ordinary skill in the art.

Many peptide toxins have a generalized eukaryotic receptor binding domain; in these instances the toxin must be modified to prevent intoxication of cells not bearing the targeted receptor (e.g., to prevent intoxication of cells not bearing the EGF receptor but having a receptor for the unmodified toxin). Any such modifications must be made in a manner which preserves the cytotoxic functions of the molecule. Potentially useful toxins include, but are not limited to: cholera toxin, ricin, Shiga-like toxin (SLT-I, SLT-II, SLT-IIV), LT toxin, C3 toxin, Shiga toxin, pertussis toxin, tetanus toxin, Pseudomonas exotoxin, alorin, saporin, modeccin, and gelanin. Diphtheria toxin can be used to produce molecules useful as described herein. Diphtheria toxin, whose sequence is known, and hybrid molecules thereof, are described in detail in U.S. Pat. No. 4,675,382 to Murphy. The natural diphtheria toxin molecule secreted by *Corynebacterium diphtheriae* consists of several functional domains which can be characterized, starting at the amino terminal end of the molecule, as enzymatically-active Fragment A (amino acids Gly1-Arg193) and Fragment B (amino acids Ser194-Ser535), which includes a translocation domain and a generalized cell binding domain (amino acid residues 475 through 535). The process by which diphtheria toxin intoxicates sensitive eukaryotic cells involves at least the following steps: (i) the binding domain of diphtheria toxin binds to specific receptors on the surface of a sensitive cell; (ii) while bound to its receptor, the toxin molecule is internalized into an endocytic vesicle; (iii) either prior to internalization, or within the endocytic vesicle, the toxin molecule undergoes a proteolytic cleavage between fragments A and B; (iv) as the pH of the endocytic vesicle decreases to below 6, the toxin crosses the endosomal membrane, facilitating the delivery of Fragment A into the cytosol; (v) the catalytic activity of Fragment A (i.e., the nicotinamide adenine dinucleotide—dependent adenosine diphosphate (ADP) ribosylation of the eukaryotic protein synthesis factor termed "Elongation Factor 2") causes the death of the intoxicated cell. A single molecule of Fragment A introduced into the cytosol is sufficient to inhibit the cell's protein synthesis machinery and kill the cell. The mechanism of cell killing by *Pseudomonas* exotoxin A, and possibly by certain other naturally-occurring toxins, is very similar.

A mixed toxin molecule is a molecule derived from two different polypeptide toxins. Generally, as discussed above in connection with diphtheria toxin, polypeptide toxins have, in addition to the domain responsible for generalized eukaryotic cell binding, an enzymatically active domain and a translocation domain. The binding and translocation domains are required for cell recognition and toxin entry respectively. Naturally-occurring proteins which are known to have a translocation domain include diphtheria toxin, *Pseudomonas* exotoxin A, and possibly other peptide toxins. The translocation domains of diphtheria toxin and *Pseudomonas* exotoxin A are well characterized (see, e.g., Hoch et al., Proc. Natl. Acad. Sci. USA 82:1692, 1985; Colombatti et al., J. Biol. Chem. 261:3030, 1986; and Deleers et al., FEBS Lett. 160: 82, 1983), and the existence and location of such a domain in other molecules may be determined by methods such as those employed by Hwang et al. (Cell 48:129, 1987); and Gray et al. (Proc. Natl. Acad. Sci. USA 81:2645, 1984).

A useful mixed toxin hybrid molecule can be formed by fusing the enzymatically active A subunit of *E. coli* Shiga-like toxin (Calderwood et al., Proc. Natl. Acad. Sci. USA 84:4364, 1987) to the translocation domain (amino acid residues 202 through 460) of diphtheria toxin, and to a molecule targeting a particular cell type, as described in U.S. Pat. No. 5,906,820 to Bacha. The targeting portion of the three-part hybrid causes the molecule to attach specifically to the targeted cells, and the diphtheria toxin translocation portion acts to insert the enzymatically active A subunit of the Shiga-like toxin into the targeted cell. The enzymatically active portion of Shiga-like toxin, like diphtheria toxin, acts on the protein synthesis machinery of the cell to prevent protein synthesis, thus killing the cell.

The targeting molecule (for example, the antibody), and the cytotoxin can be linked in several ways. If the hybrid molecule is produced by expression of a fused gene, a peptide bond serves as the link between the cytotoxin and the antibody or antibody fragment. Alternatively, the toxin and the binding ligand can be produced separately and later coupled by means of a non-peptide covalent bond. For example, the covalent linkage may take the form of a disulfide bond. In this case, the DNA encoding the antibody can be engineered to contain an extra cysteine codon. The cysteine must be positioned so as to not interfere with the binding activity of the molecule. The toxin molecule must be derivatized with a sulfhydryl group reactive with the cysteine of the modified antibody. In the case of a peptide toxin this can be accomplished by inserting a cysteine codon into the DNA sequence encoding the toxin. Alternatively, a sulhydryl group, either by itself or as part of a cysteine residue, can be introduced using solid phase polypeptide techniques. For example, the introduction of sulfhydryl groups into peptides is described by Hiskey (Peptides 3:137, 1981). The introduction of sulfhydryl groups into proteins is described in Maasen et al. (Eur. J. Biochem. 134:32, 1983). Once the correct sulfhydryl groups are present, the cytotoxin and antibody are purified, both sulfur groups are reduced; cytotoxin and ligand are mixed; (in a ratio of about 1:5 to 1:20) and disulfide bond formation is allowed to proceed to completion (generally 20 to 30 minutes) at room temperature. The mixture is then dialyzed against phosphate buffered saline or chromatographed in a resin such as Sephadex to remove unreacted ligand and toxin molecules.

Numerous types of cytotoxic compounds can be joined to proteins through the use of a reactive group on the cytotoxic compound or through the use of a cross-linking agent. A common reactive group that will form a stable covalent bond in vivo with an amine is isothiocyanate (Means, et al. Chemical modifications of proteins (Holden-Day, San Francisco 1971) pp. 105-110). This group preferentially reacts with the ε-amine group of lysine. Maleimide is a commonly used reactive group to form a stable in vivo covalent bond with the sulfhydryl group on cysteine (Ji. *Methods Enzymol* 91: 580-609 (1983)). Monoclonal antibodies are incapable of forming covalent bonds with radiometal ions, but they can be attached to the antibody indirectly through the use of chelating agents that are covalently linked to the antibodies. Chelating agents can be attached through amines (Meares, et al., *Anal. Biochem.* 142:68-78 (1984)) and sulfhydral groups (Koyama *Chem. Abstr.* 120:217262t (1994)) of amino acid residues and also through carbohydrate groups (Rodwell, et al., *Proc. Natl. Acad. Sci.* 83:2632-2636 (1986); Quadri, et al., *Nucl. Med. Biol.* 20:559-570 (1993)). Since these chelating agents contain two types of functional groups, one to bind metal ions and the other to joining the chelate to the antibody, they are commonly referred as bifunctional chelating agents (Sundberg, et al., *Nature* 250:587-588 (1974)).

Crosslinking agents have two reactive functional groups and are classified as being homo or heterobifunctional. Examples of homobifunctional crosslinking agents include bismaleimidohexane (BMH) which is reactive with sulfhydryl groups (Chen, et al. *J Biol Chem* 266: 18237-18243 (1991) and ethylene glycolbis[succinimidylsucciate] EGS which is reactive with amino groups (Browning, et al., *J. Immunol.* 143: 1859-1867 (1989)). An example of a heterobifunctional crosslinker is m-maleimidobenzoyl-N-hydroxysuccinimide ester (MBS) (Myers, et al. *J. Immunol. Meth.*121: 129-142 (1989)). These methodologies are simple and are commonly employed. There are molecules that can act like antibodies that are based on a fibronectin motif. The fibronectin type III domain (FN3) is a small autonomous folding unit. This FN3 domain can be found in numeorus proteins that bind ligand, such as animal proteins. The beta-sandwich structure of FN3 closely resembles that of immunoglobulin domains. FN3 mutants can be isolated using combinatorial approaches disclosed herein, for example phage display, that bind desired targets. Typically the libraries of FN3 molecules have been randomized in the two surface loops. Thus, FN3 can be used at least as a scaffold for engineering novel binding proteins. (Koide A, Bailey C W, Huang X, Koide S., "The fibronectin type III domain as a scaffold for novel binding proteins." J Mol Biol 1998: 284,1141-1151 which is herein incorporated by reference at least for material related to the fibronectin based novel binding proteins).

(3) Functional Nucleic Acids

Functional nucleic acids can also be used to regulate the, for example, the function of the disclosed integrins, integrin receptors, molecules that interact with the disclosed integrin receptors, and molecules in the signaling pathways of the disclosed integrin receptors.

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, Such as DNA, RNA, polypeptides, or carbohydrate chains. Thus, functional nucleic acids can interact with the mRNA of beta4 integrin for example, or the genomic DNA of alpha6 integrin for example, or they can interact with the polypeptide laminin5, or the gamma2 subunit of laminin5. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place. Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than $10^{-6}$. It is more preferred that antisense molecules bind with a $k_d$ less than $10^{-8}$. It is also more preferred that the antisense molecules bind the target molecule with a $k_d$ less than $10^{-10}$. It is also preferred that the antisense molecules bind the target molecule with a $k_d$ less than $10^{-12}$. A representative sample of methods and techniques which aid in the design and use of antisense molecules can be found in the following non-limiting list of U.S. Pat. Nos. : 5,135,917, 5,294,533, 5,627,158, 5,641,754, 5,691, 317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $k_d$s from the target molecule of less than $10^{-12}$ M. It is preferred that the aptamers bind the target molecule with a $k_d$ less than $10^{-6}$. It is more preferred that the aptamers bind the target molecule with a $k_d$ less than $10^{-8}$. It is also more preferred that the aptamers bind the target molecule with a $k_d$ less than $10^{-10}$. It is also preferred that the aptamers bind the target molecule with a $k_d$ less than $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a $k_d$ with the target molecule at least 10 fold lower than the $k_d$ with a background binding molecule. It is more preferred that the aptamer have a $k_d$ with the target molecule at least 100 fold lower than the $k_d$ with a background binding molecule. It is more preferred that the aptamer have a $k_d$ with the target molecule at least 1000 fold lower than the $k_d$ with a background binding molecule. It is preferred that the aptamer have a $k_d$ with the target molecule at least 10000 fold lower than the $k_d$ with a background binding molecule. It is preferred when doing the comparison for a polypeptide for example, that the background molecule be a different polypeptide. For example, when determining the specificity of beta4 integrin aptamers, the background protein could be bovine serum albumin. Representative examples of how to make and use aptamers to bind a variety of different target molecules can be found in the following non-limiting list of U.S. Pat. Nos.: 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (for example, but not limited to the following U.S. Pat. Nos.: 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Sproat, WO 9858057 by Ludwig and Sproat, and WO 9718312 by Ludwig and Sproat) hairpin ribozymes (for example, but not limited to the following U.S. Pat. Nos.: 5,631,115, 5,646,031, 5,683,902, 5,712,384, 5,856,188, 5,866,701, 5,869,339, and 6,022,962), and tetrahymena ribozymes (for example, but not limited to the following U.S. Pat. Nos.: 5,595,873 and 5,652,107). There are also a number of ribozymes that are not found in natural systems, but which have been engineered to catalyze specific reactions de novo (for example, but not limited to the following U.S. Pat. Nos.: 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos.: 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$. It is more preferred that the triplex forming molecules bind with a $k_d$ less than $10^{-8}$. It is also more preferred that the triplex forming molecules bind the target moelcule with a $k_d$ less than $10^{-10}$. It is also preferred that the triplex forming molecules bind the target molecule with a $k_d$ less than $10^{-12}$. Representative examples of how to make and use triplex forming molecules to bind a variety of different target molecules can be found in the following non-limiting list of U.S. Pat. Nos.: 5,176,996, 5,645,985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, *Science* 238:407-409 (1990)).

Similarly, eukaryotic EGS/RNAse P-directed cleavage of RNA can be utilized to cleave desired targets within eukaryotic cells. (Yuan et al., *Proc. Natl. Acad. Sci.* USA 89:8006-8010 (1992); WO 93/22434 by Yale; WO 95/24489 by Yale; Yuan and Altman, *EMBO J* 14:159-168 (1995), and Carrara et al., *Proc. Natl. Acad. Sci.* (*USA*) 92:2627-2631 (1995)). Representative examples of how to make and use EGS molecules to facilitate cleavage of a variety of different target molecules can be found in the following non-limiting list of U.S. Pat. Nos.: 5,168,053, 5,624,824, 5,683,873, 5,728,521, 5,869,248, and 5,877,162

(4) Small Molecules

Small molecules can also be used to regulate, for example, the function of the disclosed integrins, integrin receptors, molecules that interact with the disclosed integrin receptors, and molecules in the signaling pathways of the disclosed integrin receptors. Those of skill in the art understand how to generate small molecules of this type, and exemplary libraries and methods for isolating small molecule regulators are disclosed herein.

d) Compositions and Methods for Identifying Targets and Therapeutics

One of the main goals for R&D in biotechnology is the discovery of informative diagnostic markers and highly specific and effective drug targets, as well as cellular models for disease. The mechanisms involved in cell regulation are complex and cell behavior (or phenotype) results from integration of multiple inputs. This complicates the process of identifying ways to manipulate cell regulation and cell behavior. Typically drug discovery has been performed in a reductionistic setting, i.e. genes thought to be associated with a particular disease or phenotype are isolated and expressed or inhibited from being expressed in systems designed specifically to look at the effect of that single gene. These systems can provide information about the biochemical activity or function that the gene or gene product might have, i.e. it the gene product can function as a transcriptional regulator, but they do not necessarily replicate the environment that the gene or gene product resides in during the onset of, for example, a specific phenotype associated with the gene or gene product. This is particularly true for phenotypes, such as cancer that are multi-genic, meaning the phenotype, cellular or organismal results from mutations in more than one gene or gene product. As shown herein when different genes, each having its own mutation, having been shown previously to be associated with a particular phenotype, are put into a system, such as a cellular assay system, the phenotype of the cell differs from when the mutations are placed into cell assay system singularly. Disclosed herein are systems based on multiple variables affecting the biological response of interest, which are perturbed. Perturbations of variables are introduced both singly and in combination permitting systematic capture of non-linear regulatory events. Because of this the systems disclosed here provide better information about how to target a particular phenotype or disease therapeutically. The disclosed approach and the disclosed systems are particularly pertinent to therapeutic target discovery in multi-genic diseases such as cancer.

Carcinogenesis is associated with multiple genetic lesions, and it is well established that the emergence of the transformed phenotype requires the co-operation of several oncogenic mutations. In order to analyze the molecular mechanism underlying the mechanistic process of multi-genic disease in vitro and in vivo disclosed herein are disease models made by progressive introduction of multiple disease-relevant genetic alterations. This allows comparison of unaltered (wild type) conditions with samples containing distinct single or combinations of multiple mutations. By comparison of cell biological, biochemical and gene expression (genomic and proteomic) parameters it is possible to identify disease-relevant targets with high specificity to the multi-genic disease state that cannot be detected by analysis of single mutation effects.

By way of example, it is shown herein that when 3 genes, gene A, gene B, and gene C, associated with a particular phenotype, such as cancer, are put into a cell assay system singularly, the assay responds differently than when the genes are put into the same cell assay system together. Thus, disclosed are cell systems that have been engineered to have multiple gene mutations within them, so that the natural state of the phenotype is more closely mimicked. One example of this type of cell assay system is the system disclosed herein for assaying the role of integrin signaling in cancer. It is disclosed herein that this pathway involves an autocrine integrin signaling loop, where expression of multiple components of this pathway are induced by cooperating oncogenic mutations (such as Ras and DNp53) and play an essential role for cancer cell survival. Importantly, this signaling loop is not required for the survival of corresponding normal cells. The differences between norrnal and cancer cells were only visible in the cell assay systems having multiple gene mutations. These systems show how cancer cell-specific alterations enable selective killing of cancer cells, while maintaining the survival of normal cells, can be discovered in a rational and efficient manner by analysis of multiple variables.

Thus a cell assay system can be any cell that has been engineered to posess a particular trait. The disclosed cell assay systems typically comprise at least two genetic traits associated with a particular disease. The systems also typically start off with a cell that does not have known mutated background. Thus, for example, a Hela cell would not be used in a cell system as described herein, because the genetic background of the cell, already has many known cancer causing mutations, and may have many unknown. Thus, the systems typically will be based on normal, meaning non-immortalized cells. For example, cultured fibroblasts can be used. It is preferred that the cells forming the system are cells that mimic the cell of the diseased state. For example, if one is studying colon cancer one would use colon cells, if one is studing leukemia one would use the appropriate blood cell, if one is studying lung cancer, one would use lung cells, and so on. However, conditionally immortalized cells can also be used, as these cells have the same properties as non-immortalized cells when the immortalizing gene is not functioning. Cells of this type, will typically have an immortalizing gene(s) which are under the control of a regulatable promoter, which can be any type of regulation system, such as an activator or repressor system or a temperature controlled system. Examples of this type of cell would be one that expresses a refulatable SV40 large T or a regulatable Htert.

Any gene combination can be engineered into the disclosed systems. For example, there are many genes involved in cancer which can be engineered into the system. A variety of genetic mutations are involved in many different cancers. The following references are herein incorporated by reference for the general teachings of genes involved in cancer (e.g., BRCA1, BRCA2, p53 tumor suppressor gene,HER2/neu, and PIC3KA) (Wenham et al. Best Pract Res Clin Obstet Gynaecol August 2002;16(4):483-97); (e.g., p53, BRCA1, BRCA2, PTEN, ATM, HER2/neu, SYK, and NES1) (Buchholz T A, et al. Semin Radiat Oncol October 2002;12(4):285-95).

The following reference is herein incorporated by reference for teachings related to EGFR and cancer (Arteaga C L. Oncologist 2002;7 Suppl 4:31-9).

The erbB2 (Her2/neu) gene (GENBANK ACCESION NOS: AAB17380, AAF30295, M11730) has been associated with a variety of cancers including but not limited to breast cancer. The following references are herein incorporated by reference for teachings related to erbB2 (Her-2/neu) and cancer (Yarden Y. Oncology 2001;61 Suppl 2:1-13; Kaptain S, et al. Diagn Mol Pathol September 2001;10(3):139-52).

The p53 gene (GENBANK ACCESION NOS: M14695, M14694, and K03199) has been associated with a variety of cancers including but not limited to breast cancer, lung cancer, colorectal cancer, prostate cancer, and ovarian cancer. The following references are herein incorporated by reference for teachings relating to p53 and cancer (Holmila R, et al.,. Hum Mutat January 2003;21(1):101-2; Lutz W, et al., Int J Occup Med Environ Health 2002;15(3):209-18; Robles A I, et al. Oncogene Oct. 7, 2002;21(45):6898-907; Mizumoto K, et al. Hepatobiliary Pancreat Surg 2002;9(1):39-44; Guimaraes D P, et al. Biochimie January 2002;84(1):83-93; Bullock A N, et al. Nat Rev Cancer October 2001;1(1):68-76; Rose S L, et al. Minerva Ginecol June 2002;54(3):201-9).

The BRCA1 and BRCA2 genes (GENBANK ACCESION NOS: BRCA1 (U14680) and BRCA2 (U43746)) have been associated with a variety of cancers including but not limited to breast cancer and ovarian cancer. The following references are herein incorporated by reference for teachings related to BRCA1 and BRCA2 in cancer (Moynahan M E. Oncogene Dec. 16, 2002; 21(58):8994-9007; Jasin M. Oncogene Dec. 16, 2002 ;21(58):8981-93; Venkitaraman A R. Cell Jan. 25, 2002 ; 108(2):171-82).

PTEN (GENBANK ACCESION NOS: AH005966 and AAD38372) has been identified as being involved in a variety of cancers including but not limited to breast cancer, Cowden syndrome, and malignant thyroid disease. The following references are herein incorporated by reference for teachings related to PTEN and cancer (Eng C. Ann N Y Acad Sci June 2002;968:213-21; Mills G B, et al. Semin Oncol October 2001;28(5 Suppl 16): 125-41).

The ras gene family (GENBANK ACCESION NOS: k-ras (M54968), h-ras, (AF493916), m-ras (AF493918), RAB2 (NM_002865), RAP2A (NM_021033)) has been associated with a variety of cancers including but not limited to lung cancer and pancreatic carcinoma. The following references are herein incorporated by reference for teachings related to ras and cancer (Oxford G, et al. Cancer Lett Jan. 28, 2003; 189(2):117-28; Hilgers W, et al. Hematol Oncol Clin North Am February 2002;16(1):17-35, v; Li D. Cancer J July-August 2001;7(4):259-65; Ayllon V, et al. Mol Membr Biol April-June 2000;17(2):65-73).

The c-MYC gene (GENBANK ACCESION NOS: V00568) has been associated with a variety of cancers including but not limited to B cell lymphomas, Burkitt's lymphoma, AIDS related lymphomas, and Neuroblastoma tumors. The following references are herein incorporated by reference for teachings related to c-MYC and MYCN in cancer (Popescu N C, et al. J Cell Mol Med April-June 2002;6(2):151-9; Bown N. J Clin Pathol December 2001;54(12):897-910).

The following non-limiting list of genes has also been associated with a variety of cancers: Exo1 (Accession No: AF060479), ASPP2, (Accession No: AJ318888), C/EBPD, p16(INK4a) CDKN2A, R24P, P81L, V126D, BNIP3, MYH, PTCH, B-ras, (Accession No: AF229839 and AF229840), A-ras, PPAR (a, g, and d), Muc-1, MC1R, TP16p14/ARF, (Accession No: NM_016632), SMAD3, (Accession No: AF025293), SMAD4, (Accession No: AY119788), CDK4, p73, p15, AXIN1, raf, (Accession No: X03484), CHEK2, SHIP, HFE, p21(CIP1/WAF1), FAS, TSG101, MEN1, GSTPI, P2X7, BRAF, HPV type 16 E7 (Accession No: AF477385), P27 Cyclin E, Cyclin D, Rb (Accession No: M19701), P300, Mdm2, Fos, Jun, N-Ras, Ki-Ras, Raf-1, Abl, Bcl-2, Bcl-6, Bax, APC (Accession No: M74088), Beta catenin, E-cadherin, PI3-kinase, TGFalpha, TGFbeta, TGFbeta receptor, Src, Met, Akt, Alk, Grb2, She, and E2F 1-5. It is understood that the sequences for all of these genes can be obtained by the skilled artisan as they have been previously isolated and reported. It is further understood that these genes have allelic variants as well as functional variants which are known and understood by the skilled artisan and disclosed herein.

Classes of genes are also considered disclosed. For example, the entire Wnt gene family, and the entire EGF gene family, Growth factors, Survival factors, Growth inhibitory factors, Receptor tyrosine kinases, Tyrosine phosphatases, and Decoy receptors. It is understood that these families of genes are well understood in the art, and numerous examples of each exist. Often times these types of families are defined by homologies between the various family members.

Also disclosed are cells comprising combinations of various genes as disclosed herein. While all combinations and permutations of the disclosed genes are considered disclosed, the following are a few specific examples of combinations of genes which can be inserted into the disclosed cells or controlled in the disclosed cells. For example, combinations comprising Ras and Myc, Ras and loss of p53, Ras and loss of Rb, Ras and loss of NFkB, Ras and loss of APC, Ras and loss of Arf, Ras and E7, Ras and SV40 large T, Ras, Myc and loss of Arf, as well as SV40 large T and hTert.

It is understood that the disclosed cell systems have multiple genes and gene products controlled. It is understood that this control can occur in any way. For example, endogenous gene products can be upregulated or down regulated by addition of factors capable of controlling their expression. These factors can be protein or small molecule based or they can be themselves nucleic acids that will express the molecule capable of regulating the desired genes. It is also understood that the desired genes can themselves be supplied via nucleic acids that express the desired gene or they can be supplied as a protein. Thus, the disclosed cells comprise means for regulating specific sets of genes that are targeted.

Disclosed are cell assay systems comprising at least two manipulated genes, wherein the expression of the gene or gene product is controlled in the cell assay system, and wherein the genes are involved in a disease state. Manipulated gene as discussed herein means any gene whose expression or function of the gene product is controlled within the cell assay system. Controlled means other than the control present in the cell. Thus, the function of the gene product could be controlled using expression of a dopminant negative of the gene product or the gene producting the manipulated gene itself could have its expression reduced by expression of negative regulator of the gene. As discussed herein any way for controlling the expression of the gene or gene product is considered disclosed.

Also disclosed are cell assay systems, further comprising at least three manipulated genes, four manipulated genes, five manipulated genes, six manipulated genes, seven manipulated genes, or more manipulated genes.

Disclosed are cell assay systems wherein the disease state is cancer.

Disclosed are cell assay systems, wherein the manipulated genes are selected from the group consisting of Exo1, ASPP2, C/EBPD, FRA7G, FRA9E, p 16(INK4a) CDKN2A, R24P, P81L, V126D, BNIP3, MYH, PTCH, H-ras, B-ras, A-ras, PPAR (a, g, and d), Muc-1, MC1R, TP16, p14/ARF, SMAD3, SMAD4, CDK4, p73, p15, AXIN1, raf, CHEK2, SHIP, HFE, p21(CIP1/WAF1), FAS, TSG101, MEN1, GSTPI, P2X7, BRAF, HPV type 16 E6 and E7, P27, Cyclin E, Cyclin D, Rb, P300, Mdm2, Fos, Jun, N-Ras, Ki-Ras, Raf-1, Abl, Bcl-2, Bcl-6, Bax, APC, Beta catenin, E-cadherin, P13-kinase, TGFalpha, TGFbeta, TGFbeta receptor, Src, Met, Akt, Alk, Grb2, She, and E2F 1-5.

Also disclosed are cell assay systems, wherein the manipulated genes are selected from the group of Ras and Myc, Ras and Htert, Ras and p53, Ras and Rb, Ras and NFkB, Ras and APC, Ras and Arf, Ras and E7, Ras and SV40 large T, SV40 large T and hTert, and Ras, Myc, and Arf.

Also disclosed cell assay systems, wherein the function of p53, Rb, NFkB, APC, or Arf is reduced.

Disclosed are cell assay systems, wherein the manipulated gene is selected from a class of genes consisting of the Wnt gene family, the EGF gene family, Growth factors, Survival factors, Growth inhibitory factors, Receptor tyrosine kinases, Tyrosine phosphatases, and Decoy receptors.

Also disclosed are methods of identifying a therapeutic target comprising assaying a potential reagent for activity in any of the disclosed cell assay systems.

e) Compositions Identified by Screening with Disclosed Compositions/Combinatorial Chemistry (1) Combinatorial Chemistry The disclosed compositions can be used as targets for any combinatorial technique to identify molecules or macromolecular molecules that interact with the disclosed compositions, such as beta4 integrin, alpha6 integrin, or the gamma2 subunit of laminin5, in a desired way. The nucleic acids, peptides, and related molecules disclosed herein can be used as targets for the combinatorial approaches. Also disclosed are the compositions that are identified through combinatorial techniques or screening techniques in which the herein disclosed compositions, for example set forth in SEQ ID NOS: 1-19 or portions thereof, are used as the target or reagent in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed compositions, such as, beta4 integrin, alpa6 integrin, or the gamma2 subunit of laminin5, are also disclosed. Thus, the products produced using the combinatorial or screening approaches that involve the disclosed compositions, such as, beta4 integrin, alpha6 integrin, or the gamma2 subunit of laminin5, are also considered herein disclosed.

Combinatorial chemistry includes but is not limited to all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, *TIBS* 19:89, 1992). One synthesizes a large pool of molecules bearing random and defined sequences and subjects that complex mixture, for example, approximately $10^{15}$ individual sequences in 100 μg of a 100 nucleotide RNA, to some selection and enrichment process. Through repeated cycles of affinity chromatography and PCR amplification of the molecules bound to the ligand on the solid support, Ellington and Szostak (1990) estimated that 1 in $10^{10}$ RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry)

A preferred method for isolating proteins that have a given function is described by Roberts and Szostak (Roberts R. W. and Szostak J. W. Proc. Natl. Acad. Sci. USA, 94(23)12997-302 (1997). This combinatorial chemistry method couples the functional power of proteins and the genetic power of nucleic acids. An RNA molecule is generated in which a puromycin molecule is covalently attached to the 3'-end of the RNA molecule. An in vitro translation of this modified RNA molecule causes the correct protein, encoded by the RNA to be translated. In addition, because of the attachment of the puromycin, a peptdyl acceptor which cannot be extended, the growing peptide chain is attached to the puromycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3'-end, new peptide is translated and another functional round of selection is performed. Thus, protein selection can be performed in an iterative manner just like nucleic acid selection techniques. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostak J. W. Proc. Natl. Acad. Sci. USA, 94(23) 12997-302(1997)).

Another preferred method for combinatorial methods designed to isolate peptides is described in Cohen et al. (Cohen B. A.,et al., Proc. Natl. Acad. Sci. USA 95(24):14272-7 (1998)). This method utilizes and modifies two-hybrid technology. Yeast two-hybrid systems are useful for the detection and analysis of protein:protein interactions. The two-hybrid system, initially described in the yeast *Saccharomyces cerevisiae*, is a powerful molecular genetic technique for identifying new regulatory molecules, specific to the protein of interest (Fields and Song, *Nature* 340:245-6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain. A peptide of choice, for example a portion of beta4 or alpha6 or gamma2 or laminin5 is attached to a DNA binding domain of a transcriptional activation protein, such as Gal 4. By performing the Two-hybrid technique on this type of system, molecules that bind the portion of beta4 or alpha6 or gamma2 or laminin5 can be identified.

There are molecules that can act like antibodies, in that they can having varying binding specificities, that are based on a fibronectin motif. The fibronectin type III domain (FN3) is a small autonomous folding unit. This FN3 domain can be found in numeorus proteins that bind ligand, such as animal proteins. The beta-sandwich structure of FN3 closely resembles that of immunoglobulin domains. FN3 mutants can be isolated using combinatorial approaches disclosed herein, for example phage display, that bind desired targets. Typically the libraries of FN3 molecules have been randomized in the two surface loops. Thus, FN3 can be used at least as a scaffold for engineering novel binding proteins. (Koide A, Bailey C W, Huang X, Koide S., "The fibronectin type III domain as a scaffold for novel binding proteins." J Mol Biol 1998: 284, 1141-1151 which is herein incorporated by reference at least for material related to the fibronectin based novel binding proteins).

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449, 754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972,719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916,899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856,107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

Screening molecules similar to alpha6 for inhibition of alpha6beta4 formation is a method of identifying and isolating desired compounds that can inhibit the formation of A6B4 receptor. For example, the disclosed compositions, such as alpha6 integrin or beta4 integrin can be used as targets in a selection scheme disclosed herein, and then the counter part integrin could be used as a competitive inhibitor to isolate the desired molecules. For example, a library of molecules could be incubated with beta4 integrin, which is bound to a solid support. The solid support can be washed to remove the unbound molecules and then the solid support can be incubated with, for example, alpha6 integrin at a concentration that will saturate all beta4 binding sites. The molecules which are collected in the flowthrough after washing the solid support will be enriched for molecules that interact with beta4 integrin in a way that is competitive to the alpha6-beta4 interaction. Likewise, the solid support, bound with a target integrin, or more preferably a target integrin receptor, such as alpha6beta4 receptor, could also be washed, with for example, laminin5 or the gamma2 subunit of laminin5 at a concentration that will saturate all of the gamma2 binding sites on the beta4 integrin. Collection of the wash under these conditions will yield a population of molecules enriched for molecules that competitively interact with beta4 integrin at the beta4-gamma2 site. Another example, is the following: bind target to solid support on microtiter plate. Incubate with ligand in presence of gridded subset of library members (or single compounds), wash, identify competitor by reduction of ligand binding It is understood that the exemplary discussions of alpha6beta4 and/or beta4 are equally applicable to alpha6, as well as other alpha6betax receptors, such alpha6beta1.

Also disclosed are methods of isolating molecules that bind with a target molecule selected from the group consisting, B4 integrin, alpha6 integrin, and the gamma2 subunit of laminin5 comprising 1) contacting a library of molecules with the target molecule and 2) collecting molecules that bind the target molecule producing an enriched population of molecules.

Disclosed are methods, further comprising the step of repeating steps 1 and 2 with the enriched population of molecules, and/or wherein the library comprises a small molecule, peptide, peptide mimetic, or oligonucleotide.

As used herein combinatorial methods and libraries included traditional screening methods and libraries as well as methods and libraries used in iterative processes.

(2) Computer Assisted Design

The disclosed compositions can be used as targets for any molecular modeling technique to identify either the structure of the disclosed compositions or to identify potential or actual molecules, such as small molecules, which interact in a desired way with the disclosed compositions. The nucleic acids, peptides, and related molecules disclosed herein can be used as targets in any molecular modeling program or approach.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, such as, beta4, are also disclosed. Thus, the products produced using the molecular modeling approaches that involve the disclosed compositions, such as, beta4 integrin, alpha6 integrin, or laminin5, are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

f) Nucleic Acids

There are a variety of molecules disclosed herein that are nucleic acid based, including for example the nucleic acids that encode, for example beta4 and the gamma2 subunit of laminin5, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

(1) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl (.psi.), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Base modifications can be combined, for example, with a sugar modification, such as 2'-O-methoxyethyl, to achieve unique properties such as increased duplex stability. There are numerous U.S. Pat. Nos. such as 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH—; F—; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to —O[(CH$_2$)$_n$O]$_m$CH$_3$, —O(CH$_2$)$_n$OCH$_3$, —O(CH$_2$)$_n$NH$_2$, —O(CH$_2$)$_n$CH$_3$, —O(CH$_2$)$_n$—ONH$_2$, and —O(CH$_2$)$_n$ON [(CH$_2$)$_n$CH$_3$)]$_2$, where n and m are from 1 to 10.

Other modifications at the 2' position include but are not limited to: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones;formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331;and 5,719,262 teach how to make and use PNA molecules, each of which is herein incorporated by reference. (See also Nielsen et al., Science, 1991, 254, 1497-1500).

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Nati. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937. Numerous United States patents teach the preparation of such conjugates and include, but are not limited to U.S. Pat. Nos. 4,828,979; 4,948,882; 5,218,105; 5,525, 465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is understood that an oligonucleotide can be made from any combination of nucleotides, nucleotide analogs, or nucleotide substitutes disclosed herein or related molecules not specifically recited herein.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

(2) Sequences

There are a variety of sequences related to the beta4 integrin or the laminin5-gamma2 gene or the alpha6 integrin gene having the following Genbank Accession Numbers 6453379, 4557674, and AH006634, respectively. These sequences and others are herein incorporated by reference in their entireties as well as for individual subsequences contained therein.

One particular sequence set forth in SEQ ID NO:1 (beta4 integrin) and having Genbank accession number 6453379 is used herein, at various points, as an example, to exemplify the disclosed compositions and methods (or when another particular sequence is used as an example). It is understood that the description related to this sequence is applicable to any sequence related to beta4 integrin or any of the other molecules disclosed herein, such as alpha6 integrin, or the subunits of laminin5, such as gamma2, unless specifically indicated otherwise. Those of skill in the art understand how to resolve sequence discrepancies and differences and to adjust the compositions and methods relating to a particular sequence to other related sequences (i.e. sequences of beta4 integrin). Primers and/or probes can be designed for any beta4 integrin sequence given the information disclosed herein and known in the art.

(3) Primers and Probes

Disclosed are compositions including primers and probes, which are capable of interacting with the for example, the alpha6 gene or mRNA, beta4 gene or mRNA, or gamma2 subunit of the laminin5 ligand gene as disclosed herein or mRNA as wells as primers or probes for any of the sequences or fragments of the sequences, set forth in SEQ ID NOs:1, 3, 5, 7, 9, 11, and 13. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the beta4 gene, alpha6 gene, or laminin5-gamma2 subunit gene, for example, or region of the beta4 gene, alpha6 gene, or laminin5-gamma2 subunit gene, for example, or they hybridize with the complement of the beta4 gene, alpha6 gene, or laminin5-gamma2 subunit gene, for example, or complement of a region of the beta4 gene, alpha6 gene, or laminin5-gamma2 subunit gene, or any of the sequences or fragments of the sequences, set forth in SEQ ID NOs:1, 3, 5, 7, 9, 11, and 13, for example.

The size of the primers or probes for interaction with the beta4 gene, alpha6 gene, or laminin5-gamma2 subunit gene, for example, in certain embodiments can be any size that supports the desired enzymatic manipulation of the primer, such as DNA amplification or the simple hybridization of the probe or primer. A typical primer or probe for beta4 gene, alpha6 gene, or laminin5-gamma2 subunit gene, for example, or primer or probe for any of the sequences or fragments of the sequences, set forth in SEQ ID NOs:1, 3, 5, 7, 9, 11, and 13 would be at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments a primer or probe for beta4 gene, alpha6 gene, or laminin5-gamma2 subunit gene, for example, primer or probe or a primer or probe for any of the sequences or fragments of the sequences, set forth in SEQ ID NOs:1, 3, 5, 7, 9, 11, and 13 can be less than or equal to about 6, 7, 8, 9, 10, 11, 12 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

The primers for the beta4 gene, alpha6 gene, or laminin5-gamma2 subunit gene, or any of the sequences or fragments of the sequences, set forth in SEQ ID NOs:1, 3, 5, 7, 9, 11, and 13, for example, typically will be used to produce an amplified DNA product that contains a desired region. In general, typically the size of the product will be such that the size can be accurately determined to within 3, or 2 or 1 nucleotides.

In certain embodiments this product is at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments the product is less than or equal to about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

g) Sequence Similarities

It is understood that as discussed herein the use of the terms homology and identity mean the same thing as similarity. Thus, for example, if the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether or not they are evolutionarily related.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

It is also understood that functional fragments as well as antigenic fragments as well as fragments that can be used in selection protocols of the disclosed compositions are also disclosed. For example, integrins have domains that interact with the other integrins. It may be advantageous in certain embodiments to utilize just the integrin binding domain fragment of, for example, the beta4 integrin, in a selection protocol disclosed herein. By using this domain of the beta4 integrin as the selection target, for example, the selection protocol will be biased for molecules binding this domain of beta4 integrin.

h) Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, ifdesired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

i) Delivery of the Compositions to Cells

The disclosed compositions and methods often entail delivery of the compositions to cells. For example, antisense molecules directed to alpha6 mRNA or gamma2 mRNA can be delivered to cells via any method. A number of exemplary methods are disclosed herein. It is also understood that in certain embodiments, non-nucleic acid molecules will be and can be delivered to cells, for example an antibody to beta4 integrin, alpha6 integrin or, gamma2, or a small molecule, or a peptide. Delivery of these molecules can occur by any means, and exemplary compositions and methods for such delivery are disclosed herein.

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

(1) Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as gamma2 antisense producing molecules into the cell without degradation and include a promoter yielding expression of the gene in the cells into which it is delivered. In some embodiments the delivery vectors are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Moloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, other than Lentivirus vectors, they are typically not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

(a) Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

(b) Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586(1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

(c) Adeno-associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The vectors of the present invention thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

(d) Large Payload Viral Vectors

Molecular genetic experiments with large human herpesviruses have provided a means whereby large heterologous DNA fragments can be cloned, propagated and established in cells permissive for infection with herpesviruses (Sun et al., Nature genetics 8: 33-41, 1994; Cotter and Robertson,.Curr Opin Mol Ther 5: 633-644, 1999). These large DNA viruses (herpes simplex virus (HSV) and Epstein-Barr virus (EBV), have the potential to deliver fragments of human heterologous DNA >150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA >220 kb and to infect cells that can stably maintain DNA as episomes.

Other useful systems include, for example, replicating and host-restricted non-replicating vaccinia virus vectors.

(2) Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed nucleic acids and proteins or vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci USA* 84:7413-7417 (1987); U.S. Pat. No. 4,897, 355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution or suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog.* *Reviews,* 129:57-80, (1992); and Roffler, et al., *Biochem. Pharmacol,* 42:2062-2065, (1991)). These techniques can be used for a variety of other specific cell types. Vehicles, among others, include "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

(3) In Vivo/Ex Vivo

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

It is understood that in certain embodiments, constructs which produce an integrin signal transduction inhibitor are driven by inducible promoters, rather than constitutive promoters. inducible systems provide certain advantages, to the expression of the disclosed constructs. Any inducible system can be used. Also disclosed are cells containing the inducible systems, described herein, and in the Examples. These cells, can be used as model systems in a wide variety of assays, as well as in vivo settings.

j) Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

(1) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell Bio.* 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promoter and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

(2) Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puromycin.

k) Peptides

(1) Protein Variants

As discussed herein there are numerous variants of the beta4 integrin protein, alpha6 integrin protein, and gamma2 laminin5 protein, for example, that are known and herein contemplated. In addition, to the known functional homologue variants there are derivatives of the beta4, alpha6, and gamma2, and other disclosed proteins which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place.

Such substitutions generally are made in accordance with the following Tables 1 and 2 and are referred to as conservative substitutions.

TABLE 1

Amino Acid Abbreviations

| Amino Acid | Abbreviations | |
|---|---|---|
| alanine | Ala | A |
| allosoleucine | AIle | |
| arginine | Arg | R |
| asparagine | Asn | N |
| aspartic acid | Asp | D |
| cysteine | Cys | C |
| glutamic acid | Glu | E |
| glutamine | Gln | K |
| glycine | Gly | G |
| histidine | His | H |
| isolelucine | Ile | I |
| leucine | Leu | L |
| lysine | Lys | K |
| phenylalanine | Phe | F |
| proline | Pro | P |
| pyroglutamic acid | pGlu | |
| serine | Ser | S |
| threonine | Thr | T |
| tyrosine | Tyr | Y |
| tryptophan | Trp | W |
| valine | Val | V |

TABLE 2

Amino Acid Substitutions

| Original Residue | Exemplary Conservative Substitutions, others are known in the art. |
|---|---|
| Ala | ser |
| Arg | lys, gln |
| Asn | gln; his |
| Asp | glu |
| Cys | ser |
| Gln | asn, lys |
| Glu | asp |
| Gly | pro |
| His | asn; gln |
| Ile | leu; val |
| Leu | ile; val |
| Lys | arg; gln; |
| Met | Leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO:SEQ ID NO:5 sets forth a particular sequence of beta4 integrin cDNA and SEQ ID NO:6 sets forth a particular sequence of a beta4 integrin protein. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

It is understood that the description of conservative mutations and homology can be ombined together in any combination, such as embodiments that have at least 70% homology to a articular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. For example, one of the many nucleic acid sequences that can encode the protein sequence set forth in SEQ ID NO:6 is set forth in SEQ ID NO:5. Another nucleic acid sequence that encodes the same protein sequence set forth in SEQ ID NO:6 is set forth in SEQ ID NO:16. In addition, for example, a disclosed conservative derivative of SEQ ID NO:2 is shown in SEQ ID NO: 17, where the valine (V) at position 34 is changed to a isoleucine (I). It is understood that for this mutation all of the nucleic acid sequences that encode this particular derivative of the beta4 integrin are also disclosed including for example SEQ ID NO:18 and SEQ ID NO:19 which set forth two of the degenerate nucleic acid sequences that encode the particular polypeptide set forth in SEQ ID NO:17. It is also understood that while no amino acid sequence indicates what particular DNA sequence encodes that protein within an organism, where particular variants of a disclosed protein are disclosed herein, the known nucleic acid sequence that encodes that protein in the particular organism from which that protein arises is also known and herein disclosed and described.

I) Pharmaceutical Carriers/Delivery of Pharmaceutical Products

As described above, the compositions, for example, compositions that inhibit alpha6 function, beta4 function, or gamma2 function can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, although topical intranasal administration or administration by inhalant is typically preferred. As used herein, "topical intranasal administration" means delivery of the compositions into the nose and nasal passages through one or both of the nares and can comprise delivery by a spraying mechanism or droplet mechanism, or through aerosolization of the nucleic acid or vector. The latter may be effective when a large number of animals is to be treated simultaneously. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129: 57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

(1) Pharmaceutically Acceptable Carriers

The compositions, including antibodies, can be used therapeutically in combination with a pharmaceutically acceptable carrier.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base- addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

(2) Therapeutic Uses

The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

Other compositions which do not have a specific pharmaceutical function, but which may be used for tracking changes within cellular chromosomes or for the delivery of diagnostic tools for example can be delivered in ways similar to those described for the pharmaceutical products.

m) Chips and Micro Arrays

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

n) Computer Readable Mediums

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

Disclosed are computer readable mediums comprising the sequences and information regarding the sequences set forth herein. Also disclosed are computer readable mediums comprising the sequences and information regarding the sequences set forth herein wherein the sequences do not include SEQ ID NOs: SEQ ID NOs:1-19.

o) Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended. For example, disclosed is a kit for assessing a subject's risk for acquiring cancer, such as colon cancer, comprising the primers or probes that hybridize to the sequences set forth in SEQ ID NOs:1, 3, 5, 7, 9, 11, and 13, for example.

p) Compositions with Similar Functions

It is understood that the compositions disclosed herein have certain functions, such as inhibiting gamma2 function or binding alpha6 integrin or inhibiting beta4 function. Disclosed herein are certain structural requirements for performing the disclosed functions, and it is understood that there are a variety of structures which can perform the same function which are related to the disclosed structures, and that these structures will ultimately achieve the same result, for example stimulation or inhibition alpha6beta4 signaling or interruption of the alpha6beta4 signaling pathway.

2. Methods of Making the Compositions

The compositions disclosed herein and the compositions necessary to perform the disclosed methods can be made using any method known to those of skill in the art for that particular reagent or compound unless otherwise specifically noted.

a) Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., *Molecular Cloning. A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994).

b) Peptide Synthesis

One method of producing the disclosed proteins, or fragments of the disclosed proteins, such as a fragment of SEQ ID NO:6, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W. H. Freeman and Co., N.Y. (1992); Bodansky M and Trost B., Ed. (1993) Principles of Peptide Synthesis. Springer-Verlag Inc., N.Y. (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J.Biol.Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

The disclosed proteins and polypeptides such as that for SEQ ID NO:6, beta4 integrin, can be made using any traditional recombinant biotechnology method. Examples of such methods can be found in Sambrook et al. which is herein incorporated by reference at least for material related to production of proteins and antibodies.

c) Processes for Making the Compositions

Disclosed are processes for making the compositions as well as making the intermediates leading to the compositions. For example, disclosed are nucleic acids in SEQ ID NOs:1, 3, 5, 7, 9, 11, and 13. There are a variety of methods that can be used for making these compositions, such as synthetic chemical methods and standard molecular biology methods. It is understood that the methods of making these and the other disclosed compositions are specifically disclosed.

Disclosed are nucleic acid molecules produced by the process comprising linking in an operative way a nucleic acid molecule comprising the sequence set forth in SEQ ID Nos:1, 3, 5, 7, 9, 11, or 13 or a fragment thereof, and a sequence controlling the expression of the nucleic acid.

Also disclosed are nucleic acid molecules produced by the process comprising linking in an perative way a nucleic acid molecule comprising a sequence having at least 80% identity to a sequence set forth in SEQ ID Nos:1, 3, 5, 7, 9, 11, or 13 or a fragment thereof, and a sequence controlling the expression of the nucleic acid.

Disclosed are nucleic acid molecules produced by the process comprising linking in an operative way a nucleic acid molecule comprising a sequence that hybridizes under stringent hybridization conditions to a nucleic acid molecule comprising the sequence set forth in SEQ ID Nos:1, 3, 5, 7, 9, 11, or 13 or a fragment thereof, and a sequence controlling the expression of the nucleic acid.

Disclosed are nucleic acid molecules produced by the process comprising linking in an operative way a nucleic acid molecule comprising a sequence encoding a peptide set forth in SEQ ID Nos:2, 4, 6, 8, 10, 12, or 14 or a fragment thereof, and a sequence controlling an expression of the nucleic acid molecule.

Disclosed are nucleic acid molecules produced by the process comprising linking in an operative way a nucleic acid molecule comprising a sequence encoding a peptide having 80% identity to a peptide set forth in SEQ ID Nos:2, 4, 6, 8, 10, 12, or 14 or a fragment thereof and a sequence controlling an expression of the nucleic acid molecule.

Disclosed are nucleic acids produced by the process comprising linking in an operative way a nucleic acid molecule comprising a sequence encoding a peptide having 80% identity to a peptide set forth in SEQ ID Nos:2, 4, 6, 8, 10, 12, or 14 or a fragment thereof, wherein any change from the sequences set forth in SEQ ID Nos:2, 4, 6, 8, 10, 12, or 14 or a fragment thereof are conservative changes and a sequence controlling an expression of the nucleic acid molecule.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

Also disclose are animals produced by the process of adding to the animal any of the cells disclosed herein.

d) Products Produced from Selection Protocols

Also disclosed are methods of obtaining molecules that act as functional regulators of integrin function, integrin receptor function, and functional regulators of signaling pathways related to integrin receptors, in particular integrin alpha6beta4.

Disclosed are methods for isolating molecules that interact with the proteins set forth in SEQ ID Nos:2, 4, 6, 8, 10, 12, or 14 or a fragment thereof comprising, interacting a library of molecules with the proteins set forth in SEQ ID Nos:2, 4, 6, 8, 10, 12, or 14 or a fragment thereof, removing the unbound molecules, and collecting the molecules that are bound to at least one of the proteins set forth in SEQ ID Nos:2, 4, 6, 8, 10, 12, or 14 or a fragment thereof.

3. Methods of Using the Compositions a) Methods of Using the Compositions as Research Tools

The compositions can be used for example as targets in combinatorial chemistry protocols or other screening protocols to isolate molecules that possess desired functional properties related to A6B4 and A6B1 signaling pathways.

The disclosed compositions can also be used diagnostic tools related to diseases such as cancer, such as colon cancer.

The disclosed compositions can be used as discussed herein as either reagents in micro arrays or as reagents to probe or analyze existing microarrays. The disclosed compositions can be used in any known method for isolating or identifying single nucleotide polymorphisms. The compositions can also be used in any method for determining allelic analysis of for example, beta4 alleles having varying function, particularly allelic analysis as it relates to beta4 signaling and functions. The compositions can also be used in any known method of screening assays, related to chip/micro arrays. The compositions can also be used in any known way of using the computer readable embodiments of the disclosed compositions, for example, to study relatedness or to perform molecular modeling analysis related to the disclosed compositions.

b) Methods for Affecting Cancer

The disclosed compositions can be used to affect the growth of cancer cells because as disclosed herein, the disclosed relationships are fundamental to the ability of cancer cells to continue growing. The disclosed compositions, such as antisense constructs that will inhibit the production of either alpha6, beta4, or the gamma2 chain of laminin5 reduce the proliferation of cancer cells. In fact, the compositions cannot only reduce the proliferation of the cancer cells, but the compositions can kill the cancer cells, as shown herein.

It is understood that cancer is caused by a variety of cellular events, of which certain events related to alpha6 integrin (up regulated), beta4 integrin (upregulated) and gamma2 (up-regulated) allow the continued viability of cancer cells, and that interference of these upregulated molecules inhibits the growth and kills the cancer cells. However, there are other known events that can cause non-cancerous cells to become oncogenic. For example, Abl, Ras, EGF receptor, ErB-2, APC, beta-catenin, Arf, Mdm2, p53, Rb, Myc are known to be involved in oncogenesis, and some of these molecules (For exmaple, Ras, APC loss, p53 loss) are directly related to the disclosed target signal transduction pathways mediated by the alpha6beta4 receptor. Just as the presently disclosed compositions can be used as therapeutics targeting the disclosed relationships, so to there are other targets (For example, Abl, ErB-2) for which pharmaceutical compositions have been developed (For example, Glivec, Herceptin, respectively).

It is understood that the disclosed anti-cancer compositions can be used in combination with other anti-cancer compositions. Great benefits can be obtained from using anti-cancer compositions that target different molecules, in the same signal transduction pathway as well as, or in addition to, targeting molecules in different signal transduction pathways than those disclosed herein. Thus, the disclosed compositions which can affect the growth of cancer cells, indeed kill cancer cells, can be used in conjunction with any other chemotherapy, radiation, or any other anti-cancer therapy.

Disclosed are methods of reducing the proliferation of a cancer cell which comprises inhibiting ligand binding to an integrin receptor on the cancer cell, wherein the integrin receptor comprises an integrin.

Also disclosed are methods of reducing the proliferation of a cancer cell which comprises reducing integrin-integrin interaction, integrin receptor clustering interaction, or integrin-non-integrin protein interaction.

Also disclosed are methods of selectively reducing the proliferation of cancer cells which comprises reducing integrins from interacting with one another, integrins from clustering, or integrins from interacting with other proteins associated with cancer cells.

Disclosed are methods of reducing the proliferation of a cancer cell which comprises reducing the production of an integrin by the cancer cell.

Also disclosed are methods of reducing the proliferation of a cancer cell which comprises reducing the production of an integrin receptor ligand by the cancer cell.

Disclosed are methods of reducing the proliferation of a cancer cell which comprises interfering with an integrin signaling pathway.

Also disclosed are methods of selectively killing or reducing the proliferation of cancer cells which comprises inhibiting ligand binding to integrin receptors on the cancer cells, wherein the integrin receptor comprises a B4 integrin.

Disclosed are methods of selectively killing or reducing the proliferation of cancer cells which comprises inhibiting ligand binding to integrin receptors on the cancer cells, wherein the ligand comprises a laminin5.

Also disclosed are methods of selectively killing or reducing the proliferation of cancer cells which comprises inhibiting ligand binding to integrin receptors on the cancer cells, wherein the ligand comprises the gamma2 subunit of the laminin L5.

Disclosed are methods of selectively killing or reducing the proliferation of cancer cells which comprises inhibiting ligand binding to integrin receptors on the cancer cells, wherein the integrin receptor comprises an alpha6 integrin.

Further disclosed are methods of selectively killing or reducing the proliferation of cancer cells which comprises preventing integrin receptor subunits from interacting with one another, preventing integrin clustering, or preventing integrin receptor subunits from interacting with other proteins on cancer cells, wherein the integrin receptor comprises a B4 integrin.

Disclosed are methods of selectively killing or reducing the proliferation of cancer cells which comprises reducing the production of laminin by the cancer cells, wherein the laminin comprises laminin5, and/or any of the subunits of laininin5, such as gamma2.

Also disclosed is a method of selectively killing or reducing the proliferation of cancer cells which comprises interfering with an integrin signaling pathway, wherein the integrin signaling pathway comprises a B4 integrin or an alpha6 integrin or a beta1 integrin or a laminin or a laminin5 or the gamma2 subunit of laminin5.

Also dislcosed are methods, wherein the integrin receptor comprises integrin B4 and/or wherein the integrin receptor comprises integrin A6, and/or wherein the ligand that binds to the integrin receptor is laminin5, and/or wherein the integrin receptor is A6B4, and/or wherein the ligand comprises laminin5, and/or wherein the ligand comprises the gamma-2 subunit of laminin5, and/or wherein inhibiting ligand binding to an integrin receptor does not occur by using an antisense molecule to A6, and/or wherein inhibiting ligand binding to an integrin receptor comprises contacting a A6 integrin with a composition that inhibits ligand binding, and/or wherein inhibiting ligand binding to an integrin receptor comprises contacting a B4 integrin with a composition that inhibits ligand binding, and/or wherein inhibiting ligand binding to an integrin receptor comprises contacting a laminin5 with a composition that inhibits ligand binding, and/or wherein inhibiting ligand binding to an integrin receptor comprises contacting a gamma-2 subunit with a composition that inhibits ligand binding, and/or wherein reducing integrin-integrin interaction, integrin receptor clustering interaction, or integrin-non-integrin protein interaction does not occur by using a B4-delta-cyt, and/or wherein reducing integrin-integrin interaction, integrin receptor clustering interaction, or integrin-non-integrin protein interaction does not occur by using an antisense molecule to A6, and/or wherein reducing integrin-integrin interaction, integrin receptor clustering interaction, or integrin-non-integrin protein interaction comprises contacting a A6 integrin with a composition that inhibits an interaction between the B4 integrin and another integrin or protein molecule, and/or wherein reducing integrin-integrin interaction, integrin receptor clustering interaction, or integrin-non-integrin protein interaction comprises contacting a B4 integrin with a composition that inhibits the interaction between the B4 integrin and another integrin or protein molecule, and/or wherein reducing integrin-integrin interaction, integrin receptor clustering interaction, or integrin-non-integrin protein interaction comprises contacting a laminin5 with a composition that inhibits ligand binding, and/or wherein reducing integrin-integrin interaction, integrin receptor clustering interaction, or integrin-non-integrin protein interaction comprises contacting a gamma2 subunit with a composition that inhibits ligand binding, and/or wherein the non-integrin protein comprises a growth factor receptor, and/or wherein the non-integrin protein comprises a hemi-desomosome junction, and/or wherein the non-integrin protein comprises a SH2 domain, and/or wherein the non-integrin protein comprises a She protein, and/or wherein the non-integrin protein comprises a IRS-1 protein, and/or wherein the non-integrin protein comprises a IRS-2 protein, and/or wherein reducing the production of an integrin does not occur by using an antisense molecule to A6, and/or wherein the production of an integrin is reduced by inhibiting signaling leading to induction of expression of an integrin, and/or wherein reducing the production of an integrin comprises inhibiting alpha6 production, and/or wherein inhibiting alpha6 production further comprises using antisense molecules to alpha6 mRNA, and/or wherein reducing the production of an integrin comprises inhibiting beta4 production, and/or wherein inhibiting beta4 production further comprises using antisense molecules to beta4 mRNA, and/or wherein reducing the production of an integrin receptor ligand comprises inhibiting gamma2 production, and/or wherein reducing the production of an integrin receptor ligand comprises inhibiting laminin production, and/or wherein reducing the production of an integrin receptor ligand comprises inhibiting laminin5 production, and/or wherein interfering with an integrin signaling pathway does not occur by using a B4-delta-cyt, and/or wherein interfering with an integrin signaling pathway does not occur by using an antisense molecule to A6, and/or wherein interfering with an integrin signaling pathway comprises contacting an A6 integrin in the cell with a composition that inhibits ligand binding, and/or wherein interfering with an integrin signaling pathway comprises contacting a B4 integrin with a composition that inhibits ligand binding, and/or wherein interfering with an integrin signaling pathway comprises contacting a laminin5 with a composition that inhibits ligand binding, and/or wherein interfering with an integrin signaling pathway comprises contacting a gamma2 subunit with a composition that inhibits ligand binding, and/or wherein interfering with an integrin signaling pathway comprises contacting the cancer cell with a molecule that interferes with at least one of talin, paxillin, vinculin, a CAS family protein, CRX, NCK, FAK, ILK, Src, Fyn, She, Grb-2, Guaning nucleotide exchange factors, SOS, DOCK 180,.Vav, Syk, P-1-3 kinase, AKT, Bad, Bid, Caspase 9, Cdc42, PAK, Rac, Rho, Rho kinase, Ras, Caveolin, Tetraspan, Receptor-type protein tyrosine phosphatase, SHP-2, Alpha-actinin, Filamin, Cytohesin, Beta3-endonexin, ICAP-1, RACK-1, CIB, actin, receptor tyrosine kinase, IRS-1 or IRS-2, and/or wherein interfering with an integrin signaling pathway comprises contacting the cancer cell with an agent that interferes with post-translational modification of integrins, and/or wherein the post translational modification is glycosylation or phosphorylation.

Also disclosed are methods, wherein the integrin comprises an A6 integrin, and/or wherein the integrin comprises a B4 integrin, and/or further comprising reducing a laminin5-integrin interaction, and/or further comprising reducing a laminin5 gamma2 integrin interaction, and/or wherein the cancer cell comprises normal p53, and/or wherein the proliferation of the cancer cells is not dependent on AKT/PKB, and/or wherein reducing the proliferation of the cancer cells is selective, and/or wherein the cancer cell is not an MDA-MB-435 cell, and/or wherein the cancer cell is not an HMT-3522 cell, and/or wherein the cancer cell is not an RKO colon carcinoma line, and/or wherein the cancer cell does not express exogenous B4 integrin, and/or further comprising contacting the cancer cells with a small molecule, peptide, peptide mimetic, or oligonucleotide or synthetic analog thereof, and/or wherein the cancer cells are contacted with dominant-negative beta 4 integrin, and/or wherein the cancer cell is contacted with an antisense molecule, and/or wherein the antisense molecule is linked to a leader sequence which enables translocation across a cell membrane, and/or wherein the leader sequence binds to a cell surface protein which facilitates internalization, and/or wherein the leader sequence is TAT or antennapedia, or fragment thereof, and/or wherein the antisense molecule is an alpha6 RNA antisense molecule, and/or wherein the small molecule peptide, peptide mimetic, or oligonucleotide or synthetic analog thereof is linked to a carrier, and/or wherein the carrier is at least one of a lipidic carrier, charged carrier, retroviral carrier, TAT or fragment thereof, antennapedia or fragment thereof, or polyethylene glycol, and/or further comprising contacting the cancer cell with another agent which modulates cell signaling, a chemotherapeutic drug, or treated with radiation or angiogenesis inhibitor, and/or wherein reducing the proliferation of cancer cell is in vitro, and/or wherein reducing the proliferation of the cancer cell is in vivo, and/or wherein the cancer cell is selected from the group consisting of melanoma, adenoma, lymphoma, myeloma, carcinoma, plasmocytoma, sarcoma, glioma, thyoma, leukemia, skin cancer, retinal cancer, breast cancer, prostate cancer, colon cancer, esophageal cancer, stomac cancer, pancreas cancer, brain tumors, lung cancer, ovarian cancer, cervical cancer, hepatic cancer, gastrointestinal cancer, and head and neck cancer cells, and/or wherein the cancer cell is killed, and/or wherein the cancer cell expresses a mutated Ras, and/or wherein the cancer cell expresses a mutated Ras and a mutated p53, and/or wherein the cancer cell expresses a mutated Ras and activates the AKT/PKB protein, and/or wherein the cancer cell expresses a mutated Ras, a mutated p53, and activates the AKT/PKB protein, and/or wherein the cancer cell expresses a mutated APC, and/or wherein the cancer cell expresses a mutated Ras and mutated APC.

Disclosed are methods of reducing the proliferation of a cancer cell in a patient which comprises administering to the patient a composition which inhibits ligand binding to an integrin receptor on the cancer cell, wherein the integrin receptor comprises an integrin.

Also disclosed are methods of reducing the proliferation of a cancer cell in a patient which comprises administering to the patient a composition which reduces integrin-integrin interaction, integrin receptor clustering interaction, or integrin-non-integrin protein interaction.

Also disclosed are methods of reducing the proliferation of a cancer cell in a patient which comprises administering to the patient a composition which reduces the production of an integrin or laminin by the cancer cell.

Further disclosed are methods of reducing the proliferation of a cancer cell in a patient which comprises administering to the patient a composition which interfers with an integrin signaling pathway.

Also discisoed are methods, wherein the reduction in cancer cell proliferation is selective, and/or wherein the administering is local or systemic, and/or wherein the patient is additionally administered an agent which modulates cell signaling, a chemotherapeutic drug, or treated with radiation or angiogenesis inhibitor, and/or wherein the additional agent is administered serially or in combination, and/or wherein the local administering is direct application to cancer cells, and/or wherein the direct application to cancer cells is performed during surgery, and/or wherein the direct application to cancer cells is performed topically to cancerous tissue, and/or wherein the systemic administration is by subcutaneous, intraperitoneal, intra-arterial, intravenous, or bolus administration, or by application through a catheter or similar apparatus, and/or wherein the systemic administration comprises a long-term release formulation, and/or wherein the systemic administration is by oral administration, and/or wherein the oral administration comprises administering a pill, capsule, tablet, liquid or suspension.

Disclosed are methods of reducing the proliferation of a cancer cell in a patient which comprises administering to a patient a vector comprising coding sequence for a protein or peptide which inhibits ligand binding to integrin receptors on cancer cells wherein the coding sequence is under the control of a promoter which functions in mammalian cells.

Also disclosed are methods of reducing the proliferation of a cancer cell in a patient which comprises administering to a patient a vector comprising coding sequence for a protein or peptide which prevents integrin receptor subunits from interacting with one another, prevents integrin receptor clustering interaction, or prevents integrin receptor subunits from interacting with other proteins on cancer cells wherein the coding sequence is under the control of a promoter which functions in mammalian cells.

Further disclosed are methods of reducing the proliferation of a cancer cell in a patient which comprises administering to a patient a vector comprising coding sequence for a protein or peptide which prevents intcgrin receptor subunits from interacting with one another, prevents integrin receptor clustering interaction, or prevents integrin receptor subunits from interacting with other proteins in cancer cells wherein the coding sequence is under the control of a promoter which functions in mammalian cells.

Also disclosed are method of reducing the proliferation of a cancer cell in a patient which comprises administering to a patient a vector comprising coding sequence for a protein or peptide which interferes with integrin subunit or laminin production wherein the coding sequence is under the control of a promoter which functions in mammalian cells.

Further disclosed are methods of reducing the proliferation of a cancer cell in a patient which comprises administering to a patient a vector comprising coding sequence for a protein or peptide which interferes with an integrin signaling pathway of cells wherein the coding sequence is under the control of a promoter which functions in mammalian cells.

Also disclosed are methods, wherein the reduction in cancer cell proliferation is selective, and/or wherein the vector is administered directly to a cancer cell, and/or wherein the vector is administered directly to a normal cell, and/or wherein the vector is packaged in a viral vector or liposome, and/or wherein the vector is a retroviral vector, and/or wherein the vector is administered systemically, and/or wherein the direct administration is by topical application, and/or wherein the direct administration is by topical application, and/or wherein the direct administration is performed during surgery, and/or wherein the direct administration is performed during surgery, and/or wherein the patient is an animal, such as a mammal, mouse, rabbit, primate, chimp, ape, goriilla, and human, and/or wherein the cancer cells are selected from the group consisting of melanoma, adenoma, lymphoma, myeloma, carcinoma, plasmocytoma, sarcoma, glioma, thyoma, leukemia, skin cancer, retinal cancer, breast cancer, prostate cancer, colon cancer, esophageal cancer, stomac cancer, pancreas cancer, brain tumors, lung cancer, ovarian cancer, cervical cancer, hepatic cancer, gastrointestinal cancer, and head and neck cancer cells, and/or wherein the patient is additionally administered at least one of another agent which modulates cell signaling, a chemotherapeutic drug, an angiogenesis inhibitor or treated with radiation, and/or wherein the other agent which modifies cell signaling, chemotherapeutic drug, angiogenesis inhibitor or radiation treatment is administered serially or in combination.

c) Methods of Gene Modification and Gene Disruption

The disclosed compositions and methods can be used in targeted gene disruption and modification in any animal that can undergo these events. Gene modification and gene disruption refer to the methods, techniques, and compositions that surround the selective removal or alteration of a gene or stretch of chromosome in an animal, such as a mammal, in a way that propagates the modification through the germ line of the mammal. In general, a cell is transformed with a vector which is designed to homologously recombine with a region of a particular chromosome contained within the cell, as for example, described herein. This homologous recombination event can produce a chromosome which has exogenous DNA introduced, for example in frame, with the surrounding DNA. This type of protocol allows for very specific mutations, such as point mutations, to be introduced into the genome contained within the cell. Methods for performing this type of homologous recombination are disclosed herein.

One of the preferred characteristics of performing homologous recombination in mammalian cells is that the cells should be able to be cultured, because the desired recombination event occur at a low frequency.

Once the cell is produced through the methods described herein, an animal can be produced from this cell through either stem cell technology or cloning technology. For example, if the cell into which the nucleic acid was transfected was a stem cell for the organism, then this cell, after transfection and culturing, can be used to produce an organism which will contain the gene modification or disruption in germ line cells, which can then in turn be used to produce another animal that possesses the gene modification or disruption in all of its cells. In other methods for production of an animal containing the gene modification or disruption in all of its cells, cloning technologies can be used. These technologies generally take the nucleus of the transfected cell and either through fusion or replacement fuse the transfected nucleus with an oocyte which can then be manipulated to produce an animal. The advantage of procedures that use cloning instead of ES technology is that cells other than ES cells can be transfected. For example, a fibroblast cell, which is very easy to culture can be used as the cell which is transfected and has a gene modification or disruption event take place, and then cells derived from this cell can be used to clone a whole animal. Conditional knockouts can also be made which will conditionally delete expression of the desired molecule, for example, an A6 or integrin or the gamma2 chain of laminin5.

d) Methods of Diagnosing Cancer

Methods of diagnosing cancer using the disclosed information and the disclosed molecules. In particular disclosed are methdos of diagnoses that rely on the combined upregulation of both the ligand and the cogante integrin receptor or cognate integrins. It is understood that all of the methods of diagnosis disclosed herein, can be used with any of the disclosed compositions, but they also can be used in conjunction, where for example, both the ligand and the integrin receptor are monitored and correlated with cancer developing.

Disclosed are methods of assessing a subject's risk of developing cancer comprising determining the amount of A6 present in a target cell obtained from the subject, wherein a determination of increased levels of A6 correlates with an increased risk of cancer.

Disclosed are methods of assessing a subject's risk of acquiring cancer comprising determining the amount of B4 present in a target cell obtained from the subject, wherein a determination of increased levels of B4 correlates with an increased risk of cancer.

Disclosed are methods of assessing a subject's risk of acquiring cancer comprising determining the amount of laminin5 present in a target cell obtained from the subject, wherein a determination of increased levels of laminin5 correlates with an increased risk of cancer.

Disclosed are methods of assessing a subject's risk of acquiring cancer comprising determining the amount of gamma2 subunit present in a target cell obtained from the subject, wherein a determination of increased levels of gamma2 subunit correlates with an increased risk of cancer.

Also disclosed are methods, further comprising comparing the amount A6 present to the amount in a control cell, and wherein determining the amount of A6 present in the target cell comprises assaying the amount of A6 mRNA in the cell, and.or wherein the assaying the amount of mRNA in the cell comprises hybridizing a A6 probe to a sample of the subject's mRNA, and/or wherein the assaying the amount of mRNA in the cell comprises hybridizing a A6 primer to a sample of the subject's mRNA, and/or wherein the assaying the amount of mRNA further comprises performing an nucleic acid amplification reaction involving the primer, and/or wherein the nucleic acid amplification reaction comprises reverse transcription, producing a cDNA, and/or wherein the nucleic acid amplification reaction further comprises performing a polymerase chain reaction on the cDNA, and/or wherein determining the amount of A6 present in the target cell comprises assaying the amount of A6 protein in the cell, and/or further comprising comparing the amount B4 present to the amount in a control cell, and/or further comprising comparing the amount laminin5 present to the amount in a control cell, and/or further comprising comparing the amount gamma2 subunit present to the amount in a control cell.

C. Examples

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Colonic Epithelial Cells Dependent on alpha6beta4 Receptor Signal Transduction for Growth in the Absence of ECM Integrin alpha6 and integrin beta4 and laminin gamma2 chains are essential for tumor cell survival in vivo. The data disclosed herein indicate that interfering with integrin alpha6-mediated signaling, integrin beta 4signaling, and laminin gamma2 signaling can constitute an effective approach to induce programmed cell death in cancer cells without damaging normal cells. Ablation of integrin alpha6-dependent signaling, integrin beta4-dependent signaling, and laminin gamma2-dependent signaling in human cancer cell lines supports this.

The murine colonic epithelial transformation system introduced by D'Abaco et al. (1996) was used. In this system, control cells (control), cells containing an activated ras oncogene (Ras), a deletion in the APC gene (APCmin) or both alterations together (Ras+APCmin) can be compared with regard to their proliferation characteristics in tissue culture. The cells were derived from transgenic mice containing a temperature-sensitive allele of SV40 large T under the control of a gamma interferon-inducible promoter permitting conditional immortalization (Jat et al., 1991). All experiments were carried out with the cells being kept at non-permissive temperature in the absence of gamma interferon. As shown previously (D'Abaco et al., 1996), only the cells carrying activated Ras and the APCmin mutation were able to form colonies in soft agar in the absence of anchorage to a substratum. All other cell populations did not give rise to colonies under these conditions.

The frequency of tunel-staining cells (FIG. 2A) and caspase 3 activity (FIG. 2B) in control, Ras, APCmin and Ras+APCmin colonic epithelial cells (D'Abaco et al., 1996) in suspension was measured. Both assays show a strong suppression of apoptosis in Ras-APCmin cells, indicating that Ras and APCmin co-operate in preventing cell death in the absence of apparent ECM contacts. Activated Ras can protect cells from apoptosis via activation of the serine-threonine kinase AKT (Kauffmann-Zeh et al., 1997; Khwaja et al., 1997). However, both Ras and Ras+APCmin cells show equivalent levels of AKT phosphorylation (not shown), eliminating AKT as the relevant target of Ras+APCmin cooperation.

Although cancer cells have been thought to survive independently of integrin signaling, they frequently express high levels of alpha3 or alpha6 integrin receptors and/or their ligands (Dedhar et al., 1993; Kennel et al., 1989; Koshikawa et al., 1999; Lohi et al., 2000; Nejjari et al., 1999; Van Waes and Carey, 1992). These integrins are suspected to play a role in invasion and metastasis (Mukhopadhyay et al., 1999; Shaw et al., 1997). Ras and APCmin mutations would induce alterations in the mRNA expression patterns of integrin and ECM components. Induction of alpha6 integrin alone, was specific to Ras+APCmin cells (FIG. 3A). In addition, we found elevated expression of the laminin alpha5, gamma2 and beta2 chains induced in Ras and Ras+APCmin cells (FIG. 3B). These chains are components of laminins 5, 10 and 11 (Malinda and Kleinman, 1996), which are ligands of integrin receptors alpha6/beta4 and alpha3/beta1 (Kikkawa et al., 2000; Niessen et al., 1994). These results indicate that Ras and APCmin mutations can cooperate to induce autocrine activation of integrin receptors.

Alpha6 integrin can form functional receptors together with either beta1 or beta4 integrins (Clark and Brugge, 1995), leading to signaling through downstream effectors such as focal adhesion kinase (FAK) or the SH2 domain adapter She (Giancotti and Ruoslahti, 1999). Conversely, beta4 integrin only binds to alpha6 integrin (Clark and Brugge, 1995). In transformed colonic epithelial cells alpha6 integrin functions in conjunction with integrin beta4 and is engaged by the laminin gamma2 chain to activate She (see FIG. 4). Consistent with alpha6 integrin induction, only Ras+APCmin cells can bind a laminin gamma2-specific peptide in an alpha6 and beta4 integrin-specific manner. In contrast, an alpha3/beta1 and alpha6/beta1-specific peptide derived from the laminin gamma1 chain, only binds to control cells (FIG. 4A). In addition, only in Ras+APCmin cells is She phosphorylated in response to clustering of the integrin alpha6/beta4 receptor by beta4-specific antibodies (Mainiero et al., 1995) and by the laminin gamma2-specific peptide (FIG. 4B). In both cases p52$^{Shc}$ is the major phosphorylated form. Moreover, alpha6 integrin is required for She activation, as She phosphorylation is inhibited in response to expression of a dominant-negative beta4 integrin mutant. This mutant lacks the cytoplasmic signaling domain but selectively binds to alpha6 integrin to form a ligand binding, yet signaling-defective alpha6/beta4 integrin (Spinardi et al., 1993) (FIG. 4B)

Anti-sense RNAs specific for alpha6 integrin and gamma2 laminin, as well as dominant-negative beta4 integrin, were expressed and results indicated that integrin alpha6, integrin beta4, and laminin gamma2 expression are relevant for the survival of Ras+APCmin cells in Ras+APCmin, Ras, APC and control cells. All three constructs efficiently inhibit the growth of Ras+APCmin cells in soft agar (not shown) and when attached to plastic (FIG. 5A1). In contrast, the proliferation of wt, Ras and APCmin cells is not affected by this treatment (FIG. 5A1). Importantly, the colony formation of Ras+APC cells exposed to any of the three inhibitory constructs can be rescued by co-expression of baculovirus p35, a potent inhibitor of caspase activity and of apoptosis (Resnicoff et al., 1998) (FIG. 5A1). Similarly, co-expression of exogenous integrin alpha6 mRNA efficiently rescues Ras-APCmin cell proliferation inhibited by alpha6 anti-sense RNA (FIG. 5A1). This is mirrored by a rescue of alpha6 integrin expression on the cell surface of alpha6 anti-sense RNA expressing cells (FIG. 5B). Moreover, ectopic alpha6 integrin expression also rescues apoptosis induced by dominant-negative beta4 integrin (FIG. 5A1). The latter is expressed at constant levels (FIG. 5B). As one would expect, the cells expressing laminin gamma2 antisense RNA could not be rescued by integrin alpha6 over-expression, but showed significant rescue when plated on dishes coated with laminin gamma2 peptide (FIG. 5A1). Similarly, this peptide increases the survival of Ras+APCmin cells in suspension, as indicated by lower caspase 3 activity (FIG. 2C). In summary, the survival of Ras-APCmin cells depends on the expression of alpha6/beta4 integrin and the laminin gamma2 chain. Conversely, the inhibition of these gene activities leads to selective killing of transformed cells.

Data also indicate that cell death due to lack of alpha6/beta4 integrin receptor signaling in Ras-APCmin cells is independent of the death signaling pathway involving the induction of mitochondrial damage and caspase 9 activity. Instead, the data indicate an involvement of the Fas/TNF receptor/death domain protein/caspase8 pathway (Krtiidering and Evan, 2000) in the control of tumor cell survival by alpha6 integrin-containing integrin receptors.

Control, APCmin and Ras cells, which lack alpha6/beta4 integrin receptor signaling activity, show high levels of caspase 8 activity when kept in suspension, while at the same time caspase 9 activity cannot be detected (FIG. 2D).

Although Ras-APCmin cells can be rescued from apoptosis by caspase inhibitor baculovirus p35 (FIGS. 5A1, A2 and text above), cell death induced by expression of dominant-negative beta4 integrin cannot be prevented by expression of the survival factor Bcl2 (see FIG. 5A2). Bcl2 binds to and neutralizes BH3-domain killer proteins that cause mitochondrial damage, cytochrome C release and caspase 9 activation (Luo et al., 1998).

Ras cells which lack alpha6/beta4 integrin receptor signaling activity and cannot survive in the absence of ECM contacts, and Ras+APCmin cells which depend on alpha6/beta4 integrin receptor signaling for survival, show equivalent levels of AKT phosphorylation (data not shown). This indicates that AKT does not serve as the key target for alpha6/beta4 integrin receptor signaling. AKT has been described to promote cell survival via phosphorylation and inactivation of Bad, a BH3-domain killer protein (Datta et al., 1999).

2. Example 2

Other Cancer Cells Dependent on alpha6beta4 Receptor Signal Transduction for Growth in the Absence of ECM The survival of highly transformed primary mouse embryo fibroblasts expressing Ras and Myc oncoproteins in conjunction with a homozygous ARF null mutation (Kamijo et al., 1997) depends on expression and function of alpha6 integrin (FIG. 5C), thus demonstrating that this principle also may apply to transformed mesenchymal cells. Moreover, the human colon cancer cell line SW480 carrying multiple oncogenic mutations such as activated Ras (Fujita et al., 1988), amplified c-Myc (Cherif et al., 1988), a mutated APC allele (Munemitsu et al., 1995) and a p53 mutation (Abarzua et al., 1995) is effectively killed by anti-sense integrin alpha6 and laminin gamma2 RNAs as well as dominant-negative beta4 integrin (FIG. 4D). Similarly, integrin alpha6 ablation even leads to apoptosis of Ras/APCmin cells in the presence of active SV40 large T (not shown). Thus the survival of different types of highly transformed cells depends on alpha6 integrin expression, beta4 integrin expression and laminin5 expression irrespective of the status of major tumor supressor genes, such as arf, p53 or rb, and for at least sw480 cells, and the ras/APCmin and dnp53/ras cells, alpha6, beta4, and laminin5/gamma2 are required. The sensitivity of transformed cells to ablation of integrin signaling, for example, A6B4 integrin receptor signaling, is thus quite remarkable in its apparent generality.

Oncogenic mutations co-operate to engage autocrine integrin signaling. Importantly, this signaling mechanism, involving alpha6 integrin, beta4 integrin and the laminin gamma2 chain, becomes an essential component of the survival mechanism in transformed colonic epithelial cells. In addition, fibroblasts and human colon cancer cells also rely on integrin alpha6 for survival. In contrast, normal and partially transformed cells that express alpha6 integrin at low levels do not require this polypeptide for survival. Thus, integrin signaling inhibition can lead to selective killing of cancer cells.

The laminin-integrin receptor signaling loop is also relevant to the survival of cells transformed by other combinations of oncogenic lesions. Introduction of activated Ras together with dominant-negative p53 (Lloyd et al., 1997) into murine colonic epithelial cells (D'Abaco et al., 1996; see also above) via retroviral infection supports this. Four distinct polyclonal pools of infected cells were derived by drug selection: 1) Control (beo/neo) cells, infected with two retroviruses carrying neomycin (neo) or bleomycin (bleo) drug resistance markers, respectively; 2)Ras cells, infected with a Ras/neo virus and a virus with the bleo marker; 3) DNp53 cells, infected with a DNp53/bleo virus and a virus with the neo marker; and 4) Ras/DNp53 cells, infected with a Ras/neo virus and a DNp53/bleo virus.

As the colon epithelial cells contain temperature-sensitive SV40 large T under control of the gamma interferon promoter, all cell populations were drug-selected at the permissive temperature (33° C.) in the presence of gamma interferon. All further experiments were carried out at the non-permissive temperature for SV40 large T in the absence of gamma interferon, as described above for Ras+APCmin cells.

Similar to Ras+APCmin cells, only Ras/DNp53 cells but neither bleo/neo, Ras/bleo or DNp53/neo cells were able to grow in the absence of ECM contact in soft agar (not shown). Moreover, Ras and DNp53 cooperate in the suppression of caspase 3 activity in suspension (FIG. 2B), and in the induction of alpha6 integrin expression (FIG. 4A). In Ras/DNp53 cells passaged through a single round of soft agar growth, alpha6 integrin is expressed at even higher levels, demonstrating a correlation between the ability of the cells to survive in the absence of ECM contact and alpha6 integrin expression. In Ras/DNp53 cells beta4 integrin expression levels are also increased, when compared to controls (FIG. 4A). As expected expression of the laminin gamma2 chain is induced in Ras/bleo and Ras/DNp53 cells (FIG. 4B).

Anti-sense RNAs specific for alpha6 integrin and gamma2 laminin, as well as dominant-negative beta4 integrin were expressed in Ras/DNp53, Ras/bleo, DNp53/neo and neo/bleo cells. All three constructs efficiently inhibit the growth of Ras/DNp53 cells when attached to plastic. In contrast, the proliferation of neo/bleo, Ras/bleo and DNp53/neo cells is not affected by this treatment (FIG. 5A3). Anti-sense alpha6 integrin or dominant-negative beta4 integrin also inhibit the growth of Ras/DNp53 cells in soft agar (FIG. 5A4).

Integrin alpha6 expression can also be induced by activated Ras and DNp53 in primary murine colon crypt epithelial cells (not shown). Furthermore introduction of Ras and Myc oncoproteins into our control colon epithelial cells also leads to an induction of alpha6 expression (not shown), suggesting that induction of alpha6 integrin expression may be an integral component of distinct oncogene cooperation paradigms a) Cell Types to be Tested As described herein, there are a variety of cancer and transformed cell types that express alpha6 integrin and laminins at high levels (Dedhar et al., 1993; Koshikawa et al., 1999; Lohi et al., 2000; Van Waes and Carey, 1992). As disclosed herein the following cell lines other than the fibroblasts require alpha6 and beta4 integrin expression, as well as laminin gamma2 chain expression: (1) the human colon carcinoma cell line SW480 (data not shown), (2) Ras+APCmin-transformed murine colon epithelial cells (see FIG. 3A) Murine fibroblasts transformed by activated Ras and Myc in conjunction with homozygous Arf null mutation require alpha6 expression for their survival. These cells do not express integrin beta4, but express beta1 integrin, indicating the importance of alpha6/beta1 receptors in the transformed fibroblasts.

b) Inducible Expression of Inhibitors

To interrupt alpha6 integrin and laminin gamma2 chain-dependent signaling in tumors regulatable alpha6 integrin and laminin gamma2 antisense mRNA expression as well as regulatable expression of the beta4 integrin the dominant-negative polypeptide described in Section C were used. Constitutive expression of these inhibitors leads to rapid cell death in tissue culture. In contrast, the establishment of clonal cell lines with inducible expression of anti-sense mRNAs or dominant-negative beta4 integrin minimize such limitations.

The doxycycline (dox)-inducible reverse tetracycline transactivator (rtTA) is frequently used to overexpress transgenes in a temporally regulated fashion in vitro and in vivo (Efrat et al., 1995; Gossen et al., 1995; Ray et al., 1997). These systems are, however, often compromised by the levels of gene expression in the absence of dox administration. The tetracycline controlled transcriptional silencer (tTS), a fusion protein containing the tet repressor and the KRAB-AB domain of the kid-1 transcriptional repressor, is inhibited by doxycycline. As shown in tissue culture (Freundlieb et al., 1999) and in transgenic mice (Zhu et al., 2001), tTS tightens the control of transgene expression in rtTA-based systems, i.e. tTS effectively eliminates leaky baseline expression without altering the inducibility of rtTA-regulated genes. Thus optimal "off/on" regulation of gene expression can be accomplished with the combined use of tTS and rtTA. The complete expression system is commercially available from CLONTECH. This system can be used for the preparation of all inducible cell lines.

Another regulatable system comprising the estrogen-dependent transactivator GalER-VP16 and a promoter under the control of Gal4 DNA binding sites (Braselmann et al., 1993) can be used. (Perez-Roger et al., 1997). This particular experimental set up, was used herein to show that the induction of the beta4 integrin dominant-negative mutant in SW480 colon cancer cells induces apoptosis in vitro, as measured by caspase 3 activation (FIG. 2B). For in vivo use, however, a point mutation has to be introduced into the GalER-VP16 transactivator that eliminates its sensitivity to estrogen while retaining its response to the anti-estrogen 4OH-tamoxifen (Littlewood et al., 1995). 4OH-tamoxifen has been demonstrated to reversibly regulate in vivo the activity of another regulatable transactivator, the MycER chimera (Pelengaris et al., 1999).

Typically, inducible cell lines are first stably transfected with the anti-sense or dominant-negative constructs coupled to the regulatable promoters into the four test cell lines. Subsequently, the activator is introduced and the repressor, such as rtTA and tTS (see above) via infection using recombinant retroviruses with different selectable markers

3. Example 3

Integrin alpha6/beta4 and Laminin gamma 2 Chain Expression is Essential for Survival of Transformed Cells Anti-sense RNAs specific for alpha6 and beta4 integrins, gamma2 laminin or RNA encoding DN-beta4 integrin in Ras/APCmin and Ras/DNp53 cells were made to show that Ras/APCmin and Ras/DNp53 cooperation induces autocrine activation of integrin receptors, a mechanism that could conceivably enable the survival of transformed cells in the absence of ECM. All four constructs efficiently inhibited colony formation of both cell populations not only in suspension, but surprisingly also when grown on collagenIV-coated culture dishes in the presence of serum (FIG. 6A). The inhibitory effects of the four constructs were efficiently rescued upon co-expression of baculovirus p35, a potent inhibitor of apoptosis[21] (FIG. 6A). Taken together, we conclude that alpha6 integrin signaling is required for the survival of the transformed cells both in the absence and in the presence of ECM contacts, and when the cells are exposed to other strong survival signals contained in serum. Co-expression of exogenous integrin alpha6 mRNA efficiently rescued Ras/APCmin cells exposed to alpha6 anti-sense RNA or DN-beta4 integrin, but not laminin gamma2 anti-sense-treated cells (FIG. 6A-C). The latter were partially rescued when plated on dishes coated with the laminin gamma2 peptide (FIG. 6A) capable of activating integrin alpha6-dependent signaling, while decreasing caspase3 activity in Ras/APCmin cells kept in suspension.

In striking contrast to Ras/APCmin and Ras/DNp53 cells, colony formation of control, Ras, APCmin and DNp53 cells was not affected by any of the interfering constructs (FIG. 6A), although expression of beta4 integrin-specifc antisense RNA leads to equal reduction in surface expression of beta4 integrin in control, Ras (not shown), DNp53 and Ras/DNp53 cells (FIG. 6B).

The data indicate that the survival of Ras/APCmin and Ras/DNp53 cells depends on autocrine integrin signaling induced by cooperating oncogenic mutations. Conversely, inhibiting expression and/or function of integrin and laminin ligand components, leads to selective killing of transformed cells but not their untransformed or partially transformed counterparts. This interpretation is supported by experiments showing that integrin beta4 antibodies selectively induce apoptosis in Ras/DNp53 cells (FIG. 6D) and Ras/APCmin cells, while control, DNp53 or Ras cells remain unaffected (FIG. 6D). Moreover, the antibodies induce similar increases in apoptosis in the presence and absence of serum, suggesting that integrin function is independent of growth factors in this context.

The dependence on alpha6 integrin signaling for survival can also be found in highly malignant cancer cells. The human colon carcinoma cell line SW480 carries multiple oncogenic mutations such as activated Ras, amplified c-Myc, a mutated APC allele and a p53 mutation. Nevertheless, the cells are effectively inhibited from forming colonies in suspension by anti-sense integrin alpha6, beta4 or laminin gamma2 RNAs as well as by constitutive or inducible DN-beta4 integrin (FIG. 6E), the latter of which is also shown to induce caspase 3 activity (FIG. 6F). DN-beta4 integrin also severely inhibited transformed primary mouse embryo fibroblasts expressing Ras and Myc oncoproteins in conjunction with a homozygous $p19^{Arf}$ null mutation[22] from forming colonies on culture dishes, while Myc+$p19^{Arf}$-/- cells exposed to DN-beta4 remained virtually unaffected (FIG. 6G). Thus a variety of highly transformed cells show dependence on integrin signaling irrespective of the status of tumor suppressor genes, such as arf or p53, indicating a general dependence on integrin signaling by transformed cells.

D. References

Abarzua, P., LoSardo, J. E., Gubler, M. L. and Neri, A. (1995) Microinjection of monoclonal antibody PAb421 into human SW480 colorectal carcinoma cells restores the transcription activation function to mutant p53. Cancer Res, 55, 3490-4.

Akiyama, S. K., Nagata, K. and Yamada, K. M. (1990) Cell surface receptors for extracellular matrix components. Biochim Biophys Acta, 1031, 91-110.

Braselmann, S., Graninger, P. and Busslinger, M. (1993) A selective transcriptional induction system for mammalian cells based on Gal4-estrogen receptor fusion proteins. Proc Natl Acad Sci USA, 90, 1657-61.

Cherif, D., Le Coniat, M., Suarez, H. G., Bernheim, A. and Berger, R. (1988) Chromosomal localization of amplified c-myc in a human colon adenocarcinoma cell line with a biotinylated probe. Cancer Genet Cytogenet, 33, 245-9.

Clark, E. A. and Brugge, J. S. (1995) Integrins and signal transduction pathways: the road taken. Science, 268, 233-9.

D'Abaco, G. M., Whitehead, R. H. and Burgess, A. W. (1996) Synergy between Apc min and an activated ras mutation is sufficient to induce colon carcinomas. Mol Cell Biol, 16, 884-91.

Dedhar, S., Saulnier, R., Nagle, R. and Overall, C. M. (1993) Specific alterations in the expression of alpha 3 beta 1 and alpha 6 beta 4 integrins in highly invasive and metastatic variants of human prostate carcinoma cells selected by in vitro invasion through reconstituted basement membrane. Clin Exp Metastasis, 11, 391-400.

Efrat, S., Fusco-DeMane, D., Lemberg, H., al Emran, O. and Wang, X. (1995) Conditional transformation of a pancreatic beta-cell line derived from transgenic mice expressing a tetracycline-regulated oncogene. Proc Natl Acad Sci USA, 92, 3576-80.

Freundlieb, S., Schirra-Muller, C. and Bujard, H. (1999) A tetracycline controlled activation/repression system with increased potential for gene transfer into mammalian cells. J Gene Med, 1, 4-12.

Fujita, J., Yoshida, O., Ebi, Y., Nakayama, H., Onoue, H., Rhim, J. S. and Kitamura, Y. (1988) Detection of ras oncogenes by analysis of p21 proteins in human tumor cell lines. Urol Res, 16, 415-8.

Giancotti, F. G. and Mainiero, F. (1994) Integrin-mediated adhesion and signaling in tumorigenesis. Biochim Biophys Acta, 1198, 47-64.

Giancotti, F. G. and Ruoslahti, E. (1999) Integrin signaling. Science, 285, 1028-32.

Gossen, M., Freundlieb, S., Bender, G., Muller, G., Hillen, W. and Bujard, H. (1995) Transcriptional activation by tetracyclines in mammalian cells. Science, 268, 1766-9.

He, T. C., Sparks, A. B., Rago, C., Hermeking, H., Zawel, L., da Costa, L. T., Morin, P. J., Vogelstein, B. and Kinzler, K.

W. (1998) Identification of c-MYC as a target of the APC pathway. *Science*, 281, 1509-12.

Hynes, R. O. (1992) Integrins: versatility, modulation, and signaling in cell adhesion. *Cell*, 69, 11-25.

Jat, P. S., Noble, M. D., Ataliotis, P., Tanaka, Y., Yannoutsos, N., Larsen, L. and Kioussis, D. (1991) Direct derivation of conditionally immortal cell lines from an H-2Kb-tsA58 transgenic mouse. *Proc Natl Acad Sci USA*, 88, 5096-100.

Kamijo, T., Zindy, F., Roussel, M. F., Quelle, D. E., Downing, J. R., Ashmun, R. A., Grosveld, G. and Sherr, C. J. (1997) Tumor suppression at the mouse INK4a locus mediated by the alternative reading frame product p19ARF. *Cell*, 91, 649-59.

Kauffmann-Zeh, A., Rodriguez-Viciana, P., Ulrich, E., Gilbert, C., Coffer, P., Downward, J. and Evan, G. (1997) Suppression of c-Myc-induced apoptosis by Ras signalling through PI(3)K and PKB. *Nature*, 385, 544-8.

Kennel, S. J., Foote, L. J., Falcioni, R., Sonnenberg, A., Stringer, C. D., Crouse, C. and Hemler, M. E. (1989) Analysis of the tumor-associated antigen TSP-180. Identity with alpha 6-beta 4 in the integrin superfamily. *J Biol Chem*, 264, 15515-21.

Khwaja, A., Rodriguez-Viciana, P., Wennstrom, S., Warne, P. H. and Downward, J. (1997) Matrix adhesion and Ras transformation both activate a phosphoinositide 3-OH kinase and protein kinase B/Akt cellular survival pathway. *Embo J*, 16, 2783-93.

Kikkawa, Y., Sanzen, N., Fujiwara, H., Sonnenberg, A. and Sekiguchi, K. (2000) Integrin binding specificity of laminin-10/11: laminin-10/11 are recognized by alpha 3 beta 1, alpha 6 beta 1 and alpha 6 beta 4 integrins. *J Cell Sci*, 113, 869-76.

Koshikawa, N., Moriyama, K., Takamura, H., Mizushima, H., Nagashima, Y., Yanoma, S. and Miyazaki, K. (1999) Overexpression of laminin gamma2 chain monomer in invading gastric carcinoma cells. *Cancer Res*, 59, 5596-601.

Land, H., Parada, L. F. and Weinberg, R. A. (1983) Tumorigenic conversion of primary embryo fibroblasts requires at least two cooperating oncogenes. *Nature*, 304, 596-602.

Lee, J. W. and Juliano, R. L. (2000) alpha5beta1 integrin protects intestinal epithelial cells from apoptosis through a phosphatidylinositol 3-kinase and protein kinase B-dependent pathway. *Mol Biol Cell*, 11, 1973-87.

Lin, C. Q. and Bissell, M. J. (1993) Multi-faceted regulation of cell differentiation by extracellular matrix. *Faseb J*, 7, 737-43.

Littlewood, T. D., Hancock, D. C., Danielian, P. S., Parker, M. G. and Evan, G. I. (1995) A modified oestrogen receptor ligand-binding domain as an improved switch for the regulation of heterologous proteins. *Nucleic Acids Res*, 23, 1686-90.

Lloyd, A. C., Obermuller, F., Staddon, S., Barth, C. F., McMahon, M. and Land, H. (1997) Cooperating oncogenes converge to regulate cyclin/cdk complexes. *Genes Dev*, 11, 663-77.

Lohi, J., Oivula, J., Kivilaakso, E., Kiviluoto, T., Frojdman, K., Yamada, Y., Burgeson, R. E., Leivo, I. and Virtanen, I. (2000) Basement membrane laminin-5 is deposited in colorectal adenomas and carcinomas and serves as a ligand for alpha3beta1 integrin. *Apmis*, 108, 161-72.

Mainiero, F., Murgia, C., Wary, K. K., Curatola, A. M., Pepe, A., Blumemberg, M., Westwick, J. K., Der, C. J. and Giancotti, F. G. (1997) The coupling of alpha6beta4 integrin to Ras-MAP kinase pathways mediated by She controls keratinocyte proliferation. *Embo J*, 16, 2365-75.

Mainiero, F., Pepe, A., Wary, K. K., Spinardi, L., Mohammadi, M., Schlessinger, J. and Giancotti, F. G. (1995) Signal transduction by the alpha 6 beta 4 integrin: distinct beta 4 subunit sites mediate recruitment of She/Grb2 and association with the cytoskeleton of hemidesmosomes. *Embo J*, 14, 4470-81.

Malinda, K. M. and Kleinman, H. K. (1996) The laminins. *Int J Biochem Cell Biol*, 28, 957-9.

Marshall, M. S. (1995) Ras target proteins in eukaryotic cells. *Faseb J*, 9, 1311-8.

Morgenstern, J. P. and Land, H. (1990) Advanced mammalian gene transfer: high titre retroviral vectors with multiple drug selection markers and a complementary helper-free packaging cell line. *Nucleic Acids Res*, 18, 3587-96.

Mukhopadhyay, R., Therlault, R. L. and Price, J. E. (1999) Increased levels of alpha6 integrins are associated with the metastatic phenotype of human breast cancer cells. *Clin Exp Metastasis*, 17, 325-32.

Munemitsu, S., Albert, I., Souza, B., Rubinfeld, B. and Polakis, P. (1995) Regulation of intracellular beta-catenin levels by the adenomatous polyposis coli (APC) tumor-suppressor protein. *Proc Natl Acad Sci USA*, 92, 3046-50.

Nejjari, M., Hafdi, Z., Dumortier, J., Bringuier, A. F., Feldmann, G. and Scoazec, J. Y. (1999) alpha6beta1 integrin expression in hepatocarcinoma cells: regulation and role in cell adhesion and migration. *Int J Cancer*, 83, 518-25.

Niessen, C. M., Hogervorst, F., Jaspars, L. H., de Melker, A. A., Delwel, G. O., Hulsman, E. H., Kuikman, I. and Sonnenberg, A. (1994) The alpha 6 beta 4 integrin is a receptor for both laminin and kalinin. *Exp Cell Res*, 211, 360-7.

Parise, L. V., Lee, J. and Juliano, R. L. (2000) New aspects of integrin signaling in cancer. *Semin Cancer Biol*, 10, 407-14.

Pawson, T. and Scott, J. D. (1997) Signaling through scaffold, anchoring, and adaptor proteins. *Science*, 278, 2075-80.

Pelengaris, S., Littlewood, T., Khan, M., Elia, G. and Evan, G. (1999) Reversible activation of c-Myc in skin: induction of a complex neoplastic phenotype by a single oncogenic lesion. *Mol Cell*, 3, 565-77.

Perez-Roger, I., Kim, S. H., Griffiths, B., Sewing, A. and Land, H. (1999) Cyclins D1 and D2 mediate myc-induced proliferation via sequestration of p27(Kip1) and p21 (Cip1). *Embo J*, 18, 5310-20.

Perez-Roger, I., Solomon, D. L., Sewing, A. and Land, H. (1997) Myc activation of cyclin E/Cdk2 kinase involves induction of cyclin E gene transcription and inhibition of p27(Kip1) binding to newly formed complexes. *Oncogene*, 14, 2373-81.

Ray, P., Tang, W., Wang, P., Homer, R., Kuhn, C., 3rd, Flavell, R. A. and Elias, J. A. (1997) Regulated overexpression of interleukin 11 in the lung. Use to dissociate development-dependent and -independent phenotypes. *J Clin Invest*, 100, 2501-11.

Resnicoff, M., Valentinis, B., Herbert, D., Abraham, D., Friesen, P. D., Alnemri, E. S. and Baserga, R. (1998) The baculovirus anti-apoptotic p35 protein promotes transformation of mouse embryo fibroblasts. *J Biol Chem*, 273, 10376-80.

Roper, E., Weinberg, W., Watt, F. M. and Land, H. (2001) p19ARF-independent induction of p53 and cell cycle arrest by Raf in murine keratinocytes. *EMBO Rep*, 2, 145-50.

Ruley, H. E. (1983) Adenovirus early region 1A enables viral and cellular transforming genes to transform primary cells in culture. *Nature*, 304, 602-6.

Sewing, A., Wiseman, B., Lloyd, A. C. and Land, H. (1997) High-intensity Raf signal causes cell cycle arrest mediated by p21Cip1. *Mol Cell Biol*, 17, 5588-97.

Shaw, L. M., Rabinovitz, I., Wang, H. H., Toker, A. and Mercurio, A. M. (1997) Activation of phosphoinositide 3-OH kinase by the alpha6beta4 integrin promotes carcinoma invasion. *Cell,* 91, 949-60.

Sonnenberg, A., Linders, C. J., Daams, J. H. and Kennel, S. J. (1990) The alpha 6 beta 1 (VLA-6) and alpha 6 beta 4 protein complexes: tissue distribution and biochemical properties. *J Cell Sci,* 96, 207-17.

Spinardi, L., Ren, Y. L., Sanders, R. and Giancotti, F. G. (1993) The beta 4 subunit cytoplasmic domain mediates the interaction of alpha 6 beta 4 integrin with the cytoskeleton of hemidesmosomes. *Mol Biol Cell,* 4, 871-84.

Thompson, T. C., Southgate, J., Kitchener, G. and Land, H. (1989) Multistage carcinogenesis induced by ras and myc oncogenes in a reconstituted organ. *Cell,* 56, 917-30.

Treisman, R. (1996) Regulation of transcription by MAP kinase cascades. *Curr Opin Cell Biol,* 8, 205-15.

Van Waes, C. and Carey, T. E. (1992) Overexpression of the A9 antigen/alpha 6 beta 4 integrin in head and neck cancer. *Otolaryngol Clin North Am,* 25, 1117-39.

Wary, K. K., Mainiero, F., Isakoff, S. J., Marcantonio, E. E. and Giancotti, F. G. (1996) The adaptor protein Shc couples a class of integrins to the control of cell cycle progression. *Cell,* 87, 733-43.

Zhu, Z., Ma, B., Homer, R. J., Zheng, T. and Elias, J. A. (2001) Use of the tetracycline controlled transcriptional silencer (tTS) to eliminate transgene leak in inducible overexpression transgenic mice. *J Biol Chem,* 30, 30.

E. Sequences

1. SEQ ID NO:1 Human alpha6 integrin cds (acc# 4557674)
2. SEQ ID NO:2 Human integrin alpha6 protein sequence (acc# NP 000201):
3. SEQ ID NO:3 *Mus musculus* alpha6 integrin cds (acc# 7110658):
4. SEQ ID NO:4 *Mus musculus* alpha6 integrin protein sequence (acc# NP 032423)
5. SEQ ID NO:5 Human integrin beta4 subunit cds (acc# 6453379):
6. SEQ ID NO:6 Human beta4 integrin protein sequence (acc# CAB61345):
7. SEQ ID NO:7 Mouse integrin beta4 subunit mRNA (not only cds) (acc# L04678):
8. SEQ ID NO:8 Murine integrin beta4 protein sequence:
9. SEQ ID NO:9 Mouse beta4 dominant negative cds:
10. SEQ ID NO:10 Mouse beta4 dominant negative protein sequence:
11. SEQ ID NO:11 Murine laminin gamma2 chain complete cds (acc# U43327):
12. SEQ ID NO:12 Murine laminin gamma2 chain protein sequence (acc# AAA85256)
13. SEQ ID NO:13 Human laminin gamma2 chain complete cds (acc# AH006634)
14. SEQ ID NO:14 Human laminin gamma2 chain protein sequence (acc# AAC50457) Alternative splice form
15. SEQ ID NO:15 Human laminin gamma2 chain protein sequence (acc# AAC50456) Alternative splice form
16. Degenerate Human integrin beta4 subunit cds
17. SEQ ID NO:17 Human beta4 integrin protein sequence Variant V at 34 to I:
18. SEQ ID NO:18 Human integrin beta4 subunit cds Variant at 34 V to I:

```
   1 mpalwlgccl cfslllpaar atsrrevcdc ngksrqcifd relhrqtgng frclncndnt
  61 dgihcekckn gfyrhrerdr clpcncnskg slsarcdnsg rcsckpgvtg arcdrclpgf
 121 hmltdagctq dqrlldskcd cdpagiagpc dagrcvckpa vtgercdrcr sgyynldggn
 181 pegctqcfcy ghsascrssa eysvhkitst fhqdvdgwka vqrngspakl qwsqrhqdvf
 241 ssaqrldpvy fvapakflgn qqvsygqsls fdyrvdrggr hpsandvile gaglritapl
 301 mplgktlpcg ltktytfrln ehpsnnwspq lsyfeyrrll rnltalrira tygeystgyi
 361 dnvtlisarp vsgapapwve qcicpvgykg qfcqdcasgy krdsarlgpf gtcipcncqg
 421 ggacdpdtgd cysgdenpdi ecadcpigfy ndphdprsck pcpchngfsc svmpeteevv
 481 cnncppgvtg arcelcadgy fgdpfgehgp vrpcqpcqcn nnvdpsasgn cdrltgrclk
 541 cihntagiyc dqckagyfgd plapnpadkc racncnpmgs epvgcrsdgt cvckpgfggp
 601 ncehgafscp acynqvkiqm dqfmqqlqrm ealiskaqgg dgvvpdtele grmqqaeqal
 661 qdilrdaqis egasrslglq lakvrsqens yqsrlddlkm tvervralgs qyqnrvrdth
 721 rlitqmqlsl aeseaslgnt nipasdhyvg pngfkslaqe atrlaeshve sasnmeqltr
 781 etedyskqal slvrkalheg vgsgsgspdg avvqglvekl ektkslaqql treatqaeie
 841 adrsyqhslr lldsysrlqg vsdqsfqvee akrikqkads lstlvtrhmd efkrtqknlg
 901 nwkeeaqqll qngksgreks dqllsranla ksraqealsm gnatfyeves ilknlrefdl
 961 qvdnrkaeae eamkrlsyis qkvsdasdkt qqaeralgsa aadaqrakng agealeisse
1021 ieqeigslnl eanvtadgal amekglaslk semrevegel erkelefdtn mdavqmvite
1081 aqkvdtrakn agvtiqdtln tldgllhlmd qplsvdeegl vlleqklsra ktqinsqlrp
1141 mmseleerar qqrghlhlle tsidgiladv knlenirdnl ppgcyntqal eqq
```

19. SEQ ID NO:19 Degenerate Human integrin beta4 subunit cds variant at 34 V to I:
20. SEQ ID NO:20 adenomatosis polyposis coli (APC) mRNA (*Homo sapiens*) acc#: M74088
21. SEQ ID NO:21 adenomatosis polyposis coli (APC) protein (*Homo sapiens*)
22. SEQ ID NO:22 NFkB mRNA (*Homo sapiens*) acc#: M58603
23. SEQ ID NO:23 NFkB protein (*Homo sapiens*)
24. SEQ ID NO:24 SV40 large T large T mRNA acc#: AF169001
25. SEQ ID NO:25 SV40 large T large protein
26. SEQ ID NO:26 retinoblastoma gene (Rb) mRNA (*Homo sapiens*) acc#: M19701
27. SEQ ID NO:27 retinoblastoma (Rb) protein (*Homo sapiens*)
28. SEQ ID NO:28 HPV type 16 E7 mRNA acc#: AF477385
29. SEQ ID NO:29 HPV type 16 E7 protein
30. SEQ ID NO:30 p53 mRNA (*Homo sapiens*) acc#: M14695
31. SEQ ID NO:31 p53 protein (*Homo sapiens*)
32. SEQ ID NO:32 p53 mRNA (*mus musculus*) acc#: AF051368
33. SEQ ID NO:33 p53 protein (*mus musculus*)
34. SEQ ID NO:34 c-MYC mRNA (*Homo sapiens*) acc#: V00568
35. SEQ ID NO:35 c-MYC protein (*Homo sapiens*)
36. SEQ ID NO:36 PTEN protein (*Homo sapiens*) acc#: AAD38372
37. SEQ ID NO:37 K-ras mRNA (*Homo sapiens*) acc#: M54968
38. SEQ ID NO:38 k-ras protein
39. SEQ ID NO:39 BRCA1 mRNA (*Homo sapiens*) acc#: U14680
40. SEQ ID NO:40 BRCA1 protein (*homo sapiens*)
41. SEQ ID NO:41 BRCA2 mRNA (*homo sapiens*) acc#: U43746
42. SEQ ID NO:42 BRCA2 (*Homo sapiens*) protein
43. SEQ ID NO:43 erbB2 (*mus musculus*) protein acc#: AAB17380
44. SEQ ID NO:44 erbB (*homo sapiens*) protein acc#: AAF30295
45. SEQ ID NO:45 HER2 (*homo sapiens*) mRNA acc#: M11730

What is claimed is:

1. A method of reducing the proliferation of a cancer cell comprising contacting the cancer cell with a composition consisting of a pharmaceutical carrier and an inhibitor of a ligand binding to an integrin receptor on the cancer cell, wherein the integrin receptor comprises integrin A6, wherein the ligand comprises laminin 5, and wherein the cancer cell expresses a mutated Ras and a mutated p53.

2. The method of claim 1, wherein the integrin receptor further comprises integrin B4.

3. The method of claim 1, wherein the ligand that binds to the integrin receptor is laminin5.

4. The method of claim 1, wherein the integrin receptor is A6B4.

5. The method of claim 1, wherein the ligand comprises the gamma-2 subunit of laminin5.

6. The method of claim 1, wherein inhibiting ligand binding to an integrin receptor comprises contacting the A6 integrin with a composition that inhibits ligand binding.

7. The method of claim 1, wherein inhibiting ligand binding to an integrin receptor comprises contacting a B4 integrin with a composition that inhibits ligand binding.

8. The method of claim 1, wherein inhibiting ligand binding to an integrin receptor comprises contacting a laminin5 with a composition that inhibits ligand binding.

9. The method of claim 1, wherein inhibiting ligand binding to an integrin receptor comprises contacting a gamma-2 subunit of laminin5 with a composition that inhibits ligand binding.

10. The method of claim 1, further comprising reducing a laminin5-integrin interaction.

11. The method of claim 1, further comprising reducing a laminin5 gamma2 integrin interaction.

12. The method of claim 1, wherein reducing the proliferation of the cancer cells is selective.

13. The method of claim 1, wherein the cancer cell is not an MDA-MB-435 cell.

14. The method of claim 1, wherein the cancer cell is not an HMT-3522 cell.

15. The method of claim 1, wherein the cancer cell is not an RKO colon carcinoma line.

16. The method of claim 1, wherein the cancer cell does not express exogenous B4 integrin.

17. A method of reducing the proliferation of a cancer cell consisting of contacting the cancer cell with an oligonucleotide or synthetic analog thereof and a composition consisting of a pharmaceutical carrier and an inhibitor of a ligand binding to an integrin receptor on the cancer cell, wherein the integrin receptor comprises integrin A6, wherein the ligand comprises laminin 5, and wherein the cancer cell expresses a mutated Ras and a mutated p53.

18. The method of claim 17, wherein the cancer cells are contacted with dominant-negative beta 4 integrin.

19. The method of claim 17, wherein the oligonucleotide or synthetic analog thereof is linked to a carrier.

20. The method of claim 19, wherein the carrier is at least one of a lipidic carrier, charged carrier, retroviral carrier, TAT or fragment thereof, antennapedia or fragment thereof, or polyethylene glycol.

21. The method of claim 1, further comprising contacting the cancer cell with another agent which modulates cell signaling.

22. The method of claim 1, wherein reducing the proliferation of cancer cell is in vitro.

23. The method of claims 1, wherein reducing the proliferation of the cancer cell is in vivo.

24. The method of claim 1, wherein the cancer cell is selected from the group consisting of melanoma, adenoma, lymphoma, myeloma, carcinoma, plasmocytoma, sarcoma, glioma, thyoma, leukemia, skin cancer, retinal cancer, breast cancer, prostate cancer, colon cancer, esophageal cancer, stomach cancer, pancreas cancer, brain tumors, lung cancer, ovarian cancer, cervical cancer, hepatic cancer, gastrointestinal cancer, and head and neck cancer cells.

25. The method of claim 1, wherein the cancer cell is killed.

26. The method of claim 1, wherein the cancer cell activates the AKT/PKB protein.

27. The method of claim 1, wherein the cancer cell expresses a mutated APC.

28. The method of claim 1, wherein the inhibitor of ligand binding is an antibody.

29. The method of claim 28, wherein the antibody is specific for the ligand.

30. The method of claim 10, wherein the laminin5-integrin receptor interaction is reduced by an antibody to laminin5.

31. The method of any one of claim 1, further comprising contacting the cancer cell with a chemotherapeutic drug, or treated with radiation or angiogenesis inhibitor.

32. The method of claim 28, wherein the antibody is specific for integrin B4.

33. A method of reducing the proliferation of a cancer cell consisting of contacting the cancer cell with a composition consisting of a pharmaceutical carrier and an inhibitor of a ligand binding to an integrin receptor on the cancer cell, wherein the integrin receptor comprises integrin A6, wherein the ligand comprises laminin 5, and wherein the cancer cell expresses a mutated Ras and a mutated p53.

* * * * *